(12) United States Patent
Chong et al.

(10) Patent No.: US 11,912,992 B2
(45) Date of Patent: *Feb. 27, 2024

(54) CRISPR DNA TARGETING ENZYMES AND SYSTEMS

(71) Applicant: ARBOR BIOTECHNOLOGIES, INC., Cambridge, MA (US)

(72) Inventors: Shaorong Chong, Cambridge, MA (US); Winston X Yan, Boston, MA (US); David A. Scott, Cambridge, MA (US); David R. Cheng, Boston, MA (US); Pratyusha Hunnewell, Needham, MA (US)

(73) Assignee: ARBOR BIOTECHNOLOGIES, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/064,171

(22) Filed: Dec. 9, 2022

(65) Prior Publication Data

US 2023/0183688 A1 Jun. 15, 2023

Related U.S. Application Data

(63) Continuation of application No. 17/497,725, filed on Oct. 8, 2021, which is a continuation of application No. 17/139,678, filed on Dec. 31, 2020, now Pat. No. 11,168,324, which is a continuation of application No. 17/020,215, filed on Sep. 14, 2020, which is a continuation of application No. 16/680,104, filed on Nov. 11, 2019, now Pat. No. 10,808,245, which is a continuation of application No. PCT/US2019/022375, filed on Mar. 14, 2019.

(60) Provisional application No. 62/775,885, filed on Dec. 5, 2018, provisional application No. 62/772,038, filed on Nov. 27, 2018, provisional application No. 62/746,528, filed on Oct. 16, 2018, provisional application No. 62/740,856, filed on Oct. 3, 2018, provisional application No. 62/703,857, filed on Jul. 26, 2018, provisional application No. 62/679,628, filed on Jun. 1, 2018, provisional application No. 62/672,489, filed on May 16, 2018, provisional application No. 62/666,397, filed on May 3, 2018, provisional application No. 62/642,919, filed on Mar. 14, 2018.

(51) Int. Cl.
*C12N 15/11* (2006.01)
*C12N 9/22* (2006.01)
*C12N 15/90* (2006.01)

(52) U.S. Cl.
CPC ............ *C12N 15/11* (2013.01); *C12N 9/22* (2013.01); *C12N 15/902* (2013.01); *C12N 2310/20* (2017.05); *C12N 2310/531* (2013.01); *C12N 2800/80* (2013.01)

(58) Field of Classification Search
CPC .. C12N 9/22; C12N 2310/20; C12N 2800/80; C12N 15/113; C12N 15/63; C12N 15/111
See application file for complete search history.

(56) References Cited

U.S. PATENT DOCUMENTS

| 10,808,245 | B2 | 10/2020 | Chong et al. | |
|---|---|---|---|---|
| 2014/0186843 | A1* | 7/2014 | Zhang | G16B 20/30 435/6.12 |
| 2017/0211142 | A1 | 7/2017 | Smargon et al. | |
| 2018/0371487 | A1 | 12/2018 | Yang | |

FOREIGN PATENT DOCUMENTS

| CN | 106852157 | | 6/2017 |
|---|---|---|---|
| CN | 107250363 | A | 10/2017 |
| CN | 111690720 | A | 9/2020 |
| CN | 112195164 | A | 1/2021 |
| WO | 2012164565 | A1 | 12/2012 |
| WO | 2016106236 | A1 | 6/2016 |
| WO | 2017091630 | A1 | 6/2017 |
| WO | 2017127807 | A1 | 7/2017 |
| WO | 2017219027 | A1 | 12/2017 |
| WO | 2018035250 | A1 | 2/2018 |
| WO | 2018035388 | A1 | 2/2018 |
| WO | 2019178427 | A1 | 9/2019 |
| WO | 2019178428 | A1 | 9/2019 |
| WO | 2019201331 | A1 | 10/2019 |
| WO | 2019/217944 | A1 | 11/2019 |
| WO | 2020028823 | A1 | 2/2020 |
| WO | 2020088450 | A1 | 5/2020 |
| WO | 2020/168051 | A1 | 8/2020 |
| WO | 2020/168075 | A1 | 8/2020 |

(Continued)

OTHER PUBLICATIONS

Liu et al. "C2c1-sgRNA Complex Structure Reveals RNA-Guided DNA Cleavage Mechanism" Molecular Cell (2017) 65: 310-322 (Year: 2017).*
He et al., "Genome-editing: focus on the off-target effects" Chinese Journal of Biotechnology (2017) No. 10, pp. 104-122.
Chen et al., "CRISPR-Cas12a target binding unleashes indiscriminate single-stranded DNase activity," Science 360 (6387) 436-9 (Feb. 2018).

(Continued)

*Primary Examiner* — Neil P Hammell
*Assistant Examiner* — Kelly Nichet Hassell
(74) *Attorney, Agent, or Firm* — K&L Gates LLP

(57) ABSTRACT

The disclosure describes novel systems, methods, and compositions for the manipulation of nucleic acids in a targeted fashion. The disclosure describes non-naturally occurring, engineered CRISPR systems, components, and methods for targeted modification of nucleic acids such as DNA. Each system includes one or more protein components and one or more nucleic acid components that together target nucleic acids.

28 Claims, 68 Drawing Sheets
Specification includes a Sequence Listing.

(56) References Cited

FOREIGN PATENT DOCUMENTS

| WO | 2020/168088 A1 | 8/2020 |
| WO | 2020/168122 A1 | 8/2020 |
| WO | 2020/168132 A1 | 8/2020 |
| WO | 2020181101 A1 | 9/2020 |
| WO | 2020/236936 A1 | 11/2020 |

OTHER PUBLICATIONS

Dong et al., "The crystal structure of Cpf1 in complex with CRISPR RNA," Nature 532(7600): 522-6 (Apr. 2016).
Gaudelli et al., "Programmable base editing of A.T to G.C in genomic DNA without DNA cleavage," Nature 551 (7681): 464-71 (Oct. 2017).
Kim et al., "Efficient Transcriptional Gene Repression by Type V-A CRISPR-Cpf1 from Eubacterium eligens," ACS Synthetic Biology 6(7): 1273-82 (Apr. 2017).
Koonin et al., "Diversity, classification and evolution of CRISPR-Cas systems," Current Opinion in Microbiology 37: 67-78 (Jun. 2017).
Liu et al., "C2c1-sgRNA Complex Structure Reveals RNA-Guided DNA Cleavage Mechanism," Mol Cell. 65(2):310-22 (Dec. 2016).
Makarova et al., "An updated evolutionary classification of CRISPR-Cas systems," Nat. Rev. Microbiol. 13(11):722-36 (Sep. 2015).
Makarova et al., "Classification and Nomenclature of CRISPR-Cas Systems: Where from Here?" CRISPR J. 1(5):325-36 (Oct. 2018).
Murugan et al., "The Revolution Continues: Newly Discovered Systems Expand the CRISPR-Cas Toolkit," Molecular Cell 68(1): 15-25 (Oct. 2017).
Ran et al., "Double nicking by RNA-guided CRISPR Cas9 for enhanced genome editing specificity," Cell 154(6): 1380-9 (Aug. 2013).
Shmakov et al., "Discovery and Functional Characterization of Diverse Class 2 CRISPR-Cas Systems," Molecular Cell 60(3): 385-97 (Oct. 2015).
Stella et al., "Class 2 CRISPR-Cas RNA-guided endonucleases: Swiss Army knives of genome editing," Nature Structural & Molecular Biology 24(11): 882-92 (Oct. 2017).
Wu et al., "Structural basis of stringent PAM recognition by CRISPR-C2c1 in complex with sgRNA," Cell Res. 27(5):705-8 (Apr. 2017).
Yamano et al., "Crystal Structure of Cpf1 in Complex with Guide RNA and Target DNA," Cell 165(4):949-62 (Apr. 2016).
Yan et al., "Cas13d Is a Compact RNA-Targeting Type VI CRISPR Effector Positively Modulated by a WYL-Domain-Containing Accessory Protein," Mol. Cell 70(2)327-39.e5 (Mar. 2018).
Yan et al., "Functionally diverse type V CRISPR-Cas systems," Science 363(6422):88-91 (Dec. 2018).
Yang et al., "PAM-Dependent Target DNA Recognition and Cleavage by C2c1 CRISPR-Cas Endonuclease," Cell 167(7):1814-28 (Dec. 2016).
Zetsche et al., "Cpf1 is a single RNA-guided endonuclease of a class 2 CRISPR-Cas system," Cell 163(3), 759-71 (Sep. 2015).
International Search Report for International Application No. PCT/US2019/022375, dated Jun. 13, 2019 (6 pages).
Written Opinion of the International Searching Authority for International Application No. PCT/US2019/022375 (7 pages).
Makarova et al., "Annotation and Classification of CRISPR-Cas Systems," Methods Mol Biol (2015) vol. 1311, pp. 47-75.
Makarova et al., "Unification of Cas protein families and a simple scenario for the origin and evolution of CRISPR-Cas systems," Biology Direct (2011) vol. 6, Article 38, 27 pages.
Garrett et al., "CRISPR-based immune systems of the Sulfolobales: complexity and diversity," Biochem Soc Trans (2011) vol. 39, pp. 51-57.
Al-Shayeb et al., "Clades of huge phages from across Earth's ecosystems," Nature (2020) vol. 578, pp. 425-431 and Methods pages.
Pausch et al., "CRISPR-Cas-Phi from huge phages is a hypercompact genome editor," Science (2020) vol. 369, pp. 333-337.
Tamulaitis et al., "Type III CRISPR-Cas Immunity: Major Differences Brushed Aside," Trends Microbiol (2017) vol. 25, No. 1, pp. 49-61.
Databse EMBL Online—Speth D.R. et al. "Candidatus Scalindua brodae CHAT domain protein," retrieved from UNIPARC accession No. UPI0005442945, database Accession No. KHE91663, dated Dec. 14, 2014.
International Search Report for PCT/US2019/032750, dated Sep. 25, 2019.
Sequence Alignment of SEQ ID No. 5 with BGX25975, Search conducted on Jun. 5, 2020, 4 pages. (Year: 2020).
Sequence Alignment of SEQ ID No. 5 with BGX25978, Search conducted on Jun. 11, 2020, 7 pages. (Year: 2020).
Sequence Alignment of SEQ ID No. 5 with BGX25997, Search conducted on Jun. 11, 2020, 7 pages. (Year: 2020).
International Search Report and Written Opinion for International Application No. PCT/US2019/022376 dated Jun. 17, 2019.
Strutt et al. "RNA-dependent RNA targeting by CRISPR-Cas9" eLIFE (2018) vol. 7, e 32724, pp. 1-17.
Smargon et al. "Cas13b Is a Type VI-B CRISPR-Associated RNA-Guided RNase Differentially Regulated by Accessory Proteins Csx27 and Csx28" Molecular Cell (2017) vol. 65, No. 4, pp. 618-630.
O'Connell et al. "Programmable RNA recognition and cleavage by CRISPR/Cas9" NATURE (2014) vol. 516, No. 7530, pp. 263-266.
Abudayyeh et al. "C2c2 is a single-component programmable RNA-guided RNA-targeting CRISPR effector" SCIENCE (2016) vol. 353, No. 6299, pp. aaf5573-1-aaf5573-9.
Bisaria et al., "Lessons from Enzyme Kinetics Reveal Specificity Principles for RNA-Guided Nucleases in RNA Interference and CRISPR-Based Genome Editing," Cell Systems 4(1): 21-9 (Jan. 2017).
Boyle et al., "Quantification of Cas9 binding and cleavage across diverse guide sequences maps landscapes of target engagement," Science Advances 7(8): eabe5496 (Feb. 2021).
Chen et al., "Enhanced proofreading governs CRISPR-Cas9 targeting accuracy," Nature 550(7676)407-10 (Sep. 2017).
Huang et al., "Structural basis for two metal-ion catalysis of DNA cleavage by Cas12i2," Nature Communications 11(1): 5241 (Oct. 2020).
Jones et al., "Massively parallel kinetic profiling of natural and engineered CRISPR nucleases," Nature Biotechnology 39(1): 84-93 (Jan. 2021).
Klein et al., "Hybridization Kinetics Explains CRISPR-Cas Off-Targeting Rules," Cell Reports 22(6): 1413-23 (Feb. 2018).
Kleinstiver et al., "Engineered CRISPR-Cas12a variants with increased activities and improved targeting ranges for gene, epigenetic and base editing," Nature Biotechnology 37(3): 276-82 (Feb. 2019).
Kleinstiver et al., "High-fidelity CRISPR-Cas9 nucleases with no detectable genome-wide off-target effects," Nature 529(7587): 490-5 (Jan. 2016).
Slaymaker et al., "Rationally engineered Cas9 nucleases with improved specificity," Science 351(6268): 84-8 (Jan. 2016).
Strecker et al., "Engineering of CRISPR-Cas12b for human genome editing," Nature Communications 10(1): 212 (Jan. 2019).
Strohkendl et al., "Kinetic basis for DNA target specificity of CRISPR-Cas12a," Molecular Cell 71(5): 816-24 (Sep. 2018).
Zhang et al., "Mechanisms for target recognition and cleavage by the Cas12i RNA-guided endonuclease," Nature Structural & Molecular Biology 27:1069-76 (Sep. 2020).

* cited by examiner

Type V-I Cas12i - Functional Domains

RuvC domain architecture:

Type V-I  Cas12i2 – indels & RNA Guide designs

Representative Indels

PAM  +20bp

```
ACCCCCTTTCCAAAGCCCATTCCCTCTTTTC---GAGCCCGGGGTGTGC  (SEQ ID NO: 550)
ACCCCCTTTCCAAAGCCCATTCCCTCTTTTT---GAGCCCGGGGTGTGC  (SEQ ID NO: 551)
ACCCCCTTTCCAAAGCCCATTCCCTCTTTAT---GAGCCCGGGGTGTGC  (SEQ ID NO: 552)
ACCCCCTTTCCAAAGCCCATTCCCTCTTTA----AGAGCCCGGGTGTG   (SEQ ID NO: 553)
ACCCCCTTTCCAAAGCCCATTACCTCTTTA----AGAGCCGGGGTGTG   (SEQ ID NO: 554)
ACCCCCTTTCCAAAGCCCATTCCCTCTGTA----AGAGCCGGGGTGTG   (SEQ ID NO: 555)
```

FIG 41B

SEQUENCE LISTING

```
Sequence total quantity: 621
SEQ ID NO: 1           moltype = AA  length = 1046
FEATURE                Location/Qualifiers
REGION                 1..1046
                       note = source = /note="Description of Artificial Sequence:
                       Synthetic polypeptide"
source                 1..1046
                       mol_type = protein
                       organism = synthetic construct
SEQUENCE: 1
MVSESTIRPY TSKLAPNDPK LKMLNDTFNW LDHAYKVFFD VSVALFGAIE HETAQELIGE   60
KSKFDADLLC AIMWFRLEEK SDNPGPLQTV EQRMRLFQKY SGHEPSSFTQ EYIKGNIDSE  120
KYQWVDCRLK FIDLARNINT TQESLKIDAY TLFMNKLIPV SKDDEFNAYG LISQLFGTGK  180
KEDRSIKASM LEEISNIIED KKPNTWEEYH DLIKKTFNVD NYKELKEKLS AGSSGRDSSL  240
VIDLKEEKTG LLQPNFIKNR IVKFREDADK KRTVFLLPNR MKLREFIASQ IGPFEQNSWS  300
AVLNRSMAAI QSKNSSNILY TNEKEERNNE IQELLKKDIL SAASILGDFR RGEFNRSVVS  360
KNHLGARLNE LFEIWQELTM DDGIKKYVDL CKDKFSRRPV KALLQYIYPY FDKINAKQFL  420
DAASYNTLVE TNNRKKIHPT VTGPTVCNWG PKSTINGSIT PPNQMVKGRP AGSHGMIWVT  480
MTVIDNGRWI KHHLPFHNSR YYEEHYCYRE GLPTKNKPRT KQLGTQVGST ISAPSLAILK  540
SQEEQDRRND RKNRFKAHKS IIRSQENIEY NVAFDKSTNF DVTRKNGEFF ITISSRVATP  600
KYSYKLNIGD MIMGLDNNQT APCTYSIWRV VEKDTEGSFF HNKIWLQLVT DGKVTSIVDN  660
NRQVDQLSYA GIEYSNFAEW RKDRRQFLRS INEDYVKKSD NWRNMNLYQW NAEYSRLLLD  720
VMKENKGKNI QNTFRAEIEE LICGKFGIRL GSLFHHSLQF LTNCKSLISS YFMLNNKKEE  780
YDQELFDSDF FRLMKSIGDK RVRKRKEKSS RISSTVLQIA RENNVKSLCV EGYLPTSTKK  840
TKPKQNQKSI DWCARAVVKK LNDGCKVLGI NLQAIDPRDT SHLDPFVYYG KKSTKVGKEA  900
RYTIVEPSNI KEYMTNRFDD WHRGVTKKSK KGDVQTSTTV LLYQEALRQF ASHYKLDFDS  960
LPKMKFYELA KILGDHEKVI IPCRGGRAYL STYPVTKDSS KITFNGRERW YNESDVVAAV 1020
NIVLRGIIDE DEQPDGAKKQ ALARTK                                     1046

SEQ ID NO: 2           moltype = AA  length = 1091
FEATURE                Location/Qualifiers
REGION                 1..1091
                       note = source = /note="Description of Artificial Sequence:
                       Synthetic polypeptide"
source                 1..1091
                       mol_type = protein
                       organism = synthetic construct
SEQUENCE: 2
MFTLLLSDIS QQNFNKFLKN FFFTRNKTVV HCSSEIRHKG YRSNVMVSES TIRPYTSKLA   60
PNDPKLKMLN DTFNWLDHAY KVFFDVSVAL FGAIEHETAQ ELIGEKSKFD ADLLCAIMWF  120
RLEEKSDNPG PLQTVEQRMR LFQKYSGHEP SSFTQEYIKG NIDSEKYQWV DCRLKFIDLA  180
RNINTTQESL KIDAYTLFMN KLIPVSKDDE FNAYGLISQL FGTGKKEDRS IKASMLEEIS  240
```

```
NIIEDKKPNT  WEEYHDLIKK  TFNVDNYKEL  KEKLSAGSSG  RDSSLVIDLK  EEKTGLLQPN   300
FIKNRIVKFR  EDADKKRTVF  LLPNRMKLRE  FIASQIGPFE  QNSWSAVLNR  SMAAIQSKNS   360
SNILYTNEKE  ERNNEIQELL  KKDILSAASI  LGDFRRGEFN  RSVVSKNHLG  ARLNELFEIW   420
QELTMDDGIK  KYVDLCKDKF  SRRPVKALLQ  YIYPYFDKIN  AKQFLDAASY  NTLVETNNRK   480
KIHPTVTGPT  VCNWGPKSTI  NGSITPPNQM  VKGRPAGSHG  MIWVTMTVID  NGRWIKHHLP   540
FHNSRYYEEH  YCYREGLPTK  NKPRTKQLGT  QVGSTISAPS  LAILKSQEEQ  DRRNDRKNRF   600
KAHKSIIRSQ  ENIEYNVAFD  KSTNFDVTRK  NGEFFITISS  RVATPKYSYK  LNIGDMIMGL   660
DNNQTAPCTY  SIWRVVEKDT  EGSFFHNKIW  LQLVTDGKVT  SIVDNNRQVD  QLSYAGIEYS   720
NPAEWRKDRR  QFLRSINEDY  VKKSDNWRNM  NLYQWNAEYS  RLLLDVMKEN  KGKNIQNTFR   780
AEIEELICGK  FGIRLGSLFH  HSLQFLTNCK  SLISSYFMLN  NKKEEYDQEL  FDSDFFRLMK   840
SIGDKRVRKR  KEKSSRISST  VLQIARENNV  KSLCVEGYLP  TSTKKTKPKQ  NQKSIDWCAR   900
AVVKKLNDGC  KVLGINLQAI  DPRDTSHLDP  FVYYGKKSTK  VGKEARYTIV  EPSNIKEYMT   960
NRFDDWHRGV  TKKSKKGDVQ  TSTTVLLYQE  ALRQFASHYK  LDFDSLPKMK  FYELAKILGD  1020
HEKVIIPCRG  GRAYLSTYPV  TKDSSKITFN  GRERWYNESD  VVAAVNIVLR  GIIDEDEQPD  1080
GAKKQALART  K                                                           1091

SEQ ID NO: 3            moltype = AA  length = 1093
FEATURE                 Location/Qualifiers
REGION                  1..1093
                        note = source = /note="Description of Artificial Sequence:
                        Synthetic polypeptide"
source                  1..1093
                        mol_type = protein
                        organism = synthetic construct
SEQUENCE: 3
MSNKEKNASE  TRKAYTTKMI  PRSHDRMKLL  GNFMDYLMDG  TPIFFELWNQ  FGGGIDRDII    60
SGTANKDKIS  DDLLLAVNWF  KVMPINSKPQ  GVSPSNLANL  FQQYSGSEPD  IQAQEYFASN   120
FDTEKHQWKD  MRVEYERLLA  ELQLSRSDMH  HDLKLMYKEK  CIGLSLSTAH  YITSVMFGTG   180
AKNNRQTKHQ  FYSKVIQLLE  ESTQINSVEQ  LASIILKAGD  CDSYRKLRIR  CSRKGATPSI   240
LKIVQDYELG  TNHDDEVNVP  SLIANLKEKL  GRFEYECEWK  CMEKIKAFLA  SKVGPYYLGS   300
YSAMLENALS  PIKGMTTKNC  KFVLKQIDAK  NDIKYENEPF  GKIVEGFFDS  PYFESDTNVK   360
WVLHPHHIGE  SNIKTLWEDL  NAIHSKYEED  IASLSEDKKE  KRIKVYQGDV  CQTINTYCEE   420
VGKEAKTPLV  QLLRYLYSRK  DDIAVDKIID  GITFLSKKHK  VEKQKINPVI  QKYPSFNFGN   480
NSKLLGKIIS  PKDKLKHNLK  CNRNQVDNYI  WIEIKVLKTR  TMRWEKHHYA  LSSTRFLEEV   540
YYPATSENPP  DALAARFRTK  TNGYEGKPAL  SAEQIEQIRS  APVGLRKVKK  RQMRLEAARQ   600
QNLLPRYTWG  KDFNINICKR  GNNFEVTLAT  KVKKKKEKNY  KVVLGYDANI  VRKNTYAAIE   660
AHANGDGVID  YNDLPVKPIE  SGFVTVESQV  RDKSYDQLSY  NGVKLLYCKP  HVESRRSFLE   720
KYRNGTMKDN  RGNNIQIDFM  KDFEAIADDE  TSLYYFNMVY  CKLLQSSIRN  HSSQAKEYRE   780
EIFELLRDGK  LSVLKLSSLS  NLSFVMKFVA  KSLIGTYFGH  LLKKPKNSKS  DVKAPPITDE   840
DKQKADPEMF  ALRLAEEKR   LNKVKSKKEV  IANKIVAKAL  ELRDKYGPVL  IKGENISDTT   900
KKGKKSSTNS  FLMDWLARGV  ANKVKEMVMM  HQGLEFVEVN  PNFTSHQDPF  VHKNPENTFR   960
ARYSRCTPSE  LTEKNRKEIL  SFLSDKPSKR  PTNAYYNEGA  MAFLATYGLK  KNDVLGVSLE  1020
KFKQIMANIL  HQRSEDQLLF  PSRGGMFYLA  TYKLDADATS  VNWNGKQFWV  CNADLVAAYN  1080
VGLVDIQKDF  KKK                                                         1093

SEQ ID NO: 4            moltype = AA  length = 1033
FEATURE                 Location/Qualifiers
REGION                  1..1033
                        note = source = /note="Description of Artificial Sequence:
                        Synthetic polypeptide"
source                  1..1033
                        mol_type = protein
                        organism = synthetic construct
SEQUENCE: 4
MMSDNIILPY  NSKLAPDERK  QRLLNDTFNW  FDMCNEVFFD  FVKNLYGGVK  HEHLILVNFA    60
EKPKKVSNSK  KPKKKDQEVN  IHVEPNQAEW  VDNACATFWF  RLQAKSTVQL  DQSVQTAEER   120
IRRFRDYAGH  EPSSFAKSYL  NGNYDPEKTE  WVDCRLLYVN  FCRNLNVNLD  ADIRTMVEHN   180
LLPVLPGQDF  KTNNVFSNIF  GVGNKEDKGQ  KTNWLNTVSE  GLQSKEIWNN  DEYRDLISRS   240
TGCSTAAELR  SESIGRPSML  AVDFASEKSG  QISQEWLAER  VKSFRAAASQ  KSKIYDMPNR   300
LVLKEYIASK  IGPFKLERWS  AAAVSAYKDV  RSKNSINLLY  SKERLWRCKE  IAQILVDNTQ   360
VAEAQQILVN  YSSGDTNSFT  VENRHMGDLT  VLFKIWEKMD  MDSGIEQYSE  IYRDEYSRDP   420
ITELLRYLYN  HRHISAKTFR  AAARLNSLLL  KNDRKKIHPT  ISGRTSVSFG  HSTIKGCITP   480
PDHIVKNRKE  NAGSTGMIWV  TMQLIDNGRW  ADHHIPFHNS  RYYRDFYAYR  ADLPTISDPR   540
RKSFGHRIGN  NISDTRMINH  DCKKASKMYL  RTIQNMTHNV  AFDQQTQFAV  RRYADNNFTI   600
TIQARVVGRK  YKKEISVGDR  VMGVDQNQTT  SNTYSWEVV   AEGTENSYPY  KGNNYRLVED   660
GFIRSECSGS  DQLSYDGLDF  QDFAQWRRER  YAFLSSVGCI  LNDEIEPQIP  VSAEKAKKKK   720
KFSKWRGCSL  YSWNLCYAYY  LKGLMHENLA  NNPAGFRQEI  LNFIQGSRGV  RLCSLNHTSF   780
RLLSKAKSLI  HSFFGLNNIK  DPESQRDFDP  EIYDIMVNLT  QRKTNKRKEK  ANRITSSILQ   840
IANRLNVSRI  VIENDLPNAS  SKNKASANQR  ATDWCARNVS  EKLEYACKML  GISLWQIDPR   900
DTSHLDPFVV  GKEARFMKIK  VSDINEYTIS  NFKKWHANIA  TTSTTAPLYH  DALKAFSSHY   960
GIDWDNLPEM  KFWELKNALK  DHKEVFIPNR  GGRCYLSTLP  VTSTSEKIVF  NGRERWLNAS  1020
DIVAGVNIVL  RSV                                                         1033

SEQ ID NO: 5            moltype = AA  length = 1054
FEATURE                 Location/Qualifiers
REGION                  1..1054
                        note = source = /note="Description of Artificial Sequence:
                        Synthetic polypeptide"
source                  1..1054
```

```
                            mol_type = protein
                            organism = synthetic construct
SEQUENCE: 5
MSSAIKSYKS VLRPNERKNQ LLKSTIQCLE DGSAFFFKML QGLFGGITPE IVRFSTEQEK    60
QQQDIALWCA VNWFRPVSQD SLTHTIASDN LVEKFEEYYG GTASDAIKQY FSASIGESYY   120
WNDCRQQYYD LCRELGVEVS DLTHDLEILC REKCLAVATE SNQNNSIISV LFGTGEKEDR   180
SVKLRITKKI LEAISNLKEI PKNVAPIQEI ILNVAKATKE TFRQVYAGNL GAPSTLEKFI   240
AKDGQKEFDL KKLQTDLKKV IRGKSKERDW CCQEELRSYV EQNTIQYDLW AWGEMFNKAH   300
TALKIKSTRN YNFAKQRLEQ FKEIQSLNNL LVVKKLNDFF DSEFFSGEET YTICVHHLGG   360
KDLSKLYKAW EDDPADPENA IVVLCDDLKN NFKKEPIRNI LRYIFTIRQE CSAQDILAAA   420
KYNQQLDRYK SQKANPSVLG NQGFTWTNAV ILPEKAQRND RPNSLDLRIW LYLKLRHPDG   480
RWKKHHIPFY DTRFFQEIYA AGNSPVDTCQ FRTPRFGYHL PKLTDQTAIR VNKKHVKAAK   540
TEARIRLAIQ QGTLPVSNLK ITEISATINS KGQVRIPVKF DVGRQKGTLQ IGDRFCGYDQ   600
NQTASHAYSL WEVVKEGQYH KELGCFVRFI SSGDIVSITE NRGNQFDQLS YEGLAYPQYA   660
DWRKKASKFV SLWQITKKNK KKEIVTVEAK EKFDAICKYQ PRLYKFNKEY AYLLRDIVRG   720
KSLVELQQIR QEIFRFIEQD CGVTRLGSLS LSTLETVKAV KGIIYSYFST ALNASKNNPI   780
SDEQRKEFDP ELFALLEKLE LIRTRKKKQK VERIANSLIQ TCLENNIKFI RGEGDLSTTN   840
NATKKKANSR SMDWLARGVF NKIRQLAPMH NITLFGCGSL YTSHQDPLVH RNPDKAMKCR   900
WAAIPVKDIG DWVLRKLSQN LRAKNIGTGE YYHQGVKEFL SHYELQDLEE ELLKWRSDRK   960
SNIPCWVLQN RLAEKLGNKE AVVYIPVRGG RIYFATHKVA TGAVSIVFDQ KQVWVCNADH  1020
VAAANIALTV KGIGEQSSDE ENPDGSRIKL QLTS                              1054

SEQ ID NO: 6            moltype = DNA  length = 36
FEATURE                 Location/Qualifiers
misc_feature            1..36
                        note = source = /note="Description of Artificial Sequence:
                          Synthetic oligonucleotide"
source                  1..36
                        mol_type = other DNA
                        organism = synthetic construct
SEQUENCE: 6
cccacaatac ctgagaaatc cgtcctacgt tgacgg                               36

SEQ ID NO: 7            moltype = DNA  length = 24
FEATURE                 Location/Qualifiers
misc_feature            1..24
                        note = source = /note="Description of Artificial Sequence:
                          Synthetic oligonucleotide"
source                  1..24
                        mol_type = other DNA
                        organism = synthetic construct
SEQUENCE: 7
aattttgtg cccatcgttg gcac                                             24

SEQ ID NO: 8            moltype = DNA  length = 36
FEATURE                 Location/Qualifiers
misc_feature            1..36
                        note = source = /note="Description of Artificial Sequence:
                          Synthetic oligonucleotide"
source                  1..36
                        mol_type = other DNA
                        organism = synthetic construct
SEQUENCE: 8
ctctcaatgc cttagaaatc cgtccttggt tgacgg                               36

SEQ ID NO: 9            moltype = DNA  length = 34
FEATURE                 Location/Qualifiers
misc_feature            1..34
                        note = source = /note="Description of Artificial Sequence:
                          Synthetic oligonucleotide"
source                  1..34
                        mol_type = other DNA
                        organism = synthetic construct
SEQUENCE: 9
gcaacaccta agaaatccgt ctttcattga cggg                                 34

SEQ ID NO: 10           moltype = DNA  length = 36
FEATURE                 Location/Qualifiers
misc_feature            1..36
                        note = source = /note="Description of Artificial Sequence:
                          Synthetic oligonucleotide"
source                  1..36
                        mol_type = other DNA
                        organism = synthetic construct
SEQUENCE: 10
gttgcaaaac ccaagaaatc cgtctttcat tgacgg                               36

SEQ ID NO: 11           moltype = AA  length = 1080
FEATURE                 Location/Qualifiers
```

```
REGION                  1..1080
                        note = source = /note="Description of Artificial Sequence:
                          Synthetic polypeptide"
source                  1..1080
                        mol_type = protein
                        organism = synthetic construct
SEQUENCE: 11
MPRNYFLGIF SLQKNKSVVH CSVEIRHKGY RSSVMVSDST IRPYASKLAP NDPKLKMLND    60
TFNWLDHAYK VFFDVSVALF GAIEHETAQE LIGEKSKFDA DLICAIMWFR LEEKSDNPGP   120
LQTVEQRMRL FQKYSGHEPS SFTQEYIKGN IDSEKYEWVD CRLKFIDLAR NINTTQESLK   180
IDAYTLFMNK LIPVSKDDEF NAYGLISQLF GTGKKEDRSI KAAMLEEISN ILADKKPDTW   240
EEYHDLIKKN FNVDNYKELK EKLSAGSSGR DSSLVIDLKE EKTGLLQPNF IKNRIVKFRE   300
DADKKKTVFL LPNRMKLREF IASQIGPFEQ NSWSAVLNRS MAAIQSKNSS NILYTNEKEE   360
RNNEIQELLK KDILSAASIL GDFRRGEFNR SVVSKNHLGA RLNELFEIWQ DLTMDDGIRK   420
YVDLCKDKFS RRPVKALLQY IYPYFDKITA KQFLDAASYN TLVETNNRKK IHPTVTGPTV   480
CNWGPKSTIN GSITPPNQMV KGRPAGSHGM IWVTMTVIDN GRWIKHHLPF YNSRYYEEHY   540
CYREGLPTKN QPRTKQLGTQ VGSTISATSL AALKSQEEQD RRNDRKNRFK AHKSIIRSQE   600
NIEYNVAFDK STNFDVTRKN GEFFITISSR VATPKYSYKL NIGDMIMGLD NNQTAPCTYS   660
IWRVVEKDTE GSFFHNKIWL QLVTDGKITS IVDNNRQVDQ LSYAGIEYSN FAEWRKDRRQ   720
FLRSINEDYV KKSDNWRNMN LYQWNAEYSR LLLDVMKENK GKNIQNTFRA EIEELICGKF   780
GIRLGSLFHH SLQFLTNCKS LISSYFMLNN KKEEYDQELF DSDFFRLMKS IGDKRVRKRK   840
EKSSRISSTV LQIARENNIK SLCVEGDLPT ATKKTKPKQN QKSIDWCARA VVKKLNDGCK   900
VLGINLQAID PRDTSHLDPF VYYGKKSTKV GKEARYTIVE PSNIKEYMTN RFDDWHRGVT   960
KKSKKGDVQT STTVLLYQEA LRQFASHYEL DFDSLPKMKF YDLAKRLGDH EKVIIPCRGG  1020
RAYLSTYPVT KDSSKITFNG RERWYNESDV VAAVNIVLRG IRDEDEQPDD AKKQALARTK  1080

SEQ ID NO: 12           moltype = AA   length = 1046
FEATURE                 Location/Qualifiers
REGION                  1..1046
                        note = source = /note="Description of Artificial Sequence:
                          Synthetic polypeptide"
source                  1..1046
                        mol_type = protein
                        organism = synthetic construct
SEQUENCE: 12
MVSDSTIRPY ASKLAPNDPK LKMLNDTFNW LDHAYKVFFD VSVALFGAIE HETAQELIGE    60
KSKFDADLIC AIMWFRLEEK SDNPGPLQTV EQRMRLFQKY SGHEPSSFTQ EYIKGNIDSE   120
KYEWVDCRLK FIDLARNINT TQESLKIDAY TLFMNKLIPV SKDDEFNAYG LISQLFGTGK   180
KEDRSIKAAM LEEISNILAD KKPDTWEEYH DLIKKNFNVD NYKELKEKLS AGSSGRDSSL   240
VIDLKEEKTG LLQPNFIKNR IVKFREDADK KKTVFLLPNR MKLREFIASQ IGPFEQNSWS   300
AVLNRSMAAI QSKNSSNILY TNEKEERNNE IQELLKKDIL SAASILGDFR RGEFNRSVVS   360
KNHLGARLNE LFEIWQDLTM DDGIRKYVDL CKDKFSRRPV KALLQYIYPY FDKITAKQFL   420
DAASYNTLVE TNNRKKIHPT VTGPTVCNWG PKSTINGSIT PPNQMVKGRP AGSHGMIWVT   480
MTVIDNGRWI KHHLPYNSR YYEEHYCYRE GLPTKNQPRT KQLGTQVGST ISATSLAALK   540
SQEEQDRRND RKNRFKAHKS IIRSQENIEY NVAFDKSTNF DVTRKNGEFF ITISSRVATP   600
KYSYKLNIGD MIMGLDNNQT APCTYSIWRV VEKDTEGSFF HNKIWLQLVT DGKITSIVDN   660
NRQVDQLSYA GIEYSNFAEW RKDRRQFLRS INEDYVKKSD NWRNMNLYQW NAEYSRLLLD   720
VMKENKGKNI QNTFRAEIEE LICGKFGIRL GSLFHHSLQF LTNCKSLISS YFMLNNKKEE   780
YDQELFDSDF FRLMKSIGDK RVRKRKEKSS RISSTVLQIA RENNIKSLCV EGDLPTATKK   840
TKPKQNQKSI DWCARAVVKK LNDGCKVLGI NLQAIDPRDT SHLDPFVYYG KKSTKVGKEA   900
RYTIVEPSNI KEYMTNRFDD WHRGVTKKSK KGDVQTSTTV LLYQEALRQF ASHYELDFDS   960
LPKMKFYDLA KRLGDHEKVI IPCRGGRAYL STYPVTKDSS KITFNGRERW YNESDVVAAV  1020
NIVLRGIRDE DEQPDDAKKQ ALARTK                                      1046

SEQ ID NO: 13           moltype = AA   length = 1046
FEATURE                 Location/Qualifiers
REGION                  1..1046
                        note = source = /note="Description of Artificial Sequence:
                          Synthetic polypeptide"
source                  1..1046
                        mol_type = protein
                        organism = synthetic construct
SEQUENCE: 13
MVSESTIRPY TSKLAPNDSK LKMLNDTFNW LDHAYKVFFD VSVALFGAIE HETAQELIGE    60
KSKFDADLLC AIMWFRLEEK SDNPGPLQTV EQRMRLFQKY SGHEPSSFTQ EYIKGNIDSE   120
KYQWVDCRLK FIDLARNINT TQESLKIDAY TLFMNKLIPV SKDDEFNAYG LISQLFGTGK   180
KEDRSIKASM LEEISNILAD KNPNTWEEYQ DLIKKTFNVD NYKELKEKLS AGSSGRDGSL   240
VIDLKEEKTG LLQPNFIKNR IVKFREDADK KRTVFLLPNR MKLREFIASQ IGPFEQNSWS   300
AVLNRSMAAI QSKNSSNILY TNEKEERNNE IQELLKKDIL SAASILGDFR RGEFNRSVVS   360
KNHLGARLNE LFEIWQELTM DDGIKKYVDL CKDKFSRRPV KALLQYIYPY FDKINAKQFL   420
DAASYNTLVE TNNRKKIHPT VTGPTVCNWG PKSTINGSIT PPNQMVKGRP AGSHGMIWVT   480
MTVIDNGRWI KHHLPFHNSR YYEEHYCYRE GLPTKNKPRT KQLGTQVGST ISAPSLAILK   540
SQEEQDRRND RKNRFKAHKS IIRSQENIEY NVAFDKSTNF DVTRKNGEFF ITISSRVATP   600
KYSYKLNIGD MIMGLDNNQT APCTYSIWRV VEKDTEGSFF HNKIWLQLVT DGKVTSIVDN   660
NRQVDQLSYA GIEYSNFAEW RKDRRQFLRS INEDYVKKSD NWRNMNLYQW NAEYSRLLLD   720
VMKENKGKNI QNTFRAEIEE LICGKFGIRL GSLFHHSLQF LTNCKSLISS YFMLNNKKEE   780
YDQELFDSDF FRLMKSIGDK RVRKRKEKSS RISSTVLQIA RENNVKSLCV EGYLPTSTKK   840
TKPKQNQKSI DWCARAVVKK LNDGCKVLGI YLQAIDPRDT SHLDPFVYYG KKSTKVGKEA   900
RHTIVEPSNI KEYMTNRFDD WHRGVTKKSK KGDVQTSTTV LLYQEALRQF ASHYKLDFDS   960
```

```
LPKMKFYELA KILGDHEKVI IPCRGGRAYL STYPVTKDSS KITFNGRERW YNESDVVAAV    1020
NIVLRGIIDE DEQPDGAKKQ ATTRRT                                         1046

SEQ ID NO: 14           moltype = AA  length = 1098
FEATURE                 Location/Qualifiers
REGION                  1..1098
                        note = source = /note="Description of Artificial Sequence:
                         Synthetic polypeptide"
source                  1..1098
                        mol_type = protein
                        organism = synthetic construct
SEQUENCE: 14
MSISNNNILP YNPKLLPDDR KHKMLVDTFN QLDLIRNNLH DMIIALYGAL KYDNIKQFAS    60
KEKPHISADA LCSINWFRLV KTNERKPAIE SNQIISKFIQ YSGHTPDKYA LSHITGNHEP    120
SHKWIDCREY AINYARIMHL SFSQFQDLAT ACLNCKILIL NGTLTSSWAW GANSALFGGS    180
DKENFSVKAK ILNSFIENLK DEMNTTKFQV VEKVCQQIGS SDAADLFDLY RSTVKDGNRG    240
PATGRNPKVM NLFSQDGEIS SEQREDFIES FQKVMQEKNS KQIIPHLDKL KYHLVKQSGL    300
YDIYSWAAAI KNANSTIVAS NSSNLNTILN KTEKQQTFEE LRKDEKIVAC SKILLSVNDT    360
LPEDLHYNPS TSNLGKNLDV FFDLLNENSV HTIENKEEKN KIVKECVNQY MEECKGLNKP    420
PMPVLLTFIS DYAHKHQAQD FLSAAKMNFI DLKIKSIKVV PTVHGSSPYT WISNLSKKNK    480
DGKMIRTPNS SLIGWIIPPE EIHDQKFAGQ NPIIWAVLRV YCNNKWEMHH FPFSDSRFFT    540
EVYAYKPNLP YLPGGENRSK RFGYRHSTNL SNESRQILLD KSKYAKANKS VLRCMENMTH    600
NVVFDPKTSL NIRIKTDKNN SPVLDDKGRI TFVMQINHRI LEKYNNTKIE IGDRILAYDQ    660
NQSENHTYAI LQRTEEGSHA HQFNGWYVRV LETGKVTSIV QGLSGPIDQL NYDGMPVTSH    720
KFNCWQADRS AFVSQFASLK ISETETFDEA YQAINAQGAY TWNLFYLRIL RKALRVCHME    780
NINQFREEIL AISKNRLSPM SLGSLSQNSL KMIRAFKSII NCYMSRMSFV DELQKKEGDL    840
ELHTIMRLTD NKLNDKRVEK INRASSFLTN KAHSMGCKMI VGESDLPVAD SKTSKKQNVD    900
RMDWCARALS HKVEYACKLM GLAYRGIPAY MSSHQDPLVH LVESKRSVLR PRFVVADKSD    960
VKQHHLDNLR RMLNSKTKVG TAVYYREAVE LMCEELGIHK TDMAKGKVSL SDFVDKFIGE    1020
KAIFPQRGGR FYMSTKRLTT GAKLICYSGS DVWLSDADEI AAINIGMFVV CDQTGAFKKK    1080
KKEKLDDEEC DILPFRPM                                                 1098

SEQ ID NO: 15           moltype = AA  length = 1088
FEATURE                 Location/Qualifiers
REGION                  1..1088
                        note = source = /note="Description of Artificial Sequence:
                         Synthetic polypeptide"
source                  1..1088
                        mol_type = protein
                        organism = synthetic construct
SEQUENCE: 15
MSSQVVRPYN AKFLPDDRKH KMLTDTINQL DKISSKHFDL LVAFYGSIQH KHVSINDKQE    60
EHITPDSVCA INWFRPMSKD YAKYQVKIDS MITNFKEYAG HIPDKYAIEY MGSNIDTDRF    120
VWVDCRNFAK DYVRNMDMSF SEFQNLVDAL VFCKILALNE STSTNWAWGA ISAIYGGGDK    180
EDSQFKAKVL NTFVKALNDE NNKTKFDVIN KVCSDLGYND HLSLIEDPRS TIDENGNKKS    240
ASGSPPAIAK FTEDGEISDN YRRACISSFS KTAKEKQDKK SIPHLDILKT HMIAMCGEYN    300
TYAWTEAIKN ANTDITSRNT RNMTFIKEKI ESRNSLKYIQ TEENMKAAKI LNGINHKLTP    360
DLHYTPAPKH LGKNLKDLFE MLEEKNILAQ NEKEKKAALD ECIKQYIDDC KGLNQQPIAS    420
LLAHISNYHK EITAENFLDG AKLLVLLQKI NRQKAHPSVF SPKAYTWGSK LEKNRRAANS    480
ALLGWIVPPE EKHKDRHAGQ HPVMWVTMTL LNNGKWEKHH VPFTNSRFFS EVYAYQPELP    540
YKEGGYARNS KTATKPSQIM LPAYAESMRH HIATKGNGHK KSEKIVLRAL SNIRHNVRFD    600
PSTSFFVRIM RDKKGNHRLD TKGRITFGLQ INHRITVGKT KSEINIGDRL LAFDQNQSEN    660
HTFAIMQRVE ENTPNSHQFN GWNIRVLETG KVVSMTKGIE SYYDQLSYDG VPYETKKFED    720
WRNERKAFVK KNKDIVIKEE KTFGQMFAEI KKSSLYKWNL SYLKILRMAI RAKSGDTVSL    780
FREELISIAK NRFGPLGLGS LSASSLKMLG AFCGVIQSYF SVLNCLDDKD KSNFDSELYF    840
YLVSAFEKRV FKRNEKTSRA SSFIMAMAYN HGCKMIVCED DLPTAGAGAN KRQNSDRMDW    900
CARSLAQKIK TGCEAMSIAY RAIPAYMSSH QDPLVHLADG KTSVLCPRFA LVSKDDIKQY    960
QLDGMRRMLN SKSKIGTAVY YRAAVELLCK ELGINKTDIA KGKLSVSQFA DIVNGEILLP    1020
QRGGRVYLAT KELTNGAKLV SYNGSDVWLS NADEIAAINI GMFVVCTQTG VFGKKKKKDE    1080
QDGDIEIA                                                            1088

SEQ ID NO: 16           moltype = AA  length = 1074
FEATURE                 Location/Qualifiers
REGION                  1..1074
                        note = source = /note="Description of Artificial Sequence:
                         Synthetic polypeptide"
source                  1..1074
                        mol_type = protein
                        organism = synthetic construct
SEQUENCE: 16
MASISRPYGT KLRPDARKKE MLDKFFNTLT KGQRVFADLA LCIYGSLTLE MAKSLEPESD    60
SELVCAIGWF RLVDKTIWSK DGIKQENLVK QYEAYSGKEA SEVVKTYLNS PSSDKYVWID    120
CRQKFLRFQR ELGTRNLSED FECMLFEQYI RLTKGEIEGY AAISNMFGNG EKEDRSKKRM    180
YATRMKDWLE ANENITWEQY REALKNQLNA KNLEQVVANY KGNAGGADFP FKYSFSKEGM    240
VSKKEHAQQL DKFKTVLKNK ARDLNFPNKE KLKQYLEAEI GIPVDANVYS QMFSNGVSEV    300
QPKTTRNMSF SNEKLDLLTE LKDLNKGDGF EYAREVLNGF FDSELHTTED KFNITSRYLG    360
GDKSNRLSKL YKIWKKEGVD CEEGIQQFCE AVKDKMGQIP IRNVLKYLWQ FRETVSAEDF    420
EAAAKANHLE EKISRVKAHP IVISNRYWAF GTSALVGNIM PADKRHQGEY AGQNFKMWLE    480
AELHYDGKKA KHHLPFYNAR FFEEVYCYHP SVAEITPFKT KQFGCEIGKD IPDYVSVALK    540
```

```
DNPYKKATKR ILRAIYNPVA NTTGVDKTTN CSFMIKREND EYKLVINRKI SVDRPKRIEV  600
GRTIMGYDRN QTASDTYWIG RLVPPGTRGA YRIGEWSVQY IKSGPVLSST QGVNNSTTDQ  660
LVYNGMPSSS ERFKAWKKAR MAFIRKLIRQ LNDEGLESKG QDYIPENPSS FDVRGETLYV  720
FNSNYLKALV SKHRKAKKPV EGILDEIEAW TSKDKDSCSL MRLSSLSDAS MQGIASLKSL  780
INSYFNKNGC KTIEDKEKFN PVLYAKLVEV EQRRTNKRSE KVGRIAGSLE QLALLNGVEV  840
VIGEADLGEV EKGKSKKQNS RNMDWCAKQV AQRLEYKLAF HGIGYFGVNP MYTSHQDPFE  900
HRRVADHIVM RARFEEVNVE NIAEWHVRNF SNYLRADSGT GLYYKQATMD FLKHYGLEEH  960
AEGLENKKIK FYDFRKILED KNLTSVIIPK RGGRIYMATN PVTSDSTPIT YAGKTYNRCN 1020
ADEVAAANIV ISVLAPRSKK NEEQDDIPLI TKKAESKSPP KDRKRSKTSQ LPQK       1074

SEQ ID NO: 17          moltype = AA   length = 1031
FEATURE                Location/Qualifiers
REGION                 1..1031
                       note = source = /note="Description of Artificial Sequence:
                         Synthetic polypeptide"
source                 1..1031
                       mol_type = protein
                       organism = synthetic construct
SEQUENCE: 17
MVSDSTIRPY TSKLAPNDPK RKMLNDTFNW LDHAYKVFFD VSVALFGGID YEAAEELIDE   60
KSTFDADLLC AIMWFRLEEK SNNPGPLQTT EQRTRLFQKY SGHEPSSFAQ EYIKGNTDTE  120
KYEWVDCRLK FADLARNIHT TQESLKTDAY TLFMNKLIPV SKDDEFNAYG FISQLFGTGK  180
KEDRSVKASM LEEISNIIED KKPNTWEEYQ DLIKKTFNVS NYKELKEKLS AGSSGRDGSL  240
VIDLKEEKTG LLQPNFIKNR IVKFREDADK KRTVFSLPNR MKLREFISSQ IGPFEQNSWS  300
AVLNRSMAAI QSKNSSNILY TNQKQERNNE IQELLKEDIL SAASILNDFR RGEFNSSVVS  360
KNHLGSRLNE LFEMWQALKM NDGIEKYTDL CKDNFSRRPV SALLQYIYPY FDKITAKQFL  420
DAASYNTLVE TNNRKKIHPT VTGPTVCNWG PKSTINGSIT PPNQMVKDRP AGSHGMIWVT  480
MTVRDNGRWV KHHLPFHNSR YYEEHYCYRE GLPTKNQPRT KQLGTQVGSI ISAPSLAILK  540
SQEEQDRRND RKSRFKAHKS IIRSQENIKY NVAFDKSTNF DVTRKNGEFF ITISSRVTTP  600
KYSHKLNVGD IIMGLDNNQT APCTYSIWRI VEKDTEGSPF HNKIWLQLVT DGKITSIVDN  660
NRQVDQLSYA GVEYSNFAEW RKDRRQFLRS INEDYVKKSD NWLNMNLYQW NAEYSRLLLG  720
VMKDNKDKNI QNTFRAEIEE LICGKFGIRL GSLSHHSLQF LTNCKSLISS YPMLNNKKEE  780
HDQESFDSDF FRLMRSIDDK RIRRRKEKSS RISSSVLQIA RENNVKSLCV EGDLPTATKK  840
TKPKQNQKSI DWCARAVVKK LNDGCKVLGI NLQAIDPRDT SHLDPFVYYG KKSTKVGKEA  900
RYVIVEPSNI KEYMTKKFTD WHRGVSKKSK KGDVQTSTTA PLYQEALKQF ADHYKLDFDS  960
LPKMKFYELA KILEDHKQVI IPCRGGRAYL STYPITKDSS KINFNGRERW YNQSDVVAAV 1020
NIVLRGIRDE N                                                    1031

SEQ ID NO: 18          moltype = AA   length = 1066
FEATURE                Location/Qualifiers
REGION                 1..1066
                       note = source = /note="Description of Artificial Sequence:
                         Synthetic polypeptide"
source                 1..1066
                       mol_type = protein
                       organism = synthetic construct
SEQUENCE: 18
MPDPIKSYKS PIIIDPNNAH DVEKLDFLRE TFVYLSNGTK CFMHVFLSLL GGMNETLAKK   60
IVSLETPKKE KKKKSNKPSH KIELFLAICW FRLVKISKNE SSVLPALLGN RFEKYFGAKA  120
TPEVMEYFSA NYDEATYAWK DMREEFVSLK SKLKVSEKDL ISDIGSMINE RYIGLKFGKP  180
WGIISGLFGE GKKVDRSLKV ELLKNVLEEI EKNPPKTKDQ LAKMILKCAD CKNGQEIHAK  240
CGKIGRMSSV SNWADEVGSE KEIVLSFVKS KISQDLAKQS NERNWKCVNA LKSYILSEIG  300
NCFDQSSWSE MLNNSLSVIQ SKTTRNYNFC IEQLEEKKNL NQNHRKFGTM IEDYFSSRFF  360
TGENKFIICN FHVGDKDKVS ALLASCEGLS EEELEEKIQN FCESQKQESK MPIPALLMYL  420
NSLKDSITVD QMFQGILYNK IRDKIERQKL HPIVPNNDSF DWGMSSKING RIISPKEKAK  480
HNAQNNRSLY DSGIWIEISV LKNKEWAKHH YKISNTRFVE EFYYPSSNDE NSLDQVFRTG  540
RNGFNNPAKN NLSLEQVSNI KNAPKNRRRA IKRQMRVEAA HQQNVLPHVK WDDNYCITIS  600
KYGDKFVTFI SKKFKSKKSK EYVVFLGFDQ NQTASHTFAA VQICDSKDEN VIPYCGLFVK  660
PLECGHITSV QKVKDRSIDQ LSYSGLPWKD FISWSQERKE FVSKWRMVEV KTRNGEKLDD  720
LTVKINKLDE NKHGLYAYNS KYFWYLKSIM RKKTKDELFE IRKELLTVIK TGRLCVLRLS  780
SLNHSSFLML KNAKSAISCY FNNLLKGVSN DQEKYEADPE MFELRREVEA KRQNKCMSKK  840
NLISSQIVSK AIELRGNYGS VAIIGEDLSD YVPDKGKKST QNANLLDWLS RGVANKVKQI  900
ANMHDNISFK DVSPQWTSHQ DSFVDRNPNS ALRVRFGSCD PEEMYEKDFE SLIKFLKEDC  960
GHYTNSMNDF LSHYGVSRKD MLEIKFSAFK ILMKNILNKT GEKSLLYPKR GGRLYLATHK 1020
LGQCTRRTYN GVDFWECDAD CVAAFNIALS GIRKYYGIKS EAVSPV               1066

SEQ ID NO: 19          moltype = DNA   length = 36
FEATURE                Location/Qualifiers
misc_feature           1..36
                       note = source = /note="Description of Artificial Sequence:
                         Synthetic oligonucleotide"
source                 1..36
                       mol_type = other DNA
                       organism = synthetic construct
SEQUENCE: 19
ctagcaatga cctaatagtg tgtccttagt tgacat                             36

SEQ ID NO: 20          moltype = DNA   length = 36
FEATURE                Location/Qualifiers
```

```
                        misc_feature    1..36
                                        note = source = /note="Description of Artificial Sequence:
                                          Synthetic oligonucleotide"
                        source          1..36
                                        mol_type = other DNA
                                        organism = synthetic construct
SEQUENCE: 20
tctcaacgat agtcagacat gtgtcctcag tgacac                                   36

SEQ ID NO: 21           moltype = DNA   length = 36
FEATURE                 Location/Qualifiers
misc_feature            1..36
                        note = source = /note="Description of Artificial Sequence:
                          Synthetic oligonucleotide"
source                  1..36
                        mol_type = other DNA
                        organism = synthetic construct
SEQUENCE: 21
cctacaatac ctaagaaatc cgtcctaagt tgacgg                                   36

SEQ ID NO: 22           moltype = DNA   length = 37
FEATURE                 Location/Qualifiers
misc_feature            1..37
                        note = source = /note="Description of Artificial Sequence:
                          Synthetic oligonucleotide"
source                  1..37
                        mol_type = other DNA
                        organism = synthetic construct
SEQUENCE: 22
gtagcaatca gtacatattg tgcctttcat tggcaca                                  37

SEQ ID NO: 23           moltype = DNA   length = 36
FEATURE                 Location/Qualifiers
misc_feature            1..36
                        note = source = /note="Description of Artificial Sequence:
                          Synthetic oligonucleotide"
source                  1..36
                        mol_type = other DNA
                        organism = synthetic construct
SEQUENCE: 23
gtagcaatca gtacatattg tgcctttcat tggcac                                   36

SEQ ID NO: 24           moltype = DNA   length = 36
FEATURE                 Location/Qualifiers
misc_feature            1..36
                        note = source = /note="Description of Artificial Sequence:
                          Synthetic oligonucleotide"
source                  1..36
                        mol_type = other DNA
                        organism = synthetic construct
SEQUENCE: 24
gttggaatga ctaatttttg tgcccaccgt tggcac                                   36

SEQ ID NO: 25           moltype =       length =
SEQUENCE: 25
000

SEQ ID NO: 26           moltype =       length =
SEQUENCE: 26
000

SEQ ID NO: 27           moltype =       length =
SEQUENCE: 27
000

SEQ ID NO: 28           moltype =       length =
SEQUENCE: 28
000

SEQ ID NO: 29           moltype =       length =
SEQUENCE: 29
000

SEQ ID NO: 30           moltype =       length =
SEQUENCE: 30
000

SEQ ID NO: 31           moltype =       length =
SEQUENCE: 31
```

000

SEQ ID NO: 32        moltype =     length =
SEQUENCE: 32
000

SEQ ID NO: 33        moltype =     length =
SEQUENCE: 33
000

SEQ ID NO: 34        moltype =     length =
SEQUENCE: 34
000

SEQ ID NO: 35        moltype =     length =
SEQUENCE: 35
000

SEQ ID NO: 36        moltype =     length =
SEQUENCE: 36
000

SEQ ID NO: 37        moltype =     length =
SEQUENCE: 37
000

SEQ ID NO: 38        moltype =     length =
SEQUENCE: 38
000

SEQ ID NO: 39        moltype =     length =
SEQUENCE: 39
000

SEQ ID NO: 40        moltype =     length =
SEQUENCE: 40
000

SEQ ID NO: 41        moltype =     length =
SEQUENCE: 41
000

SEQ ID NO: 42        moltype =     length =
SEQUENCE: 42
000

SEQ ID NO: 43        moltype =     length =
SEQUENCE: 43
000

SEQ ID NO: 44        moltype =     length =
SEQUENCE: 44
000

SEQ ID NO: 45        moltype =     length =
SEQUENCE: 45
000

SEQ ID NO: 46        moltype =     length =
SEQUENCE: 46
000

SEQ ID NO: 47        moltype =     length =
SEQUENCE: 47
000

SEQ ID NO: 48        moltype =     length =
SEQUENCE: 48
000

SEQ ID NO: 49        moltype =     length =
SEQUENCE: 49
000

SEQ ID NO: 50        moltype =     length =
SEQUENCE: 50
000

SEQ ID NO: 51        moltype =     length =

-continued

| | | |
|---|---|---|
| SEQUENCE: 51 000 | | |
| SEQ ID NO: 52 SEQUENCE: 52 000 | moltype = | length = |
| SEQ ID NO: 53 SEQUENCE: 53 000 | moltype = | length = |
| SEQ ID NO: 54 SEQUENCE: 54 000 | moltype = | length = |
| SEQ ID NO: 55 SEQUENCE: 55 000 | moltype = | length = |
| SEQ ID NO: 56 SEQUENCE: 56 000 | moltype = | length = |
| SEQ ID NO: 57 SEQUENCE: 57 000 | moltype = | length = |
| SEQ ID NO: 58 SEQUENCE: 58 000 | moltype = | length = |
| SEQ ID NO: 59 SEQUENCE: 59 000 | moltype = | length = |
| SEQ ID NO: 60 SEQUENCE: 60 000 | moltype = | length = |
| SEQ ID NO: 61 SEQUENCE: 61 000 | moltype = | length = |
| SEQ ID NO: 62 SEQUENCE: 62 000 | moltype = | length = |
| SEQ ID NO: 63 SEQUENCE: 63 000 | moltype = | length = |
| SEQ ID NO: 64 SEQUENCE: 64 000 | moltype = | length = |
| SEQ ID NO: 65 SEQUENCE: 65 000 | moltype = | length = |
| SEQ ID NO: 66 SEQUENCE: 66 000 | moltype = | length = |
| SEQ ID NO: 67 SEQUENCE: 67 000 | moltype = | length = |
| SEQ ID NO: 68 SEQUENCE: 68 000 | moltype = | length = |
| SEQ ID NO: 69 SEQUENCE: 69 000 | moltype = | length = |
| SEQ ID NO: 70 SEQUENCE: 70 000 | moltype = | length = |

| | | |
|---|---|---|
| SEQ ID NO: 71<br>SEQUENCE: 71<br>000 | moltype = | length = |
| SEQ ID NO: 72<br>SEQUENCE: 72<br>000 | moltype = | length = |
| SEQ ID NO: 73<br>SEQUENCE: 73<br>000 | moltype = | length = |
| SEQ ID NO: 74<br>SEQUENCE: 74<br>000 | moltype = | length = |
| SEQ ID NO: 75<br>SEQUENCE: 75<br>000 | moltype = | length = |
| SEQ ID NO: 76<br>SEQUENCE: 76<br>000 | moltype = | length = |
| SEQ ID NO: 77<br>SEQUENCE: 77<br>000 | moltype = | length = |
| SEQ ID NO: 78<br>SEQUENCE: 78<br>000 | moltype = | length = |
| SEQ ID NO: 79<br>SEQUENCE: 79<br>000 | moltype = | length = |
| SEQ ID NO: 80<br>SEQUENCE: 80<br>000 | moltype = | length = |
| SEQ ID NO: 81<br>SEQUENCE: 81<br>000 | moltype = | length = |
| SEQ ID NO: 82<br>SEQUENCE: 82<br>000 | moltype = | length = |
| SEQ ID NO: 83<br>SEQUENCE: 83<br>000 | moltype = | length = |
| SEQ ID NO: 84<br>SEQUENCE: 84<br>000 | moltype = | length = |
| SEQ ID NO: 85<br>SEQUENCE: 85<br>000 | moltype = | length = |
| SEQ ID NO: 86<br>SEQUENCE: 86<br>000 | moltype = | length = |
| SEQ ID NO: 87<br>SEQUENCE: 87<br>000 | moltype = | length = |
| SEQ ID NO: 88<br>SEQUENCE: 88<br>000 | moltype = | length = |
| SEQ ID NO: 89<br>SEQUENCE: 89<br>000 | moltype = | length = |
| SEQ ID NO: 90<br>SEQUENCE: 90<br>000 | moltype = | length = |

```
SEQ ID NO: 91          moltype =    length =
SEQUENCE: 91
000

SEQ ID NO: 92          moltype =    length =
SEQUENCE: 92
000

SEQ ID NO: 93          moltype =    length =
SEQUENCE: 93
000

SEQ ID NO: 94          moltype =    length =
SEQUENCE: 94
000

SEQ ID NO: 95          moltype =    length =
SEQUENCE: 95
000

SEQ ID NO: 96          moltype =    length =
SEQUENCE: 96
000

SEQ ID NO: 97          moltype =    length =
SEQUENCE: 97
000

SEQ ID NO: 98          moltype =    length =
SEQUENCE: 98
000

SEQ ID NO: 99          moltype =    length =
SEQUENCE: 99
000

SEQ ID NO: 100         moltype = RNA  length = 23
FEATURE                Location/Qualifiers
misc_feature           1..23
                       note = source = /note="Description of Artificial Sequence:
                        Synthetic oligonucleotide"
source                 1..23
                       mol_type = other RNA
                       organism = synthetic construct
SEQUENCE: 100
attttttgtgc ccatcgttgg cac                                              23

SEQ ID NO: 101         moltype = RNA  length = 23
FEATURE                Location/Qualifiers
misc_feature           1..23
                       note = source = /note="Description of Artificial Sequence:
                        Synthetic oligonucleotide"
source                 1..23
                       mol_type = other RNA
                       organism = synthetic construct
SEQUENCE: 101
agaaatccgt ctttcattga cgg                                               23

SEQ ID NO: 102         moltype =    length =
SEQUENCE: 102
000

SEQ ID NO: 103         moltype =    length =
SEQUENCE: 103
000

SEQ ID NO: 104         moltype =    length =
SEQUENCE: 104
000

SEQ ID NO: 105         moltype =    length =
SEQUENCE: 105
000

SEQ ID NO: 106         moltype =    length =
SEQUENCE: 106
000
```

| | | |
|---|---|---|
| SEQ ID NO: 107<br>SEQUENCE: 107 | moltype = | length = 000 |
| SEQ ID NO: 108<br>SEQUENCE: 108 | moltype = | length = 000 |
| SEQ ID NO: 109<br>SEQUENCE: 109 | moltype = | length = 000 |
| SEQ ID NO: 110<br>SEQUENCE: 110 | moltype = | length = 000 |
| SEQ ID NO: 111<br>SEQUENCE: 111 | moltype = | length = 000 |
| SEQ ID NO: 112<br>SEQUENCE: 112 | moltype = | length = 000 |
| SEQ ID NO: 113<br>SEQUENCE: 113 | moltype = | length = 000 |
| SEQ ID NO: 114<br>SEQUENCE: 114 | moltype = | length = 000 |
| SEQ ID NO: 115<br>SEQUENCE: 115 | moltype = | length = 000 |
| SEQ ID NO: 116<br>SEQUENCE: 116 | moltype = | length = 000 |
| SEQ ID NO: 117<br>SEQUENCE: 117 | moltype = | length = 000 |
| SEQ ID NO: 118<br>SEQUENCE: 118 | moltype = | length = 000 |
| SEQ ID NO: 119<br>SEQUENCE: 119 | moltype = | length = 000 |
| SEQ ID NO: 120<br>SEQUENCE: 120 | moltype = | length = 000 |
| SEQ ID NO: 121<br>SEQUENCE: 121 | moltype = | length = 000 |
| SEQ ID NO: 122<br>SEQUENCE: 122 | moltype = | length = 000 |
| SEQ ID NO: 123<br>SEQUENCE: 123 | moltype = | length = 000 |
| SEQ ID NO: 124<br>SEQUENCE: 124 | moltype = | length = 000 |
| SEQ ID NO: 125<br>SEQUENCE: 125 | moltype = | length = 000 |
| SEQ ID NO: 126<br>SEQUENCE: 126 | moltype = | length = 000 |

| | | |
|---|---|---|
| SEQ ID NO: 127<br>SEQUENCE: 127<br>000 | moltype = | length = |
| SEQ ID NO: 128<br>SEQUENCE: 128<br>000 | moltype = | length = |
| SEQ ID NO: 129<br>SEQUENCE: 129<br>000 | moltype = | length = |
| SEQ ID NO: 130<br>SEQUENCE: 130<br>000 | moltype = | length = |
| SEQ ID NO: 131<br>SEQUENCE: 131<br>000 | moltype = | length = |
| SEQ ID NO: 132<br>SEQUENCE: 132<br>000 | moltype = | length = |
| SEQ ID NO: 133<br>SEQUENCE: 133<br>000 | moltype = | length = |
| SEQ ID NO: 134<br>SEQUENCE: 134<br>000 | moltype = | length = |
| SEQ ID NO: 135<br>SEQUENCE: 135<br>000 | moltype = | length = |
| SEQ ID NO: 136<br>SEQUENCE: 136<br>000 | moltype = | length = |
| SEQ ID NO: 137<br>SEQUENCE: 137<br>000 | moltype = | length = |
| SEQ ID NO: 138<br>SEQUENCE: 138<br>000 | moltype = | length = |
| SEQ ID NO: 139<br>SEQUENCE: 139<br>000 | moltype = | length = |
| SEQ ID NO: 140<br>SEQUENCE: 140<br>000 | moltype = | length = |
| SEQ ID NO: 141<br>SEQUENCE: 141<br>000 | moltype = | length = |
| SEQ ID NO: 142<br>SEQUENCE: 142<br>000 | moltype = | length = |
| SEQ ID NO: 143<br>SEQUENCE: 143<br>000 | moltype = | length = |
| SEQ ID NO: 144<br>SEQUENCE: 144<br>000 | moltype = | length = |
| SEQ ID NO: 145<br>SEQUENCE: 145<br>000 | moltype = | length = |
| SEQ ID NO: 146<br>SEQUENCE: 146 | moltype = | length = |

```
000

SEQ ID NO: 147          moltype =   length =
SEQUENCE: 147
000

SEQ ID NO: 148          moltype =   length =
SEQUENCE: 148
000

SEQ ID NO: 149          moltype =   length =
SEQUENCE: 149
000

SEQ ID NO: 150          moltype = RNA   length = 106
FEATURE                 Location/Qualifiers
misc_difference         37..70
                        note = a, c, u, g, unknown or other
misc_feature            1..106
                        note = source = /note="Description of Artificial Sequence:
                         Synthetic polynucleotide"
source                  1..106
                        mol_type = other RNA
                        organism = synthetic construct
SEQUENCE: 150
ctagcaatga cctaatagtg tgtccttagt tgacatnnnn nnnnnnnnnn nnnnnnnnnn   60
nnnnnnnnnn ctagcaatga cctaatagtg tgtccttagt tgacat                106

SEQ ID NO: 151          moltype = RNA   length = 107
FEATURE                 Location/Qualifiers
misc_difference         37..71
                        note = a, c, u, g, unknown or other
misc_feature            1..107
                        note = source = /note="Description of Artificial Sequence:
                         Synthetic polynucleotide"
source                  1..107
                        mol_type = other RNA
                        organism = synthetic construct
SEQUENCE: 151
ctagcaatga cctaatagtg tgtccttagt tgacatnnnn nnnnnnnnnn nnnnnnnnnn   60
nnnnnnnnnn nctagcaatg acctaatagt gtgtccttag ttgacat               107

SEQ ID NO: 152          moltype = RNA   length = 108
FEATURE                 Location/Qualifiers
misc_difference         37..72
                        note = a, c, u, g, unknown or other
misc_feature            1..108
                        note = source = /note="Description of Artificial Sequence:
                         Synthetic polynucleotide"
source                  1..108
                        mol_type = other RNA
                        organism = synthetic construct
SEQUENCE: 152
tctcaacgat agtcagacat gtgtcctcag tgacacnnnn nnnnnnnnnn nnnnnnnnnn   60
nnnnnnnnnn nntctcaacg atagtcagac atgtgtcctc agtgacac              108

SEQ ID NO: 153          moltype = RNA   length = 107
FEATURE                 Location/Qualifiers
misc_difference         37..71
                        note = a, c, u, g, unknown or other
misc_feature            1..107
                        note = source = /note="Description of Artificial Sequence:
                         Synthetic polynucleotide"
source                  1..107
                        mol_type = other RNA
                        organism = synthetic construct
SEQUENCE: 153
cctacaatac ctaagaaatc cgtcctaagt tgacggnnnn nnnnnnnnnn nnnnnnnnnn   60
nnnnnnnnnn ncctacaata cctaagaaat ccgtcctaag ttgacgg               107

SEQ ID NO: 154          moltype = RNA   length = 107
FEATURE                 Location/Qualifiers
misc_difference         38..70
                        note = a, c, u, g, unknown or other
misc_feature            1..107
                        note = source = /note="Description of Artificial Sequence:
                         Synthetic polynucleotide"
source                  1..107
                        mol_type = other RNA
```

```
                               organism = synthetic construct
SEQUENCE: 154
gtagcaatca gtacatattg tgcctttcat tggcacannn nnnnnnnnnn nnnnnnnnnn    60
nnnnnnnnnn gtagcaatca gtacatattg tgcctttcat tggcaca                 107

SEQ ID NO: 155         moltype = RNA  length = 106
FEATURE                Location/Qualifiers
misc_difference        37..70
                       note = a, c, u, g, unknown or other
misc_feature           1..106
                       note = source = /note="Description of Artificial Sequence:
                       Synthetic polynucleotide"
source                 1..106
                       mol_type = other RNA
                       organism = synthetic construct
SEQUENCE: 155
gtagcaatca gtacatattg tgcctttcat tggcacnnnn nnnnnnnnnn nnnnnnnnnn    60
nnnnnnnnnn gtagcaatca gtacatattg tgcctttcat tggcac                  106

SEQ ID NO: 156         moltype = RNA  length = 108
FEATURE                Location/Qualifiers
misc_difference        37..72
                       note = a, c, u, g, unknown or other
misc_feature           1..108
                       note = source = /note="Description of Artificial Sequence:
                       Synthetic polynucleotide"
source                 1..108
                       mol_type = other RNA
                       organism = synthetic construct
SEQUENCE: 156
gttggaatga ctaatttttg tgcccaccgt tggcacnnnn nnnnnnnnnn nnnnnnnnnn    60
nnnnnnnnnn nngttggaat gactaatttt tgtgcccacc gttggcac                108

SEQ ID NO: 157         moltype = RNA  length = 84
FEATURE                Location/Qualifiers
misc_difference        25..60
                       note = a, c, u, g, unknown or other
misc_feature           1..84
                       note = source = /note="Description of Artificial Sequence:
                       Synthetic oligonucleotide"
source                 1..84
                       mol_type = other RNA
                       organism = synthetic construct
SEQUENCE: 157
aatttttgtg cccatcgttg gcacnnnnnn nnnnnnnnnn nnnnnnnnnn nnnnnnnnnn    60
aatttttgtg cccatcgttg gcac                                          84

SEQ ID NO: 158         moltype = RNA  length = 108
FEATURE                Location/Qualifiers
misc_difference        37..72
                       note = a, c, u, g, unknown or other
misc_feature           1..108
                       note = source = /note="Description of Artificial Sequence:
                       Synthetic polynucleotide"
source                 1..108
                       mol_type = other RNA
                       organism = synthetic construct
SEQUENCE: 158
cccacaatac ctgagaaatc cgtcctacgt tgacggnnnn nnnnnnnnnn nnnnnnnnnn    60
nnnnnnnnnn nncccacaat acctgagaaa tccgtcctac gttgacgg                108

SEQ ID NO: 159         moltype = RNA  length = 108
FEATURE                Location/Qualifiers
misc_difference        37..72
                       note = a, c, u, g, unknown or other
misc_feature           1..108
                       note = source = /note="Description of Artificial Sequence:
                       Synthetic polynucleotide"
source                 1..108
                       mol_type = other RNA
                       organism = synthetic construct
SEQUENCE: 159
cccacaatac ctgagaaatc cgtcctacgt tgacggnnnn nnnnnnnnnn nnnnnnnnnn    60
nnnnnnnnnn nncccacaat acctgagaaa tccgtcctac gttgacgg                108

SEQ ID NO: 160         moltype = RNA  length = 108
FEATURE                Location/Qualifiers
misc_difference        37..72
                       note = a, c, u, g, unknown or other
```

```
misc_feature            1..108
                        note = source = /note="Description of Artificial Sequence:
                          Synthetic polynucleotide"
source                  1..108
                        mol_type = other RNA
                        organism = synthetic construct
SEQUENCE: 160
ctctcaatgc cttagaaatc cgtccttggt tgacggnnnn nnnnnnnnnn nnnnnnnnnn    60
nnnnnnnnnn nnctctcaat gccttagaaa tccgtccttg gttgacgg                108

SEQ ID NO: 161          moltype = RNA   length = 106
FEATURE                 Location/Qualifiers
misc_difference         37..70
                        note = a, c, u, g, unknown or other
misc_feature            1..106
                        note = source = /note="Description of Artificial Sequence:
                          Synthetic polynucleotide"
source                  1..106
                        mol_type = other RNA
                        organism = synthetic construct
SEQUENCE: 161
cccacaatac ctgagaaatc cgtcctacgt tgacggnnnn nnnnnnnnnn nnnnnnnnnn    60
nnnnnnnnnn cccacaatac ctgagaaatc cgtcctacgt tgacgg                  106

SEQ ID NO: 162          moltype = RNA   length = 92
FEATURE                 Location/Qualifiers
misc_difference         35..58
                        note = a, c, u, g, unknown or other
misc_feature            1..92
                        note = source = /note="Description of Artificial Sequence:
                          Synthetic oligonucleotide"
source                  1..92
                        mol_type = other RNA
                        organism = synthetic construct
SEQUENCE: 162
gcaacaccta agaaatccgt ctttcattga cgggnnnnn nnnnnnnnnn nnnnnnngc      60
aacacctaag aaatccgtct ttcattgacg gg                                  92

SEQ ID NO: 163          moltype = RNA   length = 103
FEATURE                 Location/Qualifiers
misc_difference         37..67
                        note = a, c, u, g, unknown or other
misc_feature            1..103
                        note = source = /note="Description of Artificial Sequence:
                          Synthetic polynucleotide"
source                  1..103
                        mol_type = other RNA
                        organism = synthetic construct
SEQUENCE: 163
gttgcaaaac ccaagaaatc cgtctttcat tgacggnnnn nnnnnnnnnn nnnnnnnnnn    60
nnnnnnngtt gcaaaaccca agaaatccgt ctttcattga cgg                     103

SEQ ID NO: 164          moltype =   length =
SEQUENCE: 164
000

SEQ ID NO: 165          moltype =   length =
SEQUENCE: 165
000

SEQ ID NO: 166          moltype =   length =
SEQUENCE: 166
000

SEQ ID NO: 167          moltype =   length =
SEQUENCE: 167
000

SEQ ID NO: 168          moltype =   length =
SEQUENCE: 168
000

SEQ ID NO: 169          moltype =   length =
SEQUENCE: 169
000

SEQ ID NO: 170          moltype =   length =
SEQUENCE: 170
000
```

| | | |
|---|---|---|
| SEQ ID NO: 171<br>SEQUENCE: 171<br>000 | moltype = | length = |
| SEQ ID NO: 172<br>SEQUENCE: 172<br>000 | moltype = | length = |
| SEQ ID NO: 173<br>SEQUENCE: 173<br>000 | moltype = | length = |
| SEQ ID NO: 174<br>SEQUENCE: 174<br>000 | moltype = | length = |
| SEQ ID NO: 175<br>SEQUENCE: 175<br>000 | moltype = | length = |
| SEQ ID NO: 176<br>SEQUENCE: 176<br>000 | moltype = | length = |
| SEQ ID NO: 177<br>SEQUENCE: 177<br>000 | moltype = | length = |
| SEQ ID NO: 178<br>SEQUENCE: 178<br>000 | moltype = | length = |
| SEQ ID NO: 179<br>SEQUENCE: 179<br>000 | moltype = | length = |
| SEQ ID NO: 180<br>SEQUENCE: 180<br>000 | moltype = | length = |
| SEQ ID NO: 181<br>SEQUENCE: 181<br>000 | moltype = | length = |
| SEQ ID NO: 182<br>SEQUENCE: 182<br>000 | moltype = | length = |
| SEQ ID NO: 183<br>SEQUENCE: 183<br>000 | moltype = | length = |
| SEQ ID NO: 184<br>SEQUENCE: 184<br>000 | moltype = | length = |
| SEQ ID NO: 185<br>SEQUENCE: 185<br>000 | moltype = | length = |
| SEQ ID NO: 186<br>SEQUENCE: 186<br>000 | moltype = | length = |
| SEQ ID NO: 187<br>SEQUENCE: 187<br>000 | moltype = | length = |
| SEQ ID NO: 188<br>SEQUENCE: 188<br>000 | moltype = | length = |
| SEQ ID NO: 189<br>SEQUENCE: 189<br>000 | moltype = | length = |
| SEQ ID NO: 190<br>SEQUENCE: 190 | moltype = | length = |

```
SEQ ID NO: 191         moltype =   length =
SEQUENCE: 191
000

SEQ ID NO: 192         moltype =   length =
SEQUENCE: 192
000

SEQ ID NO: 193         moltype =   length =
SEQUENCE: 193
000

SEQ ID NO: 194         moltype =   length =
SEQUENCE: 194
000

SEQ ID NO: 195         moltype =   length =
SEQUENCE: 195
000

SEQ ID NO: 196         moltype =   length =
SEQUENCE: 196
000

SEQ ID NO: 197         moltype =   length =
SEQUENCE: 197
000

SEQ ID NO: 198         moltype =   length =
SEQUENCE: 198
000

SEQ ID NO: 199         moltype =   length =
SEQUENCE: 199
000

SEQ ID NO: 200         moltype = AA   length = 7
FEATURE                Location/Qualifiers
VARIANT                1
                       note = /replace="Thr"
VARIANT                4
                       note = /replace="Leu"
VARIANT                6
                       note = /replace="Ser"
VARIANT                7
                       note = /replace="Leu"
SITE                   1..7
                       note = /note="Variant residues given in the sequence have
                        no preference with respect to those in the annotations for
                        variant positions"
REGION                 1..7
                       note = source = /note="Description of Artificial Sequence:
                        Synthetic peptide"
source                 1..7
                       mol_type = protein
                       organism = synthetic construct
SEQUENCE: 200
SSHQDPF                                                                        7

SEQ ID NO: 201         moltype = AA   length = 11
FEATURE                Location/Qualifiers
VARIANT                1
                       note = /replace="Gly" or "Ser"
MOD_RES                2
                       note = Any amino acid
MOD_RES                4
                       note = Any amino acid
VARIANT                6
                       note = /replace="Ile"
VARIANT                7
                       note = /replace="Ser" or "Val"
MOD_RES                8..10
                       note = Any amino acid
VARIANT                11
                       note = /replace="Ala"
SITE                   1..11
                       note = /note="Variant residues given in the sequence have
```

-continued

|  |  |
|---|---|
|  | no preference with respect to those in the annotations for variant positions" |
| REGION | 1..11<br>note = source = /note="Description of Artificial Sequence: Synthetic peptide" |
| source | 1..11<br>mol_type = protein<br>organism = synthetic construct |

SEQUENCE: 201
AXDXNQTXXX T                                                                11

| SEQ ID NO: 202<br>FEATURE<br>misc_difference | moltype = RNA  length = 17<br>Location/Qualifiers<br>6..11<br>note = a, c, u, g, unknown or other |
|---|---|
| misc_feature | 1..17<br>note = source = /note="Description of Artificial Sequence: Synthetic oligonucleotide" |
| source | 1..17<br>mol_type = other RNA<br>organism = synthetic construct |

SEQUENCE: 202
ccgtcnnnnn ntgacgg                                                          17

| SEQ ID NO: 203<br>FEATURE<br>misc_difference | moltype = RNA  length = 17<br>Location/Qualifiers<br>6..11<br>note = a, c, u, g, unknown or other |
|---|---|
| misc_feature | 1..17<br>note = source = /note="Description of Artificial Sequence: Synthetic oligonucleotide" |
| source | 1..17<br>mol_type = other RNA<br>organism = synthetic construct |

SEQUENCE: 203
gtgccnnnnn ntggcac                                                          17

| SEQ ID NO: 204<br>FEATURE<br>misc_difference | moltype = RNA  length = 17<br>Location/Qualifiers<br>6..11<br>note = a, c, u, g, unknown or other |
|---|---|
| misc_feature | 11<br>note = May or may not be present |
| misc_feature | 1..17<br>note = source = /note="Description of Artificial Sequence: Synthetic oligonucleotide" |
| source | 1..17<br>mol_type = other RNA<br>organism = synthetic construct |

SEQUENCE: 204
gtgtcnnnnn ntgacay                                                          17

| SEQ ID NO: 205<br>FEATURE<br>misc_feature | moltype = RNA  length = 14<br>Location/Qualifiers<br>1..14<br>note = source = /note="Description of Artificial Sequence: Synthetic oligonucleotide" |
|---|---|
| source | 1..14<br>mol_type = other RNA<br>organism = synthetic construct |

SEQUENCE: 205
tcytwvrttg acgg                                                             14

| SEQ ID NO: 206<br>FEATURE<br>misc_feature | moltype = RNA  length = 14<br>Location/Qualifiers<br>1..14<br>note = source = /note="Description of Artificial Sequence: Synthetic oligonucleotide" |
|---|---|
| source | 1..14<br>mol_type = other RNA<br>organism = synthetic construct |

SEQUENCE: 206
ccywycrttg gcac                                                             14

SEQ ID NO: 207          moltype =    length =
SEQUENCE: 207
000

SEQ ID NO: 208          moltype =    length =

```
SEQUENCE: 208
000

SEQ ID NO: 209          moltype =   length =
SEQUENCE: 209
000

SEQ ID NO: 210          moltype = AA  length = 4
FEATURE                 Location/Qualifiers
VARIANT                 1
                        note = /replace="Phe" or "Ile" or "Leu" or "Met" or "Pro"
                         or "Val" or "Trp" or "Tyr"
VARIANT                 2
                        note = /replace="Phe" or "Ile" or "Leu" or "Met" or "Pro"
                         or "Arg" or "Val" or "Trp" or "Tyr"
VARIANT                 3
                        note = /replace="Phe" or "Gly" or "Ile" or "Leu" or "Met"
                         or "Pro" or "Val" or "Trp" or "Tyr"
SITE                    1..4
                        note = /note="Variant residues given in the sequence have
                         no preference with respect to those in the annotations for
                         variant positions"
REGION                  1..4
                        note = source = /note="Description of Artificial Sequence:
                         Synthetic peptide"
source                  1..4
                        mol_type = protein
                        organism = synthetic construct
SEQUENCE: 210
CCCE                                                                            4

SEQ ID NO: 211          moltype =   length =
SEQUENCE: 211
000

SEQ ID NO: 212          moltype =   length =
SEQUENCE: 212
000

SEQ ID NO: 213          moltype =   length =
SEQUENCE: 213
000

SEQ ID NO: 214          moltype =   length =
SEQUENCE: 214
000

SEQ ID NO: 215          moltype =   length =
SEQUENCE: 215
000

SEQ ID NO: 216          moltype =   length =
SEQUENCE: 216
000

SEQ ID NO: 217          moltype =   length =
SEQUENCE: 217
000

SEQ ID NO: 218          moltype =   length =
SEQUENCE: 218
000

SEQ ID NO: 219          moltype =   length =
SEQUENCE: 219
000

SEQ ID NO: 220          moltype =   length =
SEQUENCE: 220
000

SEQ ID NO: 221          moltype =   length =
SEQUENCE: 221
000

SEQ ID NO: 222          moltype =   length =
SEQUENCE: 222
000
```

| | | |
|---|---|---|
| SEQ ID NO: 223
SEQUENCE: 223
000 | moltype = | length = |
| SEQ ID NO: 224
SEQUENCE: 224
000 | moltype = | length = |
| SEQ ID NO: 225
SEQUENCE: 225
000 | moltype = | length = |
| SEQ ID NO: 226
SEQUENCE: 226
000 | moltype = | length = |
| SEQ ID NO: 227
SEQUENCE: 227
000 | moltype = | length = |
| SEQ ID NO: 228
SEQUENCE: 228
000 | moltype = | length = |
| SEQ ID NO: 229
SEQUENCE: 229
000 | moltype = | length = |
| SEQ ID NO: 230
SEQUENCE: 230
000 | moltype = | length = |
| SEQ ID NO: 231
SEQUENCE: 231
000 | moltype = | length = |
| SEQ ID NO: 232
SEQUENCE: 232
000 | moltype = | length = |
| SEQ ID NO: 233
SEQUENCE: 233
000 | moltype = | length = |
| SEQ ID NO: 234
SEQUENCE: 234
000 | moltype = | length = |
| SEQ ID NO: 235
SEQUENCE: 235
000 | moltype = | length = |
| SEQ ID NO: 236
SEQUENCE: 236
000 | moltype = | length = |
| SEQ ID NO: 237
SEQUENCE: 237
000 | moltype = | length = |
| SEQ ID NO: 238
SEQUENCE: 238
000 | moltype = | length = |
| SEQ ID NO: 239
SEQUENCE: 239
000 | moltype = | length = |
| SEQ ID NO: 240
SEQUENCE: 240
000 | moltype = | length = |
| SEQ ID NO: 241
SEQUENCE: 241
000 | moltype = | length = |
| SEQ ID NO: 242
SEQUENCE: 242
000 | moltype = | length = |

```
SEQ ID NO: 243        moltype =    length =
SEQUENCE: 243
000

SEQ ID NO: 244        moltype =    length =
SEQUENCE: 244
000

SEQ ID NO: 245        moltype =    length =
SEQUENCE: 245
000

SEQ ID NO: 246        moltype =    length =
SEQUENCE: 246
000

SEQ ID NO: 247        moltype =    length =
SEQUENCE: 247
000

SEQ ID NO: 248        moltype =    length =
SEQUENCE: 248
000

SEQ ID NO: 249        moltype =    length =
SEQUENCE: 249
000

SEQ ID NO: 250        moltype =    length =
SEQUENCE: 250
000

SEQ ID NO: 251        moltype =    length =
SEQUENCE: 251
000

SEQ ID NO: 252        moltype =    length =
SEQUENCE: 252
000

SEQ ID NO: 253        moltype =    length =
SEQUENCE: 253
000

SEQ ID NO: 254        moltype =    length =
SEQUENCE: 254
000

SEQ ID NO: 255        moltype =    length =
SEQUENCE: 255
000

SEQ ID NO: 256        moltype =    length =
SEQUENCE: 256
000

SEQ ID NO: 257        moltype =    length =
SEQUENCE: 257
000

SEQ ID NO: 258        moltype =    length =
SEQUENCE: 258
000

SEQ ID NO: 259        moltype =    length =
SEQUENCE: 259
000

SEQ ID NO: 260        moltype =    length =
SEQUENCE: 260
000

SEQ ID NO: 261        moltype =    length =
SEQUENCE: 261
000

SEQ ID NO: 262        moltype =    length =
SEQUENCE: 262
```

-continued

000

SEQ ID NO: 263    moltype =    length =
SEQUENCE: 263
000

SEQ ID NO: 264    moltype =    length =
SEQUENCE: 264
000

SEQ ID NO: 265    moltype =    length =
SEQUENCE: 265
000

SEQ ID NO: 266    moltype =    length =
SEQUENCE: 266
000

SEQ ID NO: 267    moltype =    length =
SEQUENCE: 267
000

SEQ ID NO: 268    moltype =    length =
SEQUENCE: 268
000

SEQ ID NO: 269    moltype =    length =
SEQUENCE: 269
000

SEQ ID NO: 270    moltype =    length =
SEQUENCE: 270
000

SEQ ID NO: 271    moltype =    length =
SEQUENCE: 271
000

SEQ ID NO: 272    moltype =    length =
SEQUENCE: 272
000

SEQ ID NO: 273    moltype =    length =
SEQUENCE: 273
000

SEQ ID NO: 274    moltype =    length =
SEQUENCE: 274
000

SEQ ID NO: 275    moltype =    length =
SEQUENCE: 275
000

SEQ ID NO: 276    moltype =    length =
SEQUENCE: 276
000

SEQ ID NO: 277    moltype =    length =
SEQUENCE: 277
000

SEQ ID NO: 278    moltype =    length =
SEQUENCE: 278
000

SEQ ID NO: 279    moltype =    length =
SEQUENCE: 279
000

SEQ ID NO: 280    moltype =    length =
SEQUENCE: 280
000

SEQ ID NO: 281    moltype =    length =
SEQUENCE: 281
000

SEQ ID NO: 282    moltype =    length =

| | | |
|---|---|---|
| SEQUENCE: 282 000 | | |
| SEQ ID NO: 283 SEQUENCE: 283 000 | moltype = | length = |
| SEQ ID NO: 284 SEQUENCE: 284 000 | moltype = | length = |
| SEQ ID NO: 285 SEQUENCE: 285 000 | moltype = | length = |
| SEQ ID NO: 286 SEQUENCE: 286 000 | moltype = | length = |
| SEQ ID NO: 287 SEQUENCE: 287 000 | moltype = | length = |
| SEQ ID NO: 288 SEQUENCE: 288 000 | moltype = | length = |
| SEQ ID NO: 289 SEQUENCE: 289 000 | moltype = | length = |
| SEQ ID NO: 290 SEQUENCE: 290 000 | moltype = | length = |
| SEQ ID NO: 291 SEQUENCE: 291 000 | moltype = | length = |
| SEQ ID NO: 292 SEQUENCE: 292 000 | moltype = | length = |
| SEQ ID NO: 293 SEQUENCE: 293 000 | moltype = | length = |
| SEQ ID NO: 294 SEQUENCE: 294 000 | moltype = | length = |
| SEQ ID NO: 295 SEQUENCE: 295 000 | moltype = | length = |
| SEQ ID NO: 296 SEQUENCE: 296 000 | moltype = | length = |
| SEQ ID NO: 297 SEQUENCE: 297 000 | moltype = | length = |
| SEQ ID NO: 298 SEQUENCE: 298 000 | moltype = | length = |
| SEQ ID NO: 299 SEQUENCE: 299 000 | moltype = | length = |
| SEQ ID NO: 300 FEATURE source  SEQUENCE: 300 PKKKRKV | moltype = AA   length = 7 Location/Qualifiers 1..7 mol_type = protein organism = Simian virus 40 | 7 |

| | | |
|---|---|---|
| SEQ ID NO: 301<br>FEATURE<br>REGION<br><br>source | moltype = AA   length = 16<br>Location/Qualifiers<br>1..16<br>note = source = /note="Description of Unknown:<br>  Nucleoplasmin bipartite NLS sequence"<br>1..16<br>mol_type = protein<br>organism = unidentified | |
| SEQUENCE: 301<br>KRPAATKKAG QAKKKK | | 16 |
| SEQ ID NO: 302<br>FEATURE<br>REGION<br><br>source | moltype = AA   length = 9<br>Location/Qualifiers<br>1..9<br>note = source = /note="Description of Unknown: c-Myc NLS<br>  sequence"<br>1..9<br>mol_type = protein<br>organism = unidentified | |
| SEQUENCE: 302<br>PAAKRVKLD | | 9 |
| SEQ ID NO: 303<br>FEATURE<br>REGION<br><br>source | moltype = AA   length = 11<br>Location/Qualifiers<br>1..11<br>note = source = /note="Description of Unknown: c-Myc NLS<br>  sequence"<br>1..11<br>mol_type = protein<br>organism = unidentified | |
| SEQUENCE: 303<br>RQRRNELKRS P | | 11 |
| SEQ ID NO: 304<br>FEATURE<br>source | moltype = AA   length = 38<br>Location/Qualifiers<br>1..38<br>mol_type = protein<br>organism = Homo sapiens | |
| SEQUENCE: 304<br>NQSSNFGPMK GGNFGGRSSG PYGGGGQYFA KPRNQGGY | | 38 |
| SEQ ID NO: 305<br>FEATURE<br>REGION<br><br>source | moltype = AA   length = 42<br>Location/Qualifiers<br>1..42<br>note = source = /note="Description of Unknown: IBB domain<br>  from importin-alpha sequence"<br>1..42<br>mol_type = protein<br>organism = unidentified | |
| SEQUENCE: 305<br>RMRIZFKNKG KDTAELRRRR VEVSVELRKA KKDEQILKRR NV | | 42 |
| SEQ ID NO: 306<br>FEATURE<br>REGION<br><br>source | moltype = AA   length = 8<br>Location/Qualifiers<br>1..8<br>note = source = /note="Description of Unknown: Myoma T<br>  protein sequence"<br>1..8<br>mol_type = protein<br>organism = unidentified | |
| SEQUENCE: 306<br>VSRKRPRP | | 8 |
| SEQ ID NO: 307<br>FEATURE<br>REGION<br><br>source | moltype = AA   length = 8<br>Location/Qualifiers<br>1..8<br>note = source = /note="Description of Unknown: Myoma T<br>  protein sequence"<br>1..8<br>mol_type = protein<br>organism = unidentified | |
| SEQUENCE: 307<br>PPKKARED | | 8 |
| SEQ ID NO: 308<br>FEATURE<br>source | moltype = AA   length = 8<br>Location/Qualifiers<br>1..8<br>mol_type = protein<br>organism = Homo sapiens | |

| | | |
|---|---|---|
| SEQUENCE: 308 PQPKKKPL | | 8 |
| SEQ ID NO: 309 FEATURE source | moltype = AA length = 12 Location/Qualifiers 1..12 mol_type = protein organism = Mus sp. | |
| SEQUENCE: 309 SALIKKKKM AP | | 12 |
| SEQ ID NO: 310 FEATURE source | moltype = AA length = 5 Location/Qualifiers 1..5 mol_type = protein organism = Influenza virus | |
| SEQUENCE: 310 DRLRR | | 5 |
| SEQ ID NO: 311 FEATURE source | moltype = AA length = 7 Location/Qualifiers 1..7 mol_type = protein organism = Influenza virus | |
| SEQUENCE: 311 PKQKKRK | | 7 |
| SEQ ID NO: 312 FEATURE source | moltype = AA length = 10 Location/Qualifiers 1..10 mol_type = protein organism = Hepatitis virus | |
| SEQUENCE: 312 RKLKKKIKKL | | 10 |
| SEQ ID NO: 313 FEATURE source | moltype = AA length = 10 Location/Qualifiers 1..10 mol_type = protein organism = Mus sp. | |
| SEQUENCE: 313 REKKKFLKRR | | 10 |
| SEQ ID NO: 314 FEATURE source | moltype = AA length = 20 Location/Qualifiers 1..20 mol_type = protein organism = Homo sapiens | |
| SEQUENCE: 314 KRKGDEVDGV DEVAKKKSKK | | 20 |
| SEQ ID NO: 315 FEATURE source | moltype = AA length = 17 Location/Qualifiers 1..17 mol_type = protein organism = Homo sapiens | |
| SEQUENCE: 315 RKCLQAGMNL EARKTKK | | 17 |
| SEQ ID NO: 316 SEQUENCE: 316 000 | moltype = length = | |
| SEQ ID NO: 317 SEQUENCE: 317 000 | moltype = length = | |
| SEQ ID NO: 318 SEQUENCE: 318 000 | moltype = length = | |
| SEQ ID NO: 319 SEQUENCE: 319 000 | moltype = length = | |
| SEQ ID NO: 320 SEQUENCE: 320 000 | moltype = length = | |

| | | |
|---|---|---|
| SEQ ID NO: 321<br>SEQUENCE: 321<br>000 | moltype = | length = |
| SEQ ID NO: 322<br>SEQUENCE: 322<br>000 | moltype = | length = |
| SEQ ID NO: 323<br>SEQUENCE: 323<br>000 | moltype = | length = |
| SEQ ID NO: 324<br>SEQUENCE: 324<br>000 | moltype = | length = |
| SEQ ID NO: 325<br>SEQUENCE: 325<br>000 | moltype = | length = |
| SEQ ID NO: 326<br>SEQUENCE: 326<br>000 | moltype = | length = |
| SEQ ID NO: 327<br>SEQUENCE: 327<br>000 | moltype = | length = |
| SEQ ID NO: 328<br>SEQUENCE: 328<br>000 | moltype = | length = |
| SEQ ID NO: 329<br>SEQUENCE: 329<br>000 | moltype = | length = |
| SEQ ID NO: 330<br>SEQUENCE: 330<br>000 | moltype = | length = |
| SEQ ID NO: 331<br>SEQUENCE: 331<br>000 | moltype = | length = |
| SEQ ID NO: 332<br>SEQUENCE: 332<br>000 | moltype = | length = |
| SEQ ID NO: 333<br>SEQUENCE: 333<br>000 | moltype = | length = |
| SEQ ID NO: 334<br>SEQUENCE: 334<br>000 | moltype = | length = |
| SEQ ID NO: 335<br>SEQUENCE: 335<br>000 | moltype = | length = |
| SEQ ID NO: 336<br>SEQUENCE: 336<br>000 | moltype = | length = |
| SEQ ID NO: 337<br>SEQUENCE: 337<br>000 | moltype = | length = |
| SEQ ID NO: 338<br>SEQUENCE: 338<br>000 | moltype = | length = |
| SEQ ID NO: 339<br>SEQUENCE: 339<br>000 | moltype = | length = |
| SEQ ID NO: 340<br>SEQUENCE: 340<br>000 | moltype = | length = |

| | | |
|---|---|---|
| SEQ ID NO: 341<br>SEQUENCE: 341<br>000 | moltype = | length = |
| SEQ ID NO: 342<br>SEQUENCE: 342<br>000 | moltype = | length = |
| SEQ ID NO: 343<br>SEQUENCE: 343<br>000 | moltype = | length = |
| SEQ ID NO: 344<br>SEQUENCE: 344<br>000 | moltype = | length = |
| SEQ ID NO: 345<br>SEQUENCE: 345<br>000 | moltype = | length = |
| SEQ ID NO: 346<br>SEQUENCE: 346<br>000 | moltype = | length = |
| SEQ ID NO: 347<br>SEQUENCE: 347<br>000 | moltype = | length = |
| SEQ ID NO: 348<br>SEQUENCE: 348<br>000 | moltype = | length = |
| SEQ ID NO: 349<br>SEQUENCE: 349<br>000 | moltype = | length = |
| SEQ ID NO: 350<br>SEQUENCE: 350<br>000 | moltype = | length = |
| SEQ ID NO: 351<br>SEQUENCE: 351<br>000 | moltype = | length = |
| SEQ ID NO: 352<br>SEQUENCE: 352<br>000 | moltype = | length = |
| SEQ ID NO: 353<br>SEQUENCE: 353<br>000 | moltype = | length = |
| SEQ ID NO: 354<br>SEQUENCE: 354<br>000 | moltype = | length = |
| SEQ ID NO: 355<br>SEQUENCE: 355<br>000 | moltype = | length = |
| SEQ ID NO: 356<br>SEQUENCE: 356<br>000 | moltype = | length = |
| SEQ ID NO: 357<br>SEQUENCE: 357<br>000 | moltype = | length = |
| SEQ ID NO: 358<br>SEQUENCE: 358<br>000 | moltype = | length = |
| SEQ ID NO: 359<br>SEQUENCE: 359<br>000 | moltype = | length = |
| SEQ ID NO: 360<br>SEQUENCE: 360 | moltype = | length = |

-continued

000

SEQ ID NO: 361         moltype =    length =
SEQUENCE: 361
000

SEQ ID NO: 362         moltype =    length =
SEQUENCE: 362
000

SEQ ID NO: 363         moltype =    length =
SEQUENCE: 363
000

SEQ ID NO: 364         moltype =    length =
SEQUENCE: 364
000

SEQ ID NO: 365         moltype =    length =
SEQUENCE: 365
000

SEQ ID NO: 366         moltype =    length =
SEQUENCE: 366
000

SEQ ID NO: 367         moltype =    length =
SEQUENCE: 367
000

SEQ ID NO: 368         moltype =    length =
SEQUENCE: 368
000

SEQ ID NO: 369         moltype =    length =
SEQUENCE: 369
000

SEQ ID NO: 370         moltype =    length =
SEQUENCE: 370
000

SEQ ID NO: 371         moltype =    length =
SEQUENCE: 371
000

SEQ ID NO: 372         moltype =    length =
SEQUENCE: 372
000

SEQ ID NO: 373         moltype =    length =
SEQUENCE: 373
000

SEQ ID NO: 374         moltype =    length =
SEQUENCE: 374
000

SEQ ID NO: 375         moltype =    length =
SEQUENCE: 375
000

SEQ ID NO: 376         moltype =    length =
SEQUENCE: 376
000

SEQ ID NO: 377         moltype =    length =
SEQUENCE: 377
000

SEQ ID NO: 378         moltype =    length =
SEQUENCE: 378
000

SEQ ID NO: 379         moltype =    length =
SEQUENCE: 379
000

SEQ ID NO: 380         moltype =    length =

```
SEQUENCE: 380
000

SEQ ID NO: 381          moltype =     length =
SEQUENCE: 381
000

SEQ ID NO: 382          moltype =     length =
SEQUENCE: 382
000

SEQ ID NO: 383          moltype =     length =
SEQUENCE: 383
000

SEQ ID NO: 384          moltype =     length =
SEQUENCE: 384
000

SEQ ID NO: 385          moltype =     length =
SEQUENCE: 385
000

SEQ ID NO: 386          moltype =     length =
SEQUENCE: 386
000

SEQ ID NO: 387          moltype =     length =
SEQUENCE: 387
000

SEQ ID NO: 388          moltype =     length =
SEQUENCE: 388
000

SEQ ID NO: 389          moltype =     length =
SEQUENCE: 389
000

SEQ ID NO: 390          moltype =     length =
SEQUENCE: 390
000

SEQ ID NO: 391          moltype =     length =
SEQUENCE: 391
000

SEQ ID NO: 392          moltype =     length =
SEQUENCE: 392
000

SEQ ID NO: 393          moltype =     length =
SEQUENCE: 393
000

SEQ ID NO: 394          moltype =     length =
SEQUENCE: 394
000

SEQ ID NO: 395          moltype =     length =
SEQUENCE: 395
000

SEQ ID NO: 396          moltype =     length =
SEQUENCE: 396
000

SEQ ID NO: 397          moltype =     length =
SEQUENCE: 397
000

SEQ ID NO: 398          moltype =     length =
SEQUENCE: 398
000

SEQ ID NO: 399          moltype =     length =
SEQUENCE: 399
000
```

| | | |
|---|---|---|
| SEQ ID NO: 400 | moltype = RNA   length = 131 | |
| FEATURE | Location/Qualifiers | |
| misc_feature | 1..131<br>note = source = /note="Description of Artificial Sequence:<br>    Synthetic polynucleotide" | |
| source | 1..131<br>mol_type = other RNA<br>organism = synthetic construct | |
| SEQUENCE: 400 | | |
| gggaattttt gtgcccatcg ttggcaccct aatgcggaag tagtgggtaa cccggaattt | | 60 |
| ttgtgcccat cgttggcact ccgcaagaat tgattggctc caattctaat ttttgtgccc | | 120 |
| atcgttggca c | | 131 |

| | | |
|---|---|---|
| SEQ ID NO: 401 | moltype = RNA   length = 24 | |
| FEATURE | Location/Qualifiers | |
| misc_feature | 1..24<br>note = source = /note="Description of Artificial Sequence:<br>    Synthetic oligonucleotide" | |
| source | 1..24<br>mol_type = other RNA<br>organism = synthetic construct | |
| SEQUENCE: 401 | | |
| aatttttgtg cccatcgttg gcac | | 24 |

| | | |
|---|---|---|
| SEQ ID NO: 402 | moltype = RNA   length = 28 | |
| FEATURE | Location/Qualifiers | |
| misc_feature | 1..28<br>note = source = /note="Description of Artificial Sequence:<br>    Synthetic oligonucleotide" | |
| source | 1..28<br>mol_type = other RNA<br>organism = synthetic construct | |
| SEQUENCE: 402 | | |
| cctaatgcgg aagtagtggg taacccgg | | 28 |

| | | |
|---|---|---|
| SEQ ID NO: 403 | moltype = RNA   length = 28 | |
| FEATURE | Location/Qualifiers | |
| misc_feature | 1..28<br>note = source = /note="Description of Artificial Sequence:<br>    Synthetic oligonucleotide" | |
| source | 1..28<br>mol_type = other RNA<br>organism = synthetic construct | |
| SEQUENCE: 403 | | |
| tccgcaagaa ttgattggct ccaattct | | 28 |

| | | |
|---|---|---|
| SEQ ID NO: 404 | moltype = RNA   length = 131 | |
| FEATURE | Location/Qualifiers | |
| misc_feature | 1..131<br>note = source = /note="Description of Artificial Sequence:<br>    Synthetic polynucleotide" | |
| source | 1..131<br>mol_type = other RNA<br>organism = synthetic construct | |
| SEQUENCE: 404 | | |
| gggaattttt gtgcccatcg ttggcacagg catcatcagc attaaccacg caaacaattt | | 60 |
| ttgtgcccat cgttggcacg cgtgctggat tgcttcgatg gtctgcgaat ttttgtgccc | | 120 |
| atcgttggca c | | 131 |

| | | |
|---|---|---|
| SEQ ID NO: 405 | moltype = RNA   length = 24 | |
| FEATURE | Location/Qualifiers | |
| misc_feature | 1..24<br>note = source = /note="Description of Artificial Sequence:<br>    Synthetic oligonucleotide" | |
| source | 1..24<br>mol_type = other RNA<br>organism = synthetic construct | |
| SEQUENCE: 405 | | |
| aatttttgtg cccatcgttg gcac | | 24 |

| | | |
|---|---|---|
| SEQ ID NO: 406 | moltype = RNA   length = 28 | |
| FEATURE | Location/Qualifiers | |
| misc_feature | 1..28<br>note = source = /note="Description of Artificial Sequence:<br>    Synthetic oligonucleotide" | |
| source | 1..28<br>mol_type = other RNA<br>organism = synthetic construct | |
| SEQUENCE: 406 | | |

```
aggcatcatc agcattaacc acgcaaac                                              28

SEQ ID NO: 407          moltype = RNA  length = 28
FEATURE                 Location/Qualifiers
misc_feature            1..28
                        note = source = /note="Description of Artificial Sequence:
                        Synthetic oligonucleotide"
source                  1..28
                        mol_type = other RNA
                        organism = synthetic construct
SEQUENCE: 407
gcgtgctgga ttgcttcgat ggtctgcg                                              28

SEQ ID NO: 408          moltype = DNA  length = 128
FEATURE                 Location/Qualifiers
misc_feature            1..128
                        note = source = /note="Description of Artificial Sequence:
                        Synthetic polynucleotide"
source                  1..128
                        mol_type = other DNA
                        organism = synthetic construct
SEQUENCE: 408
catgtggacc acattaggct gcaaaactgc gcatttacga aaacgcgaaa gtttgcgtgg           60
ttaatgctga tgatgcctta acaatgccga ttcgcggtgc ggatgaacgt aatttctcga          120
ggcgtatt                                                                   128

SEQ ID NO: 409          moltype = DNA  length = 128
FEATURE                 Location/Qualifiers
misc_feature            1..128
                        note = source = /note="Description of Artificial Sequence:
                        Synthetic polynucleotide"
source                  1..128
                        mol_type = other DNA
                        organism = synthetic construct
SEQUENCE: 409
catgtggacc acattaggct tggttgttgc tgccgacgac ggtgtgatgc cgcagaccat           60
cgaagcaatc cagcacgcga aagcggcgca ggtaccggtg gtggttgcgt aatttctcga          120
ggcgtatt                                                                   128

SEQ ID NO: 410          moltype = DNA  length = 128
FEATURE                 Location/Qualifiers
misc_feature            1..128
                        note = source = /note="Description of Artificial Sequence:
                        Synthetic polynucleotide"
source                  1..128
                        mol_type = other DNA
                        organism = synthetic construct
SEQUENCE: 410
aatacgcctc gagaaattac aaagtgatgc aggcgtttcc aggtgctttc cctaatgcgg           60
aagtagtggg taacccggtg cgtaccgatg tgttggcgct gccgttgcag cctaatgtgg          120
tccacatg                                                                   128

SEQ ID NO: 411          moltype = DNA  length = 171
FEATURE                 Location/Qualifiers
misc_feature            1..171
                        note = source = /note="Description of Artificial Sequence:
                        Synthetic polynucleotide"
source                  1..171
                        mol_type = other DNA
                        organism = synthetic construct
SEQUENCE: 411
gtgccaacga tgggcacaaa aattagaatt ggagccaatc aattcttgcg gagtgccaac           60
gatgggcaca aaaattagaa ttggagccaa tcaattcttg cggagtgcca acgatgggca          120
caaaaattcc ctatagtgag tcgtattact cgagggatcc ttattacatt t                   171

SEQ ID NO: 412          moltype = DNA  length = 18
FEATURE                 Location/Qualifiers
misc_feature            1..18
                        note = source = /note="Description of Artificial Sequence:
                        Synthetic primer"
source                  1..18
                        mol_type = other DNA
                        organism = synthetic construct
SEQUENCE: 412
taatacgact cactatag                                                         18

SEQ ID NO: 413          moltype = DNA  length = 52
FEATURE                 Location/Qualifiers
misc_feature            1..52
```

```
                         note = source = /note="Description of Artificial Sequence:
                          Synthetic primer"
source                   1..52
                         mol_type = other DNA
                         organism = synthetic construct
SEQUENCE: 413
gtgccaacga tgggcacaaa aattagaatt ggagccaatc aattcttgcg ga            52

SEQ ID NO: 414           moltype = DNA  length = 171
FEATURE                  Location/Qualifiers
misc_feature             1..171
                         note = source = /note="Description of Artificial Sequence:
                          Synthetic polynucleotide"
source                   1..171
                         mol_type = other DNA
                         organism = synthetic construct
SEQUENCE: 414
gtgccaacga tgggcacaaa aattcgcaga ccatcgaagc aatccagcac gcgtgccaac    60
gatgggcaca aaaattgttt gcgtggttaa tgctgatgat gcctgtgcca acgatgggca    120
caaaaattcc ctatagtgag tcgtattact cgagggatcc ttattacatt t             171

SEQ ID NO: 415           moltype = DNA  length = 18
FEATURE                  Location/Qualifiers
misc_feature             1..18
                         note = source = /note="Description of Artificial Sequence:
                          Synthetic primer"
source                   1..18
                         mol_type = other DNA
                         organism = synthetic construct
SEQUENCE: 415
taatacgact cactatag                                                  18

SEQ ID NO: 416           moltype = DNA  length = 52
FEATURE                  Location/Qualifiers
misc_feature             1..52
                         note = source = /note="Description of Artificial Sequence:
                          Synthetic primer"
source                   1..52
                         mol_type = other DNA
                         organism = synthetic construct
SEQUENCE: 416
gtgccaacga tgggcacaaa aattcgcaga ccatcgaagc aatccagcac gc            52

SEQ ID NO: 417           moltype =   length =
SEQUENCE: 417
000

SEQ ID NO: 418           moltype =   length =
SEQUENCE: 418
000

SEQ ID NO: 419           moltype =   length =
SEQUENCE: 419
000

SEQ ID NO: 420           moltype =   length =
SEQUENCE: 420
000

SEQ ID NO: 421           moltype =   length =
SEQUENCE: 421
000

SEQ ID NO: 422           moltype =   length =
SEQUENCE: 422
000

SEQ ID NO: 423           moltype =   length =
SEQUENCE: 423
000

SEQ ID NO: 424           moltype =   length =
SEQUENCE: 424
000

SEQ ID NO: 425           moltype =   length =
SEQUENCE: 425
000
```

| | | |
|---|---|---|
| SEQ ID NO: 426<br>SEQUENCE: 426<br>000 | moltype = | length = |
| SEQ ID NO: 427<br>SEQUENCE: 427<br>000 | moltype = | length = |
| SEQ ID NO: 428<br>SEQUENCE: 428<br>000 | moltype = | length = |
| SEQ ID NO: 429<br>SEQUENCE: 429<br>000 | moltype = | length = |
| SEQ ID NO: 430<br>SEQUENCE: 430<br>000 | moltype = | length = |
| SEQ ID NO: 431<br>SEQUENCE: 431<br>000 | moltype = | length = |
| SEQ ID NO: 432<br>SEQUENCE: 432<br>000 | moltype = | length = |
| SEQ ID NO: 433<br>SEQUENCE: 433<br>000 | moltype = | length = |
| SEQ ID NO: 434<br>SEQUENCE: 434<br>000 | moltype = | length = |
| SEQ ID NO: 435<br>SEQUENCE: 435<br>000 | moltype = | length = |
| SEQ ID NO: 436<br>SEQUENCE: 436<br>000 | moltype = | length = |
| SEQ ID NO: 437<br>SEQUENCE: 437<br>000 | moltype = | length = |
| SEQ ID NO: 438<br>SEQUENCE: 438<br>000 | moltype = | length = |
| SEQ ID NO: 439<br>SEQUENCE: 439<br>000 | moltype = | length = |
| SEQ ID NO: 440<br>SEQUENCE: 440<br>000 | moltype = | length = |
| SEQ ID NO: 441<br>SEQUENCE: 441<br>000 | moltype = | length = |
| SEQ ID NO: 442<br>SEQUENCE: 442<br>000 | moltype = | length = |
| SEQ ID NO: 443<br>SEQUENCE: 443<br>000 | moltype = | length = |
| SEQ ID NO: 444<br>SEQUENCE: 444<br>000 | moltype = | length = |
| SEQ ID NO: 445<br>SEQUENCE: 445<br>000 | moltype = | length = |

| | | |
|---|---|---|
| SEQ ID NO: 446<br>SEQUENCE: 446<br>000 | moltype = | length = |
| SEQ ID NO: 447<br>SEQUENCE: 447<br>000 | moltype = | length = |
| SEQ ID NO: 448<br>SEQUENCE: 448<br>000 | moltype = | length = |
| SEQ ID NO: 449<br>SEQUENCE: 449<br>000 | moltype = | length = |
| SEQ ID NO: 450<br>SEQUENCE: 450<br>000 | moltype = | length = |
| SEQ ID NO: 451<br>SEQUENCE: 451<br>000 | moltype = | length = |
| SEQ ID NO: 452<br>SEQUENCE: 452<br>000 | moltype = | length = |
| SEQ ID NO: 453<br>SEQUENCE: 453<br>000 | moltype = | length = |
| SEQ ID NO: 454<br>SEQUENCE: 454<br>000 | moltype = | length = |
| SEQ ID NO: 455<br>SEQUENCE: 455<br>000 | moltype = | length = |
| SEQ ID NO: 456<br>SEQUENCE: 456<br>000 | moltype = | length = |
| SEQ ID NO: 457<br>SEQUENCE: 457<br>000 | moltype = | length = |
| SEQ ID NO: 458<br>SEQUENCE: 458<br>000 | moltype = | length = |
| SEQ ID NO: 459<br>SEQUENCE: 459<br>000 | moltype = | length = |
| SEQ ID NO: 460<br>SEQUENCE: 460<br>000 | moltype = | length = |
| SEQ ID NO: 461<br>SEQUENCE: 461<br>000 | moltype = | length = |
| SEQ ID NO: 462<br>SEQUENCE: 462<br>000 | moltype = | length = |
| SEQ ID NO: 463<br>SEQUENCE: 463<br>000 | moltype = | length = |
| SEQ ID NO: 464<br>SEQUENCE: 464<br>000 | moltype = | length = |
| SEQ ID NO: 465<br>SEQUENCE: 465 | moltype = | length = |

```
000

SEQ ID NO: 466           moltype =     length =
SEQUENCE: 466
000

SEQ ID NO: 467           moltype =     length =
SEQUENCE: 467
000

SEQ ID NO: 468           moltype =     length =
SEQUENCE: 468
000

SEQ ID NO: 469           moltype =     length =
SEQUENCE: 469
000

SEQ ID NO: 470           moltype =     length =
SEQUENCE: 470
000

SEQ ID NO: 471           moltype =     length =
SEQUENCE: 471
000

SEQ ID NO: 472           moltype =     length =
SEQUENCE: 472
000

SEQ ID NO: 473           moltype =     length =
SEQUENCE: 473
000

SEQ ID NO: 474           moltype =     length =
SEQUENCE: 474
000

SEQ ID NO: 475           moltype =     length =
SEQUENCE: 475
000

SEQ ID NO: 476           moltype =     length =
SEQUENCE: 476
000

SEQ ID NO: 477           moltype =     length =
SEQUENCE: 477
000

SEQ ID NO: 478           moltype =     length =
SEQUENCE: 478
000

SEQ ID NO: 479           moltype =     length =
SEQUENCE: 479
000

SEQ ID NO: 480           moltype =     length =
SEQUENCE: 480
000

SEQ ID NO: 481           moltype =     length =
SEQUENCE: 481
000

SEQ ID NO: 482           moltype =     length =
SEQUENCE: 482
000

SEQ ID NO: 483           moltype =     length =
SEQUENCE: 483
000

SEQ ID NO: 484           moltype =     length =
SEQUENCE: 484
000

SEQ ID NO: 485           moltype =     length =
```

| | | |
|---|---|---|
| SEQ ID NO: 485 | moltype = | length = |
| SEQUENCE: 485 | | |
| 000 | | |
| SEQ ID NO: 486 | moltype = | length = |
| SEQUENCE: 486 | | |
| 000 | | |
| SEQ ID NO: 487 | moltype = | length = |
| SEQUENCE: 487 | | |
| 000 | | |
| SEQ ID NO: 488 | moltype = | length = |
| SEQUENCE: 488 | | |
| 000 | | |
| SEQ ID NO: 489 | moltype = | length = |
| SEQUENCE: 489 | | |
| 000 | | |
| SEQ ID NO: 490 | moltype = | length = |
| SEQUENCE: 490 | | |
| 000 | | |
| SEQ ID NO: 491 | moltype = | length = |
| SEQUENCE: 491 | | |
| 000 | | |
| SEQ ID NO: 492 | moltype = | length = |
| SEQUENCE: 492 | | |
| 000 | | |
| SEQ ID NO: 493 | moltype = | length = |
| SEQUENCE: 493 | | |
| 000 | | |
| SEQ ID NO: 494 | moltype = | length = |
| SEQUENCE: 494 | | |
| 000 | | |
| SEQ ID NO: 495 | moltype = | length = |
| SEQUENCE: 495 | | |
| 000 | | |
| SEQ ID NO: 496 | moltype = | length = |
| SEQUENCE: 496 | | |
| 000 | | |
| SEQ ID NO: 497 | moltype = | length = |
| SEQUENCE: 497 | | |
| 000 | | |
| SEQ ID NO: 498 | moltype = | length = |
| SEQUENCE: 498 | | |
| 000 | | |
| SEQ ID NO: 499 | moltype = | length = |
| SEQUENCE: 499 | | |
| 000 | | |

```
SEQ ID NO: 500          moltype = DNA   length = 212
FEATURE                 Location/Qualifiers
misc_feature            1..212
                        note = source = /note="Description of Artificial Sequence:
                         Synthetic polynucleotide"
source                  1..212
                        mol_type = other DNA
                        organism = synthetic construct
SEQUENCE: 500
gggcagagcg cacatcgccc acagtccccg agaagtttggg gggagggggtc ggcaattgat   60
ccggtgccta gagaaggtgg cgcggggtaa actgggaaag tgatgtcgtg tactggctcc  120
gccttttttcc cgagggtggg ggagaaccgt atataagtgc agtagtcgcc gtgaacgttc  180
tttttcgcaa cgggtttgcc gccagaacac ag                                 212

SEQ ID NO: 501          moltype = DNA   length = 3375
FEATURE                 Location/Qualifiers
misc_feature            1..3375
                        note = source = /note="Description of Artificial Sequence:
                         Synthetic polynucleotide"
source                  1..3375
```

```
                        mol_type = other DNA
                        organism = synthetic construct
SEQUENCE: 501
atgaaaatcg aagaaggtaa aggtcaccat caccatcacc acatgtctaa caaggagaag    60
aatgccagcg agacccggaa ggcctacacc acaaagatga tccccaggag ccacgaccgc   120
atgaagctgc tgggcaactt tatggactat ctgatggatg gcaccccat cttctttgag    180
ctgtggaatc agttcggcgg cggcatcgac agagatatca tcagcggcac agccaacaag   240
gataagatct ccgacgatct gctgctggcc gtgaactggt ttaaagtgat gccaatcaat   300
tctaagcccc agggcgtgtc cccttctaac ctggccaatc tgttccagca gtacagcgga   360
tccgagcctg acatccaggc acaggagtat ttcgcctcca actttgacac cgagaagcac   420
cagtggaagg atatgcgggt ggagtacgag agactgctgg ccgagctgca gctgtctagg   480
agcgacatgc atcacgatct gaagctgatg tacaaggaga agtgcatcgg cctgccctg    540
tctaccgccc actatatcac aagcgtgatg tttggcaccg gcgccaagaa caatcgccag   600
acaaagcacc agttctattc caaagtgatc cagctgctgg aggagagcac ccagatccag   660
tccgtggagc agctggcctc catcatcctg aaggccggcg actgcgattc ttacaggaag   720
ctgaggatca ggtgttcccg caagggagca accccatcta tcctgaagat cgtgcaggac   780
tatgagctgg gcacaaacca cgacgatgaa gtgaatgtgc cctccctgat cgccaacctg   840
aaggagaagc tgggcaggtt tgagtacgag tgcgagtgga agtgtatgga gaagatcaag   900
gccttcctgg cctctaaagt gggcccttac tatctgggca gctattccgc catgctggag   960
aatgccctga gcccaatcaa gggcatgacc acaaagaact gtaagttcgt gctgaagcag  1020
atcgacgcca agaacgatat caagtacgag aatgagccct tggcaagat cgtggagggc   1080
ttctttgact ctccttattt cgagagcgat accaatgtga agtgggtgct gcaccctcac  1140
cacatcggcg agtctaacat caagacactg tgggaggacc tgaatgccat ccacagcaag  1200
tacgaggagg acatcgcctc tctgagcgag ataagaagg agaagcggat caaggtgtac   1260
cagggcgatg tgtgccagac catcaacaca tattgtgagg aagtgggcaa ggaggccaag  1320
accccactgg tgcagctgct gaggtacctg tattcccgca agacgatat cgccgtggac   1380
aagatcatcg atggcatcac attcctgtct aagaagcaca aggtggagaa gcagaagatc  1440
aacccagtga tccagaagta ccccagcttc aattttggca caattccaa gctgctgggc   1500
aagatcatca gcccaaagga caagctgaag cacaacctga agtgcaacag aaatcaggtg  1560
gataattaca tctggatcga gatcaaggtg ctgaacacca acaatgcg tgtgggagaag   1620
caccactatg ccctgagctc caccagattt ctggaggagg tgtactatcc cgccacatcc  1680
gagaatccac ctgacgcact ggcagcacgg ttcagaacca agacaaacgg ctacgagggc  1740
aagccagccc tgtctgccga gcagatcgag cagatcagga gcgcaccagt gggactgaga  1800
aaggtgaaga agcggcagat gagctggag gcagcaaggc agcagaatct gctgccacgc   1860
tatacctggg gcaaggattt taacatcaat atctgtagaa ggggcaacaa tttcgaggtg   1920
accctggcca caaaggtgaa gaagaagaag gagaagaact acaaggtggt gctgggctat  1980
gacgccaaca tcgtgcgcaa gaatacctac gcagcaatcg aggcacacgc aaacggcgat  2040
ggcgtgatcg actataatga tctgcctgtg aagccaatcg agtctggctt tgtgacagtg  2100
gagaccagg tgaggggaca gtcctacgat cagctgtctt ataacggcgt gaagctgctg   2160
tactcaagc ctcacgtgga gagccggaga tccttcctgg agaagtatcg gaacggcacc   2220
atgaaggaca atagaggcaa caatatccag atcgacttca tgaaggattt tgaggccatc  2280
gccgacgatg agacaagcct gtactactcc aacatgaagt actgtaagct gctgcagtct  2340
agcatccgca accactcctc tcaggccaag gagtataggg aggagatctt cgagctgctg  2400
cgcgatggca agctgtccgt gctgaagctg agctccctgt ctaatctgag cttcgtgatg  2460
tttaaggtgg ccaagtctct gatcggcacc tactttggcc acctgctgaa gaagcctaag  2520
aactccaagt ctgacgtgaa ggccccaccc atcacagacg aggataagca gaaggccgat  2580
ccagagatgt tcgcactgcg gctggcactg gaggagaaga gactgaataa ggtgaagagc  2640
aagaaggaag tgatcgccaa caagatcgtg gccaaggcac tggagctgag ggacaagtac  2700
ggaccagtgc tgatcaaggg cgagaatatc agcgatacca aaagaaggg caagaagtct  2760
agcaccaatt ccttcctgat ggactggctg ccagaggctg tggccaacaa ggtgaaggag  2820
atggtcatga tgcaccaggg cctggagttc gtggaggtga accccaattt tacctcccac  2880
caggatcctt tcgtgcacaa gaacccagag aataccttcc gggcaaggta cagcaggtgc  2940
accccttccg agctgacaga gaagaaccgc aaggagatcc tgtccttcct gtctgacaag  3000
cccagcaagc ggcctactaa cgcctactat aatgagggcg ccatggcctt tctggccaca  3060
tatgcctga agaagaatga cgtgctgggc gtgtccctgg agaagttcaa gcagatcatg  3120
gccaacatcc tgcaccagcg gtccgaggat cagctgctgt ttccctctag aggcggcatg  3180
ttctacctgg ccacctataa gctggacgcc gatgccacaa gcgtgaactg gaatggcaag  3240
cagttttggg tgtgtaacgc cgacctggtg ccgcctaca atgtgggcct ggtggacatc  3300
cagaaggatt tcaagaagaa gaaaaggccg gcggccacga aaaaggccgg ccaggcaaaa  3360
aagaaaaagt aataa                                                  3375

SEQ ID NO: 502        moltype = DNA   length = 3258
FEATURE               Location/Qualifiers
misc_feature          1..3258
                        note = source = /note="Description of Artificial Sequence:
                        Synthetic polynucleotide"
source                1..3258
                        mol_type = other DNA
                        organism = synthetic construct
SEQUENCE: 502
atgaaaatcg aagaaggtaa aggtcaccat caccatcacc acatgagctc cgccatcaag    60
tcctacaagt ctgtgctgcg gccaaacgag agaaagaatc agctgctgaa gagccaccatc  120
cagtgcctga aggacggctc cgccttcttt tcaagatgc tgcagggcct gtttggcggc   180
atcacccccg agatcgtgag attcagcaca gagcaggaga agcagcag ggatatcgcc    240
ctgtggtgtg ccgtgaattg gttcaggcct gtgagccagg actccctgac ccacacaatc  300
gcctccgata acctggtgga agtttgag gagtactatg cggcacagc cagcgacgcc    360
atcaagcagt acttcagcgc ctccatcggc agtcctact attggaatga ctgccgccaa  420
cagtactatg atctgtgtcg ggagctgggc gtggaggtgt ctgacctgac ccacgatctg  480
gagatcctgt gccgggagaa gtgtctggcc gtggccacag agcaaccaga aacaattct   540
```

```
atcatcagcg tgctgtttgg caccggcgag aaggaggata ggtctgtgaa gctgcgcatc   600
acaaagaaga tcctggaggc catcagcaac ctgaaggaga tcccaaagaa tgtggccccc   660
atccaggaga tcatcctgaa tgtggccaag gccaccaagg agacattcag acaggtgtac   720
gcaggaaacc tgggagcacc atccaccctg gagaagttta tcgccaagga cggccagaag   780
gagttcgatc tgaagaagct gcagacagac ctgaagaaag tgatccgggg caagtctaag   840
gagagagatt ggtgctgtca ggaggagctg aggagctacg tggagcagaa taccatccag   900
tatgacctgt gggcctgggg cgagatgttc aacaaggccc acaccgccct gaagatcaag   960
tccacaagaa actacaattt tgccaagcag aggctggagc agttcaagga gatccagtct  1020
ctgaacaatc tgctggtggt gaagaagctg aacgactttt tcgatagcga gttttttctcc  1080
ggcgaggaga cctacacaat ctgcgtgcac cacctgggcg gcaaggacct gtccaagctg  1140
tataaggcct gggaggacga tcccgccgat cctgagaatg ccatcgtggt gctgtgcgac  1200
gatctgaaga acaattttaa gaaggagcct atcaggaaca tcctgcgcta catcttcacc  1260
atccgccagg agtgtagcgc acaggacatc ctggcagcag caagtacaa tcagcagctg  1320
gatcggtata agagccagaa ggccaaccca tccgtgctgg gcaatcaggg cttttacctgg  1380
acaaacgccg tgatcctgcc agagaaggcc cagcggaacg acagacccaa ttctctggat  1440
ctgcgcatct ggctgtacct gaagctgcgc caccctgacg gcagatggaa gaagcaccac  1500
atcccattct acgatacccg gttttttccag gagatctatg ccgccggcaa tagccctgtg  1560
gacacctgtc agtttaggac accccgcttc ggctatcacc tgcctaagct gaccgatcag  1620
acagccatcc gcgtgaacaa gaagcacgtg aaggcagcaa agaccgaggc acggatcaga  1680
ctggccatcc agcagggcac actgccagtg tccaatctga agatcaccga gatctccgcc  1740
acaatcaact ctaaggggcca ggtgcgcatc cccgtgaagt tgacgtgggg aaggcagaag  1800
ggaaccctgc agatcgagtc ccggttctgc ggctacgatc agaaccagac agcctctcac  1860
gcctatagcc tgtgggaggt ggtgaaggag ggccagtacc acaaggagct gggctgtttt  1920
gtgcgcttca tctctagcgg cgacatcgtg tccatcaccg agaacggggg caatcagttt  1980
gatcagctgt cttatgaggg cctggcctac ccccagtatg ccgactggag aaagaaggcc  2040
tccaagttcg tgtctctgtg gcagatcacc aagaagaaga gatcgtgaca  2100
gtggaggcca aggagaagtt tgacgccatc tgcaagtacc agcctaggct gtataagttc  2160
aacaaggagt acgcctatct gctgcgggat atcgtgagag caagagcct ggtggagctg  2220
cagcagatca ggcaggagat cttcgcttc atcgagcagg actgtggagt gacccgcctg  2280
ggatctctga gcctgtccac cctggagaca gtgaagggcat catctactcc  2340
tatttttcta cagccctgaa tgcctctaag aacaatccca tcagcgacga gcagcggaag  2400
gagtttgatc ctgagctgtt cgccctgctg gagaagctgg agctgatcag gactcggaag  2460
aagaagcaga aggtggagag aatcgccaat agcctgatcc agacatgcct ggagaacaat  2520
atcaagttca tcaggggcga gggcgacctg tccaccacaa acaatgccac caagaagaag  2580
gccaactcta ggagcatgga ttggctggcc agaggcgtgt taataagat ccggcagctg  2640
gccccaatgc acaacatcac cctgttcggc tgcggcagcc tgtacacatc ccaccaggac  2700
cctctggtgc acagaaaccc agataaggcc atgaagtgta gatgggcagc aatcccagtg  2760
aaggacatcg gcgattgggt gctgagaaag ctgtcccaga acctgagggc caagaatatc  2820
ggcaccggcg agtactatca ccagggcgtg aaggagttcc tgtctcacta tgagctgcag  2880
gacctggagg aggagctgct gaagtggcgg tctgatagaa agagcaacat cccttgctgg  2940
gtgctgcaga atagactggc cgagaagctg ggcaacaagg aggccgtggt gtacatccca  3000
gtgaggggcg gccgcatcta ttttgcaacc cacaaggtgg caacaggagc cgtgagcatc  3060
gtgttcgacc agaagcaagt gtgggtgtgt aatgcagatc acgtggcagc agcaaacatc  3120
gcactgaccg tgaagggcat cggcgagcag tcctctgacg aggagaaccc cgatggctcc  3180
aggatcaagc tgcagctgac atctaaaagg ccggcggcca cgaaaaaggc cggccaggca  3240
aaaaagaaaa agtaataa                                                 3258

SEQ ID NO: 503         moltype = DNA   length = 228
FEATURE                Location/Qualifiers
misc_feature           1..228
                       note = source = /note="Description of Artificial Sequence:
                       Synthetic polynucleotide"
source                 1..228
                       mol_type = other DNA
                       organism = synthetic construct
SEQUENCE: 503
cgactgtgcc ttctagttgc cagccatctg ttgtttgccc ctcccccgtg ccttccttga    60
ccctggaagg tgccactccc actgtccttt cctaataaaa tgaggaaatt gcatcgcatt   120
gtctgagtag gtgtcattct attctggggg gtgggtggg gcaggacagc aaggggagg    180
attgggaaga caatagcagg catgctgggg atgcggtggg ctctatgg              228

SEQ ID NO: 504         moltype =   length =
SEQUENCE: 504
000

SEQ ID NO: 505         moltype =   length =
SEQUENCE: 505
000

SEQ ID NO: 506         moltype =   length =
SEQUENCE: 506
000

SEQ ID NO: 507         moltype =   length =
SEQUENCE: 507
000

SEQ ID NO: 508         moltype =   length =
SEQUENCE: 508
```

000

SEQ ID NO: 509     moltype =     length =
SEQUENCE: 509
000

SEQ ID NO: 510     moltype =     length =
SEQUENCE: 510
000

SEQ ID NO: 511     moltype =     length =
SEQUENCE: 511
000

SEQ ID NO: 512     moltype =     length =
SEQUENCE: 512
000

SEQ ID NO: 513     moltype =     length =
SEQUENCE: 513
000

SEQ ID NO: 514     moltype =     length =
SEQUENCE: 514
000

SEQ ID NO: 515     moltype =     length =
SEQUENCE: 515
000

SEQ ID NO: 516     moltype =     length =
SEQUENCE: 516
000

SEQ ID NO: 517     moltype =     length =
SEQUENCE: 517
000

SEQ ID NO: 518     moltype =     length =
SEQUENCE: 518
000

SEQ ID NO: 519     moltype =     length =
SEQUENCE: 519
000

SEQ ID NO: 520     moltype =     length =
SEQUENCE: 520
000

SEQ ID NO: 521     moltype =     length =
SEQUENCE: 521
000

SEQ ID NO: 522     moltype =     length =
SEQUENCE: 522
000

SEQ ID NO: 523     moltype =     length =
SEQUENCE: 523
000

SEQ ID NO: 524     moltype =     length =
SEQUENCE: 524
000

SEQ ID NO: 525     moltype =     length =
SEQUENCE: 525
000

SEQ ID NO: 526     moltype =     length =
SEQUENCE: 526
000

SEQ ID NO: 527     moltype =     length =
SEQUENCE: 527
000

SEQ ID NO: 528     moltype =     length =

| | | |
|---|---|---|
| SEQUENCE: 528 000 | | |
| SEQ ID NO: 529 SEQUENCE: 529 000 | moltype = | length = |
| SEQ ID NO: 530 SEQUENCE: 530 000 | moltype = | length = |
| SEQ ID NO: 531 SEQUENCE: 531 000 | moltype = | length = |
| SEQ ID NO: 532 SEQUENCE: 532 000 | moltype = | length = |
| SEQ ID NO: 533 SEQUENCE: 533 000 | moltype = | length = |
| SEQ ID NO: 534 SEQUENCE: 534 000 | moltype = | length = |
| SEQ ID NO: 535 SEQUENCE: 535 000 | moltype = | length = |
| SEQ ID NO: 536 SEQUENCE: 536 000 | moltype = | length = |
| SEQ ID NO: 537 SEQUENCE: 537 000 | moltype = | length = |
| SEQ ID NO: 538 SEQUENCE: 538 000 | moltype = | length = |
| SEQ ID NO: 539 SEQUENCE: 539 000 | moltype = | length = |
| SEQ ID NO: 540 SEQUENCE: 540 000 | moltype = | length = |
| SEQ ID NO: 541 SEQUENCE: 541 000 | moltype = | length = |
| SEQ ID NO: 542 SEQUENCE: 542 000 | moltype = | length = |
| SEQ ID NO: 543 SEQUENCE: 543 000 | moltype = | length = |
| SEQ ID NO: 544 SEQUENCE: 544 000 | moltype = | length = |
| SEQ ID NO: 545 SEQUENCE: 545 000 | moltype = | length = |
| SEQ ID NO: 546 SEQUENCE: 546 000 | moltype = | length = |
| SEQ ID NO: 547 SEQUENCE: 547 000 | moltype = | length = |

```
SEQ ID NO: 548         moltype =    length =
SEQUENCE: 548
000

SEQ ID NO: 549         moltype =    length =
SEQUENCE: 549
000

SEQ ID NO: 550         moltype = DNA  length = 45
FEATURE                Location/Qualifiers
misc_feature           1..45
                       note = source = /note="Description of Artificial Sequence:
                        Synthetic oligonucleotide"
source                 1..45
                       mol_type = other DNA
                       organism = synthetic construct
SEQUENCE: 550
acccccttc caaagcccat tccctctttt cgagccgggg tgtgc              45

SEQ ID NO: 551         moltype = DNA  length = 45
FEATURE                Location/Qualifiers
misc_feature           1..45
                       note = source = /note="Description of Artificial Sequence:
                        Synthetic oligonucleotide"
source                 1..45
                       mol_type = other DNA
                       organism = synthetic construct
SEQUENCE: 551
acccccttc caaagcccat tccctctttt tgagccgggg tgtgc              45

SEQ ID NO: 552         moltype = DNA  length = 45
FEATURE                Location/Qualifiers
misc_feature           1..45
                       note = source = /note="Description of Artificial Sequence:
                        Synthetic oligonucleotide"
source                 1..45
                       mol_type = other DNA
                       organism = synthetic construct
SEQUENCE: 552
acccccttc caaagcccat tcctgtttta tgagccgggg tgtgc              45

SEQ ID NO: 553         moltype = DNA  length = 44
FEATURE                Location/Qualifiers
misc_feature           1..44
                       note = source = /note="Description of Artificial Sequence:
                        Synthetic oligonucleotide"
source                 1..44
                       mol_type = other DNA
                       organism = synthetic construct
SEQUENCE: 553
acccccttc caaagcccat tccctcttta agagccgggg tgtg               44

SEQ ID NO: 554         moltype = DNA  length = 44
FEATURE                Location/Qualifiers
misc_feature           1..44
                       note = source = /note="Description of Artificial Sequence:
                        Synthetic oligonucleotide"
source                 1..44
                       mol_type = other DNA
                       organism = synthetic construct
SEQUENCE: 554
acccccttc caaagcccat tacctcttta agagccgggg tgtg               44

SEQ ID NO: 555         moltype = DNA  length = 44
FEATURE                Location/Qualifiers
misc_feature           1..44
                       note = source = /note="Description of Artificial Sequence:
                        Synthetic oligonucleotide"
source                 1..44
                       mol_type = other DNA
                       organism = synthetic construct
SEQUENCE: 555
acccccttc caaagcccat tccctctgta agagccgggg tgtg               44

SEQ ID NO: 556         moltype =    length =
SEQUENCE: 556
000

SEQ ID NO: 557         moltype =    length =
```

-continued

```
SEQUENCE: 557
000

SEQ ID NO: 558         moltype =    length =
SEQUENCE: 558
000

SEQ ID NO: 559         moltype =    length =
SEQUENCE: 559
000

SEQ ID NO: 560         moltype =    length =
SEQUENCE: 560
000

SEQ ID NO: 561         moltype =    length =
SEQUENCE: 561
000

SEQ ID NO: 562         moltype =    length =
SEQUENCE: 562
000

SEQ ID NO: 563         moltype =    length =
SEQUENCE: 563
000

SEQ ID NO: 564         moltype =    length =
SEQUENCE: 564
000

SEQ ID NO: 565         moltype =    length =
SEQUENCE: 565
000

SEQ ID NO: 566         moltype =    length =
SEQUENCE: 566
000

SEQ ID NO: 567         moltype =    length =
SEQUENCE: 567
000

SEQ ID NO: 568         moltype =    length =
SEQUENCE: 568
000

SEQ ID NO: 569         moltype =    length =
SEQUENCE: 569
000

SEQ ID NO: 570         moltype =    length =
SEQUENCE: 570
000

SEQ ID NO: 571         moltype =    length =
SEQUENCE: 571
000

SEQ ID NO: 572         moltype =    length =
SEQUENCE: 572
000

SEQ ID NO: 573         moltype =    length =
SEQUENCE: 573
000

SEQ ID NO: 574         moltype =    length =
SEQUENCE: 574
000

SEQ ID NO: 575         moltype =    length =
SEQUENCE: 575
000

SEQ ID NO: 576         moltype =    length =
SEQUENCE: 576
000
```

| | | |
|---|---|---|
| SEQ ID NO: 577<br>SEQUENCE: 577<br>000 | moltype = | length = |
| SEQ ID NO: 578<br>SEQUENCE: 578<br>000 | moltype = | length = |
| SEQ ID NO: 579<br>SEQUENCE: 579<br>000 | moltype = | length = |
| SEQ ID NO: 580<br>SEQUENCE: 580<br>000 | moltype = | length = |
| SEQ ID NO: 581<br>SEQUENCE: 581<br>000 | moltype = | length = |
| SEQ ID NO: 582<br>SEQUENCE: 582<br>000 | moltype = | length = |
| SEQ ID NO: 583<br>SEQUENCE: 583<br>000 | moltype = | length = |
| SEQ ID NO: 584<br>SEQUENCE: 584<br>000 | moltype = | length = |
| SEQ ID NO: 585<br>SEQUENCE: 585<br>000 | moltype = | length = |
| SEQ ID NO: 586<br>SEQUENCE: 586<br>000 | moltype = | length = |
| SEQ ID NO: 587<br>SEQUENCE: 587<br>000 | moltype = | length = |
| SEQ ID NO: 588<br>SEQUENCE: 588<br>000 | moltype = | length = |
| SEQ ID NO: 589<br>SEQUENCE: 589<br>000 | moltype = | length = |
| SEQ ID NO: 590<br>SEQUENCE: 590<br>000 | moltype = | length = |
| SEQ ID NO: 591<br>SEQUENCE: 591<br>000 | moltype = | length = |
| SEQ ID NO: 592<br>SEQUENCE: 592<br>000 | moltype = | length = |
| SEQ ID NO: 593<br>SEQUENCE: 593<br>000 | moltype = | length = |
| SEQ ID NO: 594<br>SEQUENCE: 594<br>000 | moltype = | length = |
| SEQ ID NO: 595<br>SEQUENCE: 595<br>000 | moltype = | length = |
| SEQ ID NO: 596<br>SEQUENCE: 596<br>000 | moltype = | length = |

```
SEQ ID NO: 597           moltype =    length =
SEQUENCE: 597
000

SEQ ID NO: 598           moltype =    length =
SEQUENCE: 598
000

SEQ ID NO: 599           moltype =    length =
SEQUENCE: 599
000

SEQ ID NO: 600           moltype =    length =
SEQUENCE: 600
000

SEQ ID NO: 601           moltype = AA   length = 7
FEATURE                  Location/Qualifiers
REGION                   1..7
                         note = source = /note="Description of Artificial Sequence:
                          Synthetic peptide"
source                   1..7
                         mol_type = protein
                         organism = synthetic construct
SEQUENCE: 601
GSGGGGS                                                                   7

SEQ ID NO: 602           moltype = AA   length = 15
FEATURE                  Location/Qualifiers
REGION                   1..15
                         note = source = /note="Description of Artificial Sequence:
                          Synthetic peptide"
source                   1..15
                         mol_type = protein
                         organism = synthetic construct
SEQUENCE: 602
GGGGSGGGGS GGGGS                                                          15

SEQ ID NO: 603           moltype = AA   length = 18
FEATURE                  Location/Qualifiers
REGION                   1..18
                         note = source = /note="Description of Artificial Sequence:
                          Synthetic peptide"
source                   1..18
                         mol_type = protein
                         organism = synthetic construct
SEQUENCE: 603
GGSGGSGGSG GSGGSGGS                                                       18

SEQ ID NO: 604           moltype = AA   length = 32
FEATURE                  Location/Qualifiers
REGION                   1..32
                         note = source = /note="Description of Artificial Sequence:
                          Synthetic polypeptide"
source                   1..32
                         mol_type = protein
                         organism = synthetic construct
SEQUENCE: 604
SGGSSGGSSG SETPGTSESA TPESSGGSSG GS                                       32

SEQ ID NO: 605           moltype = AA   length = 167
FEATURE                  Location/Qualifiers
REGION                   1..167
                         note = source = /note="Description of Artificial Sequence:
                          Synthetic polypeptide"
source                   1..167
                         mol_type = protein
                         organism = synthetic construct
SEQUENCE: 605
MSEVEFSHEY WMRHALTLAK RAWDEREVPV GAVLVHNNRV IGEGWNRPIG RHDPTAHAEI         60
MALRQGGLVM QNYRLIDATL YVTLEPCVMC AGAMIHSRIG RVVFGARDAK TGAAGSLMDV         120
LHHPGMNHRV EITEGILADE CAALLSDFFR MRRQEIKAQK KAQSSTD                      167

SEQ ID NO: 606           moltype = AA   length = 167
FEATURE                  Location/Qualifiers
REGION                   1..167
                         note = source = /note="Description of Artificial Sequence:
                          Synthetic polypeptide"
```

```
                              -continued source                  1..167
                        mol_type = protein
                        organism = synthetic construct
SEQUENCE: 606
MSEVEFSHEY WMRHALTLAK RAWDEREVPV GAVLVHNNRV IGEGWNRPIG RHDPTAHAEI   60
MALRQGGLVM QNYRLIDATL YVTLEPCVMC AGAMIHSRIG RVVFGARDAK TGAAGSLMDV  120
LHHPGMNHRV EITEGILADE CAALLSDFFR MRRQEIKAQK KAQSSTD               167

SEQ ID NO: 607          moltype = AA  length = 198
FEATURE                 Location/Qualifiers
REGION                  1..198
                        note = source = /note="Description of Artificial Sequence:
                         Synthetic polypeptide"
source                  1..198
                        mol_type = protein
                        organism = synthetic construct
SEQUENCE: 607
MDSLLMNRRK FLYQFKNVRW AKGRRETYLC YVVKRRDSAT SFSLDFGYLR NKNGCHVELL   60
FLRYISDWDL DPGRCYRVTW FTSWSPCYDC ARHVADFLRG NPNLSLRIFT ARLYFCEDRK  120
AEPEGLRRLH RAGVQIAIMT FKDYFYCWNT FVENHERTFK AWEGLHENSV RLSRQLRRIL  180
LPLYEVDDLR DAFRTLGL                                               198

SEQ ID NO: 608          moltype = AA  length = 208
FEATURE                 Location/Qualifiers
REGION                  1..208
                        note = source = /note="Description of Artificial Sequence:
                         Synthetic polypeptide"
source                  1..208
                        mol_type = protein
                        organism = synthetic construct
SEQUENCE: 608
MTDAEYVRIH EKLDIYTFKK QFFNNKKSVS HRCYVLFELK RRGERRACFW GYAVNKPQSG   60
TERGIHAEIF SIRKVEEYLR DNPGQFTINW YSSWSPCADC AEKILEWYNQ ELRGNGHTLK  120
IWACKLYYEK NARNQIGLWN LRDNGVGLNV MVSEHYQCCR KIFIQSSHNQ LNENRWLEKT  180
LKRAEKRRSE LSIMIQVKIL HTTKSPAV                                    208

SEQ ID NO: 609          moltype = AA  length = 229
FEATURE                 Location/Qualifiers
REGION                  1..229
                        note = source = /note="Description of Artificial Sequence:
                         Synthetic polypeptide"
source                  1..229
                        mol_type = protein
                        organism = synthetic construct
SEQUENCE: 609
MSSETGPVAV DPTLRRRIEP HEFEVFFDPR ELRKETCLLY EINWGGRHSI WRHTSQNTNK   60
HVEVNFIEKF TTERYFCPNT RCSITWFLSW SPCGECSRAI TEFLSRYPHV TLFIYIARLY  120
HHADPRNRQG LRDLISSGVT IQIMTEQESG YCWRNFVNYS PSNEAHWPRY PHLWVRLYVL  180
ELYCIILGLP PCLNILRRKQ PQLTFFTIAL QSCHYQRLPP HILWATGLK             229

SEQ ID NO: 610          moltype = AA  length = 4
FEATURE                 Location/Qualifiers
REGION                  1..4
                        note = source = /note="Description of Unknown: KDEL motif
                         sequence"
source                  1..4
                        mol_type = protein
                        organism = unidentified
SEQUENCE: 610
KDEL                                                                4

SEQ ID NO: 611          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 611
EAAAK                                                               5

SEQ ID NO: 612          moltype = DNA  length = 44
FEATURE                 Location/Qualifiers
misc_difference         24..44
                        note = a, c, t, g, unknown or other
misc_feature            1..44
                        note = source = /note="Description of Artificial Sequence:
                         Synthetic oligonucleotide"
```

```
source                    1..44
                          mol_type = other DNA
                          organism = synthetic construct
SEQUENCE: 612
attttttgtgc ccatcgttgg cacnnnnnnnn nnnnnnnnnn nnnn                              44

SEQ ID NO: 613            moltype = RNA   length = 44
FEATURE                   Location/Qualifiers
misc_difference           24..44
                          note = a, c, u, g, unknown or other
misc_feature              1..44
                          note = source = /note="Description of Artificial Sequence:
                          Synthetic oligonucleotide"
source                    1..44
                          mol_type = other RNA
                          organism = synthetic construct
SEQUENCE: 613
agaaatccgt ctttcattga cggnnnnnnnn nnnnnnnnnn nnnn                               44

SEQ ID NO: 614            moltype = DNA   length = 36
FEATURE                   Location/Qualifiers
misc_feature              1..36
                          note = source = /note="Description of Artificial Sequence:
                          Synthetic oligonucleotide"
source                    1..36
                          mol_type = other DNA
                          organism = synthetic construct
SEQUENCE: 614
ttcgcgtgct ggattgcttc gatggtctgc ggcatc                                        36

SEQ ID NO: 615            moltype = DNA   length = 36
FEATURE                   Location/Qualifiers
misc_feature              1..36
                          note = source = /note="Description of Artificial Sequence:
                          Synthetic oligonucleotide"
source                    1..36
                          mol_type = other DNA
                          organism = synthetic construct
SEQUENCE: 615
gatgccgcag accatcgaag caatccagca cgcgaa                                        36

SEQ ID NO: 616            moltype = RNA   length = 28
FEATURE                   Location/Qualifiers
misc_feature              1..28
                          note = source = /note="Description of Artificial Sequence:
                          Synthetic oligonucleotide"
source                    1..28
                          mol_type = other RNA
                          organism = synthetic construct
SEQUENCE: 616
gcgtgctgga ttgcttcgat ggtctgcg                                                 28

SEQ ID NO: 617            moltype = RNA   length = 34
FEATURE                   Location/Qualifiers
misc_feature              1..34
                          note = source = /note="Description of Artificial Sequence:
                          Synthetic oligonucleotide"
source                    1..34
                          mol_type = other RNA
                          organism = synthetic construct
SEQUENCE: 617
gcaacaccta agaaatccgt ctttcattga cggg                                          34

SEQ ID NO: 618            moltype = RNA   length = 36
FEATURE                   Location/Qualifiers
misc_feature              1..36
                          note = source = /note="Description of Artificial Sequence:
                          Synthetic oligonucleotide"
source                    1..36
                          mol_type = other RNA
                          organism = synthetic construct
SEQUENCE: 618
gttgcaaaac ccaagaaatc cgtctttcat tgacgg                                        36

SEQ ID NO: 619            moltype = RNA   length = 24
FEATURE                   Location/Qualifiers
misc_feature              1..24
                          note = source = /note="Description of Artificial Sequence:
                          Synthetic oligonucleotide"
```

```
source            1..24
                  mol_type = other RNA
                  organism = synthetic construct
SEQUENCE: 619
aatttttgtg cccatcgttg gcac                                          24

SEQ ID NO: 620    moltype = RNA  length = 36
FEATURE           Location/Qualifiers
misc_feature      1..36
                  note = source = /note="Description of Artificial Sequence:
                  Synthetic oligonucleotide"
source            1..36
                  mol_type = other RNA
                  organism = synthetic construct
SEQUENCE: 620
ctctcaatgc cttagaaatc cgtccttggt tgacgg                             36

SEQ ID NO: 621    moltype = RNA  length = 36
FEATURE           Location/Qualifiers
misc_feature      1..36
                  note = source = /note="Description of Artificial Sequence:
                  Synthetic oligonucleotide"
source            1..36
                  mol_type = other RNA
                  organism = synthetic construct
SEQUENCE: 621
cccacaatac ctgagaaatc cgtcctacgt tgacgg                             36
```

CRISPR DNA TARGETING ENZYMES AND SYSTEMS

CROSS REFERENCE TO RELATED APPLICATIONS

This application is a continuation of U.S. application Ser. No. 17/497,725, filed Oct. 8, 2021 which is a continuation of U.S. application Ser. No. 17/139,678, filed Dec. 31, 2020, which is a continuation of U.S. application Ser. No. 17/020, 215, filed Sep. 14, 2020, which is a continuation of U.S. application Ser. No. 16/680,104, filed Nov. 11, 2019, which is a continuation of International Application No. PCT/US2019/022375, filed Mar. 14, 2019, which claims the benefit of priority of U.S. Application No. 62/642,919, filed Mar. 14, 2018; U.S. Application No. 62/666,397, filed May 3, 2018; U.S. Application No. 62/672,489, filed May 16, 2018; U.S. Application No. 62/679,628, filed Jun. 1, 2018; U.S. Application No. 62/703,857, filed Jul. 26, 2018; U.S. Application No. 62/740,856, filed Oct. 3, 2018; U.S. Application No. 62/746,528, filed Oct. 16, 2018; U.S. Application No. 62/772,038, filed Nov. 27, 2018; and U.S. Application No. 62/775,885, filed Dec. 5, 2018. The content of each of the foregoing applications is hereby incorporated by reference in its entirety.

SEQUENCE LISTING

The instant application contains a Sequence Listing which has been submitted electronically in XML format and is hereby incorporated by reference in its entirety. Said XML copy, created on Mar. 2, 2023, is named A2186-701124FT_SL.xml and is 285,599 bytes in size.

FIELD OF THE INVENTION

The present disclosure relates to systems, methods, and compositions used for the control of gene expression involving sequence targeting and nucleic acid editing, which uses vector systems related to Clustered Regularly Interspaced Short Palindromic Repeats (CRISPR) and components thereof.

BACKGROUND

Recent application of advances in genome sequencing technologies and analysis have yielded significant insights into the genetic underpinning of biological activities in many diverse areas of nature, ranging from prokaryotic biosynthetic pathways to human pathologies. To fully understand and evaluate the vast quantities of information produced by genetic sequencing technologies, equivalent increases in the scale, efficacy, and ease of technologies for genome and epigenome manipulation are needed. These novel genome and epigenome engineering technologies will accelerate the development of novel applications in numerous areas, including biotechnology, agriculture, and human therapeutics.

Clustered Regularly Interspaced Short Palindromic Repeats (CRISPR) and the CRISPR-associated (Cas) genes, collectively known as the CRISPR-Cas or CRISPR/Cas systems, are currently understood to provide immunity to bacteria and archaea against phage infection. The CRISPR-Cas systems of prokaryotic adaptive immunity are an extremely diverse group of proteins effectors, non-coding elements, as well as loci architectures, some examples of which have been engineered and adapted to produce important biotechnologies.

The components of the system involved in host defense include one or more effector proteins capable of modifying DNA or RNA and an RNA guide element that is responsible to targeting these protein activities to a specific sequence on the phage DNA or RNA. The RNA guide is composed of a CRISPR RNA (crRNA) and may require an additional trans-activating RNA (tracrRNA) to enable targeted nucleic acid manipulation by the effector protein(s). The crRNA consists of a direct repeat responsible for protein binding to the crRNA and a spacer sequence that is complementary to the desired nucleic acid target sequence. CRISPR systems can be reprogrammed to target alternative DNA or RNA targets by modifying the spacer sequence of the crRNA.

CRISPR-Cas systems can be broadly classified into two classes: Class 1 systems are composed of multiple effector proteins that together form a complex around a crRNA, and Class 2 systems consist of a single effector protein that complexes with the RNA guide to target DNA or RNA substrates. The single-subunit effector composition of the Class 2 systems provides a simpler component set for engineering and application translation, and have thus far been an important source of programmable effectors. Thus, the discovery, engineering, and optimization of novel Class 2 systems may lead to widespread and powerful programmable technologies for genome engineering and beyond.

CRISPR-Cas systems are adaptive immune systems in archaea and bacteria that defend the species against foreign genetic elements. The characterization and engineering of Class 2 CRISPR-Cas systems, exemplified by CRISPR-Cas9, have paved the way for a diverse array of biotechnology applications in genome editing and beyond. Nevertheless, there remains a need for additional programmable effectors and systems for modifying nucleic acids and polynucleotides (i.e., DNA, RNA, or any hybrid, derivative, or modification) beyond the current CRISPR-Cas systems that enable novel applications through their unique properties.

Citation or identification of any document in this application is not an admission that such document is available as prior art to the present invention.

SUMMARY

This disclosure provides non-naturally-occurring, engineered systems and compositions for new single-effector Class 2 CRISPR-Cas systems, together with methods for computational identification from genomic databases, development of the natural loci into an engineered system, and experimental validation and application translation. These new effectors are divergent in sequence to orthologs and homologs of existing Class 2 CRISPR effectors, and also have unique domain organizations. They provide additional features that include, but are not limited to, 1) novel DNA/RNA editing properties and control mechanisms, 2) smaller size for greater versatility in delivery strategies, 3) genotype triggered cellular processes such as cell death, and 4) programmable RNA-guided DNA insertion, excision, and mobilization. Adding the novel DNA-targeting systems described herein to the toolbox of techniques for genome and epigenome manipulation enables broad applications for specific, programmed perturbations.

In general, this disclosure relates to new CRISPR-Cas systems including newly discovered enzymes and other components used to create minimal systems that can be used in non-natural environments, e.g., in bacteria other than those in which the system was initially discovered.

In one aspect, the disclosure provides engineered, non-naturally occurring CRISPR-Cas systems that include: i) one or more Type V-I (CLUST.029130) RNA guides or one or more nucleic acids encoding the one or more Type V-I RNA guides, wherein a Type V-I RNA guide includes or consists of a direct repeat sequence and a spacer sequence capable of hybridizing to a target nucleic acid; and ii) a Type V-I (CLUST.029130) CRISPR-Cas effector protein or a nucleic acid encoding the Type V-I CRISPR-Cas effector protein, wherein the Type V-I CRISPR-Cas effector protein is capable of binding to a Type V-I RNA guide and of targeting the target nucleic acid sequence complementary to the spacer sequence, wherein the target nucleic acid is a DNA. As used herein, the Type V-I (CLUST.029130) CRISPR-Cas effector proteins are also referred to as Cas12i effector proteins, and these two terms are used interchangeably in this disclosure.

In some embodiments of any of the systems described herein, the Type V-I CRISPR-Cas effector protein is about 1100 amino acids or less in length (excluding any amino acid signal sequence or peptide tag fused thereto) and includes at least one RuvC domain. In some embodiments, none, one, or more of the RuvC domains are catalytically inactivated. In some embodiments, the Type V-I CRISPR-Cas effector protein includes or consists of the amino acid sequence $X_1SHX_4DX_6X_7$ (SEQ ID NO: 200), wherein $X_1$ is S or T, $X_4$ is Q or L, $X_6$ is P or S, and $X_7$ is F or L.

In some embodiments, the Type V-I CRISPR-Cas effector protein includes or consists of the amino acid sequence $X_1XDXNX_6X_7XXXX_{11}$ (SEQ ID NO: 201), wherein $X_1$ is A or G or S, X is any amino acid, $X_6$ is Q or I, $X_7$ is T or S or V, and $X_{10}$ is T or A. In some embodiments, the Type V-I CRISPR-Cas effector protein includes or consists of the amino acid sequence X1X2X3E (SEQ ID NO: 210), wherein X1 is C or F or I or L or M or P or V or W or Y, X2 C or F or I or L or M or P or R or V or W or Y, and X3 C or F or G or I or L or M or P or V or W or Y.

In some embodiments, the Type V-I CRISPR-Cas effector protein includes more than one sequence from the set SEQ ID NO: 200, SEQ ID NO: 201, and SEQ ID NO: 210. In some embodiments, the Type V-I CRISPR-Cas effector protein includes or consists of an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence provided in Table 4 (e.g., SEQ ID NOs: 1-5, and 11-18).

In some embodiments of any of the systems described herein, the Type V-I CRISPR-Cas effector protein includes or consists of an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of Cas12i1 (SEQ ID NO: 3) or Cas12i2 (SEQ ID NO: 5). In some embodiments, the Type V-I CRISPR-Cas effector protein is Cas12i1 (SEQ ID NO: 3) or Cas12i2 (SEQ ID NO: 5).

In some embodiments, the Type V-I CRISPR-Cas effector protein is capable of recognizing a protospacer adjacent motif (PAM), and the target nucleic acid includes or consists of a PAM including or consisting of the nucleic acid sequence 5'-TTN-3' or 5'-TTH-3' or 5'-TTY-3' or 5'-TTC-3'.

In some embodiments of any of the systems described herein, the Type V-I CRISPR-Cas effector protein includes one or more amino acid substitutions within at least one of the RuvC domains. In some embodiments, the one or more amino acid substitutions include a substitution, e.g., an alanine substitution, at an amino residue corresponding to D647 or E894 or D948 of SEQ ID NO: 3. In some embodiments, the one or more amino acid substitutions include an alanine substitution at an amino residue corresponding to D599 or E833 or D886 of SEQ ID NO: 5. In some embodiments, the one or more amino acid substitutions result in a reduction of the nuclease activity of the Type V-I CRISPR-Cas effector protein as compared to the nuclease activity of the Type V-I CRISPR-Cas effector protein without the one or more amino acid substitutions.

In some embodiments of any of the systems described herein, the Type V-I RNA guide includes a direct repeat sequence that includes a stem-loop structure proximal to the 3' end (immediately adjacent to the spacer sequence). In some embodiments, the Type V-I RNA guide direct repeat includes a stem loop proximal to the 3' end where the stem is 5 nucleotides in length. In some embodiments, the Type V-I RNA guide direct repeat includes a stem loop proximal to the 3' end where the stem is 5 nucleotides in length and the loop is 7 nucleotides in length. In some embodiments, the Type V-I RNA guide direct repeat includes a stem loop proximal to the 3' end where the stem is 5 nucleotides in length and the loop is 6, 7, or 8 nucleotides in length.

In some embodiments, the Type V-I RNA guide direct repeat includes the sequence 5'-CCGUCNNNNN-NUGACGG-3' (SEQ ID NO: 202) proximal to the 3' end, wherein N refers to any nucleobase. In some embodiments, the Type V-I RNA guide direct repeat includes the sequence 5'-GUGCCNNNNNNUGGCAC-3' (SEQ ID NO: 203) proximal to the 3' end, wherein N refers to any nucleobase.

In some embodiments, the Type V-I RNA guide direct repeat includes the sequence 5'-GUGUCN$_{5-6}$UGACAX$_1$-3' (SEQ ID NO: 204) proximal to the 3' end, wherein N5-6 refers to a contiguous sequence of any 5 or 6 nucleobases, and $X_1$ refers to C or T or U. In some embodiments, the Type V-I RNA guide direct repeat includes the sequence 5'-UCX$_3$UX$_5$X$_6$X$_7$UUGACGG-3' (SEQ ID NO: 205) proximal to the 3' end, wherein $X_3$ refers to C or T or U, $X_5$ refers to A or T or U, $X_6$ refers to A or C or G, and $X_7$ refers to A or G. In some embodiments, the Type V-I RNA guide direct repeat includes the sequence 5'-CCX$_3$X$_4$X$_5$CX$_7$UUGGCAC-3' (SEQ ID NO: 206) proximal to the 3' end, wherein $X_3$ refers to C or T or U, $X_4$ refers to A or T or U, $X_5$ refers to C or T or U, and $X_7$ refers to A or G.

In some embodiments, the Type V-I RNA guide includes a direct repeat sequence including or consisting of a nucleotide sequence that is at least 80% identical, e.g., 85%, 90%, 91%, 92%, 93%, 94%, 95%, 96%, 97%, 98%, 99%, or 100% identical, to a nucleotide sequence provided in Table 5A (e.g., SEQ ID NOs: 6-19, and 19-24).

In some embodiments, the Type V-I RNA guide includes or consists of a nucleotide sequence or subsequence thereof provided in Table 5B (e.g., SEQ ID Nos: 150-163). In some embodiments, the Type V-I RNA guide includes or consists of a nucleotide sequence constructed by the concatenation of a direct repeat, spacer, direct repeat sequence wherein the direct repeat sequence is provided in Table 5A and the length of the spacer is provided in the Spacer Lens 1 column in Table 5B. In some embodiments, the Type V-I RNA guide includes or consists of a nucleotide sequence constructed by the concatenation of a direct repeat, spacer, direct repeat sequence wherein the direct repeat sequence is provided in Table 5A and the length of the spacer is provided in the Spacer Lens 2 column in Table 5B. In some embodiments, the Type V-I RNA guide includes or consists of a nucleotide sequence constructed by the concatenation of a direct repeat, spacer, direct repeat sequence wherein the direct repeat sequence is provided in Table 5A and the length of the spacer is provided in the Spacer Lens 3 column in Table 5B.

In some embodiments of any of the systems described herein, the spacer sequence of the Type V-I RNA guide includes or consists of between about 15 to about 34 nucleotides (e.g., 16, 17, 18, 19, 20, 21, or 22 nucleotides). In some embodiments of any of the systems described herein, the spacer is between 17 nucleotides and 31 nucleotides in length.

In some embodiments of any of the systems provided herein, the target nucleic acid is a DNA. In some embodiments of any of the systems described herein, the target nucleic acid includes a protospacer adjacent motif (PAM), e.g., a PAM including or consisting of the nucleic acid sequence 5'-TTN-3' or 5'-TTH-3' or 5'-TTY-3' or 5'-TTC-3'.

In certain embodiments of any of the systems provided herein, the targeting of the target nucleic acid by the Type V-I CRISPR-Cas effector protein and RNA guide results in a modification (e.g., a single-stranded or a double-stranded cleavage event) in the target nucleic acid. In some embodiments, the modification is a deletion event. In some embodiments, the modification is an insertion event. In some embodiments, the modification results in cell toxicity and/or cell death.

In some embodiments, the Type V-I CRISPR-Cas effector protein has non-specific (i.e., "collateral") nuclease (e.g., DNase) activity. In certain embodiments of any of the systems provided herein, the system further includes a donor template nucleic acid (e.g., a DNA or a RNA).

In some embodiments of any of the systems provided herein, the system is within a cell (e.g., a eukaryotic cell (e.g., a mammalian cell) or a prokaryotic cell (e.g., a bacterial cell)).

In another aspect, the disclosure provides methods of targeting and editing a target nucleic acid, wherein the methods include contacting the target nucleic acid with any of the systems described herein. These can be carried out ex vivo or in vitro methods. In some embodiments, the methods described herein do not modify the germ line genetic identity of a human being.

In other aspects, the disclosure provides methods of targeting the insertion of a payload nucleic acid at a site of a target nucleic acid, wherein the methods include contacting the target nucleic acid with any of the systems described herein.

In yet another aspect, the disclosure provides methods of targeting the excision of a payload nucleic acid from a site at a target nucleic acid, wherein the methods include contacting the target nucleic acid with any of the systems described herein.

In another aspect, the disclosure provides methods of targeting and nicking a non-target strand (non-spacer complementary strand) of a double-stranded target DNA upon recognition of a target strand (spacer complementary strand) of the double-stranded target DNA. The method includes contacting the double-stranded target DNA with any of the systems described herein.

In yet another aspect, the disclosure provides methods of targeting and cleaving a double-stranded target DNA, the method including contacting the double-stranded target DNA with any of the systems described herein.

In some embodiments of the methods of targeting and cleaving a double-stranded target DNA, a non-target strand (non-spacer complementary strand) of the double-stranded target DNA is nicked before a target strand (spacer complementary strand) of the double-stranded target nucleic acid is nicked.

In yet another aspect, the disclosure provides methods of specifically editing a double-stranded nucleic acid, the methods including: contacting (a) a Type V-I effector protein and one other enzyme with sequence-specific nicking activity; (b) a Type V-I RNA guide that guides the Type V-I effector protein to nick the opposing strand relative to the activity of the other sequence-specific nickase; and (c) the double-stranded nucleic acid, wherein the method results in reduced likelihood of off-target modification.

In some embodiments, the Type V-I effector protein further includes a linker sequence. In some embodiments, the Type V-I effector protein includes one or more mutations or amino acid substitutions that render the CRISPR-associated protein unable to cleave DNA.

In yet another aspect, the disclosure provides methods of base editing a double-stranded nucleic acid, the method including: contacting (a) a fusion protein comprising a Type V-I effector protein and a protein domain with DNA modifying activity (e.g., cytidine deamination); (b) a Type V-I RNA guide targeting the double-stranded nucleic acid, and (c) the double-stranded nucleic acid. The Type V-I effector of the fusion protein can be modified to nick non-target strand of the double-stranded nucleic acid. In some embodiments, the Type V-I effector of the fusion protein can be modified to be nuclease deficient. zzz In another aspect, the disclosure provides methods of modifying a DNA molecule, the methods including contacting the DNA molecule with a system described herein.

In some embodiments of any of the methods described herein (and compositions for use in such methods), the cell is a eukaryotic cell. In some embodiments, the cell is an animal cell. In some embodiments, the cell is a cancer cell (e.g., a tumor cell). In some embodiments, the cell is an infectious agent cell or a cell infected with an infectious agent. In some embodiments, the cell is a bacterial cell, a cell infected with a virus, a cell infected with a prion, a fungal cell, a protozoan, or a parasite cell.

In another aspect, the disclosure provides methods of treating a condition or disease in a subject in need thereof and compositions for use in such methods. The methods include administering to the subject a system described herein, wherein the spacer sequence is complementary to at least 15 nucleotides of a target nucleic acid associated with the condition or disease, wherein the Type V-I CRISPR-Cas effector protein associates with the RNA guide to form a complex, wherein the complex binds to a target nucleic acid sequence that is complementary to the at least 15 nucleotides of the spacer sequence, and wherein upon binding of the complex to the target nucleic acid sequence the Type V-I CRISPR-Cas effector protein cleaves or silences the target nucleic acid, thereby treating the condition or disease in the subject.

In some embodiments of the methods described herein (and compositions for use in such methods), the condition or disease is a cancer or an infectious disease. In some embodiments, the condition or disease is cancer, wherein the cancer is selected from the group consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

In some embodiments, the Type V-I effector protein includes or consists of at least one (e.g., two, three, four, five, six, or more) nuclear localization signal (NLS). In some embodiments, the Type V-I effector protein includes or consists of at least one (e.g., two, three, four, five, six, or more) nuclear export signal (NES). In some embodiments, the Type V-I effector protein includes at least one (e.g., two, three, four, five, six, or more) NLS and at least one (e.g., two, three, four, five, six, or more) NES.

In some embodiments, the systems described herein include a nucleic acid encoding one or more RNA guides. In some embodiments, the nucleic acid encoding the one or more RNA guides is operably linked to a promoter (e.g., a constitutive promoter or an inducible promoter).

In some embodiments, the systems described herein include a nucleic acid encoding a target nucleic acid (e.g., a target DNA). In some embodiments, the nucleic acid encoding the target nucleic acid is operably linked to a promoter (e.g., a constitutive promoter or an inducible promoter).

In some embodiments, the systems described herein include a nucleic acid encoding a Type V-I CRISPR-Cas effector protein in a vector. In some embodiments, the system further includes one or more nucleic acids encoding an RNA guide present in the vector.

In some embodiments, the vectors included in the systems are viral vectors (e.g., retroviral vectors, lentiviral vectors, adenoviral vectors, adeno-associated vectors, and herpes simplex vectors. In some embodiments, the vectors included in the system are phage vectors.

In some embodiments, the systems provided herein are in a delivery system. In some embodiments, the delivery system is a nanoparticle, a liposome, an exosome, a microvesicle, and a gene-gun.

The disclosure also provides a cell (e.g., a eukaryotic cell or a prokaryotic cell (e.g., a bacterial cell)) comprising a system described herein. In some embodiments, the eukaryotic cell is a mammalian cell (e.g., a human cell) or a plant cell. The disclosure also provides animal models (e.g., rodent, rabbit, dog, monkey, or ape models) and plant model that include the cells. In some embodiments, the methods are used to treat a subject, e.g., a mammal, such as a human patient. The mammalian subject can also be a domesticated mammal, such as a dog, cat, horse, monkey, rabbit, rat, mouse, cow, goat, or sheep In yet another aspect, the disclosure provides methods of detecting a target nucleic acid (e.g., DNA or RNA) in a sample, the methods including: (a) contacting the sample with a system provided herein and a labeled reporter nucleic acid, wherein hybridization of the crRNA to the target nucleic acid causes cleavage of the labeled reporter nucleic acid; and (b) measuring a detectable signal produced by cleavage of the labeled reporter nucleic acid, thereby detecting the presence of the target nucleic acid in the sample.

In some embodiments, the methods of detecting a target nucleic acid can also include comparing a level of the detectable signal with a reference signal level, and determining an amount of target nucleic acid in the sample based on the level of the detectable signal.

In some embodiments, the measuring is performed using gold nanoparticle detection, fluorescence polarization, colloid phase transition/dispersion, electrochemical detection, or semiconductor based-sensing.

In some embodiments, the labeled reporter nucleic acid can include a fluorescence-emitting dye pair, a fluorescence resonance energy transfer (FRET) pair, or a quencher/fluorophore pair, wherein cleavage of the labeled reporter nucleic acid by the effector protein results in an increase or a decrease of the amount of signal produced by the labeled reporter nucleic acid.

Turning to another aspect, the disclosure includes methods of modifying a target DNA, which include contacting the target DNA with a complex comprising a Cas12i effector protein and an engineered Type V-I RNA guide, which is designed to hybridize with (e.g., is at least 70%, 75%, 80%, 85%, 90%, 95%, 96%, 97%, 98%, 99%, or 100% complementary to) a target sequence of the target DNA, and the system is distinguished by (a) the lack of a tracrRNA in the system, and (b) the Cas12i effector protein and Type V-I RNA guide form a complex that associates with the target DNA, thereby modifying the target DNA.

In certain embodiments, modifying the target DNA includes cleaving at least one strand of the target DNA (e.g., creating a single-strand break or "nick," or creating a double strand break). Alternatively, or additionally, modification of the target DNA includes either (i) binding to the target DNA, thereby preventing the target DNA from associating with another biomolecule or complex, or (ii) unwinding a portion of the target DNA. In some instances, the target DNA includes a protospacer adjacent motif (PAM) sequence that is recognized by the Cas12i effector protein, such as 5'-TTN-3' or 5'-TTH-3' or 5'-TTY-3' or 5'-TTC-3'. The Cas12 effector protein is, in certain embodiments, a Cas12i1 effector protein or a Cas12i2 effector protein.

Continuing with this aspect of the disclosure, in certain embodiments the contacting of the target DNA with the complex occurs in a cell, for instance by (a) contacting the cell with the complex, which complex is formed in vitro, or (b) contacting the cell with one or more nucleic acids encoding the Cas12i effector protein and the Type V-I RNA guide, which are then expressed by the cell and which form the complex within the cell. In some cases, the cell is a prokaryotic cell; in other cases, it is a eukaryotic cell.

In another aspect, this disclosure relates to methods of altering a target DNA, including contacting the target DNA within the cell with a genome editing system including a Cas12i protein and a Type V-I RNA guide (e.g., a crRNA, guide RNA or like structure, optionally comprising one or more nucleotide, nucleobase or backbone modifications) comprising a 15-24 nucleotide spacer sequence having at least 70%, 75%, 80%, 85%, 90%, 91%, 92%, 93%, 94%, 95%, 96%, 97%, 98%, 99%, or 100% complementarity to a sequence in the target DNA, but which system does not comprise a tracrRNA. In various embodiments, the Cas12i protein includes or consists of an amino acid sequence having at least 95%, e.g., 96%, 97%, 98%, 99%, or 100%, sequence identity to SEQ ID NO: 3 and the Type V-I RNA guide comprises a direct repeat sequence with at least 95%, e.g., 96%, 97%, 98%, 99%, or 100%, sequence identity to one of SEQ ID NOS: 7 or 24; or the Cas12i protein includes or consists of an amino acid sequence having at least 95%, e.g., 96%, 97%, 98%, 99%, or 100%, sequence identity to SEQ ID NO: 5 and the Type V-I RNA guide comprises a direct repeat sequence with at least 95% e.g., 96%, 97%, 98%, 99%, or 100%, sequence identity to one of SEQ ID NOS: 9 or 10. The target DNA is optionally a cellular DNA, and the contacting optionally occurs within a cell such as a prokaryotic cell or a eukaryotic cell (e.g., a mammalian cell, a plant cell, or a human cell).

In some embodiments, the Type V-I CRISPR-Cas effector protein comprises an amino acid sequence having at least 90%, or at least 95%, sequence identity to one of SEQ ID NOs: 1-5 or 11-18. According to certain embodiments, the Type V-I CRISPR-Cas effector protein comprises an amino acid sequence given by SEQ ID NO: 3, or an amino acid sequence given by SEQ ID NO: 5. The total length of the CRISPR-Cas effector protein according to certain embodiments is less than 1100 amino acids, excluding any amino acid signal sequence or peptide tag fused thereto. In some cases, the CRISPR-Cas effector protein comprises an amino acid substitution, for instance a substitution at an amino acid residue corresponding to D647, E894, or D948 of SEQ ID NO: 3 or a substitution at an amino acid residue corresponding to D599, E833, or D886 of SEQ ID NO: 5. The substitution is optionally an alanine.

In yet another aspect, this disclosure relates to an engineered, non-naturally occurring CRISPR-Cas systems, including or consisting of a Cas12i effector protein, and an engineered Type V-I RNA guide (e.g., a crRNA, guide RNA or like structure, optionally including one or more nucleotide, nucleobase or backbone modifications) having a 15-34 nucleotide spacer sequence that is at least 80%, e.g., 85%, 90%, 91%, 92%, 93%, 94%, 95%, 96%, 97%, 98%, 99%, or 100%, complementary to a target sequence. The systems do not include a tracrRNA, and the Cas12i effector protein and the Type V-I RNA guide form a complex that associates with the target sequence. In some instances, the complex of the Cas12i effector protein and Type V-I RNA guide causes cleavage of at least one strand of a DNA comprising the target sequence. The target sequence can include a protospacer adjacent motif (PAM) sequence recognized by the Cas12i effector protein, which PAM sequence is optionally 5'-TTN-3', 5'-TTY-3' or 5'-TTH-3' or 5'-TTC-3'. The Type V-I RNA guide can include a direct repeat sequence having at least 95%, e.g., 96%, 97%, 98%, 99%, or 100%, sequence identity to one of SEQ ID NOS: 7, 9, 10, 24, 100, or 101.

In certain embodiments, the Cas12i effector protein comprises an amino acid sequence having at least 95% sequence identity to SEQ ID NO: 3 and the direct repeat sequence has at least 95% sequence identity to SEQ ID NO: 100, or the Cas12i effector protein comprises an amino acid sequence having at least 95% sequence identity to SEQ ID NO: 5 and the direct repeat sequence has at least 95% sequence identity to SEQ ID NO: 101. Alternatively, or additionally, the Cas12i effector protein comprises an amino acid substitution (optionally, an alanine substitution) selected from the group consisting of (a) a substitution at an amino acid residue corresponding to D647, E894, or D948 of SEQ ID NO: 3; and (b) a substitution at an amino acid residue corresponding to D599, E833, or D886 of SEQ ID NO: 5.

In still another aspect, this disclosure relates to a composition comprising one or more nucleic acids encoding a CRISPR-Cas system (or a genome editing system) according to one of the aspects of the disclosure. And in another aspect, the disclosure relates to a viral vector encoding a CRISPR-Cas system (or a genome editing system) according to one of the aspects of the disclosure.

The disclosure also includes methods of targeting and nicking a non-spacer complementary strand of a double-stranded target DNA upon recognition of a spacer complementary strand of the double-stranded target DNA, the method comprising contacting the double-stranded target DNA with any of the systems described herein.

In another aspect, the disclosure includes methods of targeting and cleaving a double-stranded target DNA, the method comprising contacting the double-stranded target DNA with a system as described herein. In these methods, a non-spacer complementary strand of the double-stranded target DNA is nicked before a spacer complementary strand of the double-stranded target nucleic acid is nicked.

In other embodiments, the disclosure includes methods of detecting a target nucleic acid in a sample, the method comprising: (a) contacting the sample with a system as described herein and a labeled reporter nucleic acid, wherein hybridization of the crRNA to the target nucleic acid causes cleavage of the labeled reporter nucleic acid; and (b) measuring a detectable signal produced by cleavage of the labeled reporter nucleic acid, thereby detecting the presence of the target nucleic acid in the sample. These methods can further include comparing a level of the detectable signal with a reference signal level, and determining an amount of target nucleic acid in the sample based on the level of the detectable signal. In some embodiments, the measuring is performed using gold nanoparticle detection, fluorescence polarization, colloid phase transition/dispersion, electrochemical detection, or semiconductor based-sensing. In some embodiments, the labeled reporter nucleic acid comprises a fluorescence-emitting dye pair, a fluorescence resonance energy transfer (FRET) pair, or a quencher/fluorophore pair, wherein cleavage of the labeled reporter nucleic acid by the effector protein results in an increase or a decrease of the amount of signal produced by the labeled reporter nucleic acid.

In another aspect, the methods herein include specifically editing a double-stranded nucleic acid, the method comprising contacting, under sufficient conditions and for a sufficient amount of time, (a) a Type V-I CRISPR-Cas effector and one other enzyme with sequence-specific nicking activity, and a crRNA that guides the the Type V-I CRISPR-Cas effector to nick the opposing strand relative to the activity of the other sequence-specific nickase; and (b) the double-stranded nucleic acid; wherein the method results in the formation of a double-stranded break.

Another aspect includes methods of editing a double-stranded nucleic acid, the method comprising contacting, under sufficient conditions and for a sufficient amount of time, (a) a fusion protein comprising a the Type V-I CRISPR-Cas effector and a protein domain with DNA modifying activity and an RNA guide targeting the double-stranded nucleic acid; and (b) the double-stranded nucleic acid; wherein the the Type V-I CRISPR-Cas effector of the fusion protein is modified to nick a non-target strand of the double-stranded nucleic acid.

Another aspect includes methods of inducing genotype-specific or transcriptional-state-specific cell death or dormancy in a cell, the method comprising contacting a cell, e.g., a prokaryotic or eukaryotic cell, with any system disclosed herein, wherein the RNA guide hybridizing to the target DNA causes a collateral DNase activity-mediated cell death or dormancy. For example, the cell can be a mammalian cell, e.g., a cancer cell. The cell can be an infectious cell or a cell infected with an infectious agent, e.g., a cell infected with a virus, a cell infected with a prion, a fungal cell, a protozoan, or a parasite cell.

In another aspect, the disclosure provides methods of treating a condition or disease in a subject in need thereof, the method comprising administering to the subject any of the systems described herein, wherein the spacer sequence is complementary to at least 15 nucleotides of a target nucleic acid associated with the condition or disease; wherein the Type V-I CRISPR-Cas effector protein associates with the RNA guide to form a complex; wherein the complex binds to a target nucleic acid sequence that is complementary to the at least 15 nucleotides of the spacer sequence; and wherein upon binding of the complex to the target nucleic acid sequence the Type V-I CRISPR-Cas effector protein cleaves the target nucleic acid, thereby treating the condition or disease in the subject. For example, the condition or disease can be a cancer or an infectious disease. For example, the condition or disease can be cancer, and wherein the cancer is selected from the group consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

The disclosure also includes the systems or cells as described herein for use as a medicament, or for use in the treatment or prevention of a cancer or an infectious disease, e.g., wherein the cancer is selected from the group consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

The disclosure also provides the use of the systems or cells as described herein in vitro or ex vivo methods of:
a) targeting and editing a target nucleic acid;
b) non-specifically degrading single-stranded DNA upon recognition of a DNA target nucleic acid;
c) targeting and nicking a non-spacer complementary strand of a double-stranded target DNA upon recognition of a spacer complementary strand of the double-stranded target DNA;
d) targeting and cleaving a double-stranded target DNA;
e) detecting a target nucleic acid in a sample;
f) specifically editing a double-stranded nucleic acid;
g) base editing a double-stranded nucleic acid;
h) inducing genotype-specific or transcriptional-state-specific cell death or dormancy in a cell.
i) creating an indel in a double-stranded target DNA;
j) inserting a sequence into a double-stranded target DNA, or
k) deleting or inverting a sequence in a double-stranded target DNA.

In another aspect, the disclosure provides the use of the systems or cells described herein in methods of:
a) targeting and editing a target nucleic acid;
b) non-specifically degrading single-stranded DNA upon recognition of a DNA target nucleic acid;
c) targeting and nicking a non-spacer complementary strand of a double-stranded target DNA upon recognition of a spacer complementary strand of the double-stranded target DNA;
d) targeting and cleaving a double-stranded target DNA;
e) detecting a target nucleic acid in a sample;
f) specifically editing a double-stranded nucleic acid;
g) base editing a double-stranded nucleic acid;
h) inducing genotype-specific or transcriptional-state-specific cell death or dormancy in a cell;
i) creating an indel in a double-stranded target DNA;
j) inserting a sequence into a double-stranded target DNA, or
k) deleting or inverting a sequence in a double-stranded target DNA, wherein the method does not comprise a process for modifying the germ line genetic identity of a human being and does not comprise a method of treatment of the human or animal body.

In the methods described herein, cleaving the target DNA or target nucleic acid results in the formation of an indel, or wherein cleaving the target DNA or target nucleic acid results in the insertion of a nucleic acid sequence, or, wherein cleaving the target DNA or target nucleic acid comprises cleaving the target DNA or target nucleic acid in two sites, and results in the deletion or inversion of a sequence between the two sites.

The various systems described herein can lack a tracrRNA. In some embodiments, the Type V-I CRISPR-Cas effector protein and Type V-I RNA guide form a complex that associates with the target nucleic acid, thereby modifying the target nucleic acid.

In some embodiments of the systems described herein, the spacer sequence is between 15 and 47 nucleotides in length, e.g., between 20 and 40 nucleotides in length, or between 24 and 38 nucleotides in length.

In another aspect, the disclosure provides eukaryotic cells, e.g., mammalian cells, e.g., human cells, comprising a modified target locus of interest, wherein the target locus of interest has been modified according to a method or via use of a composition of any one of the preceding claims. For example, the modification of the target locus of interest can result in:
(i) the eukaryotic cell comprising altered expression of at least one gene product;
(ii) the eukaryotic cell comprising altered expression of at least one gene product, wherein the expression of the at least one gene product is increased;
(iii) the eukaryotic cell comprising altered expression of at least one gene product, wherein the expression of the at least one gene product is decreased; or
(iv) the eukaryotic cell comprising an edited genome.

In another aspect, the disclosure provides a eukaryotic cell line of or comprising the eukaryotic cells described herein, or progeny thereof, or a multicellular organism comprising one or more eukaryotic cells described herein.

The disclosure also provides plant or animal models comprising one or more cells as described herein.

In another aspect, the disclosure provides methods of producing a plant, having a modified trait of interest encoded by a gene of interest, the method comprising contacting a plant cell with any of the systems described herein, thereby either modifying or introducing said gene of interest, and regenerating a plant from the plant cell.

The disclosure also provides methods of identifying a trait of interest in a plant, wherein the trait of interest is encoded by a gene of interest, the method comprising contacting a plant cell with any of the systems described herein, thereby identifying the gene of interest. For example, the method can further comprising introducing the identified gene of interest into a plant cell or plant cell line or plant germ plasm and generating a plant therefrom, whereby the plant contains the gene of interest. The method can include having the plant exhibit the trait of interest.

The disclosure also includes methods of targeting and cleaving a single-stranded target DNA, the method comprising contacting the target nucleic acid with any of the systems described herein. The methods can include the condition or disease being infectious, and wherein the infectious agent is selected from the group consisting of human immunodeficiency virus (HIV), herpes simplex virus-1 (HSV1), and herpes simplex virus-2 (HSV2).

In some of the method described herein, both strands of target DNA can be cleaved at different sites, resulting in a staggered cut. In other embodiments, both strands of target DNA are cleaved at the same site, resulting in a blunt double-strand break (DSB).

In some of the therapeutic methods described herein, the condition or disease is selected from the group consisting of Cystic Fibrosis, Duchenne Muscular Dystrophy, Becker Muscular Dystrophy, Alpha-1-antitrypsin Deficiency, Pompe Disease, Myotonic Dystrophy, Huntington Disease, Fragile X Syndrome, Friedreich's ataxia, Amyotrophic Lateral Sclerosis, Frontotemporal Dementia, Hereditary Chronic Kidney Disease, Hyperlipidemia, Hypercholesterolemia, Leber Congenital Amaurosis, Sickle Cell Disease, and Beta Thalassemia.

The term "cleavage event," as used herein, refers to a DNA break in a target nucleic acid created by a nuclease of a CRISPR system described herein. In some embodiments, the cleavage event is a double-stranded DNA break. In some embodiments, the cleavage event is a single-stranded DNA break.

The term "CRISPR-Cas system," "Type V-I CRISPR-Cas system," or "Type V-I system" as used herein refers to a Type V-I CRISPR-Cas effector protein (i.e., Cas12i effector protein) and one or more Type V-I RNA guides, and/or nucleic acids encoding the Type V-I CRISPR-Cas effector protein or the one or more Type V-I RNA guides, and optionally promoters operably linked to the expression of the CRISPR effector or to the RNA guide or to both.

The term "CRISPR array" as used herein refers to the nucleic acid (e.g., DNA) segment that includes CRISPR repeats and spacers, starting with the first nucleotide of the first CRISPR repeat and ending with the last nucleotide of the last (terminal) CRISPR repeat. Typically, each spacer in a CRISPR array is located between two repeats. The terms "CRISPR repeat," or "CRISPR direct repeat," or "direct repeat," as used herein, refer to multiple short direct repeating sequences, which show very little or no sequence variation within a CRISPR array. Suitably, a Type V-I direct repeat may form a stem-loop structure.

A "stem-loop structure" refers to a nucleic acid having a secondary structure that includes a region of nucleotides that are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. As is known in the art, a stem-loop structure does not require exact base-pairing. Thus, the stem may include one or more base mismatches. Alternatively, the base-pairing may be exact, i.e., not include any mismatches. The predicted stem loop structures of some Type V-I direct repeats are illustrated in FIG. 3. The stem for the Type V-I direct repeat contained within the RNA guide is composed of 5 complementary nucleobases that hybridize to each other, and the loop is 6, 7, or 9 nucleotides in length.

The term "CRISPR RNA" or "crRNA" as used herein refers to an RNA molecule comprising a guide sequence used by a CRISPR effector to target a specific nucleic acid sequence. Typically, crRNAs contains a spacer sequence that mediates target recognition and a direct repeat sequence (referred to herein as a direct repeat or "DR" sequence) that forms a complex with a CRISPR-Cas effector protein.

The term "donor template nucleic acid," as used herein refers to a nucleic acid molecule that can be used by one or more cellular proteins to alter the structure of a target nucleic acid after a CRISPR enzyme described herein has altered a target nucleic acid. In some embodiments, the donor template nucleic acid is a double-stranded nucleic acid. In some embodiments, the donor template nucleic acid is a single-stranded nucleic acid. In some embodiments, the donor template nucleic acid is linear. In some embodiments, the donor template nucleic acid is circular (e.g., a plasmid). In some embodiments, the donor template nucleic acid is an exogenous nucleic acid molecule. In some embodiments, the donor template nucleic acid is an endogenous nucleic acid molecule (e.g., a chromosome).

The term "CRISPR-Cas effector," "CRISPR effector," "effector," "CRISPR-associated protein," or "CRISPR enzyme," "Type V-I CRISPR-Cas effector protein," "Type V-I CRISPR-Cas effector," "Type V-I effector," or Cas12i effector protein" as used herein refers to a protein that carries out an enzymatic activity or that binds to a target site on a nucleic acid specified by an RNA guide. A CRISPR-Cas Type V-I effector protein associated within a Type V-I CRISPR-Cas system can also be referred to herein as "Cas12i" or "Cas12i enzyme." A Cas12i enzyme can recognize a short motif associated in the vicinity of a target DNA called a Protospacer Adjacent Motif (PAM). Suitably, a Cas12i enzyme of the present disclosure can recognize a PAM comprising or consisting of TTN, wherein N denotes any nucleotide. For example, the PAM may be TTN, TTH, TTY or TTC.

In some embodiments, a Type V-I CRISPR-Cas effector protein has endonuclease activity, nickase activity, and/or exonuclease activity.

The terms "CRISPR effector complex," "effector complex," "binary complex," or "surveillance complex" as used herein refer to a complex containing a Type V-I CRISPR-Cas effector protein and a Type V-I RNA guide.

The term "RNA guide" as used herein refers to any RNA molecule that facilitates the targeting of a protein described herein to a target nucleic acid. Exemplary "RNA guides" include, but are not limited to, crRNAs, pre-crRNAs (e.g. DR-spacer-DR), and mature crRNAs (e.g. mature_DR-spacer, mature DR-spacer-mature_DR).

As used herein, the term "targeting" refers to the ability of a complex including a CRISPR-associated protein and an RNA guide, such as a crRNA, to preferentially or specifically bind to, e.g., hybridize to, a specific target nucleic acid compared to other nucleic acids that do not have the same or similar sequence as the target nucleic acid.

As used herein, the term "target nucleic acid" refers to a specific nucleic acid substrate that contains a nucleic acid sequence complementary to the entirety or a part of the spacer in an RNA guide. In some embodiments, the target nucleic acid comprises a gene or a sequence within a gene. In some embodiments, the target nucleic acid comprises a non-coding region (e.g., a promoter). In some embodiments, the target nucleic acid is single-stranded. In some embodiments, the target nucleic acid is double-stranded.

The terms "activated CRISPR complex," "activated complex," or "ternary complex" as used herein refer to a CRISPR effector complex after it has bound to or has modified a target nucleic acid.

The terms "collateral RNA" or "collateral DNA" as used herein refer to a nucleic acid substrate that is cleaved non-specifically by an activated CRISPR complex.

The term "collateral DNase activity," as used herein in reference to a CRISPR enzyme, refers to non-specific DNase activity of an activated CRISPR complex.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF FIGURE DESCRIPTION

The figures include a series of schematics and nucleic acid and amino acid sequences that represent the results of locus analysis of various protein clusters.

FIGS. 1A-B together depict a classification tree of Type V effectors (Cas12 proteins). The corresponding CRISPR-Cas loci organization is shown for each branch, with the need for a tracrRNA depicted by a white rectangle adjacent to a CRISPR array. CLUST.029130 (Type V-I) systems are depicted as Cas12i.

FIG. 2A is a schematic representation of the functional domains of the CLUST.029130 (Type V-I) effector, designated Cas12i. The solid grey shading indicates the location of the C-terminal RuvC domain, with the catalytic residues in the three conserved sequence motifs (I, II and III) indicated and shown to scale. The location of the bridge helix domain is indicated with the superscript h.

Figure 4A:
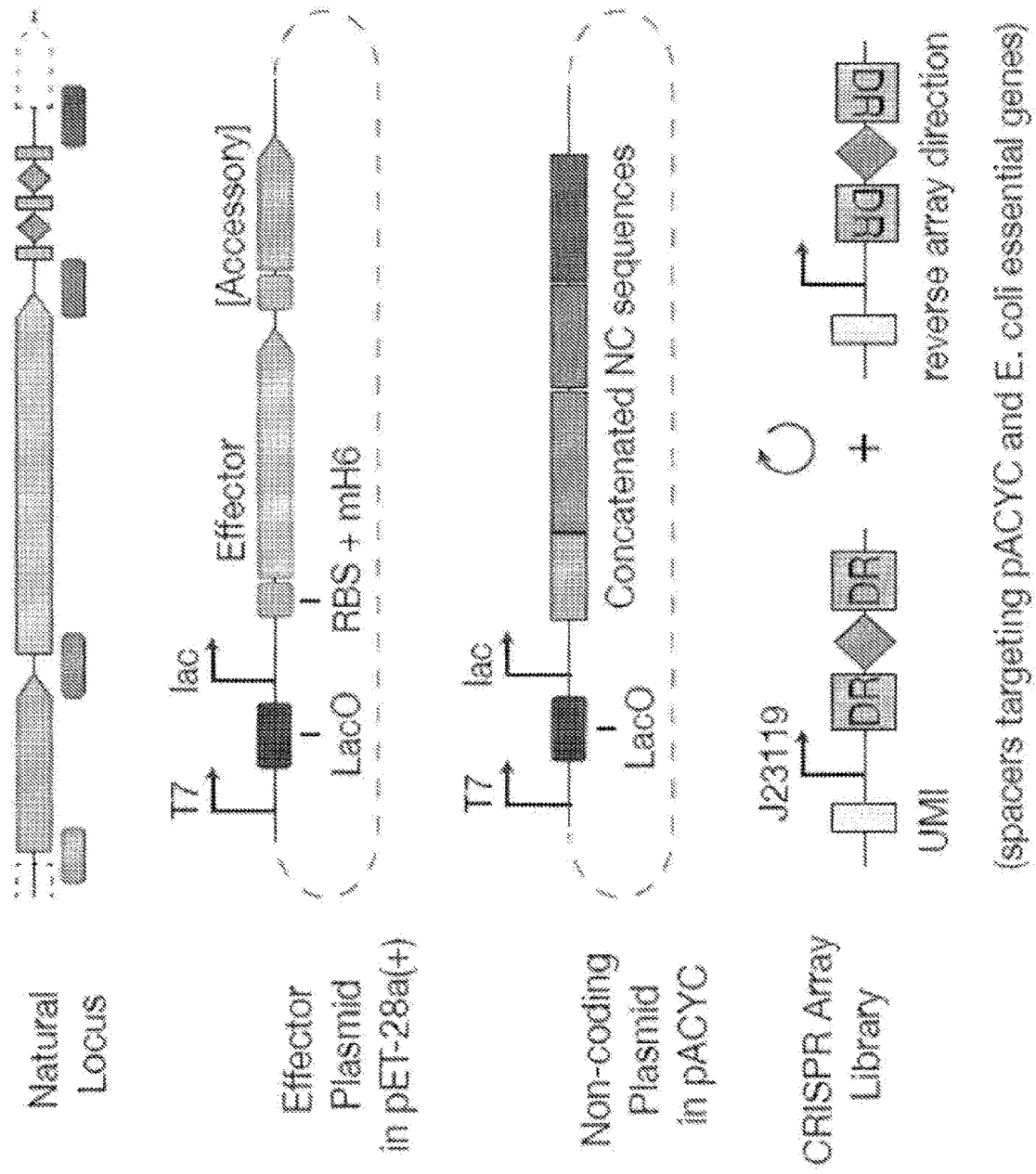
FIG. 4A is a schematic representation of the design of in vivo screen Effector and Non-coding Plasmids. CRISPR array libraries were designed including non-repetitive spacers uniformly sampled from both strands of pACYC184 or E. coli essential genes flanked by two DRs and expressed by J23119.
Figure 4B:
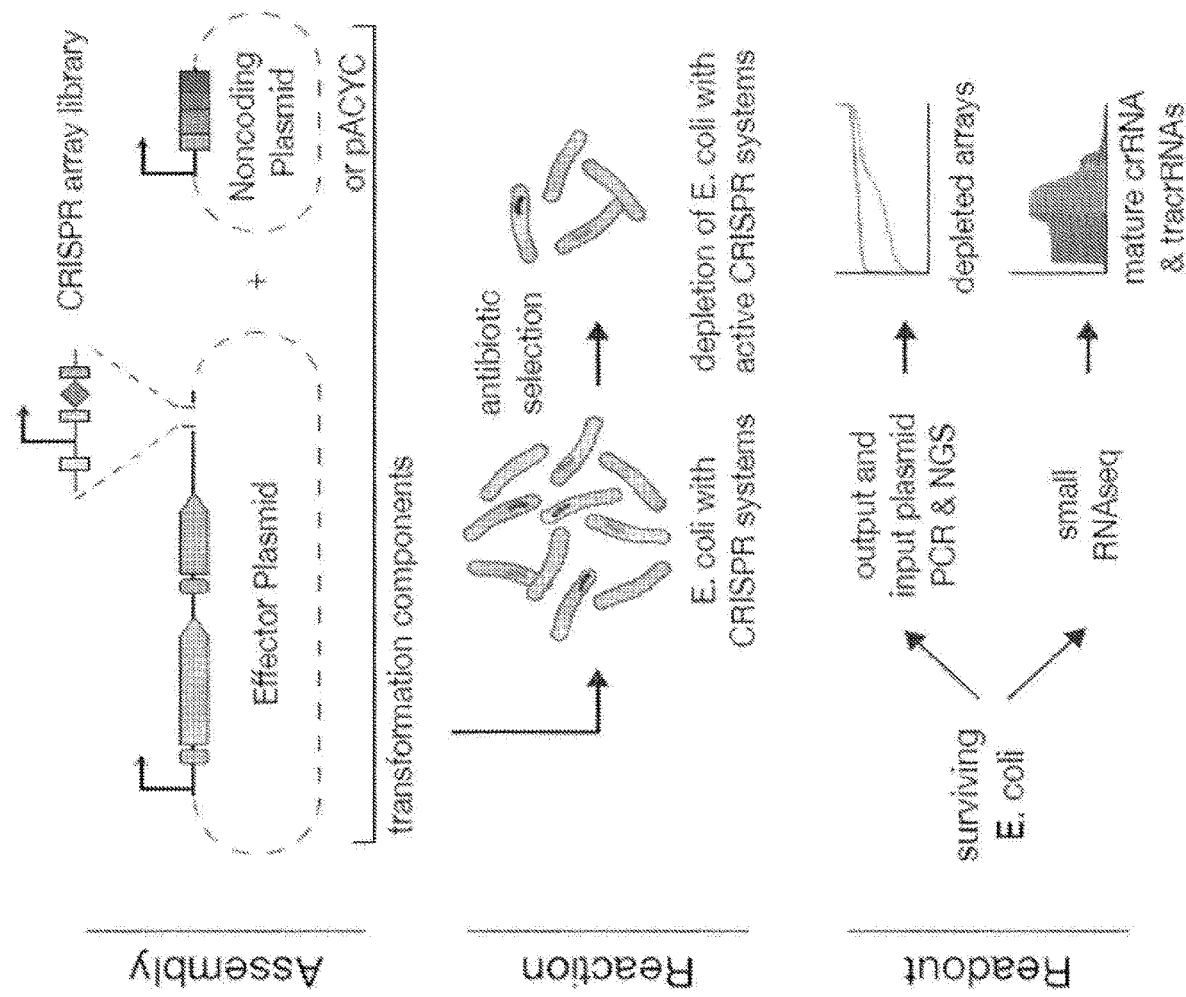
Figure 5A:
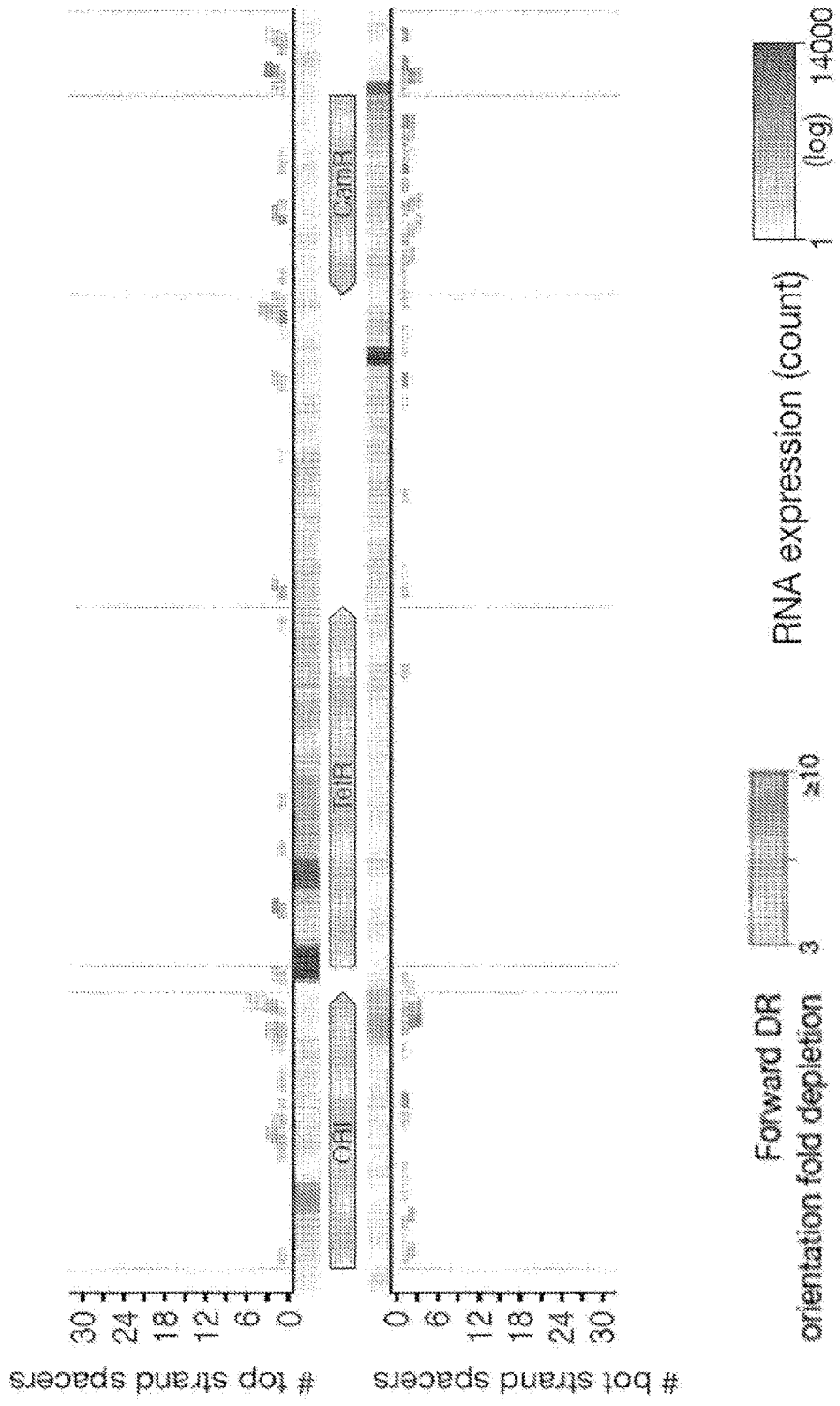
Figure 5B:
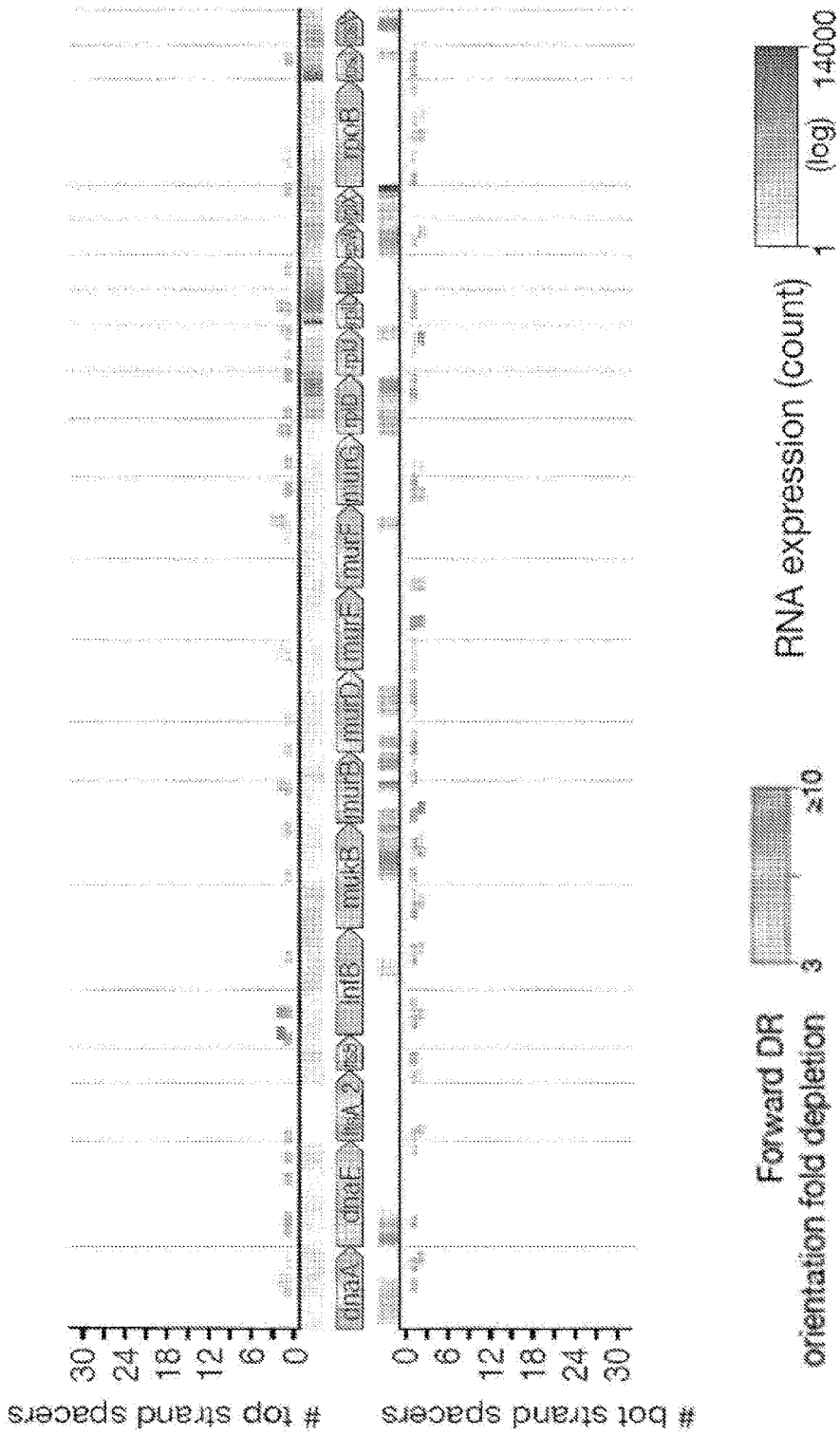
Figure 5C:
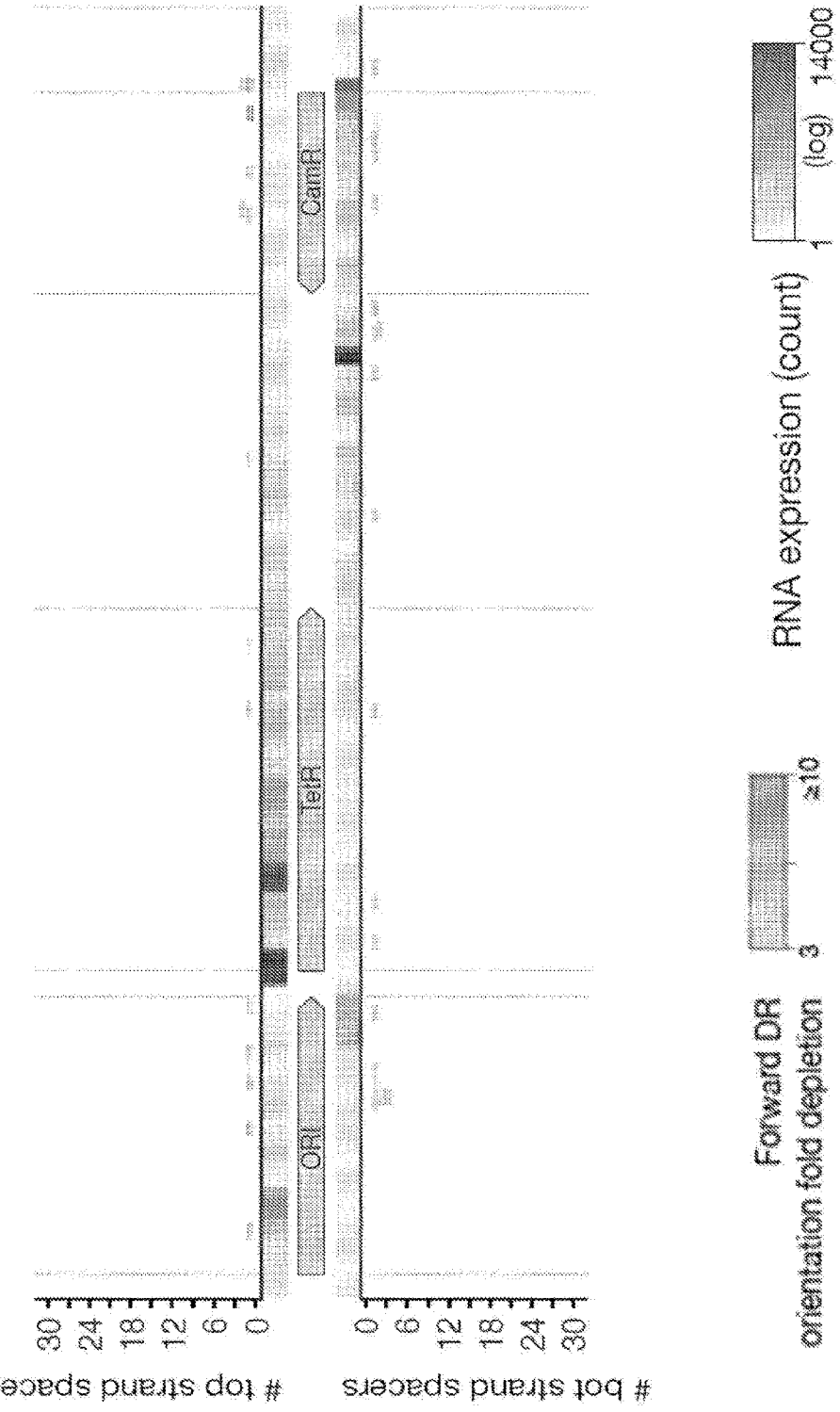
Figure 5D:
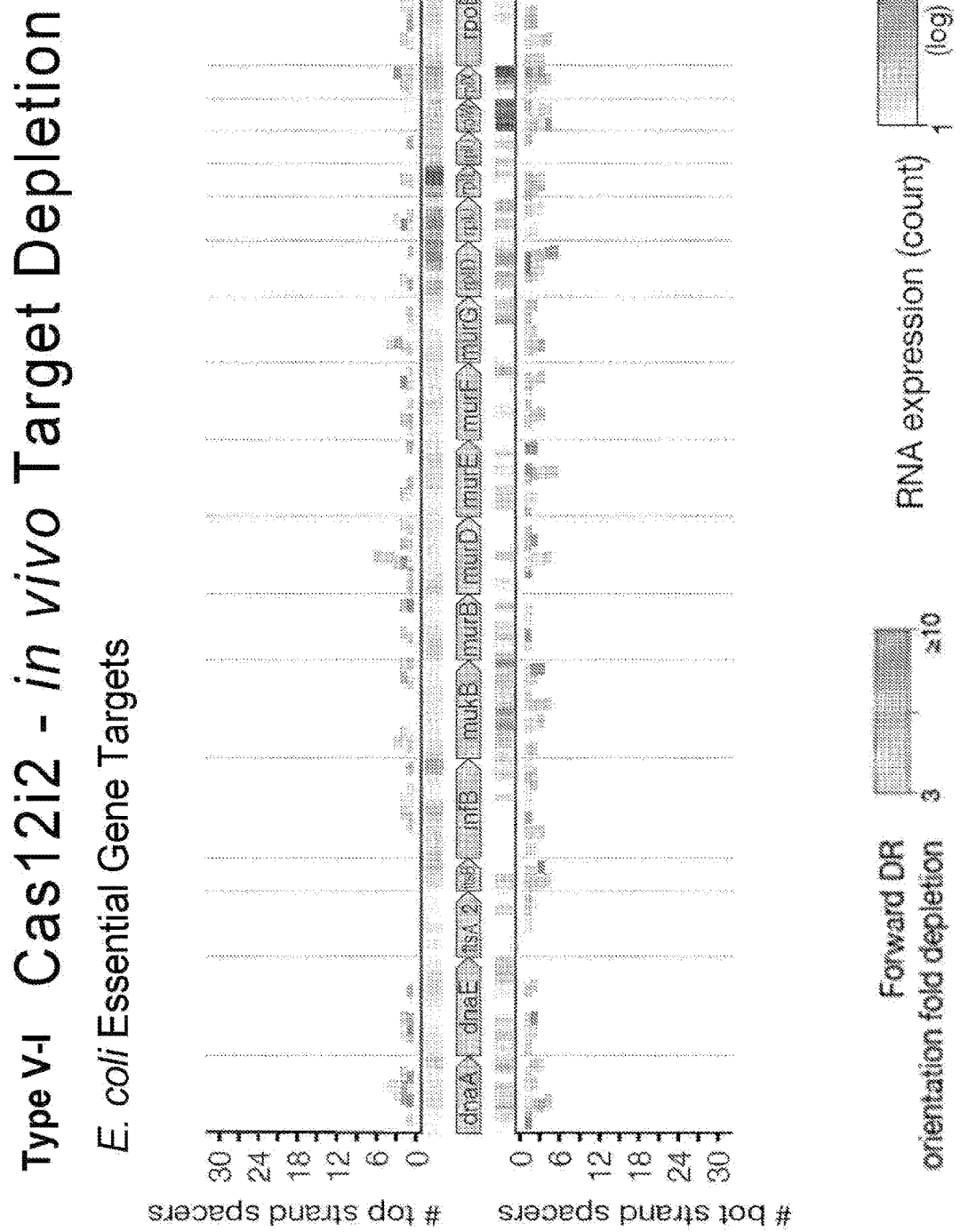

FIG. 4B is a schematic representation of the negative selection screening workflow; 1) CRISPR array libraries were cloned into the Effector Plasmid, 2) the Effector Plasmid and, when present, the Non-coding Plasmid were transformed into E. coli followed by outgrowth for negative selection of CRISPR arrays conferring interference against DNA or RNA transcripts from pACYC184 or E. coli essential genes, 3) Targeted sequencing of the Effector Plasmid was used to identify depleted CRISPR arrays and small RNA sequencing was used to identify mature crRNAs and tracrRNAs.

FIGS. 5A-B and FIGS. 5C-D are graphic representations that show the density of depleted and non-depleted targets for Cas12i1 and Cas12i2, respectively. Strongly depleted spacers targeting both pACYC184 and E. coli essential genes are depicted in separate plots. Targets on the top strand and bottom strand are shown separately, and in relation to the orientation of the annotated genes.

Figure 6A:
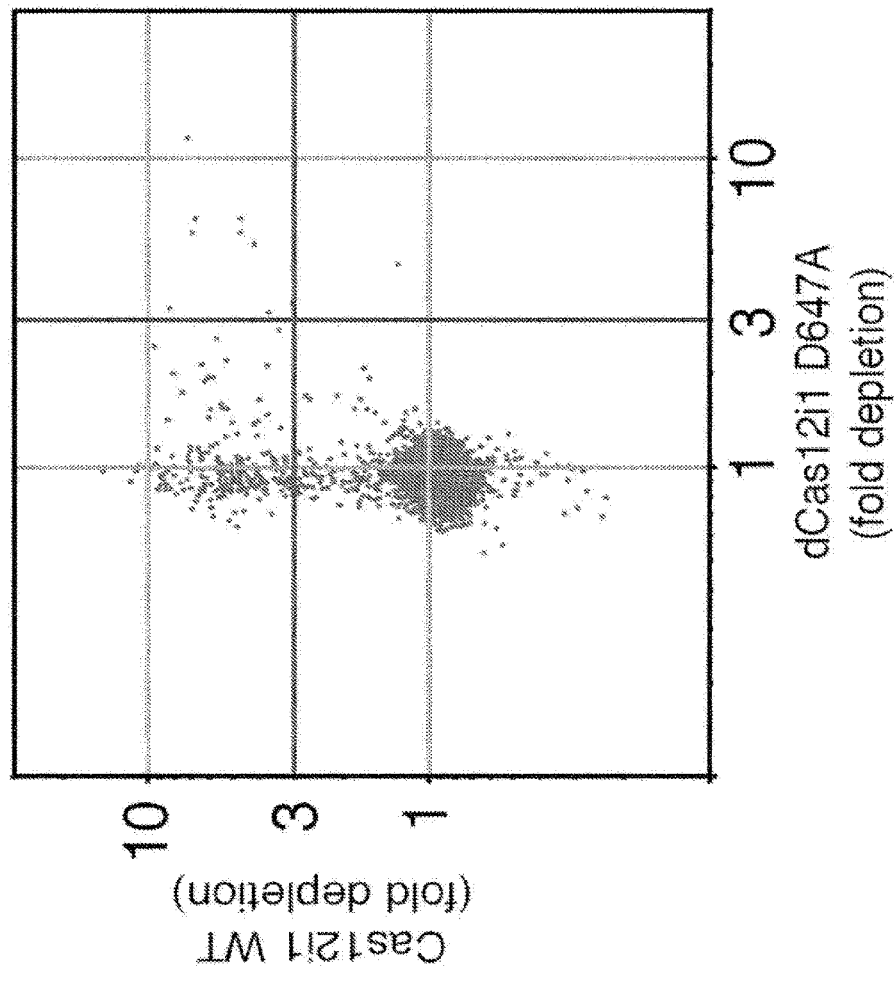
Figure 6B:
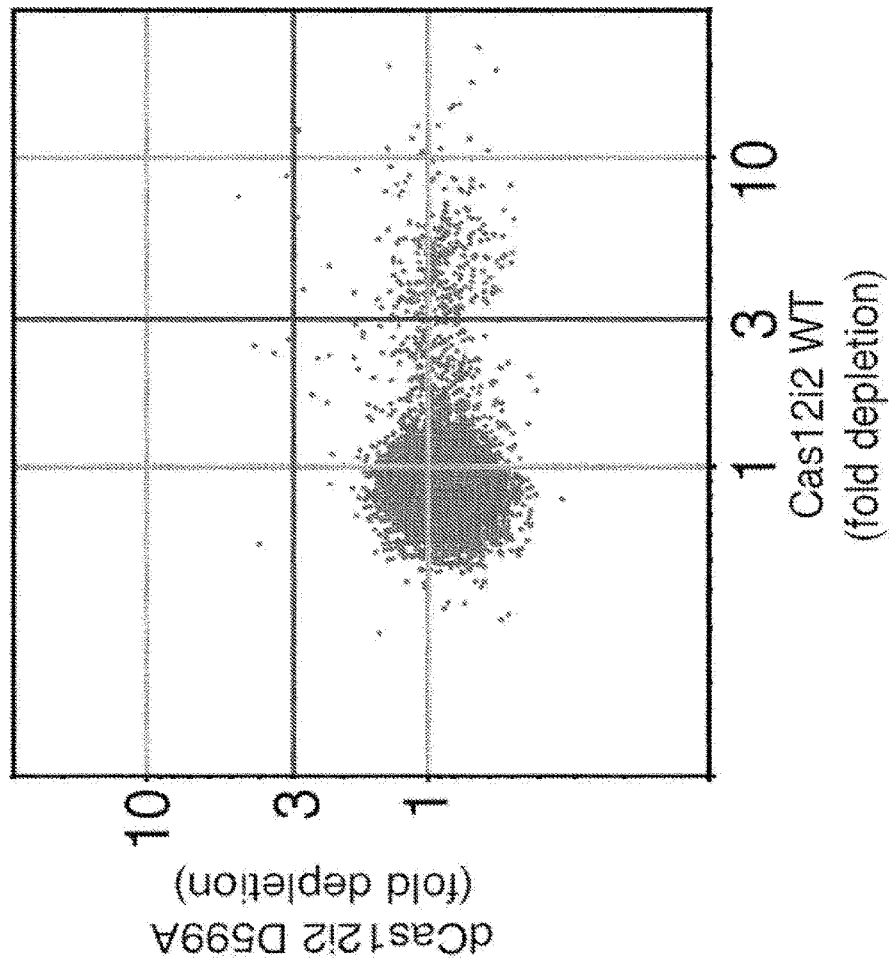

FIGS. 6A and 6B are scatter plots that show the effect of mutating the RuvC-I catalytic residue aspartate (in location 647 for Cas12i1, and 599 for Cas12i2) to alanine. Each point represents a spacer, and the value indicates the fold depletion under the condition specified for the axis (wild type vs mutant). Higher values indicate stronger depletion (i.e. fewer surviving colonies).

Figure 7A:
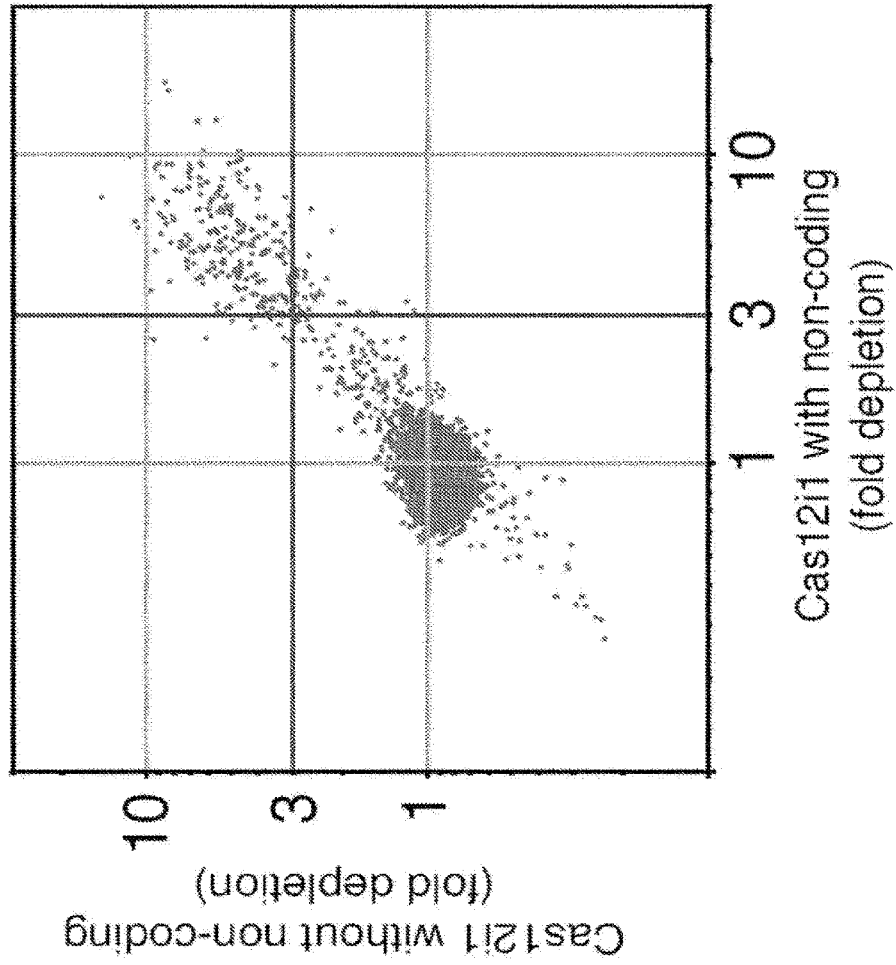
Figure 7B:
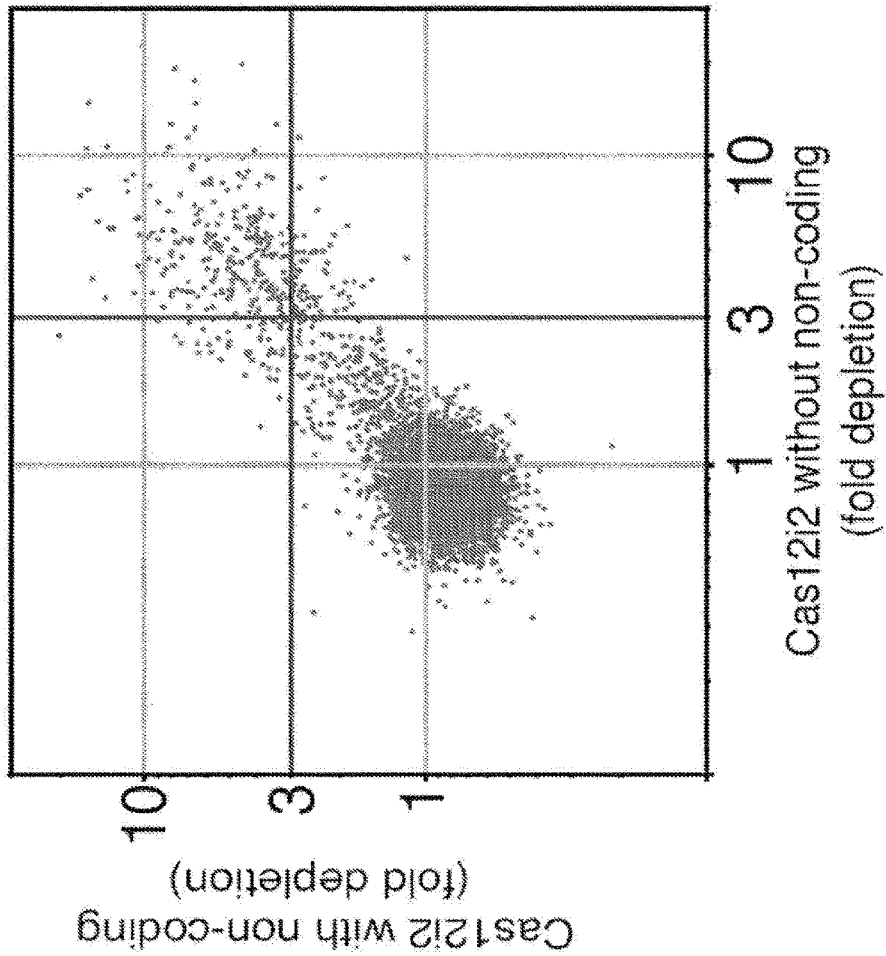

FIGS. 7A and 7B are scatter plots that show the effect of adding or removing the non-coding sequences to the Type V-I CRISPR-Cas system being screened. Each point represents a spacer, and the value indicates the fold depletion under the condition specified for the axis (wild type vs mutant). Higher values indicate stronger depletion (i.e., fewer surviving colonies).

Figure 8A:
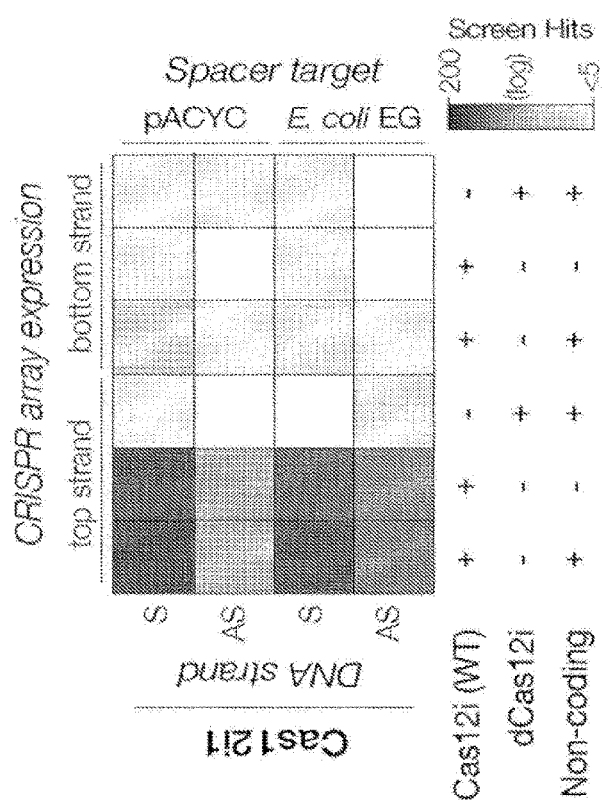
Figure 8B:
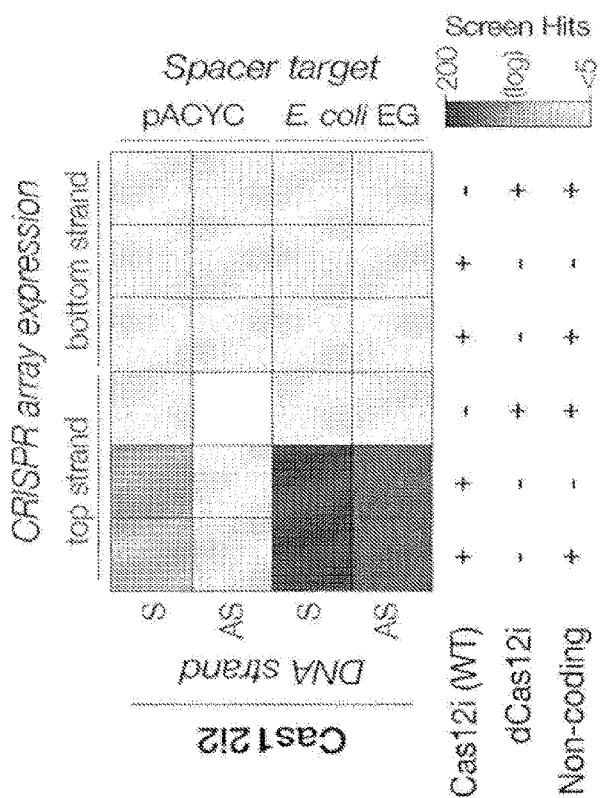

FIGS. 8A and 8B are heatmaps of the aggregate screening results for Cas12i1 and Cas12i2, respectively. The heatmap is decomposed into dependencies such as the orientation of the direct repeat, necessity of noncoding sequence, as well as the requirement of the intact RuvC domain (where dCas12i refers to a point mutant in a catalytically active residue of the RuvC-I domain). The Y-axis decomposes the library targets into the constituent features of targeting pACYC184, E. coli essential genes (E. coli EG), or strand-edness of targeting (S, sense; AS, antisense). Cas12i1 and Cas12i2 in vivo screens were run in Endura Stbl3 and E. Cloni® competent cell strains, respectively. CRISPR arrays strongly depleted in negative controls without Cas2i1 or Cas12i2 effectors are subtracted from the respective analyses.

Figure 9A:
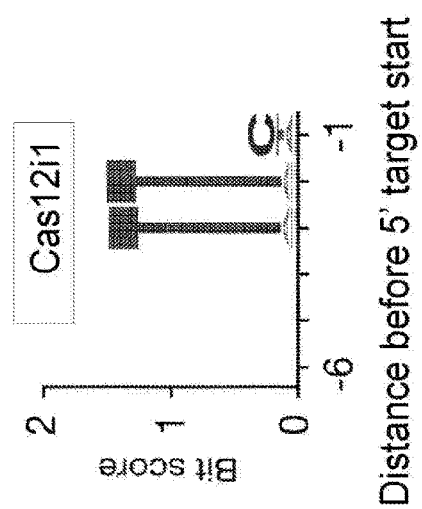
Figure 9B:
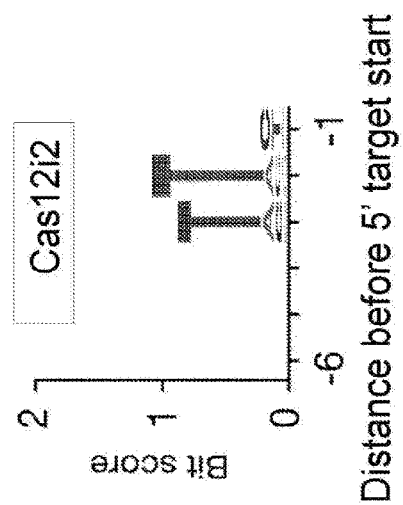

FIGS. 9A and 9B are weblogos of 5' PAM motifs identified from sequences flanking targets for strongly depleted spacers from Cas12i1 and Cas12i2 in vivo screens, respectively.

Figure 10A:
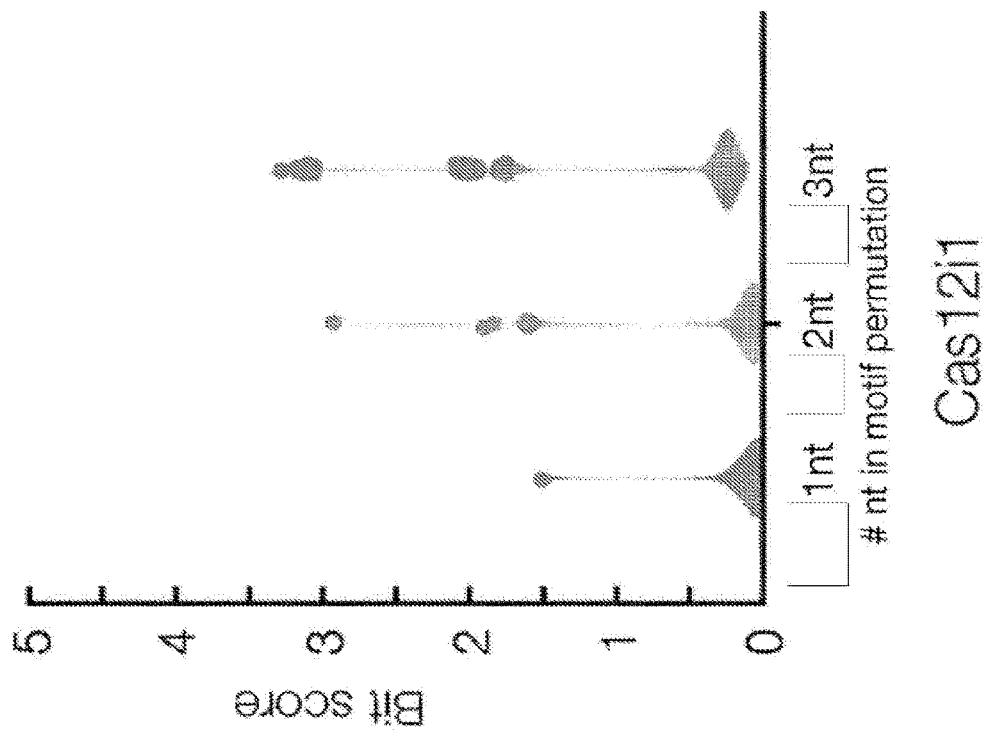
Figure 10B:
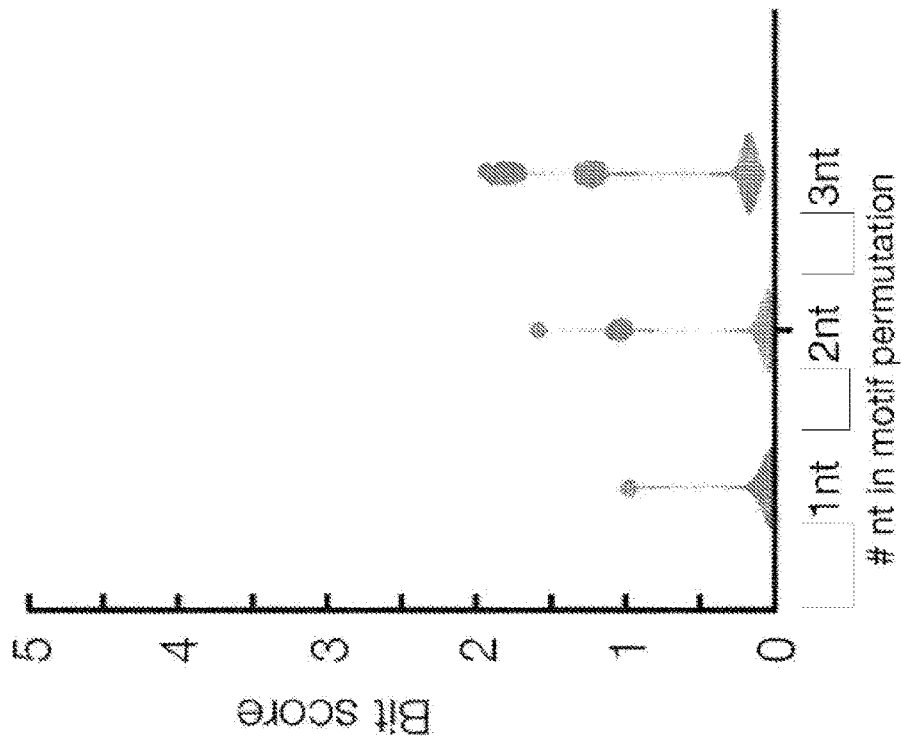

FIGS. 10A and 10B are violin plots of bit scores for all possible permutations of target and flanking nucleotides, confirming that Cas12i1 and Cas12i2 each have a preference for only a single 2-nt PAM motif at the 2nd and 3rd positions 5' of spacer targets.

Figure 11A:
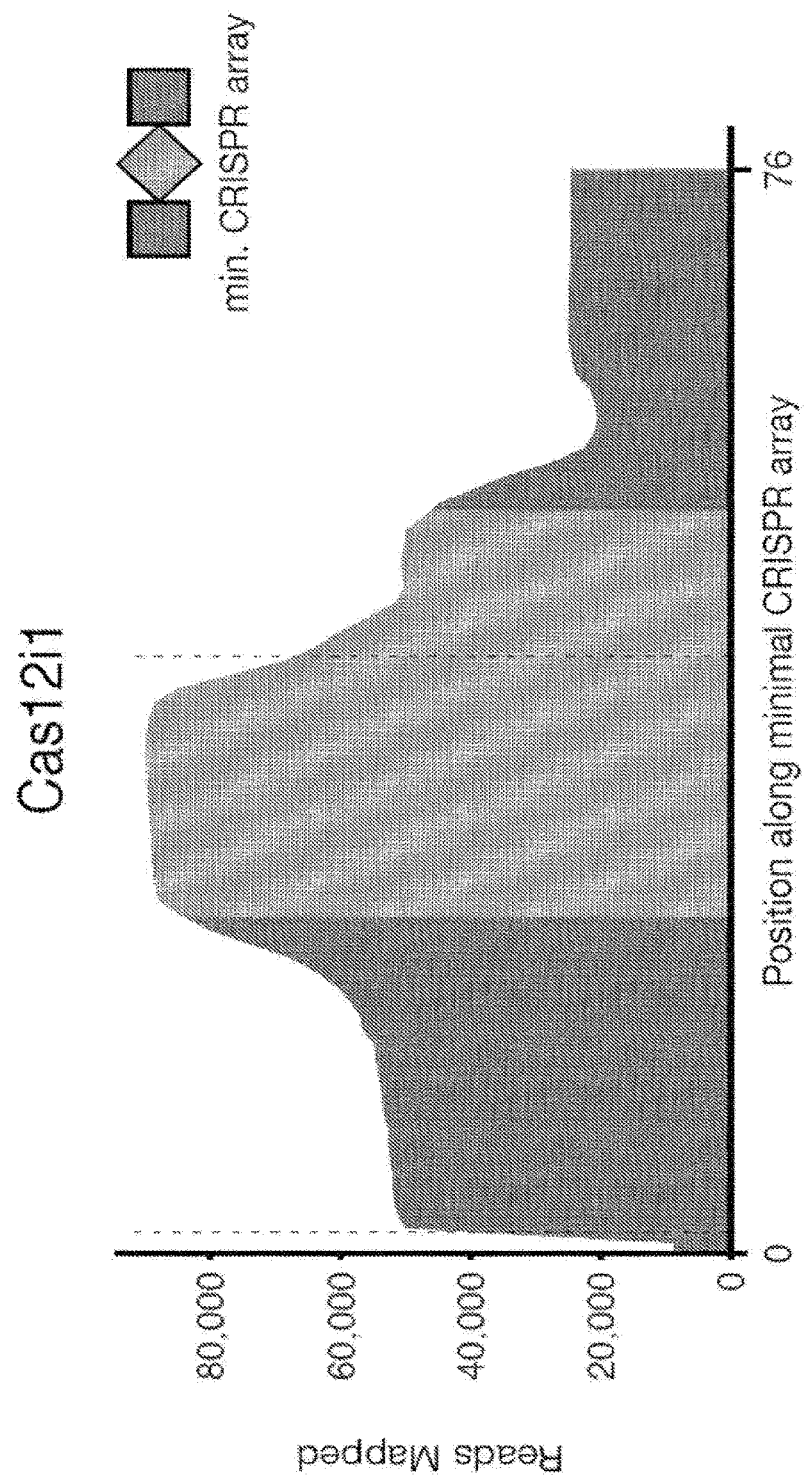
Figure 11B:
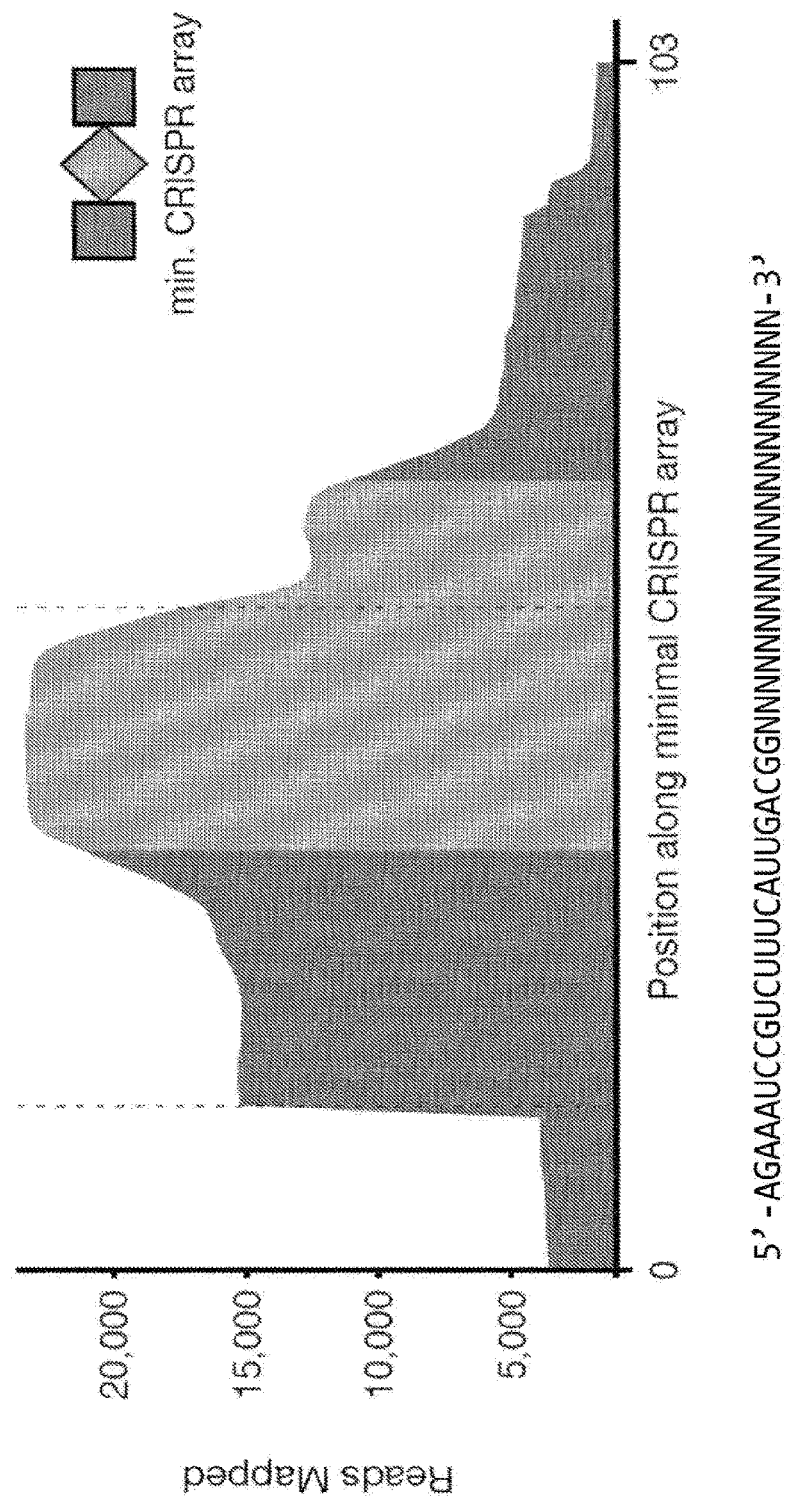

FIGS. 11A and 11B depict the read mapping of small RNA sequencing of in vivo screening samples of the minimal Cas12i systems, revealing the mature crRNA of Cas12i1 and Cas12i2 systems respectively.

Figure 12:
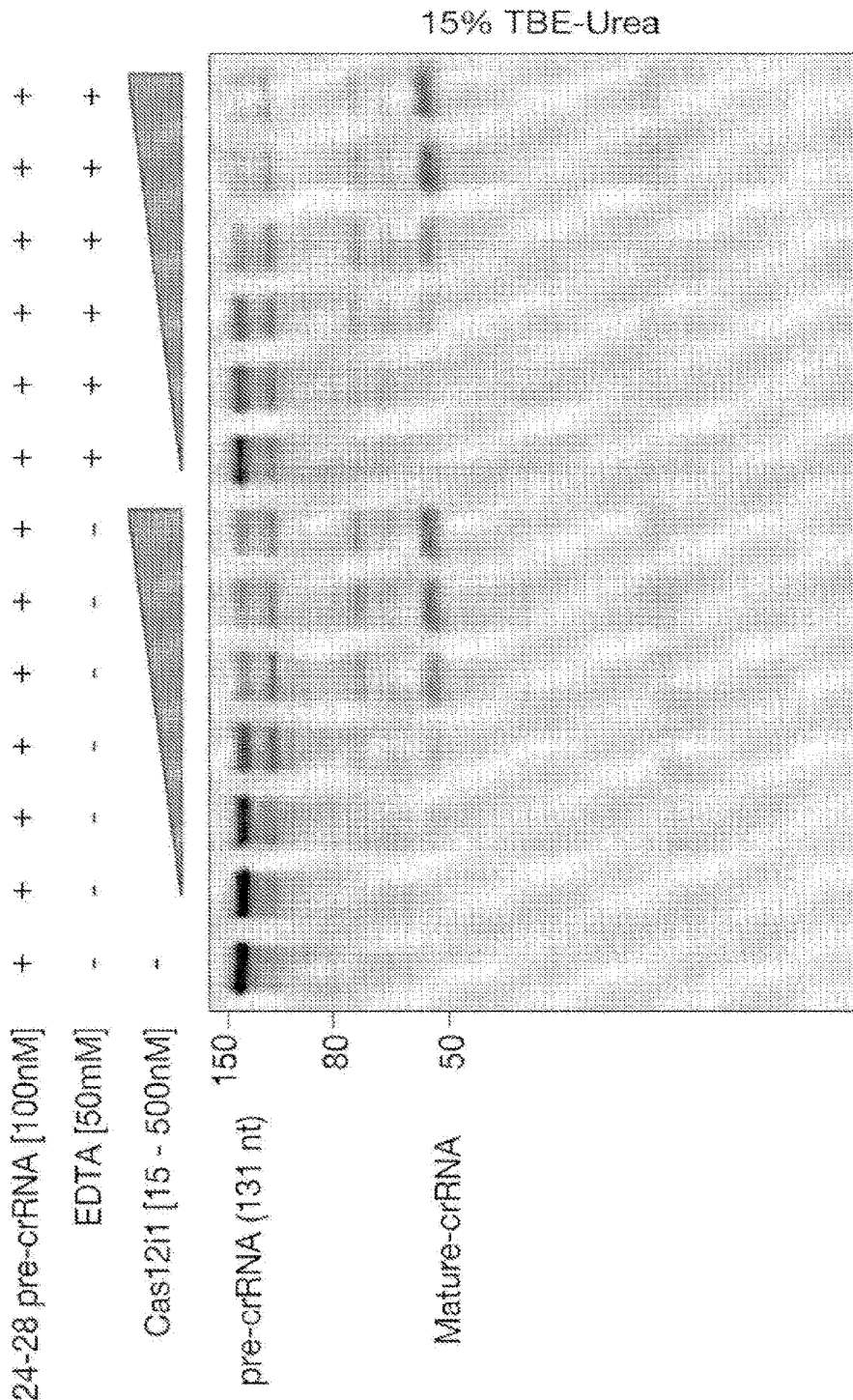

FIG. 12 is a denaturing gel showing pre-crRNA processing by Cas12i1 effector protein. Magnesium independent processing of pre-crRNA expressed from a minimal CRISPR array (repeat-spacer-repeat-spacer-repeat) with a 24nt repeat and 28nt spacer by Cas12i1. pre-crRNA was incubated with Cas12i1 for 30 minutes at 37° C. and analyzed on a 15% TBE-Urea gel.

Figure 13:
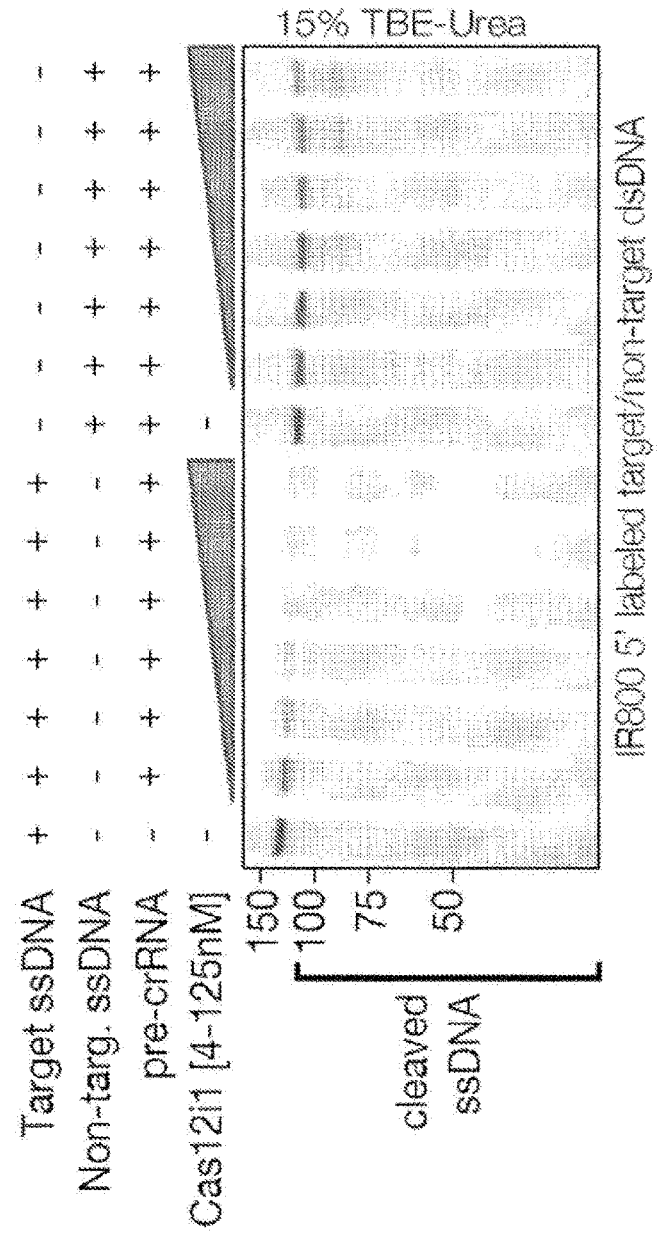

FIG. 13 is a representation of a gel that show the manipulation of IR800 dye-labeled target (left) or non-target (right) ssDNA by increasing doses of Cas12i1 binary complex. Samples were analyzed by 15% TBE-urea denaturing gel electrophoresis.

Figure 14:
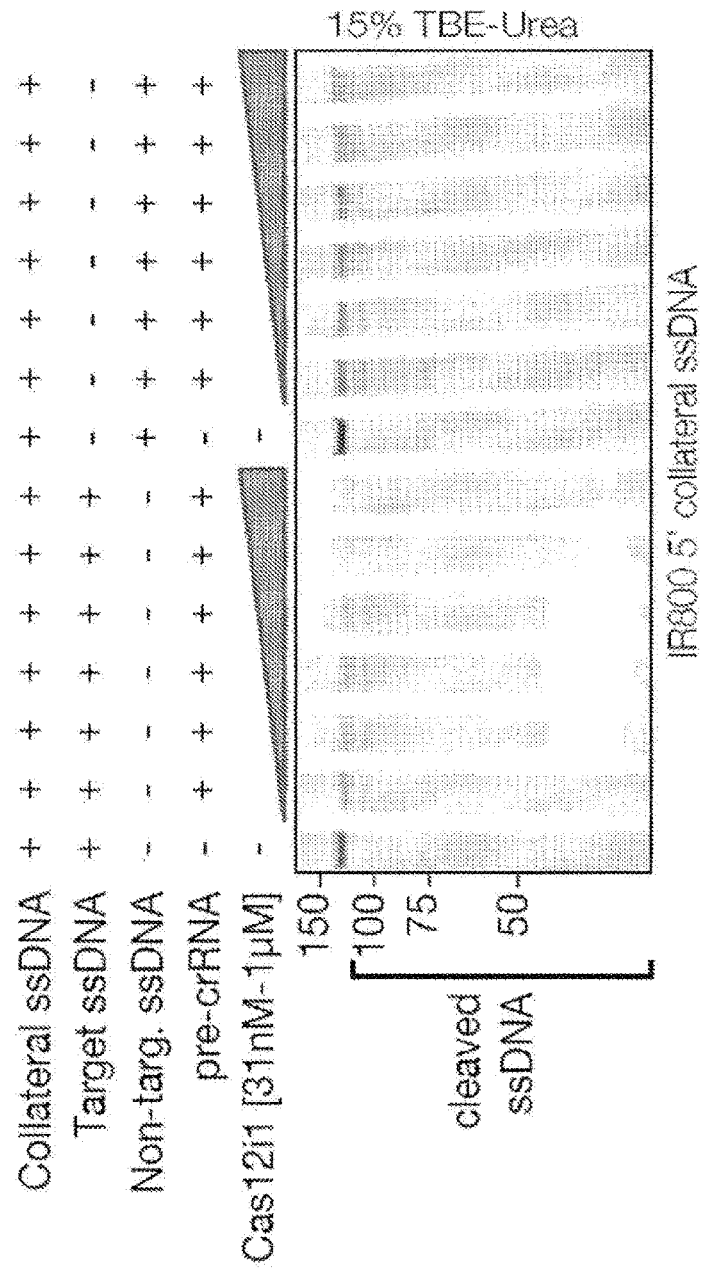

FIG. 14 is a representation of a gel that shows the manipulation of IR800 dye-labeled collateral ssDNA (with no sequence similarity to the target) in the presence of unlabeled target (left) or non-target (right) ssDNA by increasing doses of Cas12i1 binary complex. Samples were analyzed by 15% TBE-urea denaturing gel electrophoresis.

Figure 15:
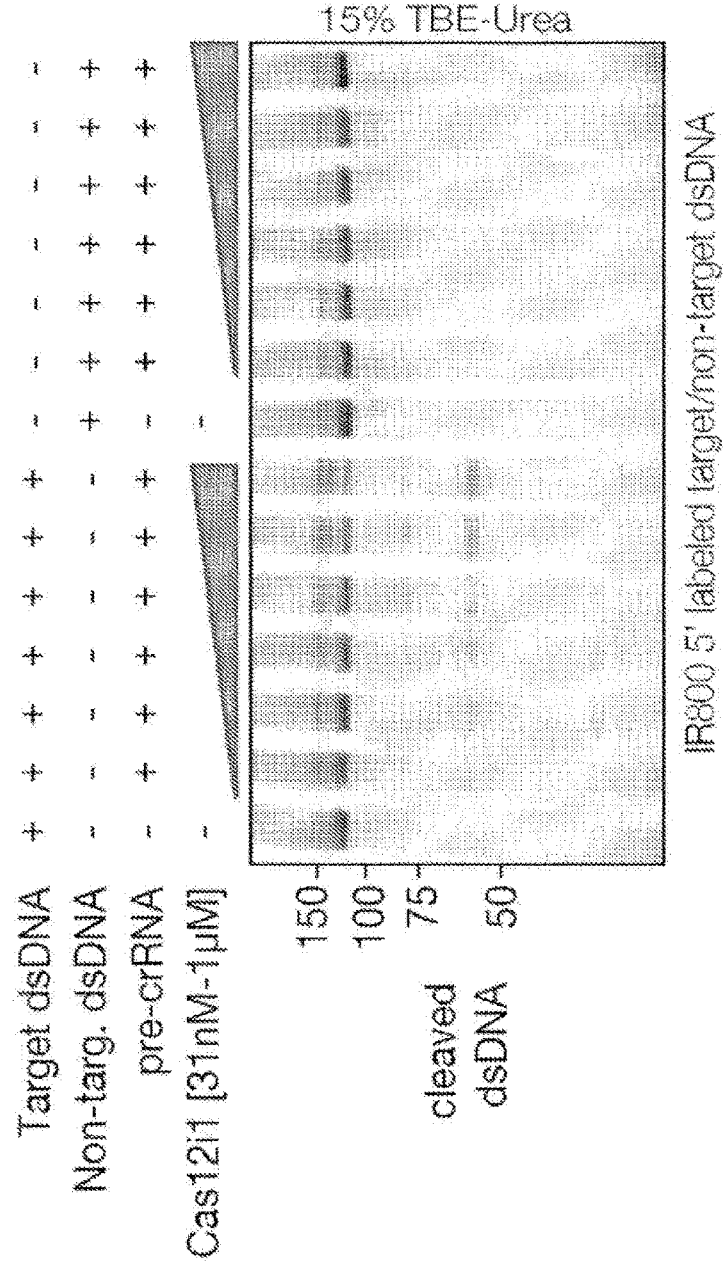

FIG. 15 is a representation of a gel that shows the manipulation of IR800 dye-labeled target (left) or non-target (right) dsDNA by increasing doses of Cas12i1 binary complex. Samples were analyzed by 15% TBE-urea denaturing gel electrophoresis.

Figure 16:
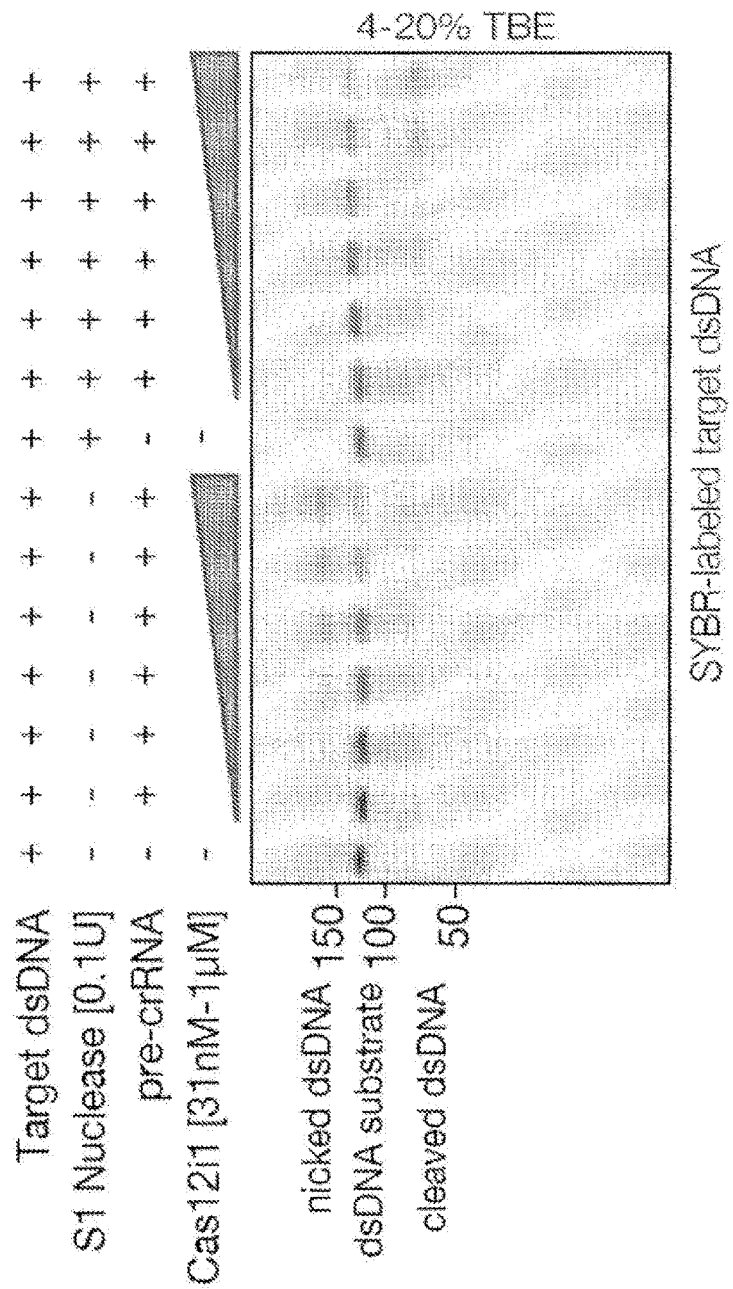

FIG. 16 is a representation of a gel that shows the manipulation of IR800 dye-labeled target dsDNA by increasing doses of Cas12i1 binary complex and quenched directly (left) or treated with S1 nuclease before quenching (right). Samples were analyzed by 4-20% TBE non-denaturing gel electrophoresis.

Figure 17A:
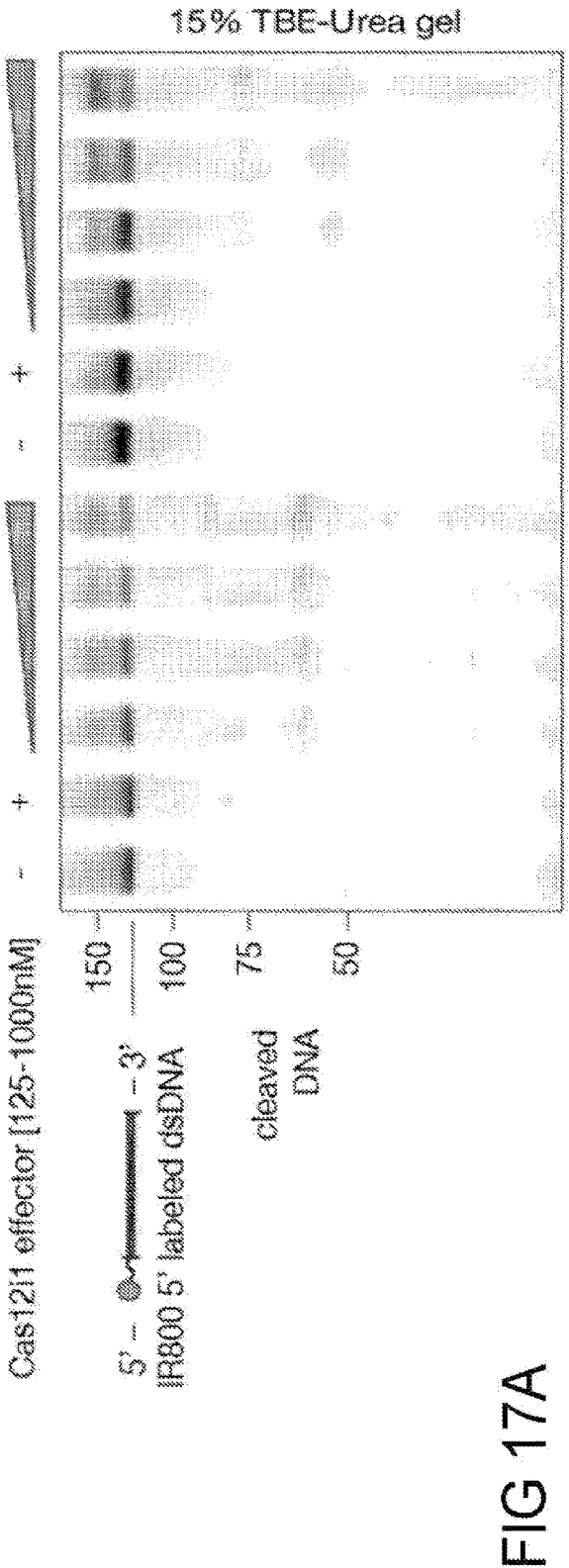
Figure 17B:
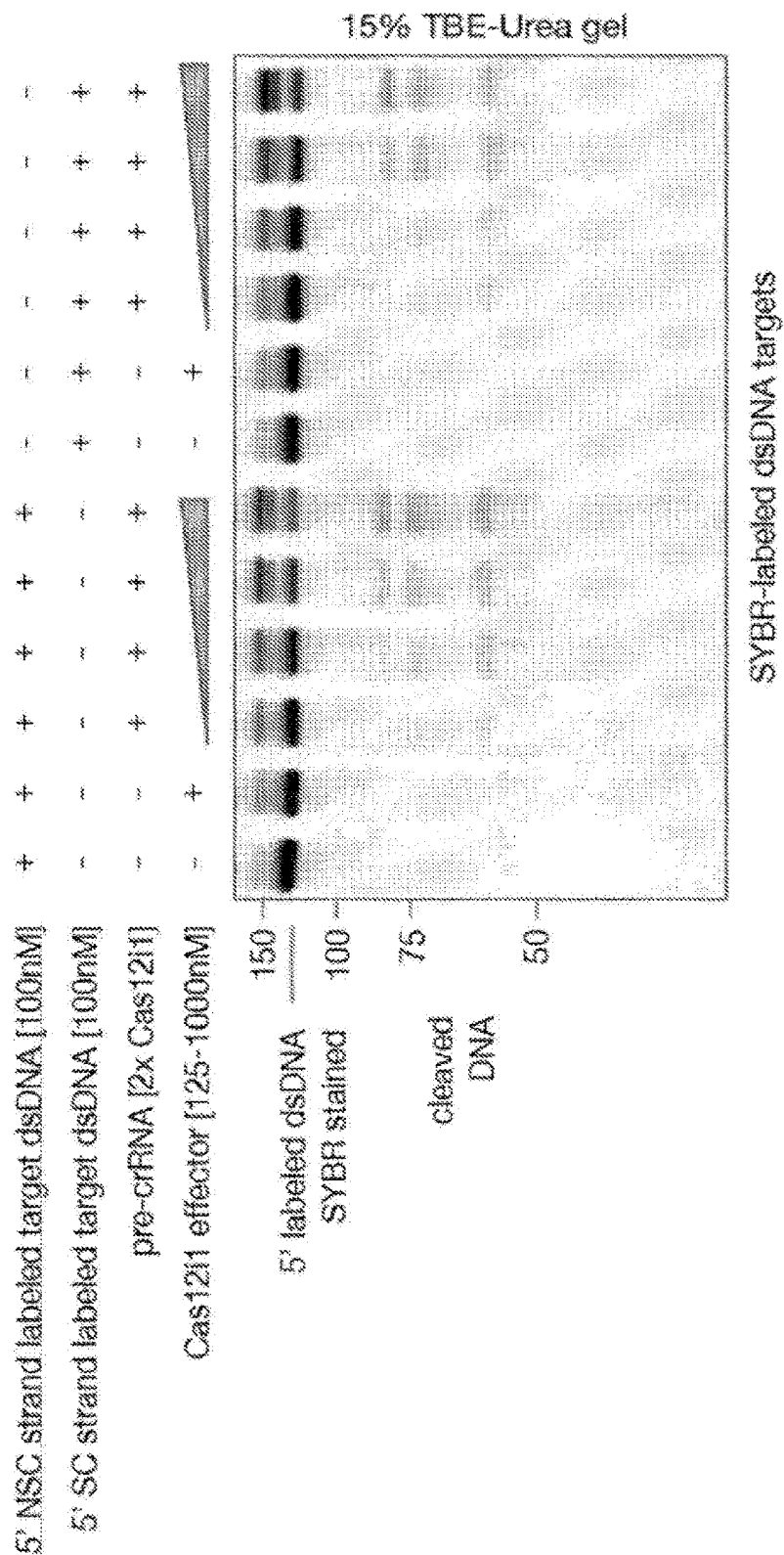

FIGS. 17A and 17B are representations of gels that show the asymmetric cleavage efficiency of dsDNA target strand (spacer complementary; "SC") versus non-target strand (non-spacer complementary; "NSC"). FIG. 17A is a denaturing gel imaged by IR800 (only labeled DNA), while FIG. 17B is a denaturing gel imaged by SYBR stain (total DNA). Each gel depicts cleavage or nicking activity on dsDNA with 5' IR800-labeled NSC strand (left), or 5' IR800-labeled SC strand (right), with increasing concentrations of Cas12i1 binary complex. Cas12i1 binary complex was formed by pre-incubating Cas12i1 with pre-crRNA for 10 minutes at 37° C. prior to adding to the substrates and incubating for 1 hour at 37° C.

Figure 18A:
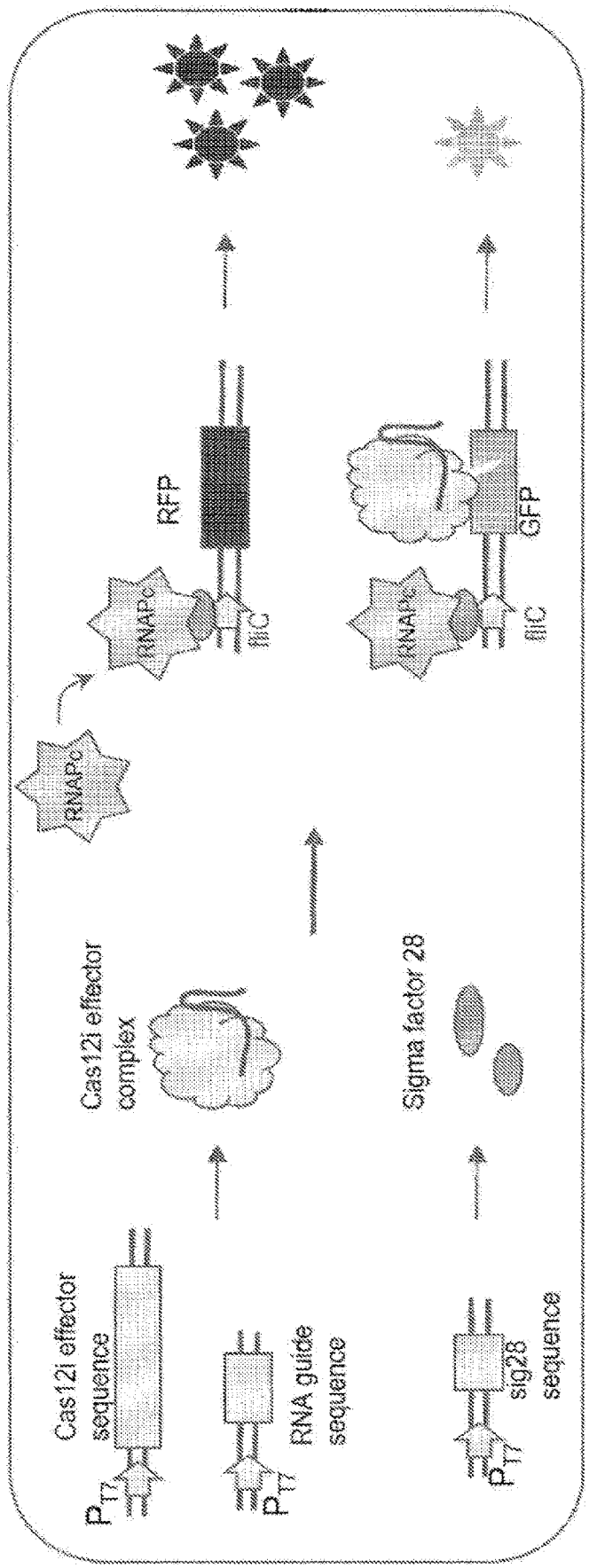

FIG. 18A is a schematic representation of the design of an in vitro assay to detect gene silencing. In a one pot reaction (depicted by the outer boundary), linear DNA templates encoding the Cas12i effector, RNA guide, and sigma factor 28 are combined with a reconstituted IVTT (in vitro transcription and translation) reagent and *E. coli* RNA polymerase core enzyme (denoted by RNAPc). A DNA plasmid encoding GFP targeted by the RNA guide is included, as is a non-target linear DNA template expressing RFP as an internal control. Both GFP and RFP are expressed from the sigma factor 28 promoter (fliC), and the GFP and RFP fluorescence is measured every 5 minutes for up to 12 hours.

Figure 18B:
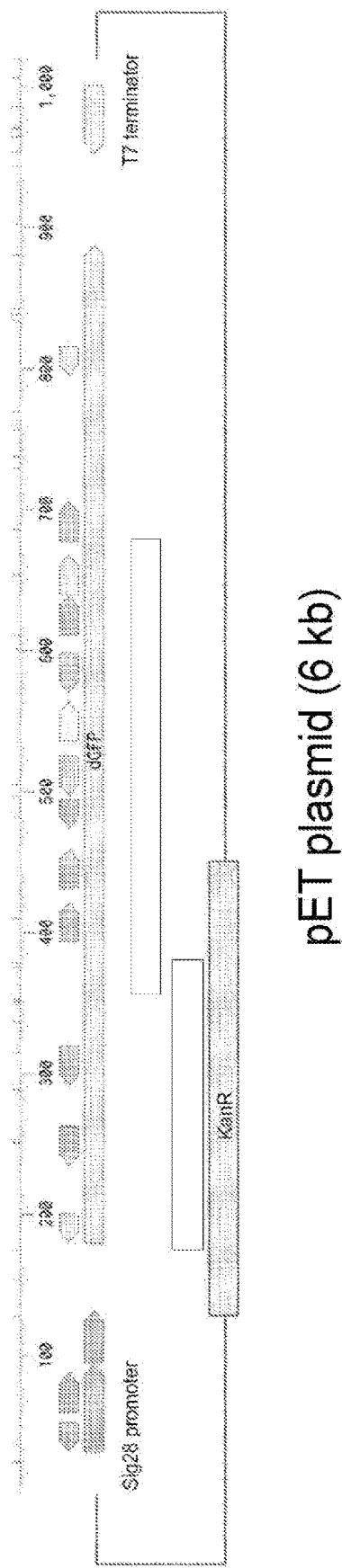

FIG. 18B is a schematic representation of the design of the GFP-encoding plasmid used as a substrate in the in vitro gene silencing assay. The plasmid encodes GFP under the sig28 promoter, and engineered RNA guides are designed to target both strands of the promoter region and the GFP gene (denoted by short chevrons in both orientations).

Figure 19A:
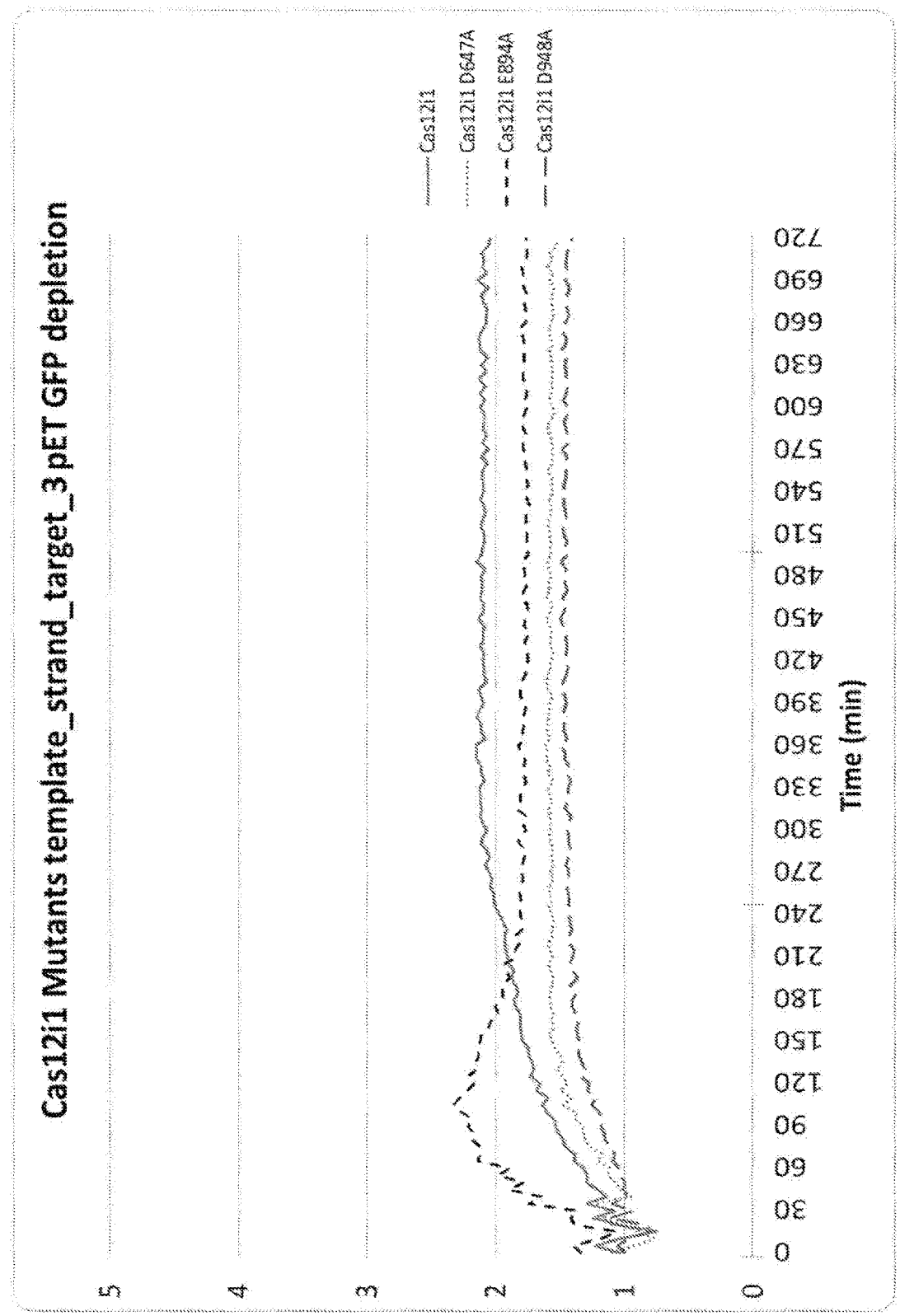
Figure 19B:
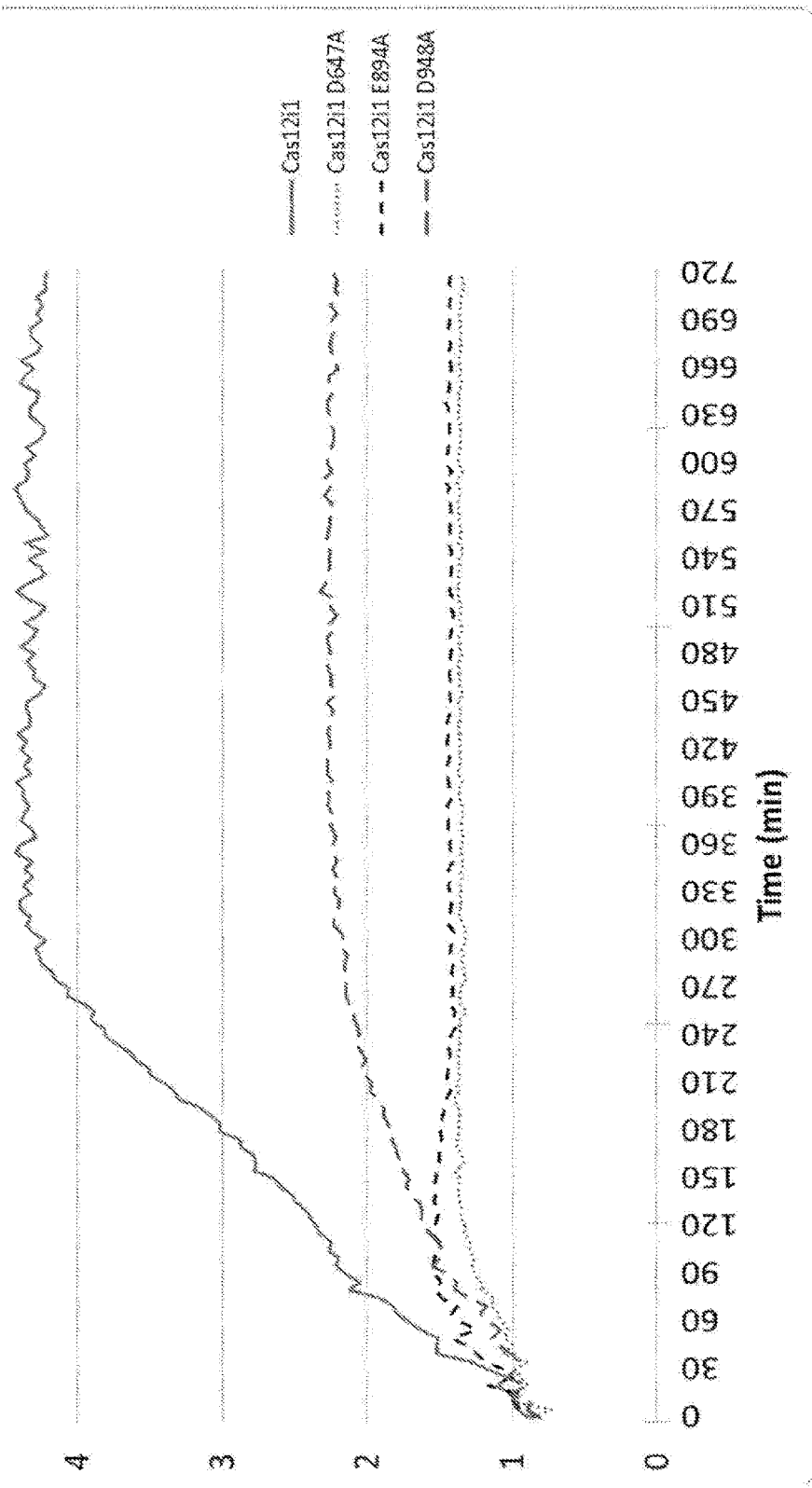

FIGS. 19A and 19B are graphs that show the GFP fluorescence fold depletion (y-axis) over 12 hours (720 minutes, x-axis) with the Type V-I effector as indicated in a complex with a guide containing a sequence complementary to the template strand (FIG. 19A) and coding strand (FIG. 19B) of the substrate GFP-coding region. GFP fluorescence fold depletion is calculated as the ratio of the normalized GFP fluorescence with the Type V-I effector in a complex with a non-target RNA guide over that of the Type V-I effector in a complex with a GFP-targeting RNA guide. Cas12i1 (solid line) shows greater depletion (gene silencing) compared to the activity of each of the mutant forms Cas12i1 D647A or Cas12i1 E894A or Cas12i1 D948A.

Figure 20:
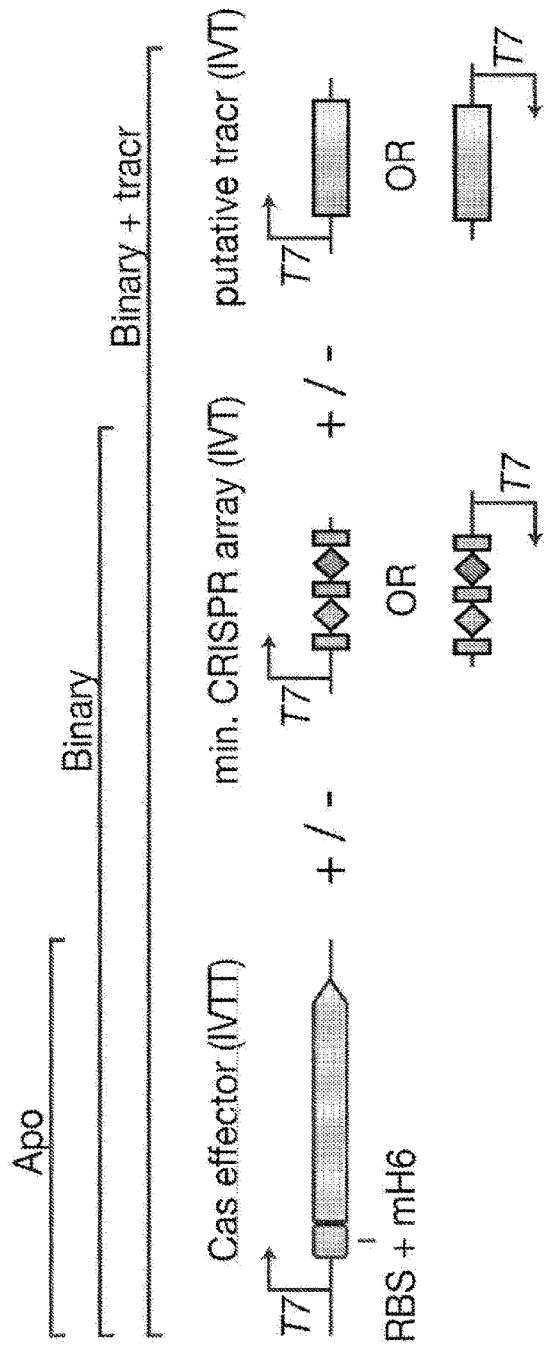

FIG. 20 shows the different forms of protein and/or RNAs in the in vitro reconstitution of the CRISPR-Cas system used in in vitro pooled screening. Transcriptional directions are indicated by the orientation of the T7 promoter arrow.

Figure 21:
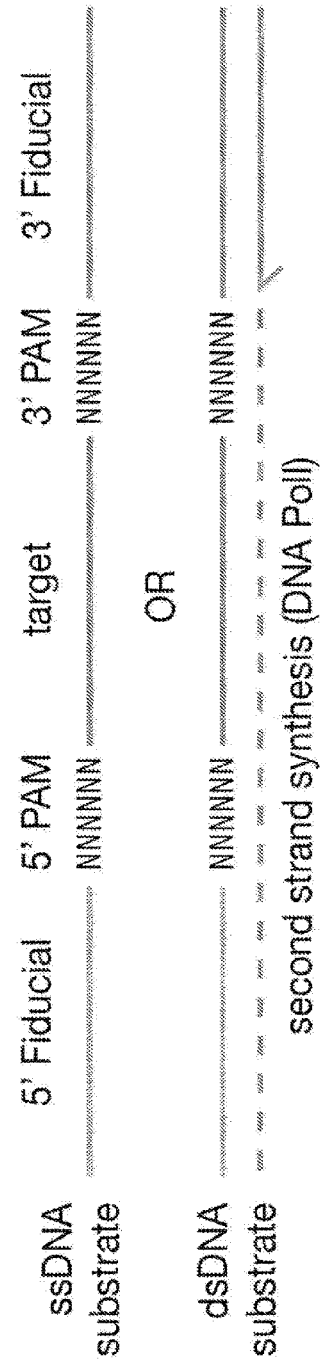

FIG. 21 shows one embodiment of the ssDNA and dsDNA substrates for in vitro pooled screening. The target sequence is flanked by 6 degenerate bases ("N") on both the 5' and 3' side, which are adjacent to a common region used as a fiducial mark for downstream data analysis following next generation sequencing. In the dsDNA substrate, the second strand synthesis is completed using a DNA polymerase I fill-in after annealing a primer to the 3' fiducial mark.

Figure 22:
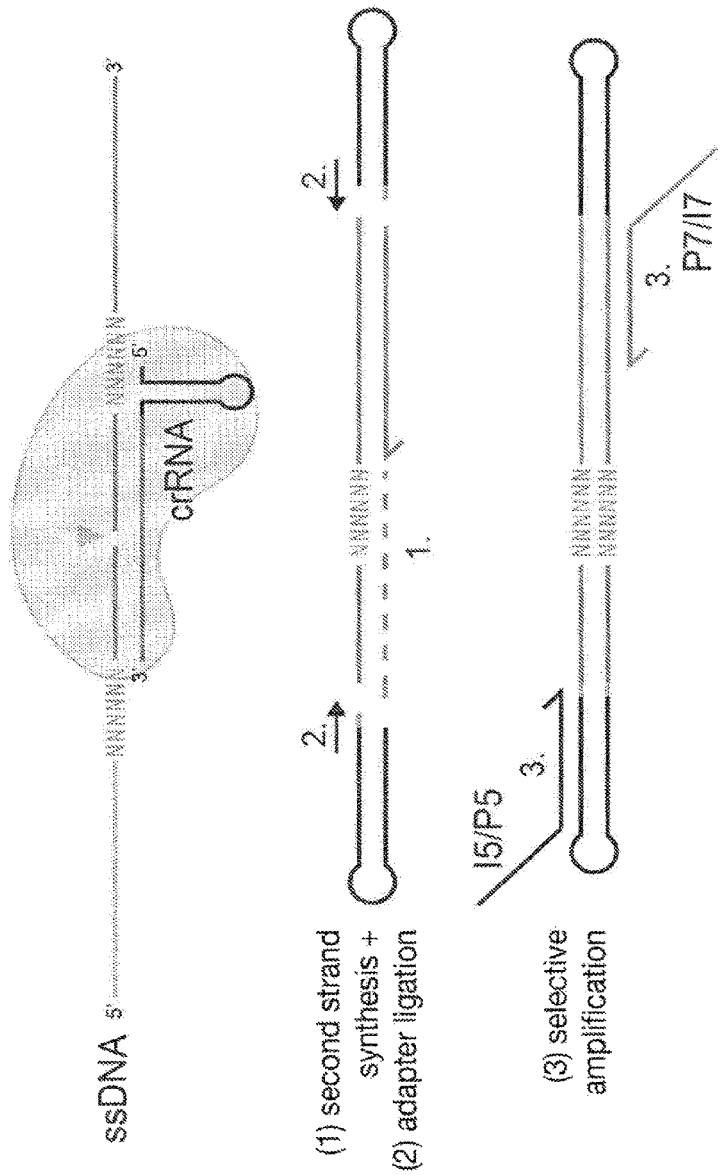

FIG. 22 displays a schematic of the unidirectional sequencing library preparation of the ssDNA fragments post incubation with the reconstituted CRISPR-Cas system.

Figure 23:
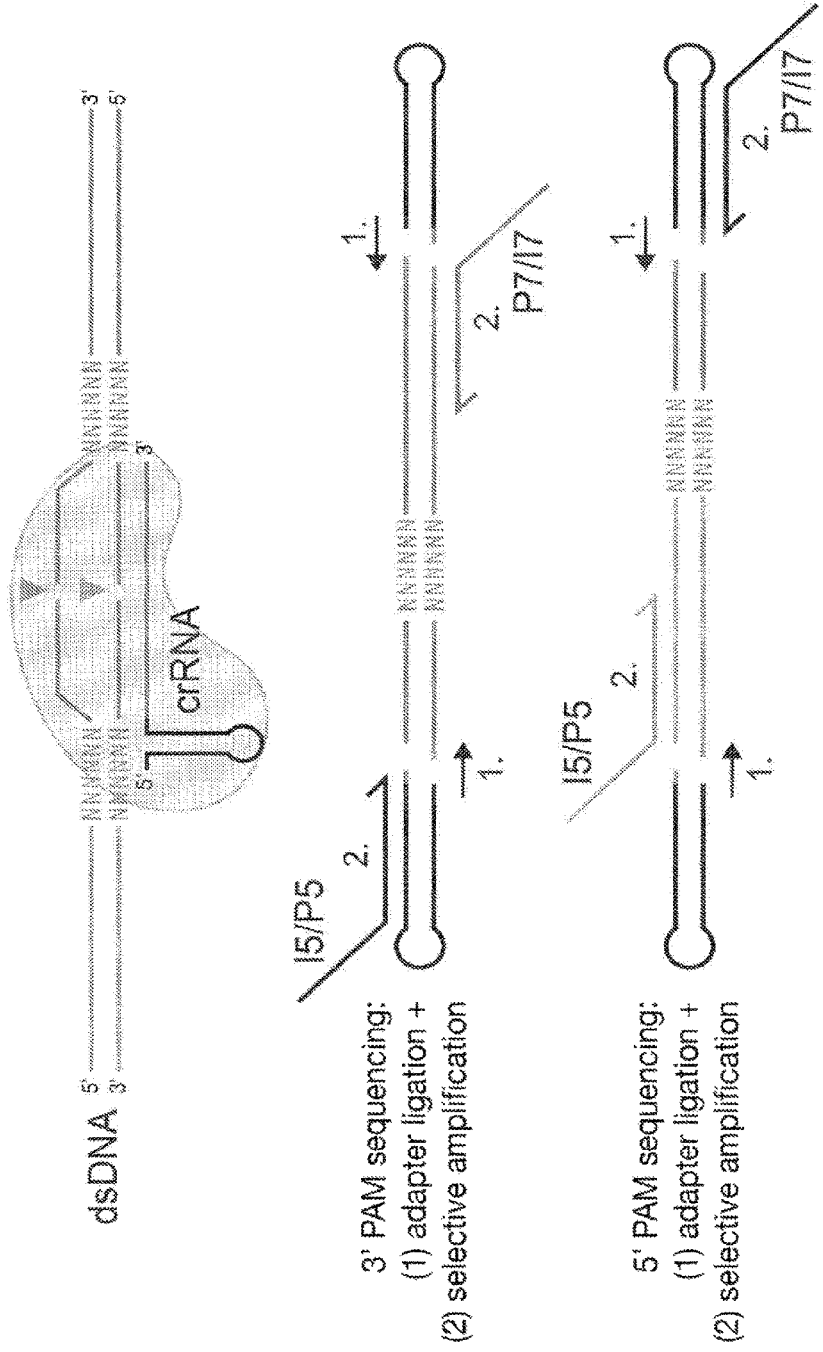

FIG. 23 displays a schematic of the bidirectional sequencing library preparation possible with the dsDNA fragments post incubation with the reconstituted CRISPR-Cas systems. The sequencing adaptor can be ligated to both cut fragments, and then selected for using a combination of primers common to the adaptor and common to the dsDNA substrate.

Figure 24A:
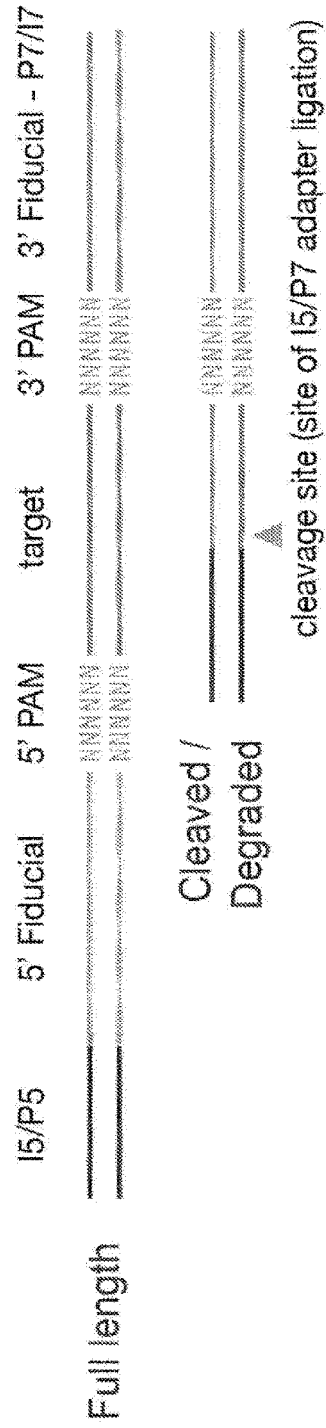
Figure 24B:
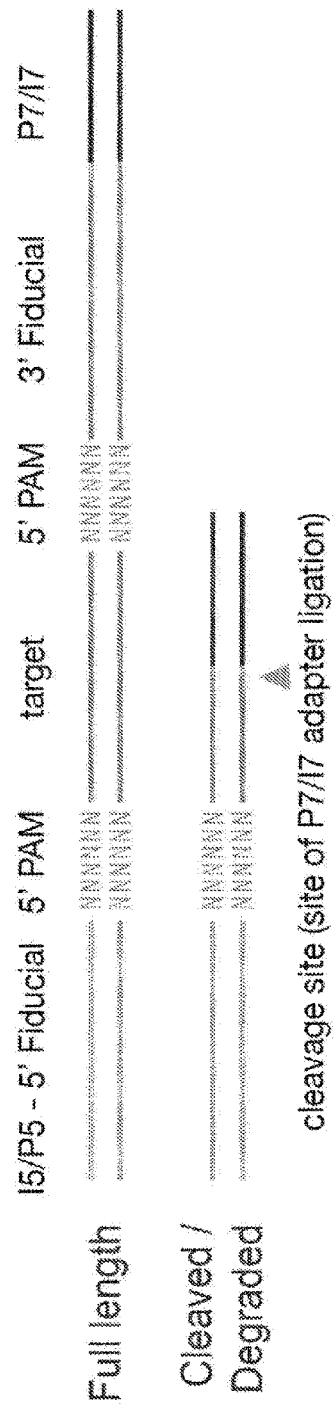

FIGS. 24A-B show the forms of the full length and cleaved products captured by the next generation sequencing library preparation and readout using A) I5/P5 ligation adapter and 3' fiducial for targeted amplification and addition of I7/P7, or B) I7/P7 ligation adapter and 5' fiducial for targeted amplification and addition of I5/P5.

Figure 25A:
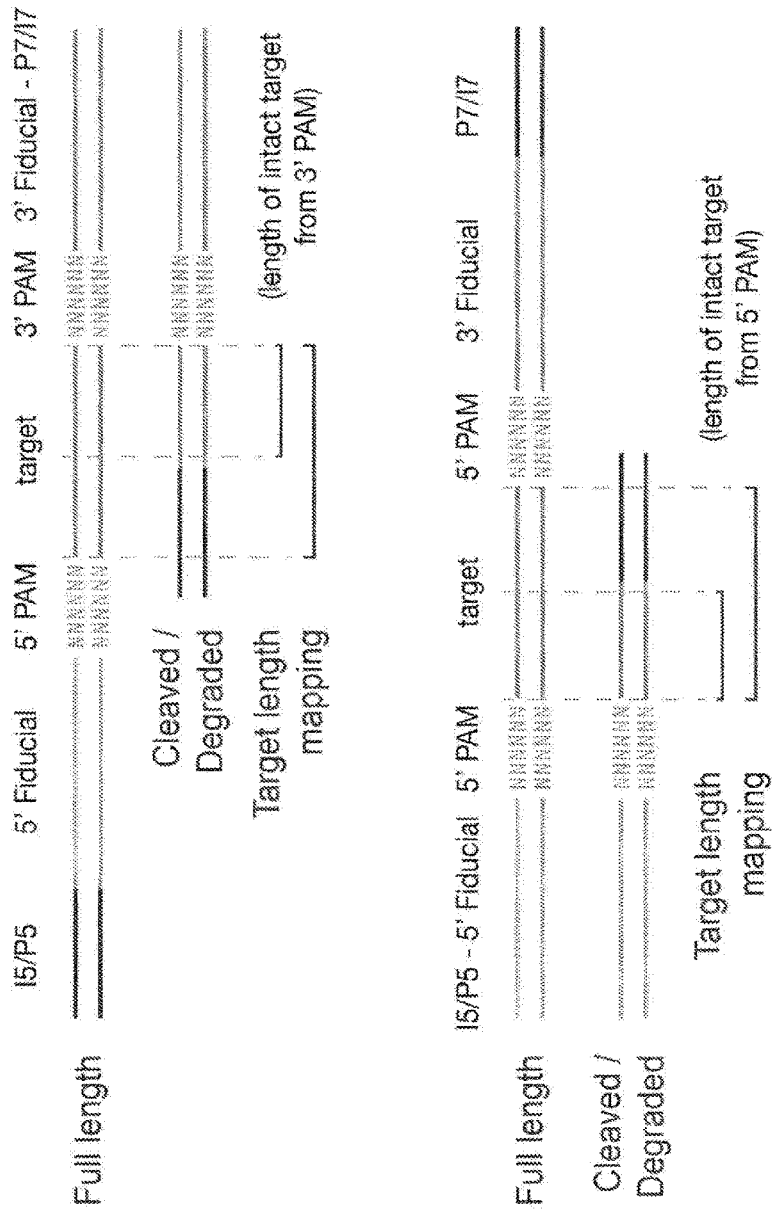
Figure 25B:
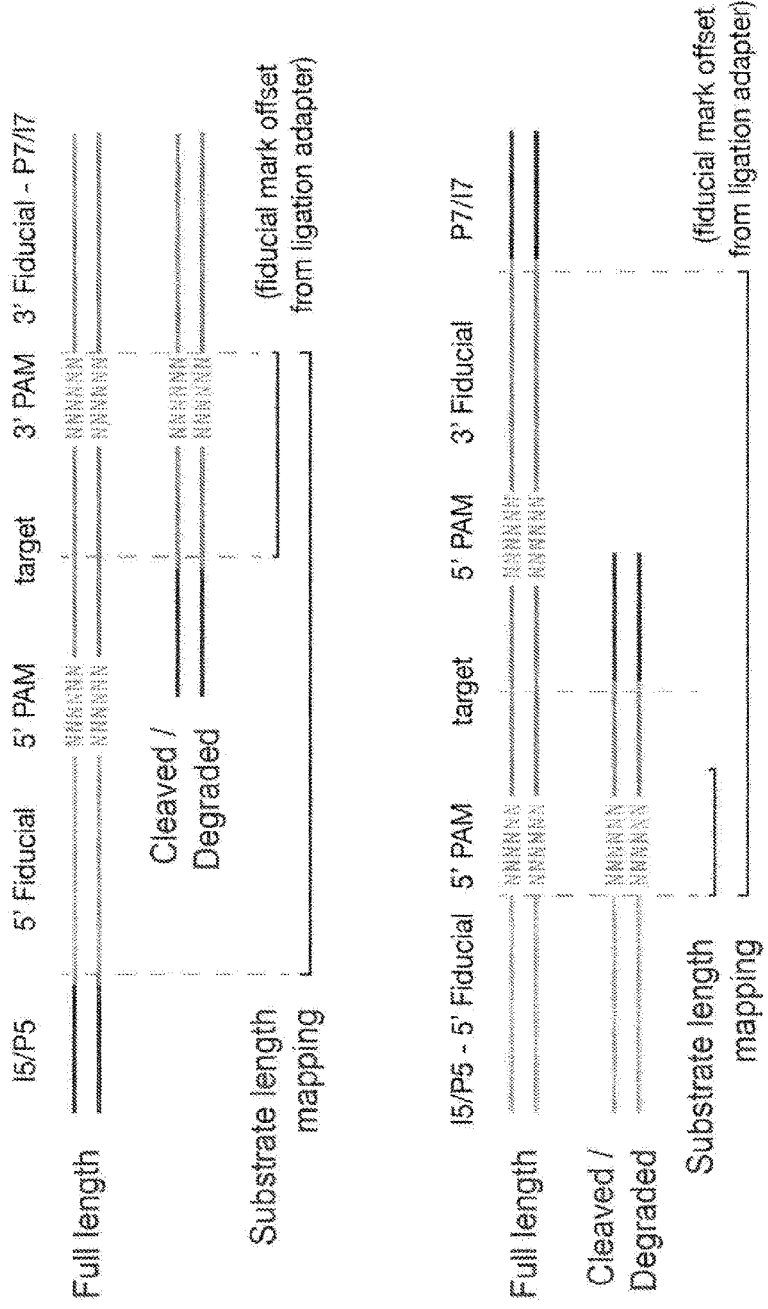

FIGS. 25A-B show a schematic for A) ssDNA target length mapping and B) substrate length mapping, respectively.

Figure 26A:
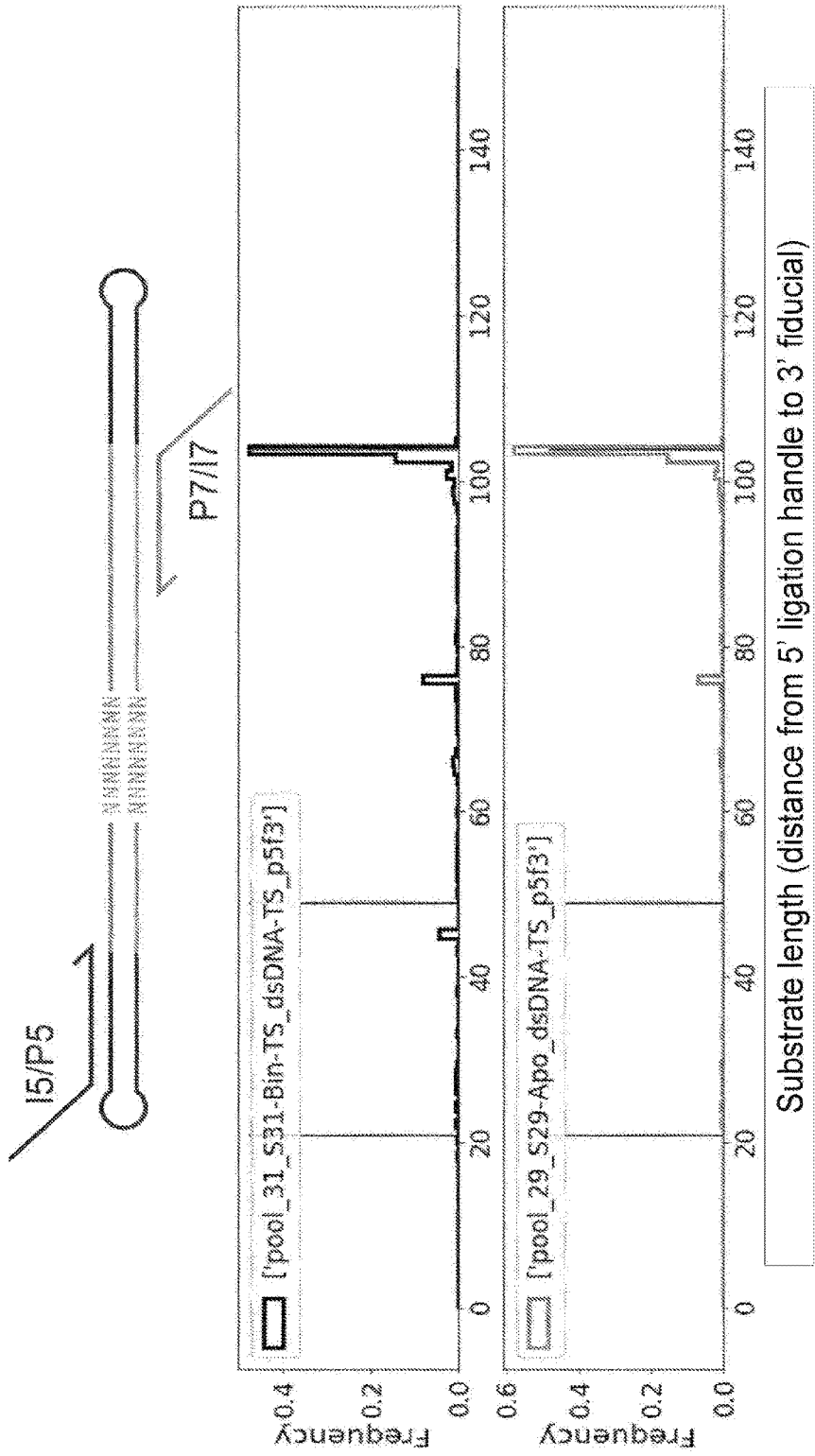
Figure 26B:
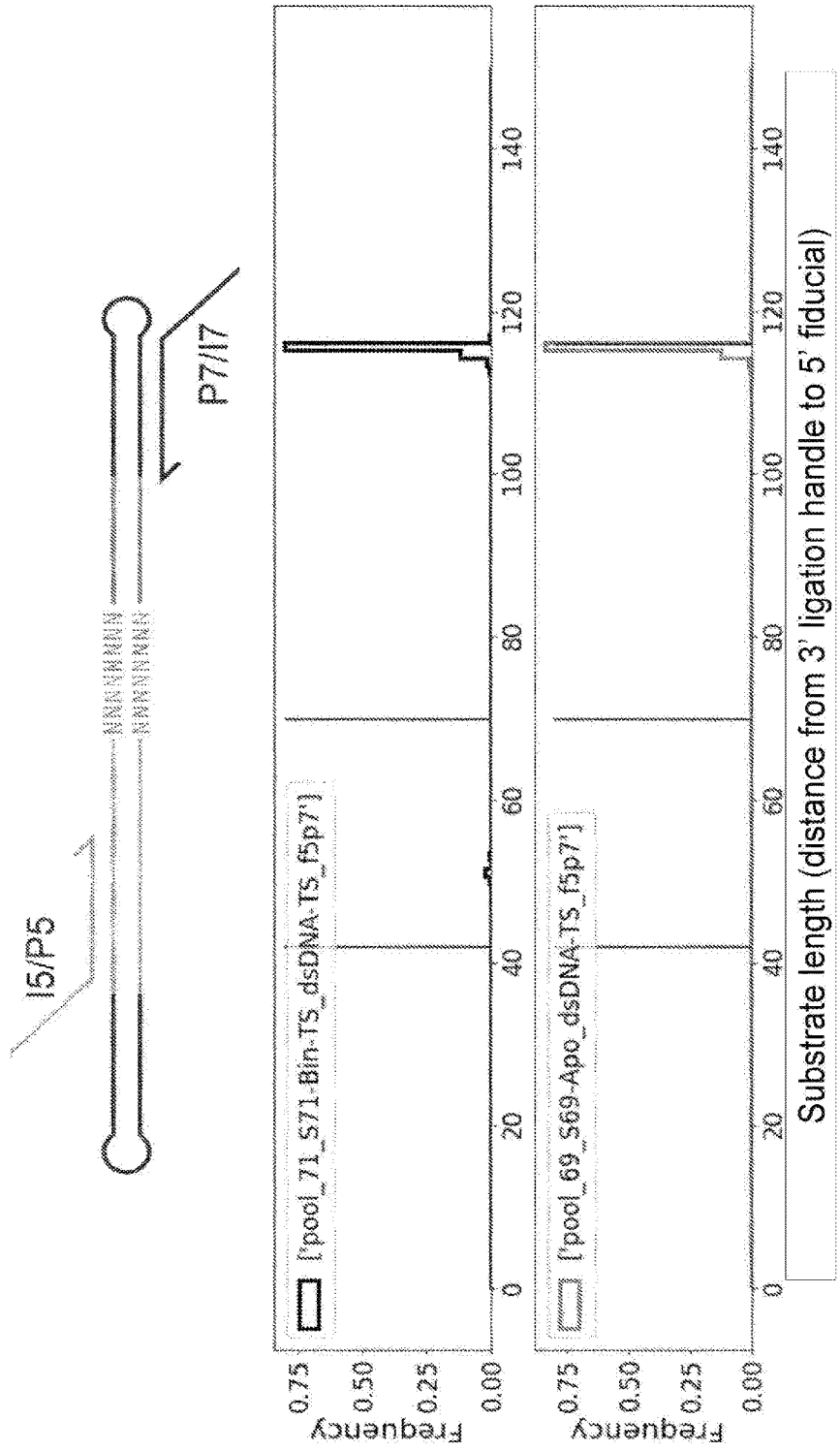

FIGS. 26A-B show the distribution of dsDNA substrate lengths for IVTT-expressed Cas12i1 in complex with a top-strand (active orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 27A:
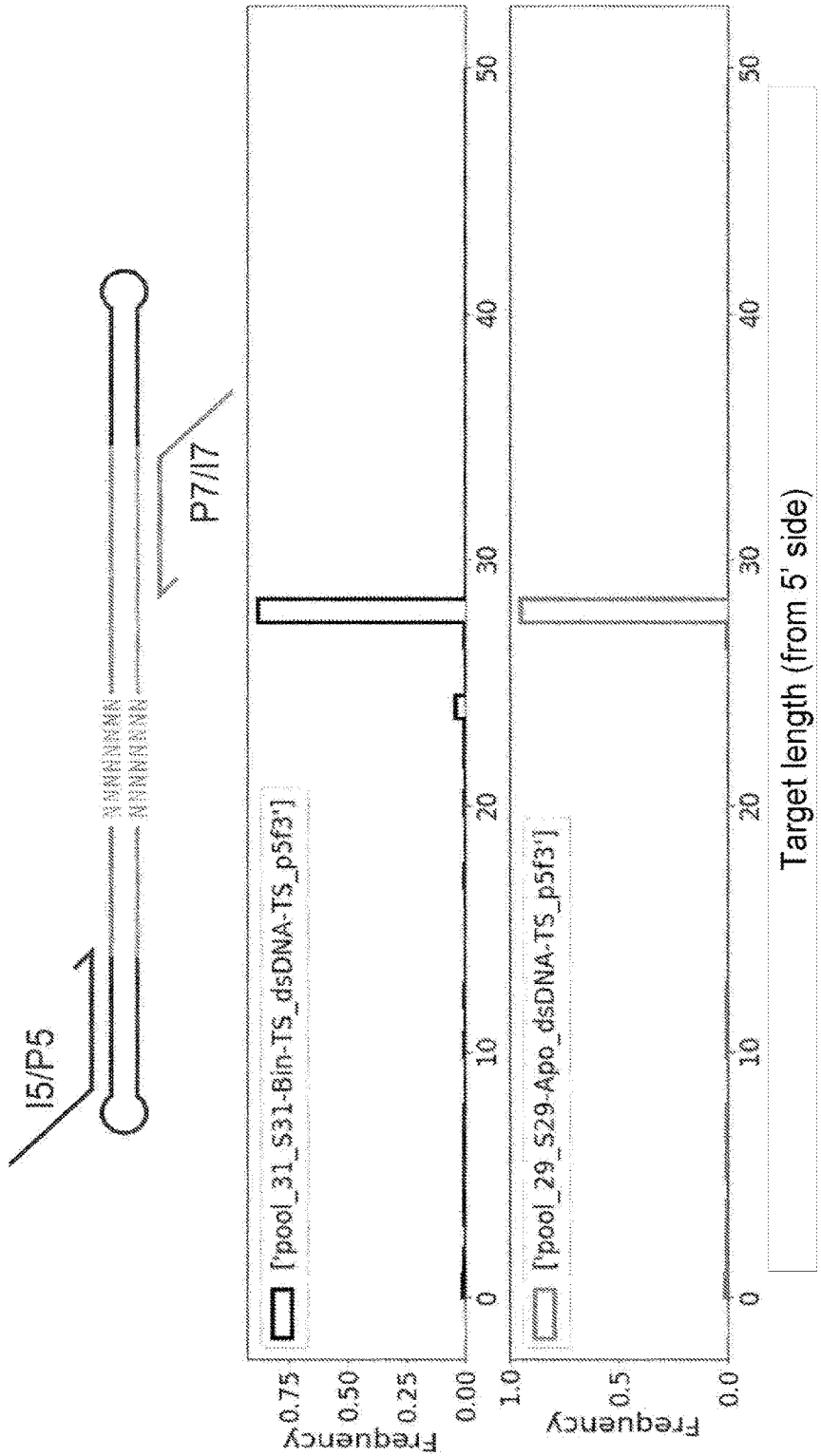
Figure 27B:
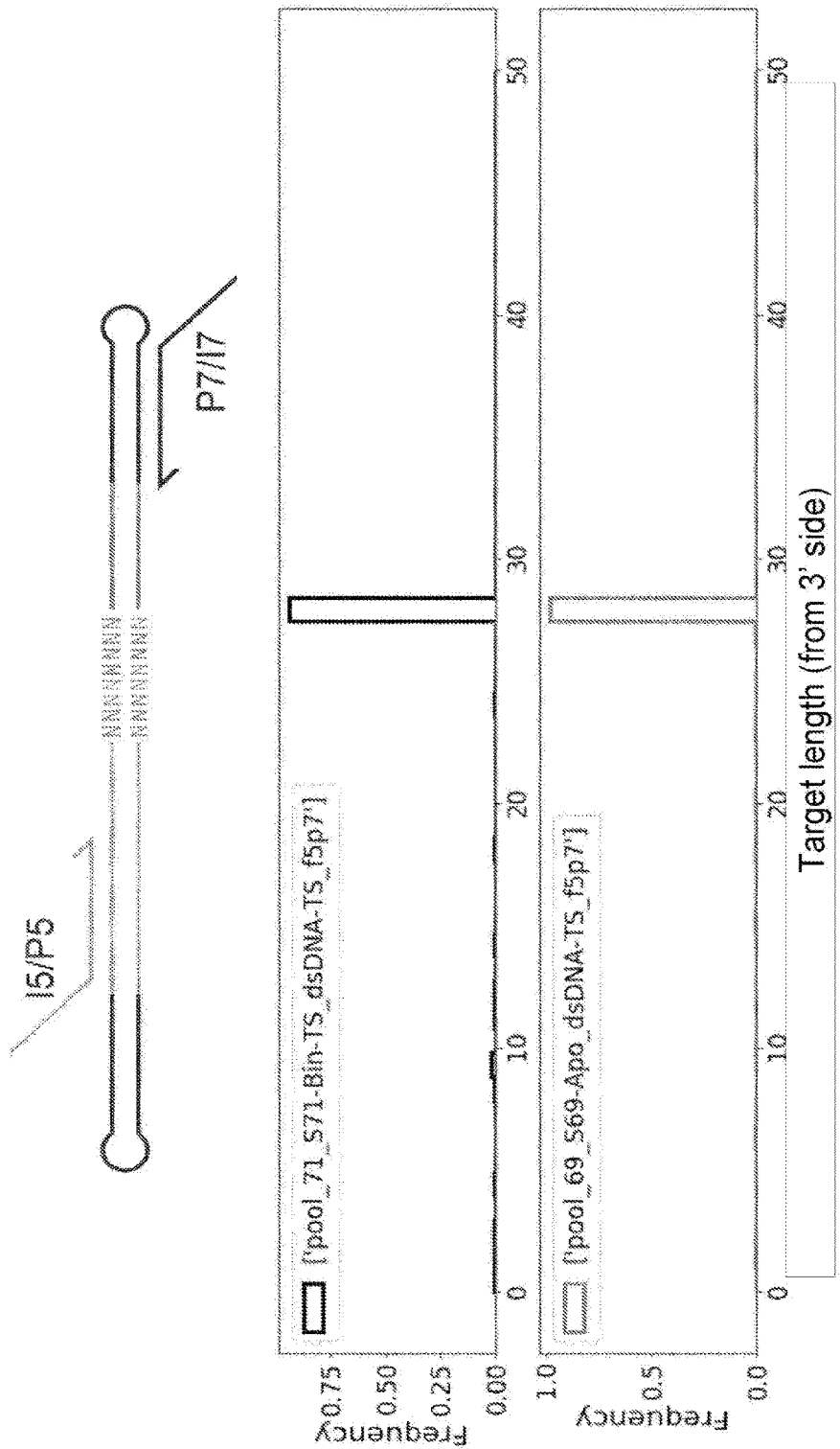

FIGS. 27A-B show the distribution of dsDNA target lengths for IVTT-expressed Cas12i1 in complex with a top-strand (active orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 28A:
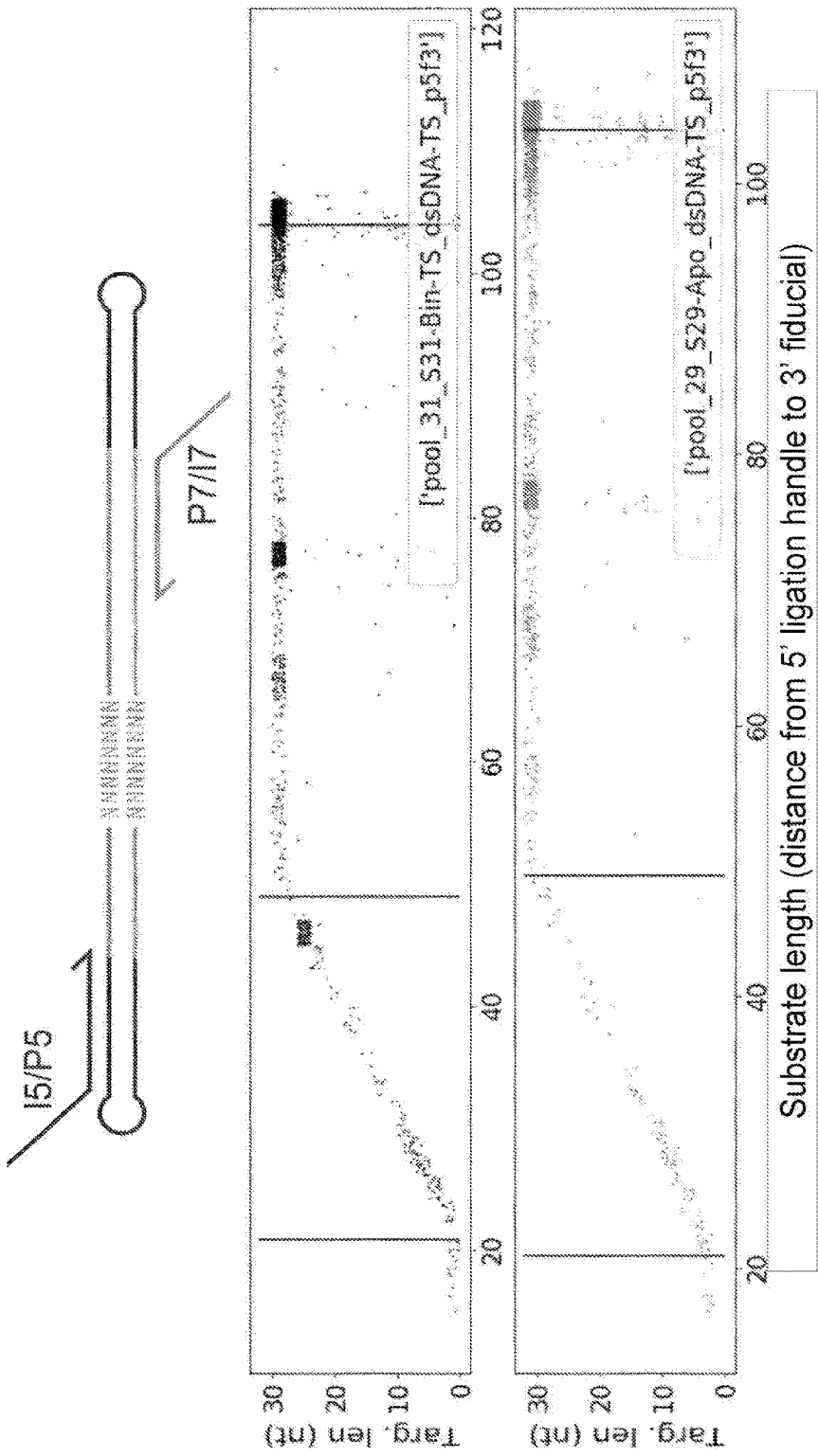
Figure 28B:
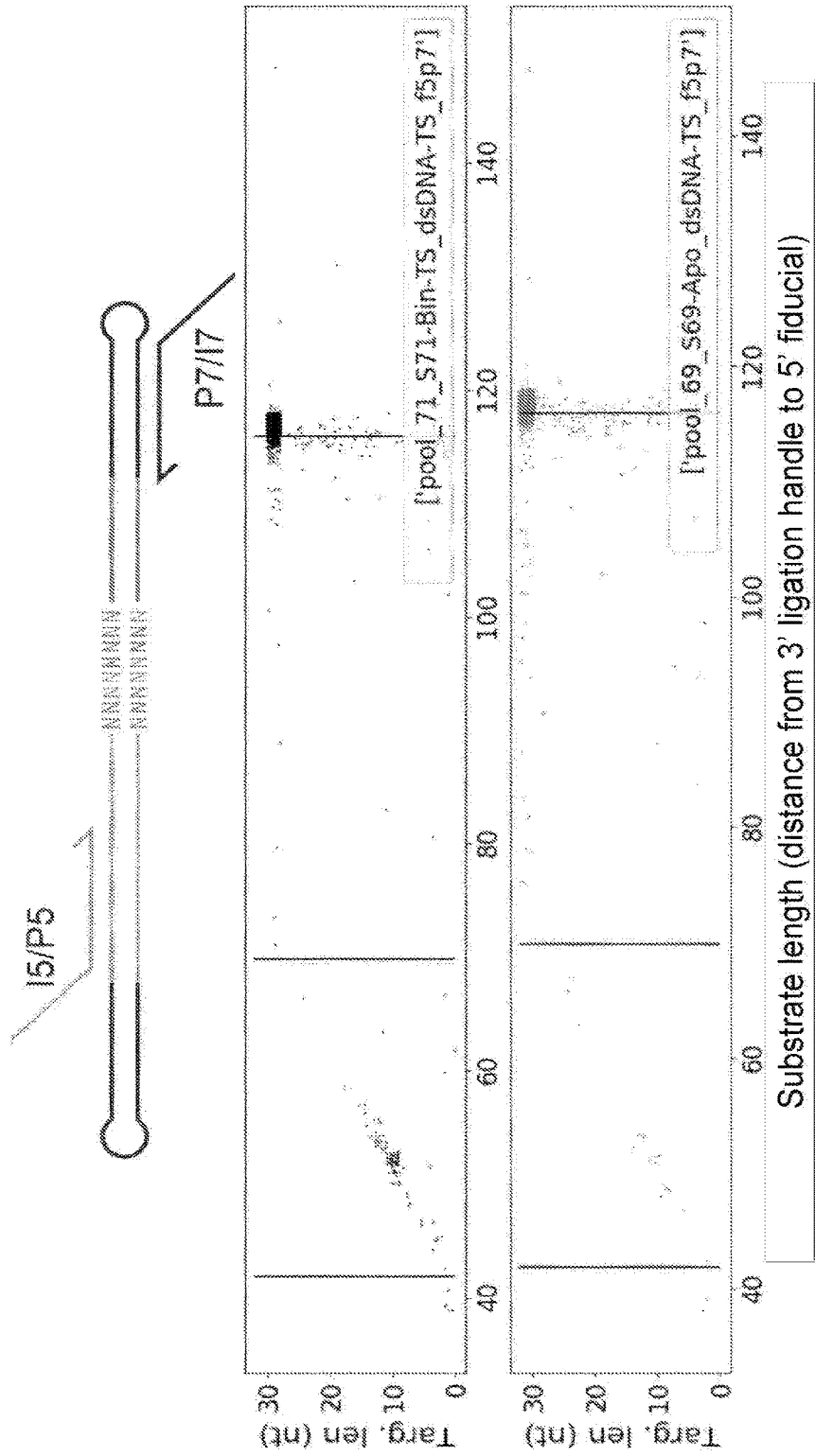

FIGS. 28A-B show the distribution of dsDNA substrate lengths (X) vs target lengths (Y) for IVTT-expressed Cas12i1 in complex with a top-strand (active orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 29:
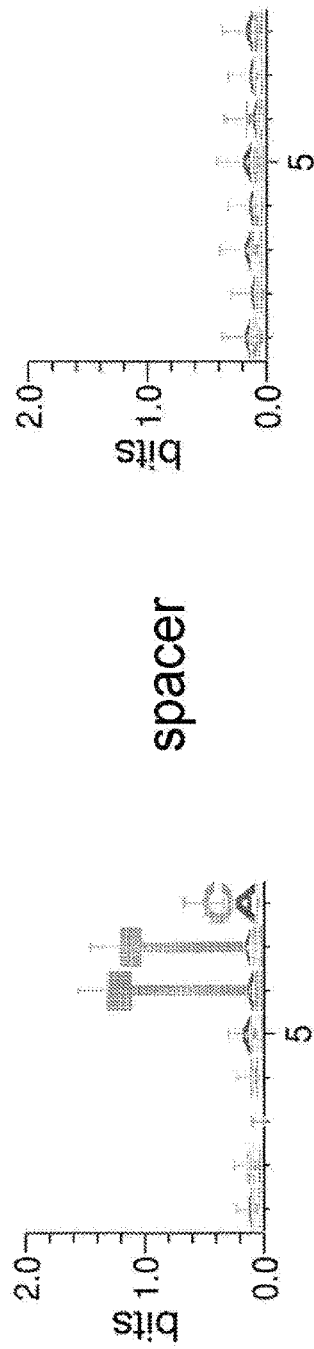

FIG. 29 shows a weblogo indicating a 5' TTN PAM R motif (left of the target sequence) for Cas12i1 associated with non-target strand cleavage between the +24/+25 nucleotides relative to the PAM. No PAM sequence requirement is observed on the right side of the Cas12i1 target.

Figure 30:
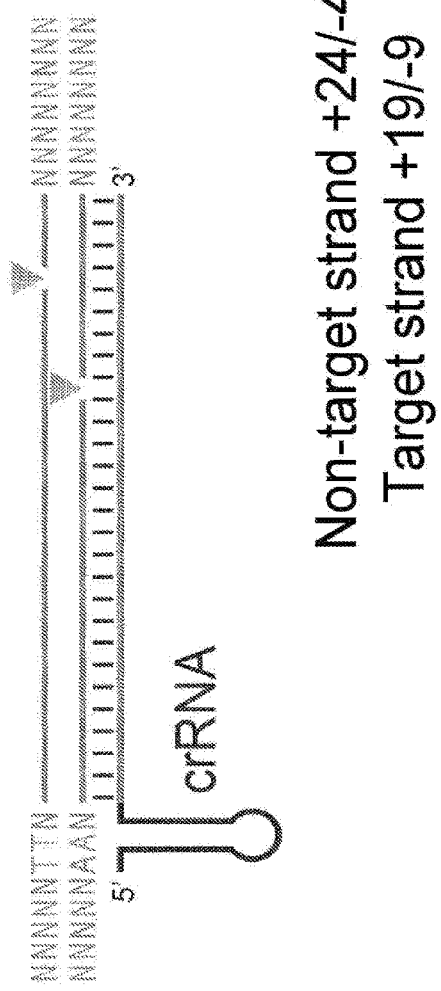

FIG. 30 shows a 5nt 3' overhang associated with double stranded DNA cleavage by Cas12i1 indicated by cleavage observed between the +24/+25 nucleotides of the non-target strand relative to the PAM and cleavage between the +19/+20 nucleotides of the target strand relative to the PAM.

Figure 31A:
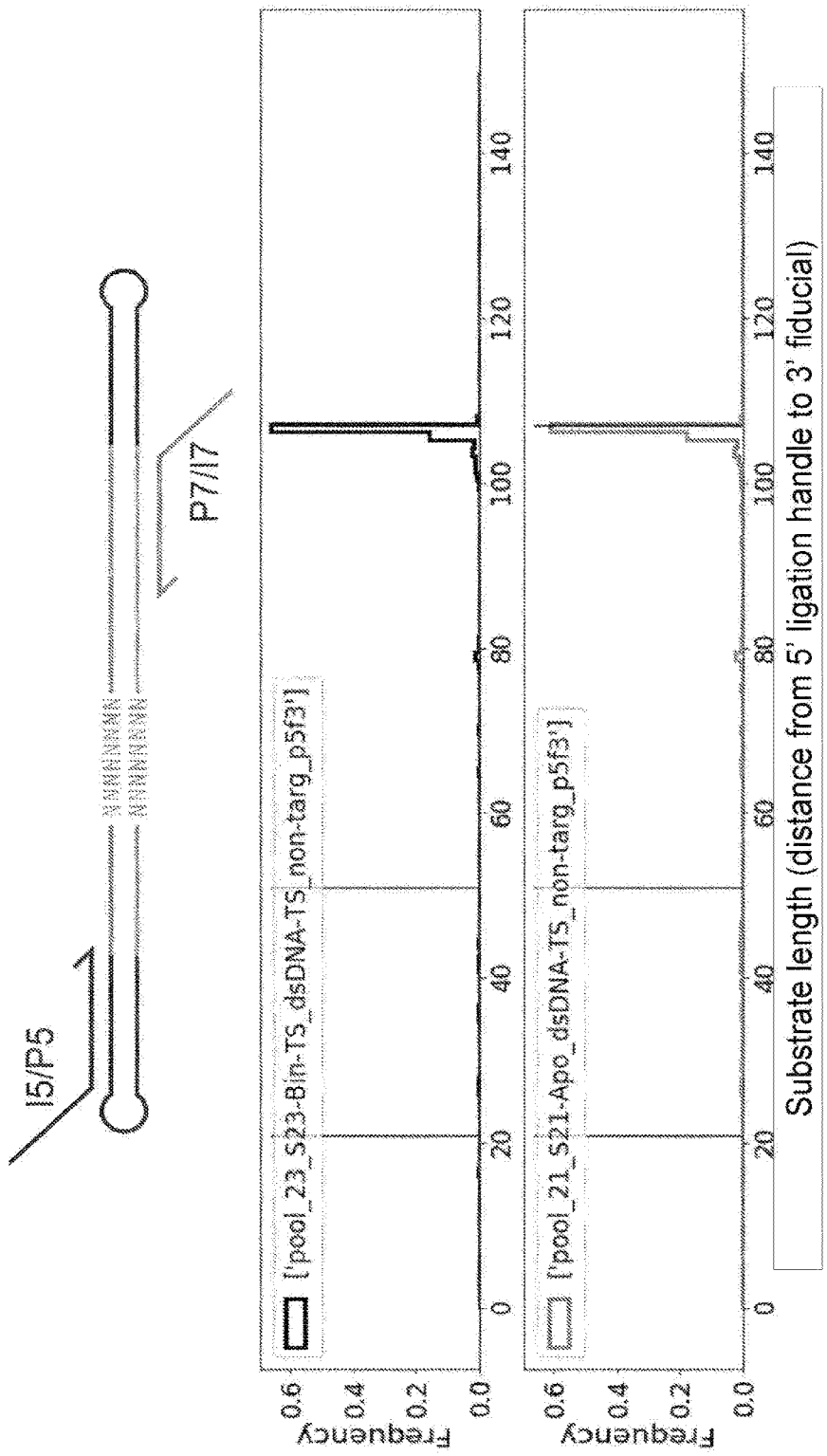
Figure 31B:
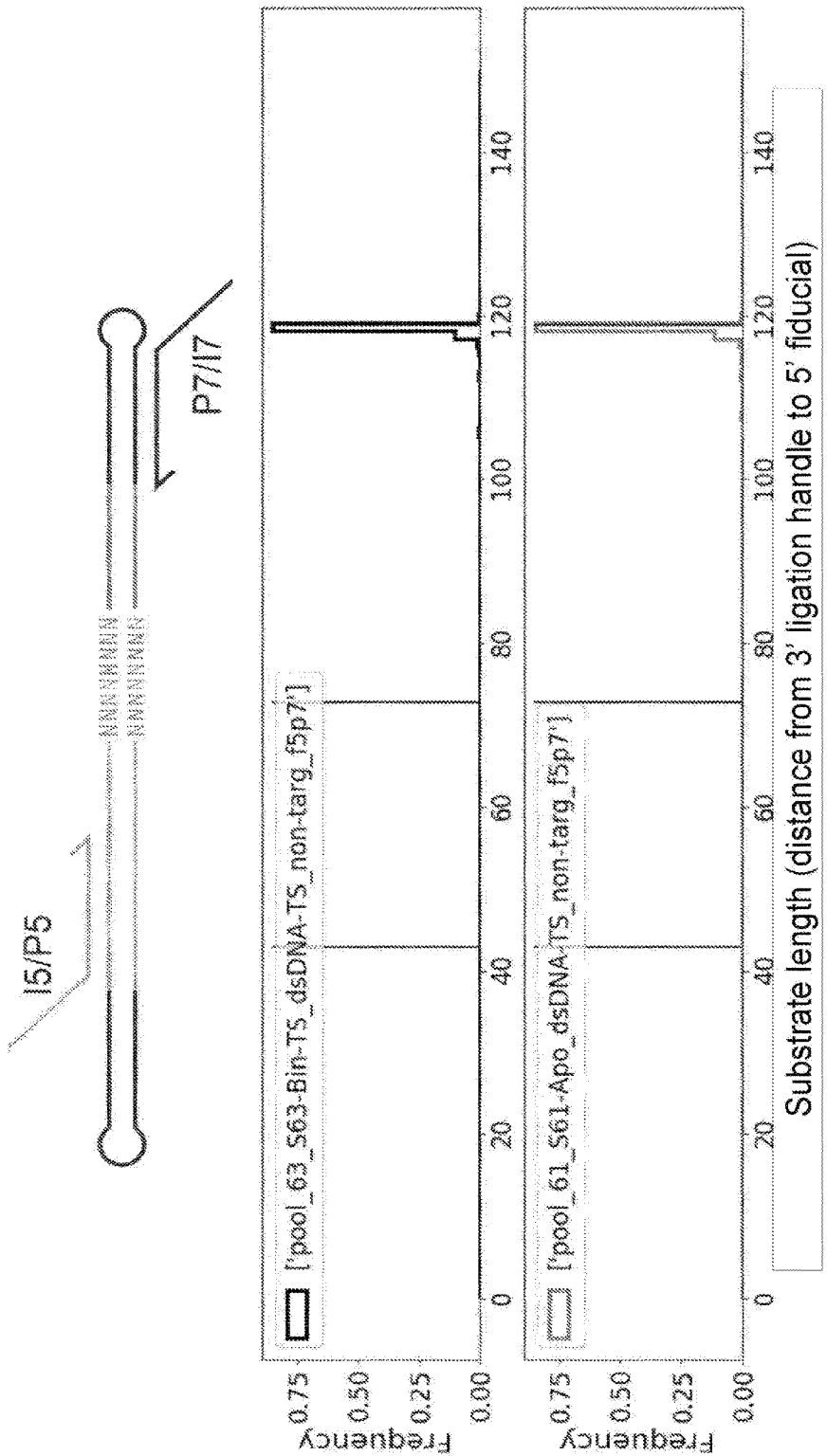

FIGS. 31A-B show the distribution of dsDNA substrate lengths for IVTT-expressed Cas12i1 in complex with a non-target crRNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 32A:
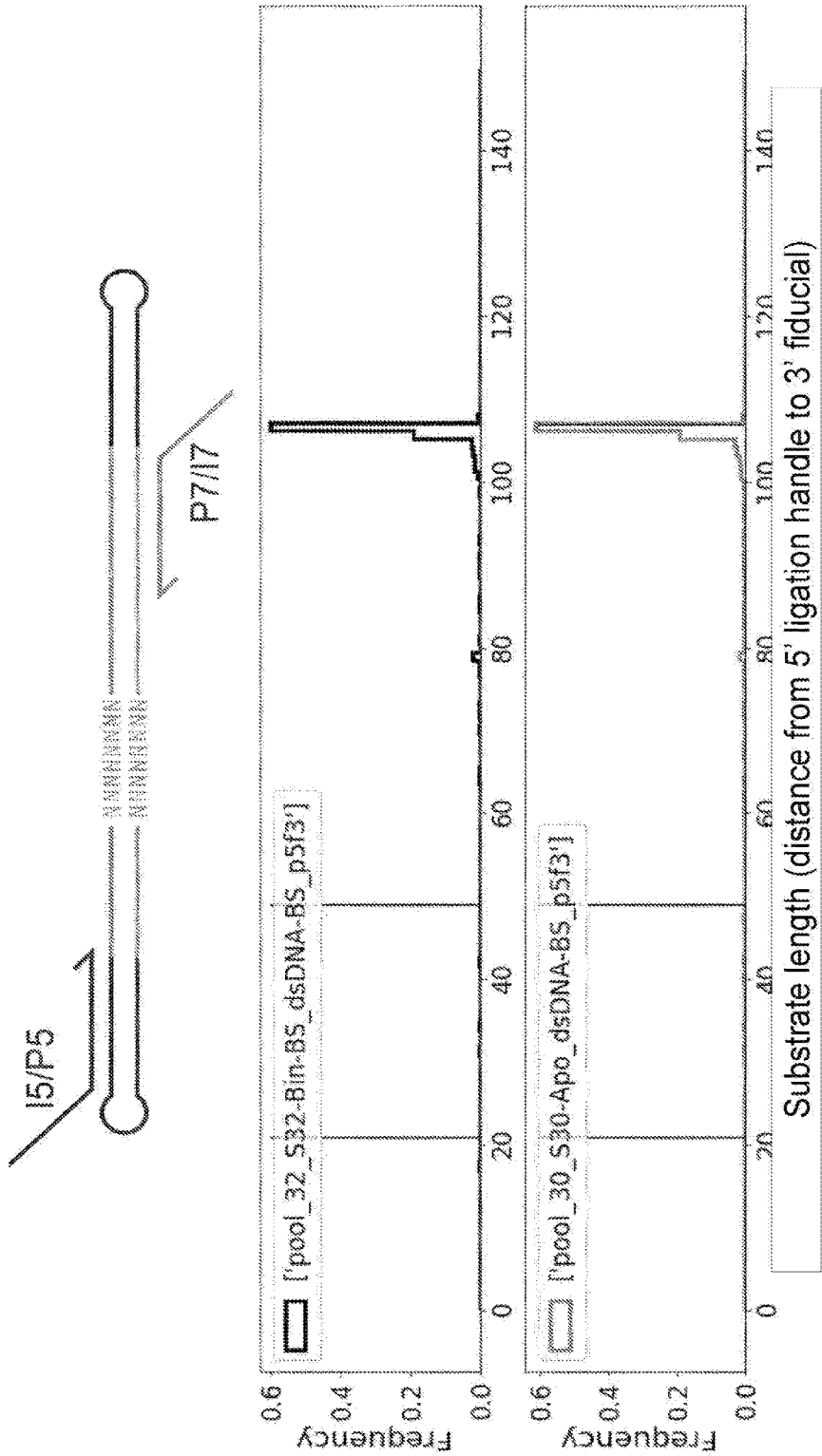
Figure 32B:
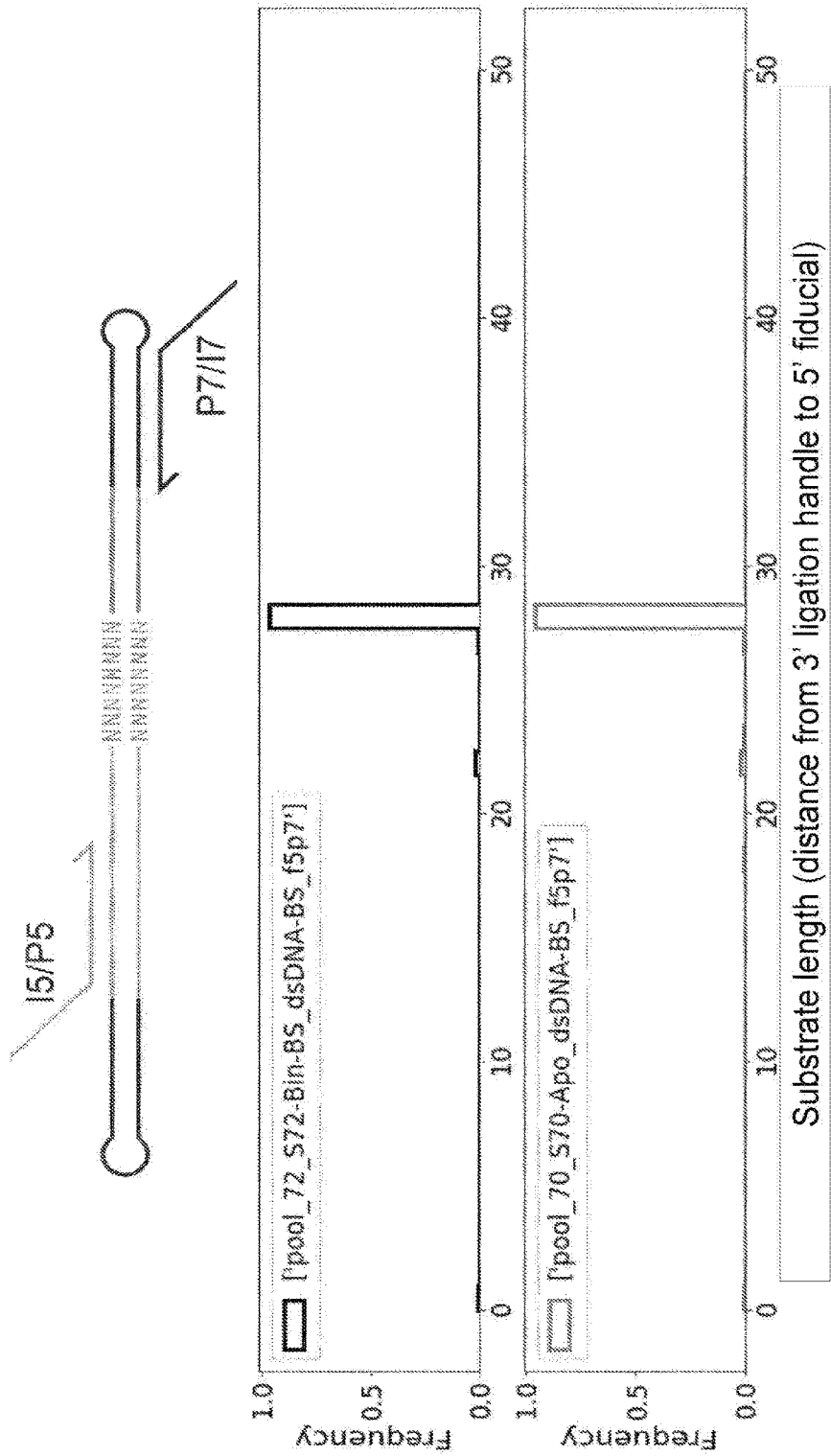

FIGS. 32A-B show the distribution of dsDNA substrate lengths for IVTT-expressed Cas12i1 in complex with a bottom-strand (inactive orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 33A:
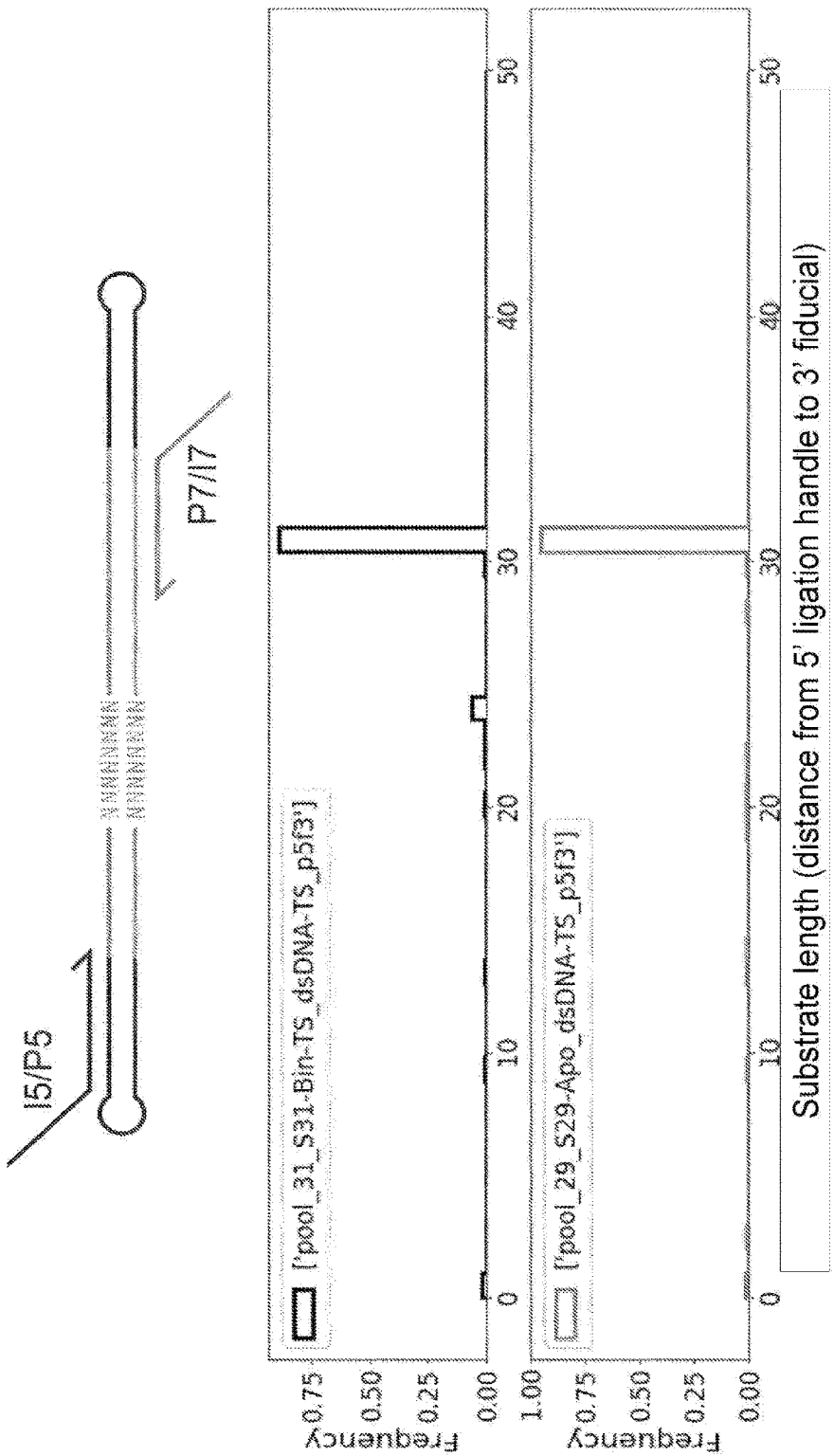
Figure 33B:
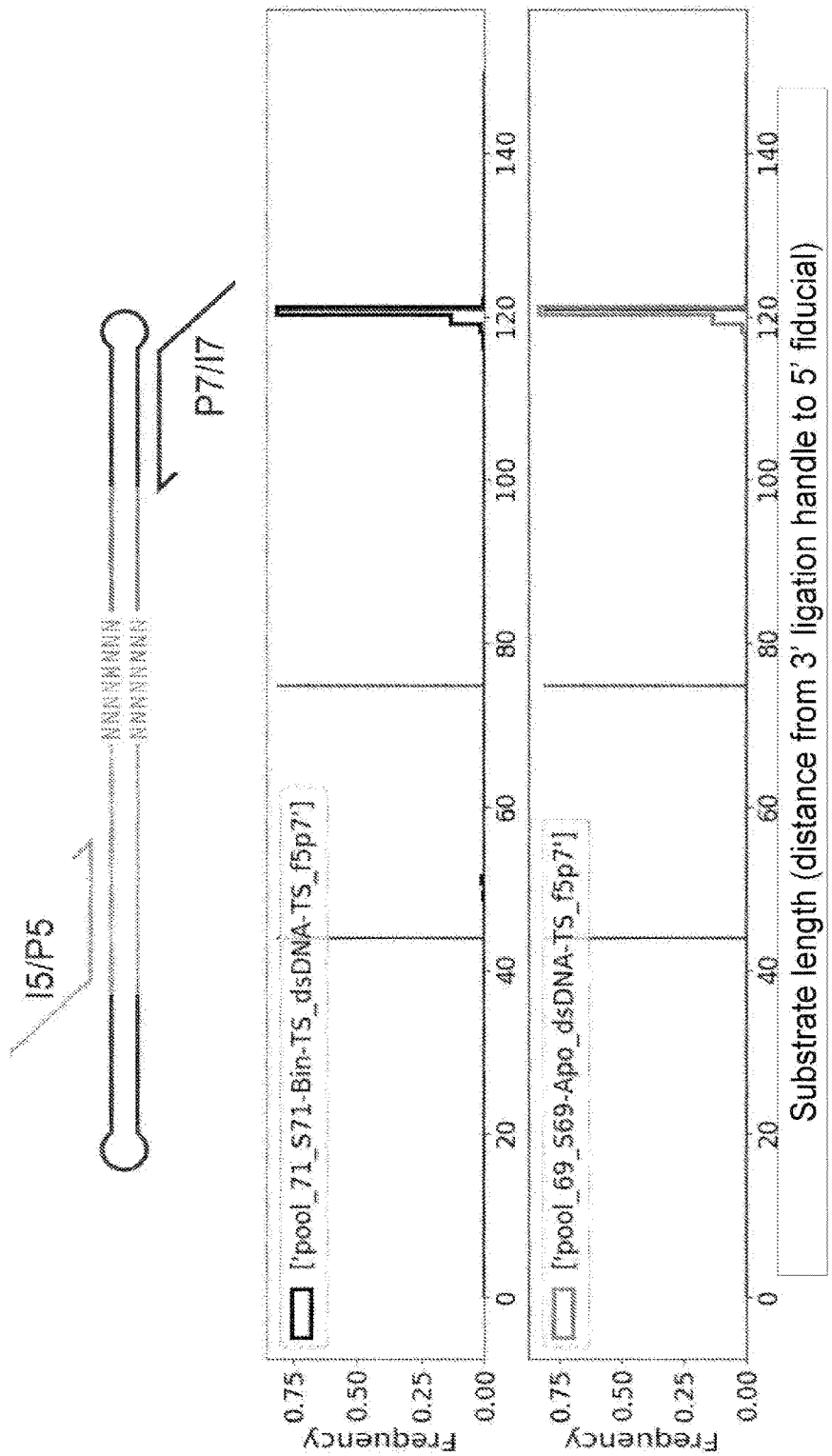

FIGS. 33A-B show the distribution of dsDNA substrate lengths for IVTT-expressed Cas12i2 in complex with a top-strand (active orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 34A:
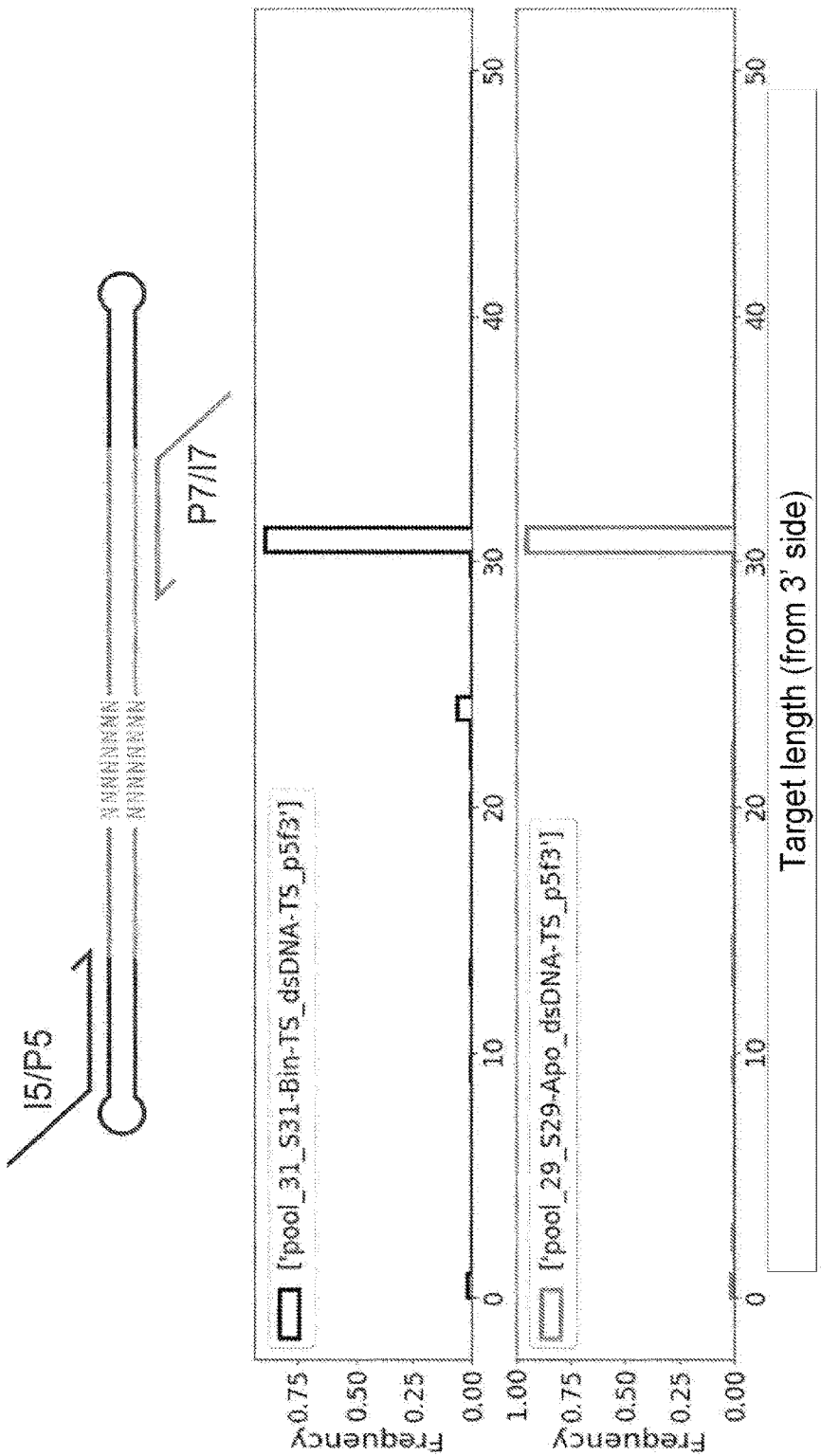
Figure 34B:
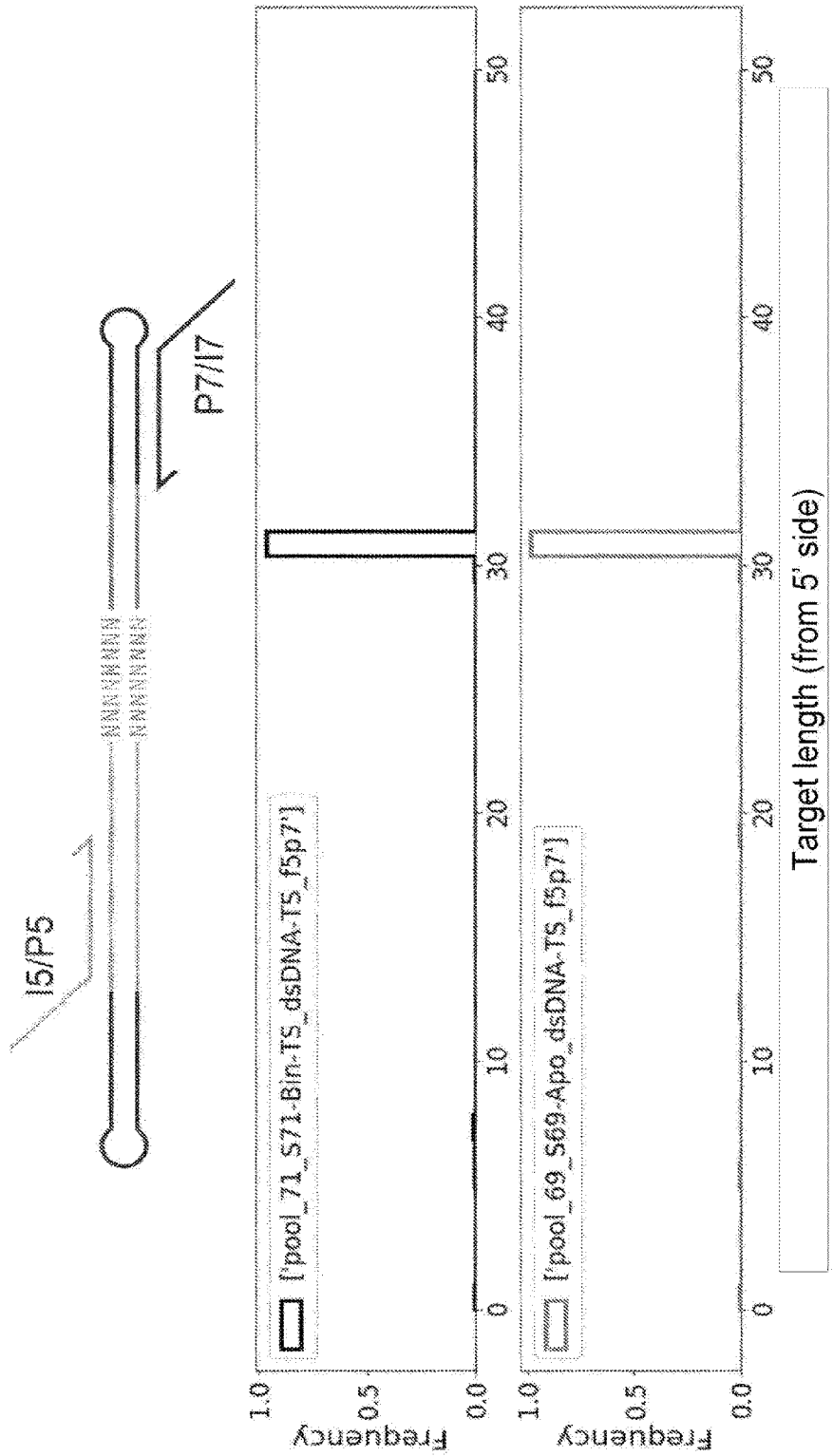

FIGS. 34A-B show the distribution of dsDNA target lengths for IVTT-expressed Cas12i2 in complex with a top-strand (active orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 35A:
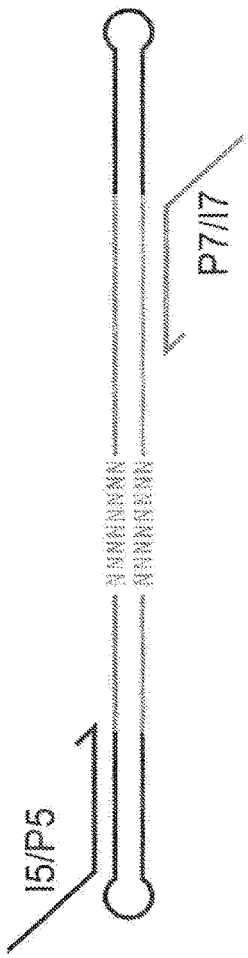
Figure 35A:
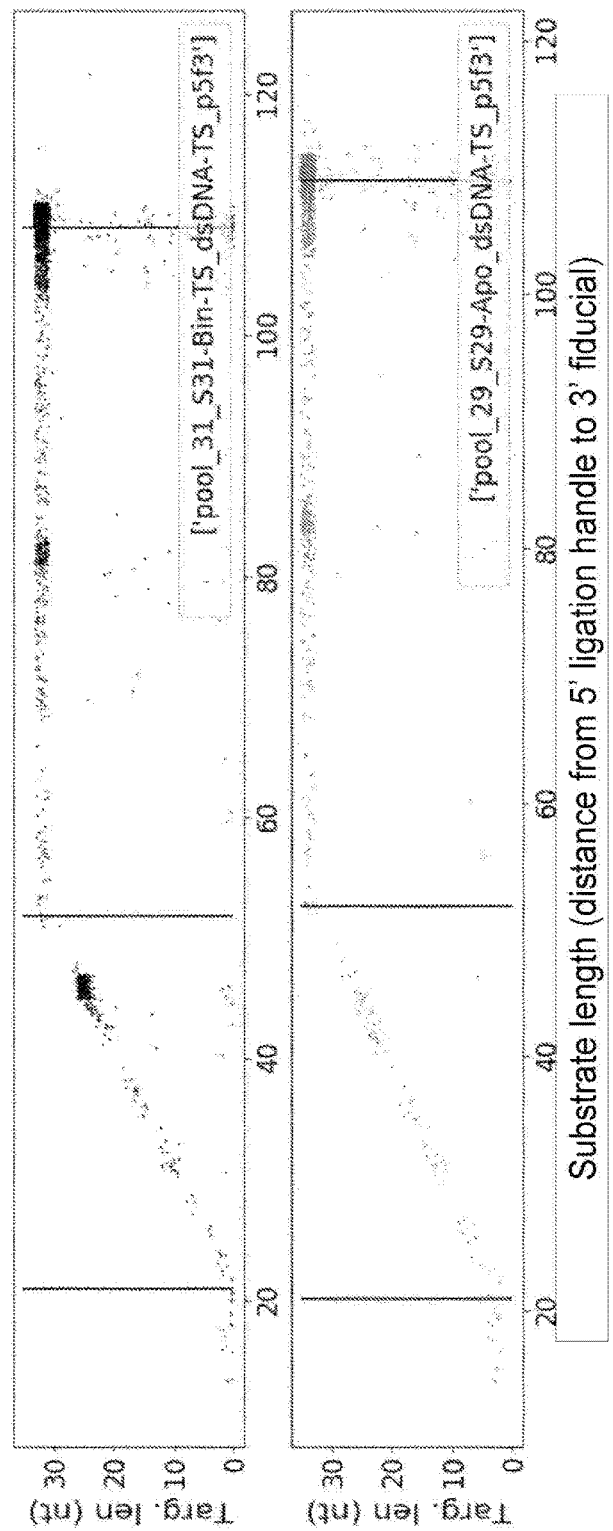
Figure 35B:
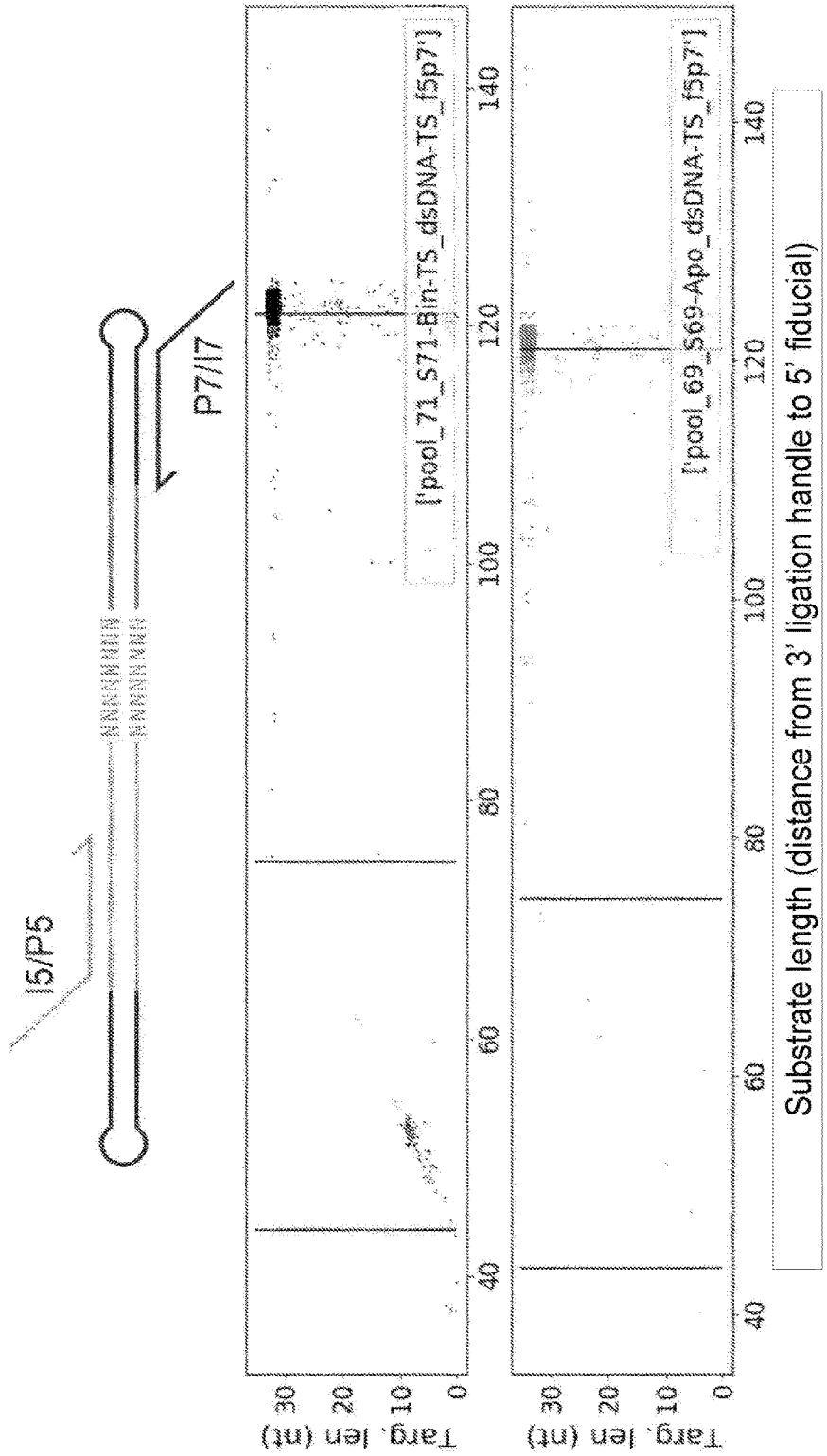

FIGS. 35A-B show the distribution of dsDNA substrate lengths (X) vs target lengths (Y) for IVTT-expressed Cas12i2 in complex with a top-strand (active orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P17 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 36:
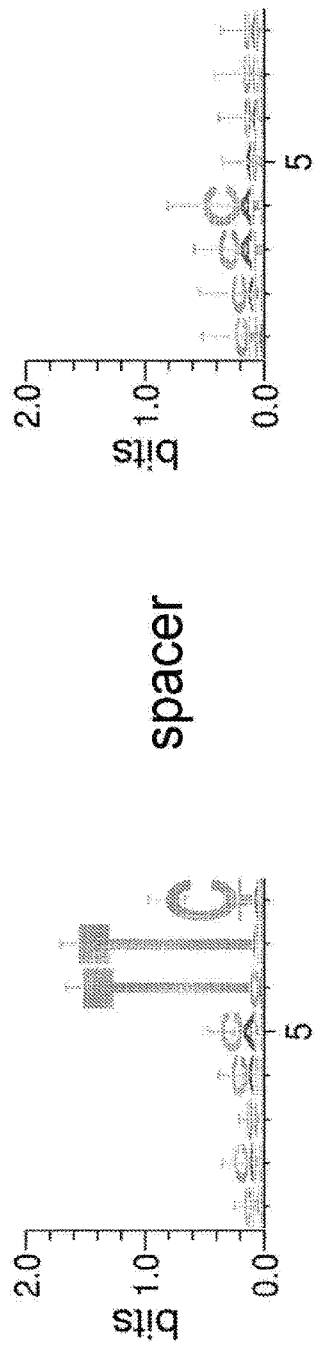

FIG. 36 shows a weblogo indicating a 5' TTN PAM/1 motif (left of the target sequence) for Cas12i2 associated with non-target strand cleavage between the +24/+/+25 nucleotides relative to the PAM. No PAM sequence requirement is observed on the right side of the Cas12i2 target.

Figure 37:
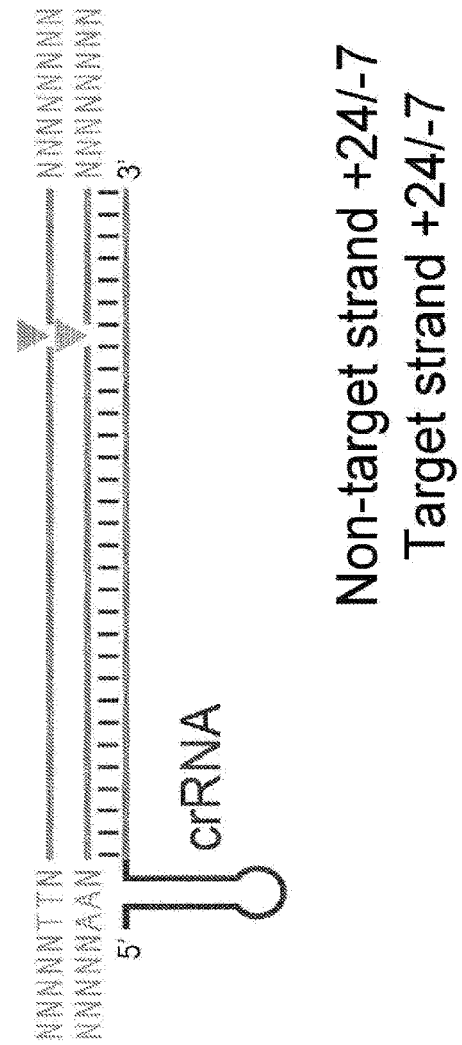

FIG. 37 shows a blunt cut associated with double stranded DNA cleavage by Cas12i2 indicated by cleavage observed between the +24/+25 nucleotides of the non-target strand relative to the PAM and cleavage between the +24/+25 nucleotides of the target strand relative to the PAM.

Figure 38A:
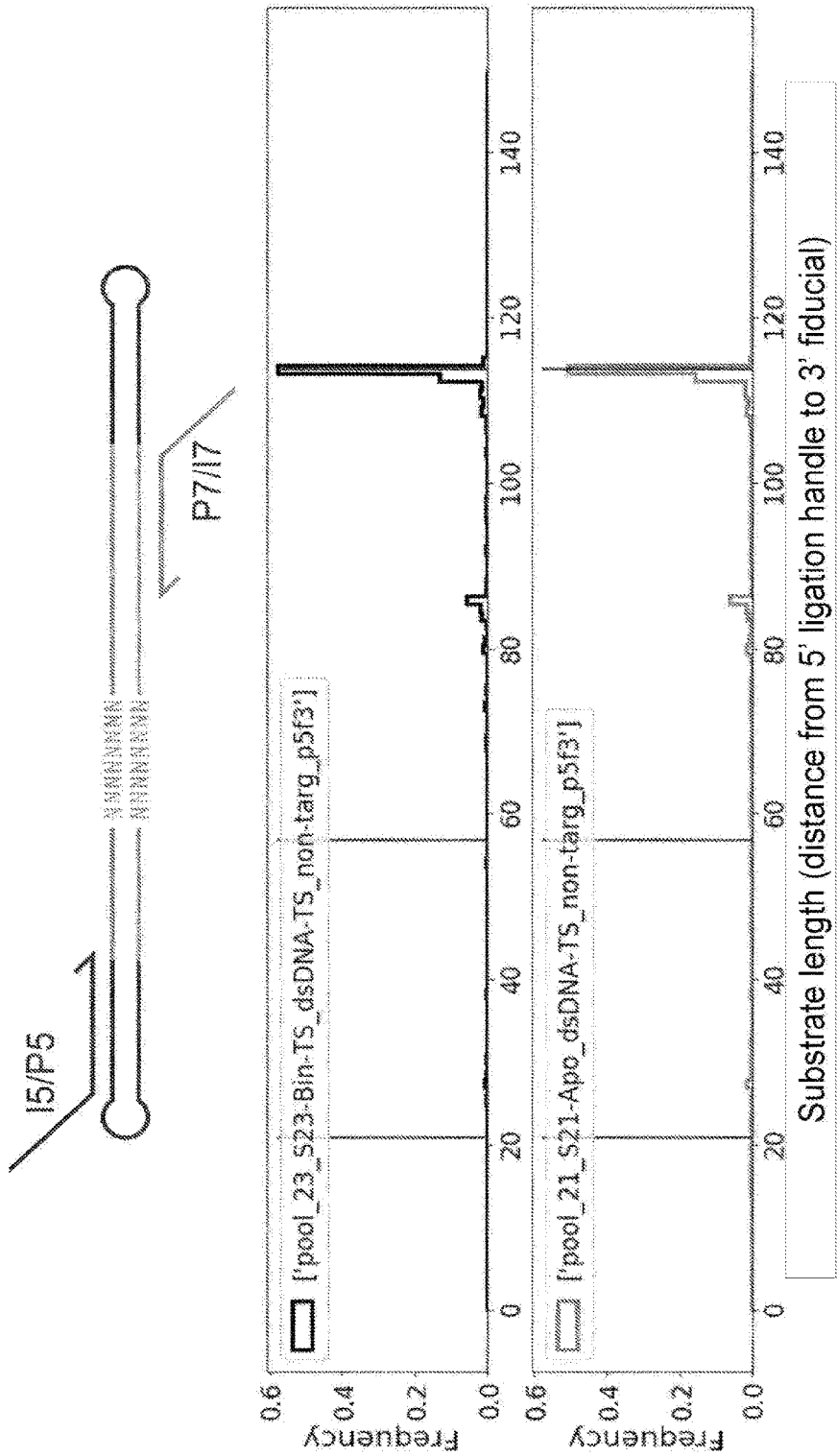
Figure 38B:
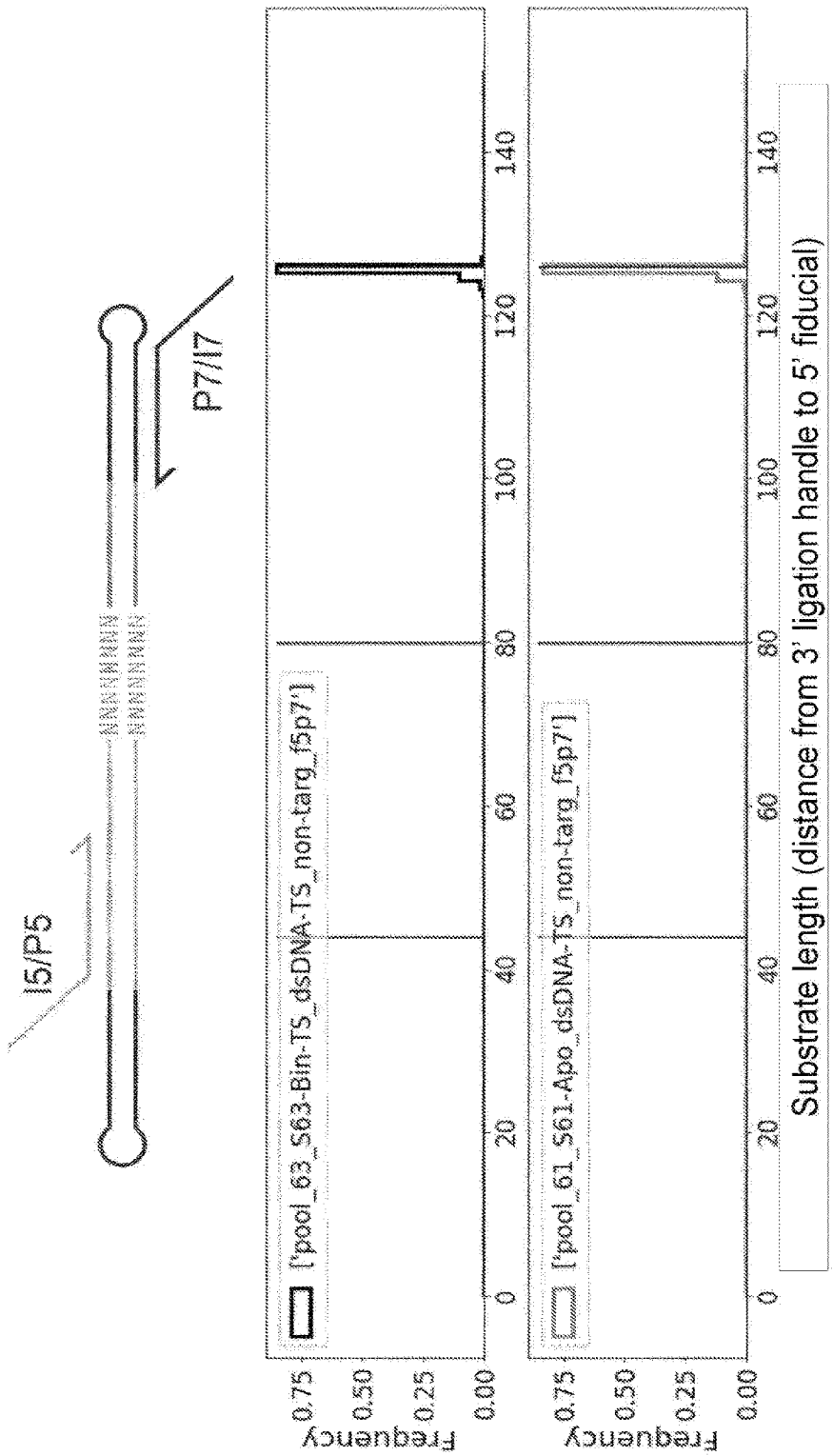

FIGS. 38A-B show the distribution of dsDNA substrate lengths for IVTT-expressed Cas12i2 in complex with a non-target crRNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 39A:
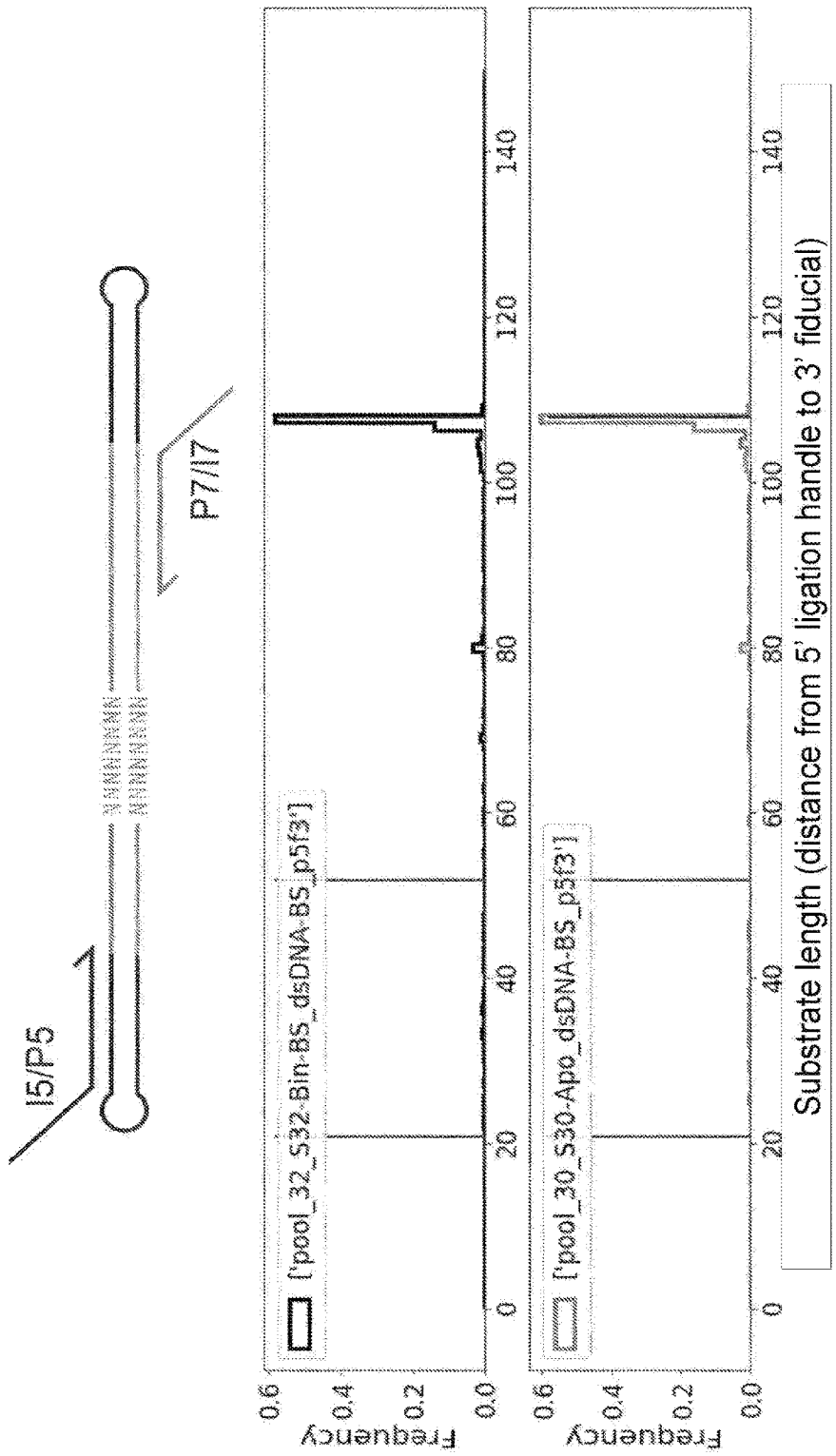
Figure 39B:
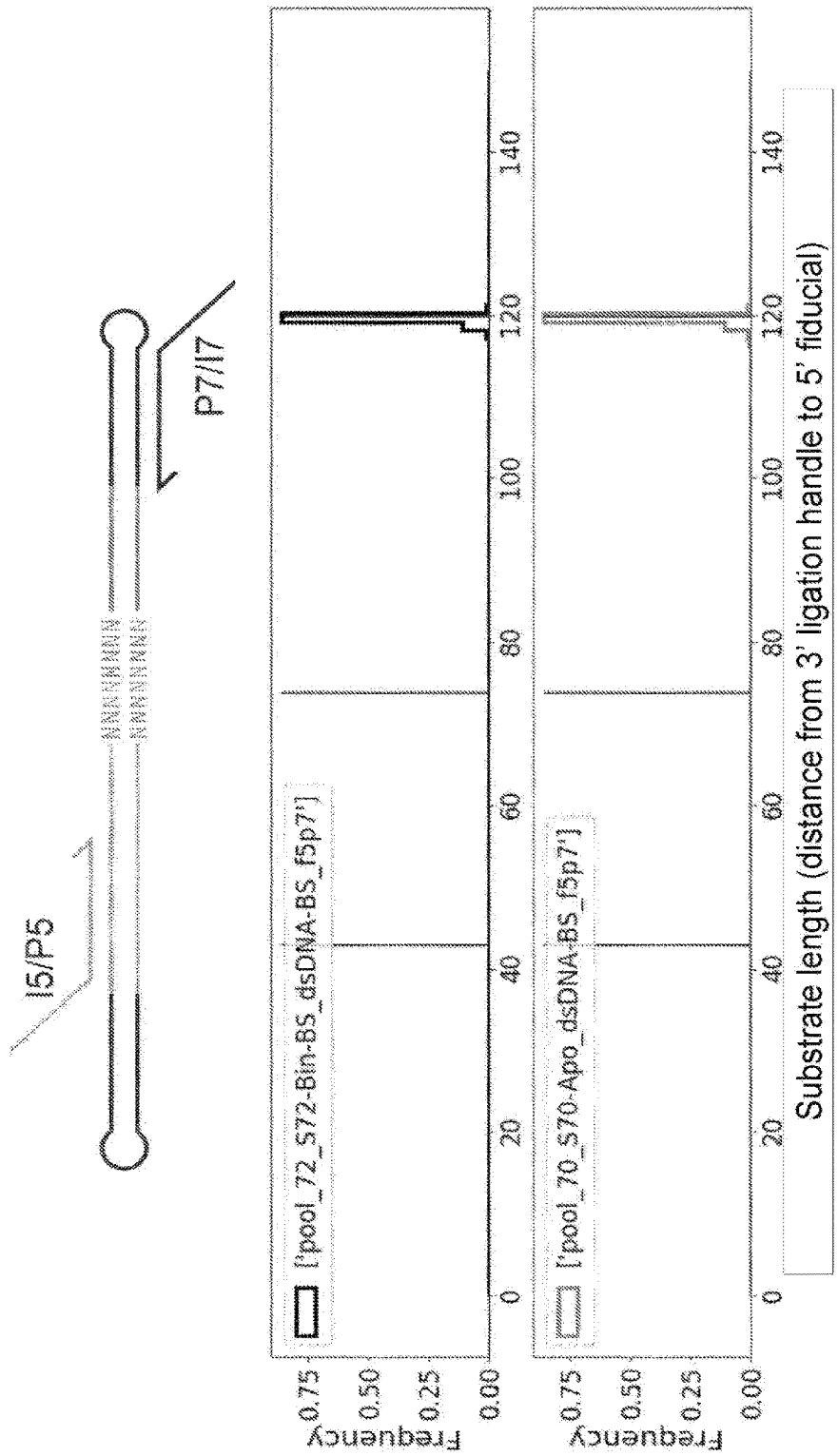

FIGS. 39A-B show the distribution of dsDNA substrate lengths for IVTT-expressed Cas12i2 in complex with a bottom-strand (inactive orientation) crRNA targeting dsDNA (red) vs. apo (effector-only) controls (blue). (A) Next generation sequencing libraries for readout were prepared with a first primer complementary to a handle ligated to the 5' end of the full length or cleaved substrate (and containing I5/P5 sequences) and a second primer complementary to the 3' fiducial sequence of the substrate (and containing I7/P7 sequences). (B) Next generation sequencing libraries for readout were prepared with a first primer complementary to the 5' fiducial sequence of the substrate (and containing I5/P5 sequences) and a second primer complementary to a handle ligated to the 3' end of the full length or cleaved substrate (and containing I7/P7 sequences).

Figure 40:
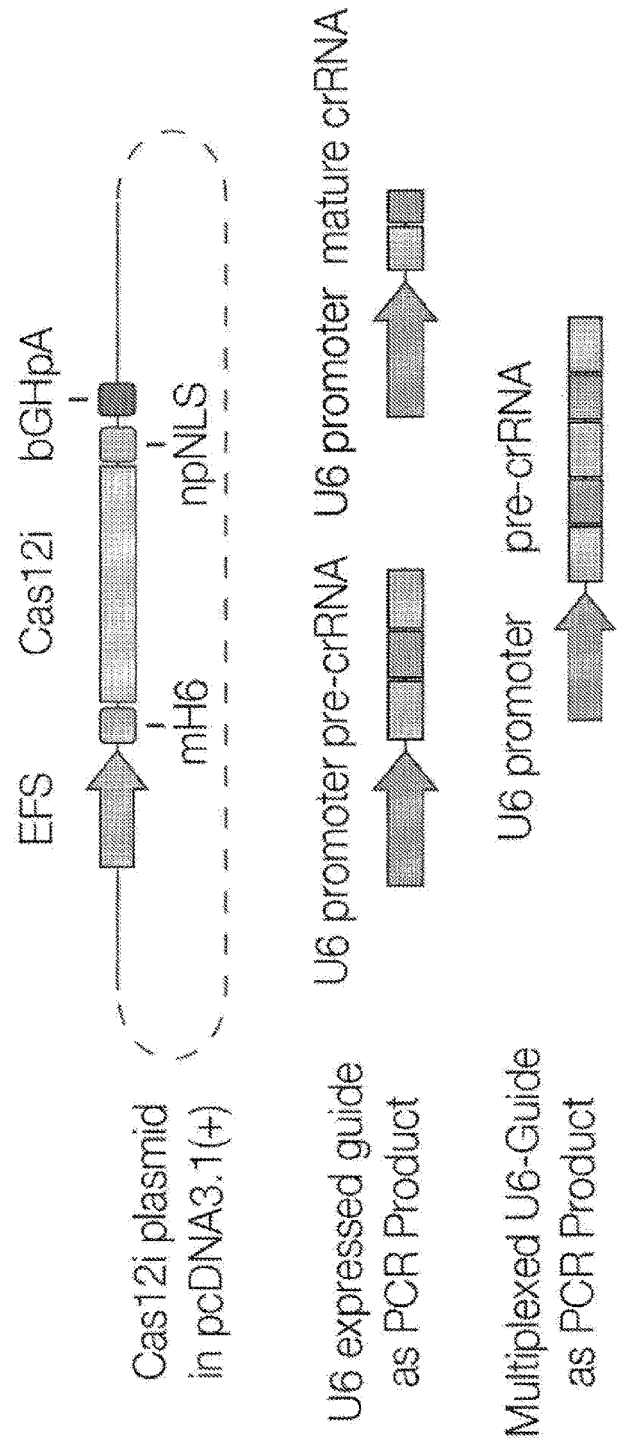

FIG. 40 is a schematic of the constructs used for mammalian validation of the Type V-I CRISPR systems as described herein. The effector is mammalian codon optimized and a nucleoplasmin nuclear localization sequence (npNLS) is appended to the C-terminus of the protein. Mammalian expression from the plasmid uses a EF1 alpha-short promoter (EFS) and a polyA sequence from bGH (bGHpA). The RNA guide is expressed from a linear dsDNA fragment, driven by a RNA polymerase 111 promoter (U6). The schematic describes different implementations, with the RNA guide expressed as either a pre-crRNA bearing a single target, mature crRNA, or multiplexed with multiple targets in the shown configuration.

Figure 41A:
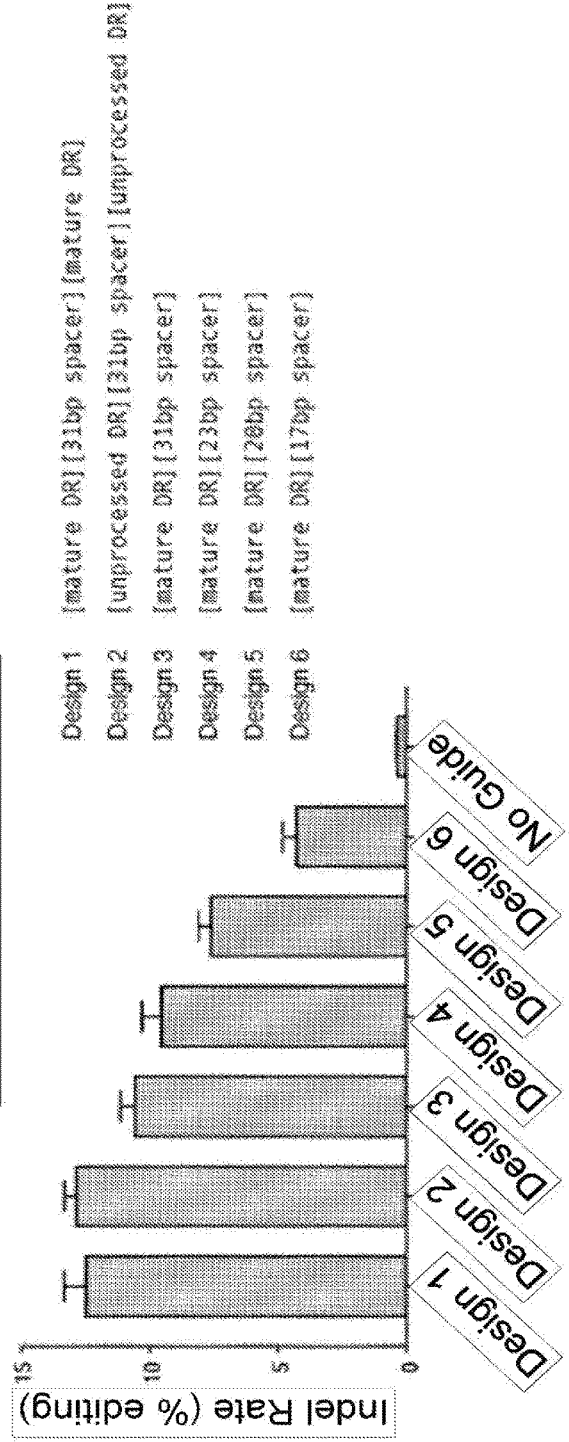

FIG. 41A is a bar graph that shows indel activity induced by the Cas12i2 CRISPR effector targeted to the VEGFA locus in the 293T cell line 72 hours post transient transfection of effector and RNA guide constructs described in FIG. 40. Different RNA guide designs were assayed and display varying degrees of efficacy. The error bars represent the S.E.M., with 3 replicates.

FIG. 41B is a representation of representative indels from next generation sequencing. Labeled are the TTC PAM sequence, and the representative indels occurring ≥20 bp downstream of the PAM.

DETAILED DESCRIPTION

The broad natural diversity of CRISPR-Cas defense systems contain a wide range of activity mechanisms and functional elements that can be harnessed for programmable biotechnologies. In a natural system, these mechanisms and parameters enable efficient defense against foreign DNA and viruses while providing self vs. non-self discrimination to avoid self-targeting. In an engineered system, the same mechanisms and parameters also provide a diverse toolbox of molecular technologies and define the boundaries of the targeting space. For instance, systems Cas9 and Cas13a have canonical DNA and RNA endonuclease activity and their targeting spaces are defined by the protospacer adjacent motif (PAM) on targeted DNA and protospacer flanking sites (PFS) on targeted RNA, respectively.

The methods described herein have been used to discover additional mechanisms and parameters within single subunit Class 2 effector systems that can expand the capabilities of RNA-programmable nucleic acid manipulation.

In one aspect, the disclosure relates to the use of computational methods and algorithms to search for and identify novel protein families that exhibit a strong co-occurrence pattern with certain other features within naturally occurring genome sequences. In certain embodiments, these computational methods are directed to identifying protein families that co-occur in close proximity to CRISPR arrays. However, the methods disclosed herein are useful in identifying proteins that naturally occur within close proximity to other features, both non-coding and protein-coding (e.g., fragments of phage sequences in non-coding areas of bacterial loci; or CRISPR Cas1 proteins). It is understood that the methods and calculations described herein may be performed on one or more computing devices.

In some embodiments, a set of genomic sequences is obtained from genomic or metagenomic databases. The databases comprise short reads, or contig level data, or assembled scaffolds, or complete genomic sequences of organisms. Likewise, the database may comprise genomic sequence data from prokaryotic organisms, or eukaryotic organisms, or may include data from metagenomic environmental samples. Examples of database repositories include the National Center for Biotechnology Information (NCBI) RefSeq, NCBI GenBank, NCBI Whole Genome Shotgun (WGS), and the Joint Genome Institute (JGI) Integrated Microbial Genomes (IMG).

In some embodiments, a minimum size requirement is imposed to select genome sequence data of a specified minimum length. In certain exemplary embodiments, the minimum contig length may be 100 nucleotides, 500 nt, 1 kb, 1.5 kb, 2 kb, 3 kb, 4 kb, 5 kb, 10 kb, 20 kb, 40 kb, or 50 kb.

In some embodiments, known or predicted proteins are extracted from the complete or a selected set of genome sequence data. In some embodiments, known or predicted proteins are taken from extracting coding sequence (CDS) annotations provided by the source database. In some embodiments, predicted proteins are determined by applying a computational method to identify proteins from nucleotide sequences. In some embodiments, the GeneMark Suite is used to predict proteins from genome sequences. In some embodiments, Prodigal is used to predict proteins from genome sequences. In some embodiments, multiple protein prediction algorithms may be used over the same set of sequence data with the resulting set of proteins de-duplicated.

In some embodiments, CRISPR arrays are identified from the genome sequence data. In some embodiments, PILER-CR is used to identify CRISPR arrays. In some embodiments, CRISPR Recognition Tool (CRT) is used to identify CRISPR arrays. In some embodiments, CRISPR arrays are identified by a heuristic that identifies nucleotide motifs repeated a minimum number of times (e.g. 2, 3, or 4 times), where the spacing between consecutive occurrences of a repeated motif does not exceed a specified length (e.g. 50, 100, or 150 nucleotides). In some embodiments, multiple CRISPR array identification tools may be used over the same set of sequence data with the resulting set of CRISPR arrays de-duplicated.

In some embodiments, proteins in close proximity to CRISPR arrays are identified. In some embodiments, proximity is defined as a nucleotide distance, and may be within 20 kb, 15 kb, or 5 kb. In some embodiments, proximity is defined as the number of open reading frames (ORFs) between a protein and a CRISPR array, and certain exemplary distances may be 10, 5, 4, 3, 2, 1, or 0 ORFs. The proteins identified as being within close proximity to a CRISPR array are then grouped into clusters of homologous proteins. In some embodiments, blastclust is used to form protein clusters. In certain other embodiments, mmseqs2 is used to form protein clusters.

To establish a pattern of strong co-occurrence between the members of a protein cluster with CRISPR arrays, a BLAST search of each member of the protein family may be performed over the complete set of known and predicted proteins previously compiled. In some embodiments, UBLAST or mmseqs2 may be used to search for similar proteins. In some embodiments, a search may be performed only for a representative subset of proteins in the family.

In some embodiments, the clusters of proteins within close proximity to CRISPR arrays are ranked or filtered by a metric to determine co-occurrence. One exemplary metric is the ratio of the number of elements in a protein cluster against the number of BLAST matches tip to a certain E value threshold. In some embodiments, a constant E value threshold may be used. In other embodiments, the E value threshold may be determined by the most distant members of the protein cluster. In some embodiments, the global set of proteins is clustered and the co-occurrence metric is the ratio of the number of elements of the CRISPR associated cluster against the number of elements of the containing global cluster(s).

In some embodiments, a manual review process is used to evaluate the potential functionality and the minimal set of components of an engineered system based on the naturally occurring locus structure of the proteins in the cluster. In some embodiments, a graphical representation of the protein cluster may assist in the manual review, and may contain information including pairwise sequence similarity, phylogenetic tree, source organisms/environments, predicted functional domains, and a graphical depiction of locus structures. In some embodiments, the graphical depiction of locus structures may filter for nearby protein families that have a high representation. In some embodiments, representation may be calculated by the ratio of the number of related nearby proteins against the size(s) of the containing global cluster(s). In certain exemplary embodiments, the graphical representation of the protein cluster may contain a depiction of the CRISPR array structures of the naturally occurring loci. In some embodiments, the graphical representation of the protein cluster may contain a depiction of the number of conserved direct repeats versus the length of the putative CRISPR array, or the number of unique spacer sequences versus the length of the putative CRISPR array. In some embodiments, the graphical representation of the protein cluster may contain a depiction of various metrics of co-occurrence of the putative effector with CRISPR arrays predict new CRISPR-Cas systems and identify their components.

Pooled-Screening

To efficiently validate the activity of the engineered novel CRISPR-Cas systems and simultaneously evaluate in an unbiased manner different activity mechanisms and functional parameters, a new pooled-screening approach is used in E. coli. First, from the computational identification of the conserved protein and noncoding elements of the novel CRISPR-Cas system, DNA synthesis and molecular cloning is used to assemble the separate components into a single artificial expression vector, which in one embodiment is based on a pET-28a+ backbone. In a second embodiment, the effectors and noncoding elements are transcribed on a single mRNA transcript, and different ribosomal binding sites are used to translate individual effectors.

Second, the natural crRNA and targeting spacers are replaced with a library of unprocessed crRNAs containing non-natural spacers targeting a second plasmid, pACYC184. This crRNA library is cloned into the vector backbone containing the protein effectors and noncoding elements (e.g. pET-28a+), and then subsequently transformed the library into E. coli along with the pACYC184 plasmid target. Consequently, each resulting E. coli cell contains no more than one targeting spacer. In an alternate embodiment, the library of unprocessed crRNAs containing non-natural spacers additionally target E. coli essential genes, drawn from resources such as those described in Baba el al. (2006) Mol. Syst Biol. 2: 2006.0008; and Gerdes et al. (2003) J. Bacteriol. 185(19): 5673-84, the entire contents of each of which are incorporated herein by reference. In this embodiment, positive, targeted activity of the novel CRISPR-Cas systems that disrupts essential gene function results in cell death or growth arrest. In some embodiments, the essential gene targeting spacers can be combined with the pACYC184 targets to add another dimension to the assay. In other embodiments, the non-coding sequences flanking the CRISPR array, putative effector or accessory open reading frames, and predicted anti-repeats indicative of tracrRNA elements were concatenated together and cloned into pACYC184 and expressed by lac and IPTG-inducible T7 promoters Third, the E. coli are grown under antibiotic selection. In one embodiment, triple antibiotic selection is used: kanamycin for ensuring successful transformation of the pET-28a+ vector containing the engineered CRISPR-Cas effector system, and chloramphenicol and tetracycline for ensuring successful co-transformation of the pACYC184 target vector. Since pACYC184 normally confers resistance to chloramphenicol and tetracycline, under antibiotic selection, positive activity of the novel CRISPR-Cas system targeting the plasmid will eliminate cells that actively express the effectors, noncoding elements, and specific active elements of the crRNA library. Examining the population of surviving cells at a later time point compared to an earlier time point typically provides a depleted signal compared to the inactive crRNAs. In some embodiments, double antibiotic selection is used. For example, withdrawal of either chloramphenicol or tetracycline to remove selective pressure can provide novel information about the targeting substrate, sequence specificity, and potency. In some embodiments, only kanamycin is used to ensure successful transformation of the pET-28a+ vector containing the engineered CRISPR-Cas effector system. This embodiment is suitable for libraries containing spacers targeting E. coli essential genes, as no additional selection beyond kanamycin is needed to observe growth alterations. In this embodiment, chloramphenicol and tetracycline dependence is removed, and their targets (if any) in the library provides an additional source of negative or positive information about the targeting substrate, sequence specificity, and potency.

Since the pACYC184 plasmid contains a diverse set of features and sequences that may affect the activity of a CRISPR-Cas system, mapping the active crRNAs from the pooled screen onto pACYC184 provides patterns of activity that can be suggestive of different activity mechanisms and functional parameters in a broad, hypothesis-agnostic manner. In this way, the features required for reconstituting the novel CRISPR-Cas system in a heterologous prokaryotic species can be more comprehensively tested and studied.

Certain important advantages of the in vivo pooled-screen described herein include:

(1) Versatility—plasmid design allows multiple effectors and/or noncoding elements to be expressed; library cloning strategy enables both transcriptional directions of the computationally predicted crRNA to be expressed:

(2) Comprehensive tests of activity mechanisms and functional parameters can be used to evaluate diverse interference mechanisms, including DNA or RNA cleavage; to examine co-occurrence of features such as transcription, plasmid DNA replication; and flanking sequences for a crRNA library to reliably determine PAMs with complexity equivalence of 4N's;

(3) Sensitivity—pACYC184 is a low copy plasmid, enabling high sensitivity for CRISPR-Cas activity, because even modest interference rates can eliminate the antibiotic resistance encoded by the plasmid; and (4) Efficiency—the pooled-screening includes optimized molecular biology steps that enable greater speed and throughput for RNA-sequencing and the protein expression samples can be directly harvested from the surviving cells in the screen.

As discussed in more detail in the Examples below, the novel CRISPR-Cas families described herein were evaluated using this in vivo pooled-screen to evaluate their operational elements, mechanisms and parameters, as well as their ability to be active and reprogrammed in an engineered system outside of their natural cellular environment.

In Vitro Pooled Screening

In vitro pooled screening approaches can also be used and are complementary to in vivo pooled screens. In vitro pooled screens enable rapid biochemical characterization and reduction of a CRISPR system to the essential components necessary for the system's activity. In one embodiment, a cell-free in vitro transcription and translation (IVTT) system is used to directly synthesize RNA and protein from DNA encoding the noncoding and effector proteins of the CRISPR system, thus enabling a faster and higher throughput method to evaluate a larger number of distinct separate CRISPR-Cas effector systems than conventional biochemical assays reliant on FPLC-purified proteins. In addition to enabling greater throughput and efficiency of biochemical reactions, the in vitro screening has several advantages that make it complementary to the in vivo pooled screening approach described above.

(1) Direct observation of both enrichment and depletion signals—in vitro pooled screening enables a readout of both cleavage enrichment, in which the cleavage products can be directly captured and sequenced to identify specific cut sites, cleavage patterns, and sequence motifs for active effector systems, as well as target depletion, in which the negative signal from the depletion of specific targets within the uncleaved population is used as a proxy for activity. As the in vivo pooled screen utilizes a target depletion readout, the enrichment mode offers additional insight into the effector activity.

(2) Greater control of the reaction components and environment—the well-defined components and activity of the proprietary IVTT enables precise control of the reaction components to identify the minimal components necessary for further activity translation, as compared to the complex E. coli cellular milieu for an in vivo screen. Additionally, non-natural modifications may be made to reaction components for enhanced activity or easier readout; for instance, adding phosphorothioated bonds onto the ssDNA and dsDNA substrates to reduce noise by limiting exonuclease degradation of substrates.

(3) Robustness to toxic/growth inhibiting proteins—for proteins that may be toxic to E. coli cell growth, the in vitro pooled screen enables functional screening without being subject to the growth constraints of a live cell. This ultimately enables greater versatility in protein selection and screening.

The novel CRISPR-Cas families described herein were evaluated using a combination of in vivo and in vitro pooled-screens to evaluate their operational elements, mechanisms and parameters, as well as their ability to be active and reprogrammed in an engineered system outside of their natural cellular environment.

Class 2 CRISPR-Cas Effectors Having a RuvC Domain

In one aspect, the disclosure provides Class 2 CRISPR-Cas systems referred to herein as CLUST.029130 (Type V-I) CRISPR-Cas systems. These Class 2 CRISPR-Cas systems include an isolated CRISPR-associated protein having a RuvC domain and an isolated crRNA, also referred to as an RNA guide, guide RNA, or gRNA, comprising a spacer sequence that is complementary to a target nucleic acid sequence such as a DNA sequence.

Suitably, a CRISPR-Cas effector protein having a RuvC domain may include one or motifs from the set of: the RuvC III motif, $X_1SHX_4DX_6X_7$ (SEQ ID NO: 200), wherein $X_1$ is S or T, X4 is Q or L, $X_6$ is P or S, and $X_7$ is F or L; the RuvC I motif, $X_1XDXNX_6X_7XXXX_{11}$ (SEQ ID NO: 201), wherein $X_1$ is A or G or S, X is any amino acid, $X_6$ is Q or I, $X_7$ is T or S or V, and $X_{11}$ is T or A; and the RuvC II motif, $X_1X_2X_3E$ (SEQ ID NO: 210), wherein $X_1$ is C or F or I or L or M or P or V or W or Y, $X_2$ is C or F or I or L or M or P or R or V or W or Y, and $X_3$ is C or F or G or I or L or M or P or V or W or Y.

Suitably, a Type V-I CRISPR-Cas system includes a CRISPR-Cas effector having a RuvC domain and a Type V-I crRNA. Suitably, the Cas12i effector is about 1100 amino acids or less in length, and includes a functional PAM interacting domain that recognizes the PAM in the target DNA. Type V-I CRISPR-Cas effector proteins are capable of binding to a Type V-I RNA guide to form a Type V-I CRISPR-Cas system, wherein the Type V-I RNA guide includes a stem-loop structure with a 5-nucleotide stem and a loop of 6, 7, or 8 nucleotides. Type V-I CRISPR-Cas systems are capable of targeting and binding to sequence-specific DNA without the presence of a tracrRNA.

In some embodiments, the Type V-I CRISPR-Cas effector protein and the Type V-I RNA guide form a binary complex that may include other components. The binary complex is activated upon binding to a nucleic acid substrate that is complementary to a spacer sequence in the RNA guide (i.e., a sequence-specific substrate or target nucleic acid). In some embodiments, the sequence-specific substrate is a double-stranded DNA. In some embodiments, the sequence-specific substrate is a single-stranded DNA. In some embodiments, the sequence-specificity requires a complete match of the spacer sequence in the RNA guide (e.g., crRNA) to the target substrate. In other embodiments, the sequence specificity requires a partial (contiguous or non-contiguous) match of the spacer sequence in the RNA guide (e.g., crRNA) to the target substrate. Sequence specificity in certain embodiments further requires a complete match between a proto-spacer adjacent motif ("PAM") sequence proximate to the spacer sequence, and a canonical PAM sequence recognized by the CRISPR-associated protein. In some instances, a complete PAM sequence match is not required, and a partial match is sufficient for sequence-specific association of the binary complex and the DNA substrate.

In some embodiments, the target nucleic acid substrate is a double stranded DNA (dsDNA). In some embodiments, the target nucleic acid substrate is a dsDNA and includes a PAM. In some embodiments, the binary complex modifies the target sequence-specific dsDNA substrate upon binding to it. In some embodiments, the binary complex preferentially nicks the non-target strand of the target dsDNA substrate. In some embodiments, the binary complex cleaves both strands of the target dsDNA substrate it. In some embodiments, the binary complex cleaves both strands of target dsDNA substrate with a staggered cut. In some embodiments, the binary complex creates a blunt double-stranded break (DSB) on the target dsDNA substrate.

In some embodiments, the target nucleic acid substrate is a single stranded DNA (ssDNA). In some embodiments, the target nucleic acid substrate is a ssDNA and does not include a PAM. In some embodiments, the binary complex modifies the target sequence-specific ssDNA substrate upon binding to it. In some embodiments, the binary complex cleaves the target ssDNA substrate.

In some embodiments, the binary complex becomes activated upon binding to the target substrate. In some embodiments, the activated complex exhibits "multiple turnover" activity, whereby upon acting on (e.g., cleaving) the target substrate the activated complex remains in an activated state. In some embodiments, the binary complex exhibits "single turnover" activity, whereby upon acting on the target substrate the binary complex reverts to an inactive state. In some embodiments, the activated complex exhibits non-specific (i.e., "collateral") cleavage activity whereby the activated complex cleaves nucleic acids with no sequence similarity to the target. In some embodiments, the collateral nucleic acid substrate is a ssDNA.

CRISPR Enzyme Modifications

Nuclease-Deficient CRISPR Enzymes

Where the CRISPR enzymes described herein have nuclease activity, the CRISPR enzymes can be modified to have diminished nuclease activity, e.g., nuclease inactivation of at least 50%, at least 60%, at least 70%, at least 80%, at least 90%, at least 95%, at least 97%, or 100% as compared with the wild type CRISPR enzymes. The nuclease activity can be diminished by several methods, e.g., introducing mutations into the nuclease or PAM interacting domains of the CRISPR enzymes. In some embodiments, catalytic residues for the nuclease activities are identified, and these amino acid residues can be substituted by different amino acid residues (e.g., glycine or alanine) to diminish the nuclease activity. Examples of such mutations for Cas12i1 include D647A or E894A or D948A. Examples of such mutations for Cas12i2 include D599A or E833A or D886A.

The inactivated CRISPR enzymes can comprise (e.g., via fusion protein, linker peptides, Gly4Ser (GS) peptide linkers, etc.) or be associated (e.g., via co-expression of multiple proteins) with one or more functional domains. These functional domains can have various activities, e.g., methylase activity, demethylase activity, transcription activation activity, transcription repression activity, transcription release factor activity, histone modification activity, RNA cleavage activity, DNA cleavage activity, nucleic acid binding activity, and switch activity (e.g., light inducible). In some embodiments, the functional domains are Krüppel associated box (KRAB), VP64, VP16, Fok1, P65, HSF1, MyoD1, and biotin-APEX.

The positioning of the one or more functional domains on the inactivated CRISPR enzymes allows for correct spatial orientation for the functional domain to affect the target with the attributed functional effect. For example, if the functional domain is a transcription activator (e.g., VP16, VP64, or p65), the transcription activator is placed in a spatial orientation that allows it to affect the transcription of the target. Likewise, a transcription repressor is positioned to affect the transcription of the target, and a nuclease (e.g., Fok1) is positioned to cleave or partially cleave the target. In some embodiments, the functional domain is positioned at the N-terminus of the CRISPR enzyme. In some embodiments, the functional domain is positioned at the C-terminus of the CRISPR enzyme. In some embodiments, the inactivated CRISPR enzyme is modified to comprise a first functional domain at the N-terminus and a second functional domain at the C-terminus.

Split Enzymes

The present disclosure also provides a split version of the CRISPR enzymes described herein. The split version of the CRISPR enzymes may be advantageous for delivery. In some embodiments, the CRISPR enzymes are split to two parts of the enzymes, which together substantially comprises a functioning CRISPR enzyme.

The split can be done in a way that the catalytic domain(s) are unaffected. The CRISPR enzymes may function as a nuclease or may be inactivated enzymes, which are essentially RNA-binding proteins with very little or no catalytic activity (e.g., due to mutation(s) in their catalytic domains).

In some embodiments, the nuclease lobe and α-helical lobe are expressed as separate polypeptides. Although the lobes do not interact on their own, the RNA guide recruits them into a complex that recapitulates the activity of full-length CRISPR enzymes and catalyzes site-specific DNA cleavage. The use of a modified RNA guide abrogates split-enzyme activity by preventing dimerization, allowing for the development of an inducible dimerization system. The split enzyme is described, e.g., in Wright, Addison V., et al. "Rational design of a split-Cas9 enzyme complex," Proc. Nat'l. Acad. Sci., 112.10 (2015): 2984-2989, which is incorporated herein by reference in its entirety.

In some embodiments, the split enzyme can be fused to a dimerization partner, e.g., by employing rapamycin sensitive dimerization domains. This allows the generation of a chemically inducible CRISPR enzyme for temporal control of CRISPR enzyme activity. The CRISPR enzymes can thus be rendered chemically inducible by being split into two fragments and rapamycin-sensitive dimerization domains can be used for controlled reassembly of the CRISPR enzymes.

The split point is typically designed in silico and cloned into the constructs. During this process, mutations can be introduced to the split enzyme and non-functional domains can be removed. In some embodiments, the two parts or fragments of the split CRISPR enzyme (i.e., the N-terminal and C-terminal fragments), can form a full CRISPR enzyme, comprising, e.g., at least 70%, at least 80%, at least 90%, at least 95%, or at least 99% of the sequence of the wild-type CRISPR enzyme.

Self-Activating or Inactivating Enzymes

The CRISPR enzymes described herein can be designed to be self-activating or self-inactivating. In some embodiments, the CRISPR enzymes are self-inactivating. For example, the target sequence can be introduced into the CRISPR enzyme coding constructs. Thus, the CRISPR enzymes can cleave the target sequence, as well as the construct encoding the enzyme thereby self-inactivating their expression. Methods of constructing a self-inactivating CRISPR system is described, e.g., in Epstein, Benjamin E., and David V. Schaffer. "Engineering a Self-Inactivating CRISPR System for AAV Vectors," Mol. Ther., 24 (2016): S50, which is incorporated herein by reference in its entirety.

In some other embodiments, an additional RNA guide, expressed under the control of a weak promoter (e.g., 7SK promoter), can target the nucleic acid sequence encoding the CRISPR enzyme to prevent and/or block its expression (e.g., by preventing the transcription and/or translation of the nucleic acid). The transfection of cells with vectors expressing the CRISPR enzyme, RNA guides, and RNA guides that target the nucleic acid encoding the CRISPR enzyme can lead to efficient disruption of the nucleic acid encoding the CRISPR enzyme and decrease the levels of CRISPR enzyme, thereby limiting the genome editing activity.

In some embodiments, the genome editing activity of the CRISPR enzymes can be modulated through endogenous RNA signatures (e.g., miRNA) in mammalian cells. The CRISPR enzyme switch can be made by using a miRNA-complementary sequence in the 5'-UTR of mRNA encoding the CRISPR enzyme. The switches selectively and efficiently respond to miRNA in the target cells. Thus, the switches can differentially control the genome editing by sensing endogenous miRNA activities within a heterogeneous cell population. Therefore, the switch systems can provide a framework for cell-type selective genome editing and cell engineering based on intracellular miRNA information (Hirosawa, Moe et al. "Cell-type-specific genome editing with a microRNA-responsive CRISPR-Cas9 switch," Nucl. Acids Res., 2017 Jul. 27; 45(13): e118).

Inducible CRISPR Enzymes

The CRISPR enzymes can be inducible, e.g., light inducible or chemically inducible. This mechanism allows for activation of the functional domain in the CRISPR enzymes with a known trigger. Light inducibility can be achieved by various methods known in the art, e.g., by designing a fusion complex wherein CRY2PHR/CIBN pairing is used in split CRISPR Enzymes (see, e.g., Konermann et al. "Optical control of mammalian endogenous transcription and epigenetic states," *Nature*, 500.7463 (2013): 472). Chemical inducibility can be achieved, e.g., by designing a fusion complex wherein FKBP/FRB (FK506 binding protein/FKBP rapamycin binding domain) pairing is used in split CRISPR Enzymes. Rapamycin is required for forming the fusion complex, thereby activating the CRISPR enzymes (see, e.g., Zetsche, Volz, and Zhang, "A split-Cas9 architecture for inducible genome editing and transcription modulation," *Nature Biotech.*, 33.2 (2015): 139-142).

Furthermore, expression of the CRISPR enzymes can be modulated by inducible promoters, e.g., tetracycline or doxycycline controlled transcriptional activation (Tet-On and Tet-Off expression systems), hormone inducible gene expression system (e.g., an ecdysone inducible gene expression system), and an arabinose-inducible gene expression system. When delivered as RNA, expression of the RNA targeting effector protein can be modulated via a riboswitch, which can sense a small molecule like tetracycline (see, e.g., Goldfless, Stephen J. et al. "Direct and specific chemical control of eukaryotic translation with a synthetic RNA-protein interaction," *Nucl. Acids Res.*, 40.9 (2012): e64-e64).

Various embodiments of inducible CRISPR enzymes and inducible CRISPR systems are described, e.g., in U.S. Pat. No. 8,871,445, US20160208243, and WO2016205764, each of which is incorporated herein by reference in its entirety.

Functional Mutations

Various mutations or modifications can be introduced into CRISPR enzymes as described herein to improve specificity and/or robustness. In some embodiments, the amino acid residues that recognize the Protospacer Adjacent Motif (PAM) are identified. The CRISPR enzymes described herein can be modified further to recognize different PAMs, e.g., by substituting the amino acid residues that recognize PAM with other amino acid residues. In some embodiments, the CRISPR enzymes can recognize alternative PAMs, e.g., as described herein.

In some embodiments, the CRISPR-associated proteins include at least one (e.g., 1, 2, 3, 4, 5, 6, 7, 8, 9, or 10) Nuclear Localization Signal (NLS) attached to the N-terminal or C-terminal of the protein. Non-limiting examples of NLSs include an NLS sequence derived from: the NLS of the SV40 virus large T-antigen, having the amino acid sequence PKKKRKV (SEQ ID NO: 300); the NLS from nucleoplasmin (e.g., the nucleoplasmin bipartite NLS with the sequence KRPAATKKAGQAKKKK (SEQ ID NO: 301)); the c-myc NLS having the amino acid sequence PAAKRVKLD (SEQ ID NO: 302) or RQRRNELKRSP (SEQ ID NO: 303); the hRNPA1 M9 NLS having the sequence NQSSNFGPMKGGNFGGRSSGPYGGGGQYFAKPRNQGGY (SEQ ID NO: 304); the sequence RMRIZFKNKGKDTAELRRRRVEVSVELRKAKKDEQILKRRNV (SEQ ID NO: 305) of the IBB domain from importin-alpha; the sequences VSRKRPRP (SEQ ID NO: 306) and PPKKARED (SEQ ID NO: 307) of the myoma T protein; the sequence PQPKKKPL (SEQ ID NO: 308) of human p53; the sequence SALIKKKKKMAP (SEQ ID NO: 309) of mouse c-abl IV; the sequences DRLRR (SEQ ID NO: 310) and PKQKKRK(SEQ ID NO: 311) of the influenza virus NS1; the sequence RKLKKKIKKL (SEQ ID NO: 312) of the Hepatitis virus delta antigen; the sequence REKKKFLKRR (SEQ ID NO: 313) of the mouse Mx1 protein; the sequence KRKGDEVDGVDEVAKKKSKK (SEQ ID NO: 314) of the human poly(ADP-ribose) polymerase; and the sequence RKCLQAGMNLEARKTKK (SEQ ID NO: 315) of the human glucocorticoid receptor. In some embodiments, the CRISPR-associated protein includes at least one (e.g., 1, 2, 3, 4, 5, 6, 7, 8, 9, or 10) Nuclear Export Signal (NES) attached the N-terminal or C-terminal of the protein. In a preferred embodiment, a C-terminal and/or N-terminal NLS or NES is attached for optimal expression and nuclear targeting in eukaryotic cells, e.g., human cells.

In some embodiments, the CRISPR enzymes described herein are mutated at one or more amino acid residues to alter one or more functional activities. For example, in some embodiments, the CRISPR enzyme is mutated at one or more amino acid residues to alter its helicase activity. In some embodiments, the CRISPR enzyme is mutated at one or more amino acid residues to alter its nuclease activity (e.g., endonuclease activity or exonuclease activity). In some embodiments, the CRISPR enzyme is mutated at one or more amino acid residues to alter its ability to functionally associate with a RNA guide. In some embodiments, the CRISPR enzyme is mutated at one or more amino acid residues to alter its ability to functionally associate with a target nucleic acid.

In some embodiments, the CRISPR enzymes described herein are capable of cleaving a target nucleic acid molecule. In some embodiments, the CRISPR enzyme cleaves both strands of the target nucleic acid molecule. However, in some embodiments, the CRISPR enzyme is mutated at one or more amino acid residues to alter its cleaving activity. For example, in some embodiments, the CRISPR enzyme may comprise one or more mutations which render the enzyme incapable of cleaving a target nucleic acid. In other embodiments, the CRISPR enzyme may comprise one or more mutations such that the enzyme is capable of cleaving a single strand of the target nucleic acid (i.e., nickase activity). In some embodiments, the CRISPR enzyme is capable of cleaving the strand of the target nucleic acid that is complementary to the strand that the RNA guide hybridizes to. In some embodiments, the CRISPR enzyme is capable of cleaving the strand of the target nucleic acid that the RNA guide hybridizes to.

In some embodiments, a CRISPR enzyme described herein may be engineered to comprise a deletion in one or more amino acid residues to reduce the size of the enzyme while retaining one or more desired functional activities (e.g., nuclease activity and the ability to interact functionally with a RNA guide). The truncated CRISPR enzyme may be advantageously used in combination with delivery systems having load limitations.

In one aspect, the present disclosure provides nucleic acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the nucleic sequences described herein. In another aspect, the present disclosure also provides amino acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the amino acid sequences described herein.

In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are the same as the sequences described herein. In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from the sequences described herein.

In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as the sequences described herein. In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from the sequences described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general, the length of a reference sequence aligned for comparison purposes should be at least 80% of the length of the reference sequence, and in some embodiments is at least 90%, 95%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blosum 62 scoring matrix with a gap penalty of 12, a gap extend penalty of 4, and a frameshift gap penalty of 5.

Beyond the biochemical and diagnostic applications described herein, programmable Type V-I CRISPR-Cas systems described herein have important applications in eukaryotic cells such as therapeutic modification of the genome, with examples of modifications including, but not limited to; genotype correction, gene knockout, genetic sequence insertion/deletion (by homology directed repair or otherwise), single nucleotide modification, or gene regulation. These gene modification modalities can use the nuclease activity of Cas12i, double nicking, or programmable DNA binding of catalytically inactive Cas12i fused to additional effector domains.

In some embodiments, the CRISPR-associated proteins and accessory proteins described herein can be fused to one or more peptide tags, including a His-tag, GST-tag, FLAG-tag, or myc-tag. In some embodiments, the CRISPR-associated proteins or accessory proteins described herein can be fused to a detectable moiety such as a fluorescent protein (e.g., green fluorescent protein or yellow fluorescent protein). And in some embodiments, CRISPR-associated proteins or accessory proteins of this disclosure are fused to a peptide or non-peptide moiety that allows these proteins to enter or localize to a tissue, a cell, or a region of a cell. For instance, a CRISPR-associated protein or accessory protein of this disclosure (such as Cas12i) may comprise a nuclear localization sequence (NLS) such as an SV40 (simian virus 40) NLS, c-Myc NLS, or other suitable monopartite NLS. The NLS may be fused to an N-terminal and/or a C-terminal of the CRISPR-associated protein or accessory protein, and may be fused singly (i.e., a single NLS) or concatenated (e.g., a chain of 2, 3, 4, etc. NLS).

In those embodiments where a tag is fused to a CRISPR-associated protein, such tag may facilitate affinity-based or charge-based purification of the CRISPR-associated protein, e.g., by liquid chromatography or bead separation utilizing an immobilized affinity or ion-exchange reagent. As a non-limiting example, a recombinant CRISPR-associated protein of this disclosure (such as Cas12i) comprises a polyhistidine (His) tag, and for purification is loaded onto a chromatography column comprising an immobilized metal ion (e.g. a $Zn^{2+}$, $Ni^{2+}$, $Cu^{2+}$ ion chelated by a chelating ligand immobilized on the resin, which resin may be an individually prepared resin or a commercially available resin or ready to use column such as the HisTrap FF column commercialized by GE Healthcare Life Sciences, Marlborough, Massachusetts). Following the loading step, the column is optionally rinsed, e.g., using one or more suitable buffer solutions, and the His-tagged protein is then eluted using a suitable elution buffer. Alternatively or additionally, if the recombinant CRISPR-associated protein of this disclosure utilizes a FLAG-tag, such protein may be purified using immunoprecipitation methods known in the industry. Other suitable purification methods for tagged CRISPR-associated proteins or accessory proteins of this disclosure will be evident to those of skill in the art.

The proteins described herein (e.g., CRISPR-associated proteins or accessory proteins) can be delivered or used as either nucleic acid molecules or polypeptides. When nucleic acid molecules are used, the nucleic acid molecule encoding the CRISPR-associated proteins can be codon-optimized, as discussed in further detail below. The nucleic acid can be codon optimized for use in any organism of interest, in particular human cells or bacteria. For example, the nucleic acid can be codon-optimized for any non-human eukaryote including mice, rats, rabbits, dogs, livestock, or non-human primates. Codon usage tables are readily available, for example, at the "Codon Usage Database" available at World Wide Web address kazusa.orjp/codon/ and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, PA).

In some instances, nucleic acids of this disclosure which encode CRISPR-associated proteins or accessory proteins for expression in eukaryotic (e.g., human, or other mammalian cells) cells include one or more introns, i.e., one or more non-coding sequences comprising, at a first end (e.g., a 5' end), a splice-donor sequence and, at second end (e.g., the 3' end) a splice acceptor sequence. Any suitable splice donor/splice acceptor can be used in the various embodiments of this disclosure, including without limitation simian virus 40 (SV40) intron, beta-globin intron, and synthetic introns. Alternatively or additionally, nucleic acids of this disclosure encoding CRISPR-associated proteins or accessory proteins may include, at a 3' end of a DNA coding sequence, a transcription stop signal such as a polyadenylation (polyA) signal. In some instances, the polyA signal is located in close proximity to, or adjacent to, an intron such as the SV40 intron.

RNA Guides

In some embodiments, the CRISPR systems described herein include at least one Type V-I RNA guide. The architecture of many RNA guides is known in the art (see, e.g., International Publication Nos. WO 2014/093622 and WO 2015/070083, the entire contents of each of which are incorporated herein by reference). In some embodiments, the CRISPR systems described herein include multiple RNA guides (e.g., two, three, four, five, six, seven, eight, or more RNA guides).

In some embodiments, the CRISPR systems described herein include at least one Type V-I RNA guide or a nucleic acid encoding at least one Type V-I RNA guide. In some embodiments, the RNA guide includes a crRNA. Generally, the crRNAs described herein include a direct repeat sequence and a spacer sequence. In certain embodiments, the crRNA includes, consists essentially of, or consists of a direct repeat sequence linked to a guide sequence or spacer sequence. In some embodiments, the crRNA includes a direct repeat sequence, a spacer sequence, and a direct repeat sequence (DR-spacer-DR), which is typical of precursor crRNA (pre-crRNA) configurations in other CRISPR systems. In some embodiments, the crRNA includes a truncated direct repeat sequence and a spacer sequence, which is typical of processed or mature crRNA. In some embodiments, the CRISPR-Cas effector protein forms a complex with the RNA guide, and the spacer sequence directs the complex to a sequence-specific binding with the target nucleic acid that is complementary to the spacer sequence.

Suitably, CRISPR systems described herein comprise at least one Type V-I RNA guide or nucleic acids encoding a Type V-I RNA guide, wherein the RNA guide comprises a direct repeat. Suitably, the Type V-I RNA guide may form a secondary structure such as a stem loop structure, e.g., as described herein.

Figure 3:
FIG. 3 is a group of schematic diagrams that show predicted secondary structure of the RNA transcript of examples of Type V-I direct repeat sequences.

The direct repeat can include two stretches of nucleotides that may be complementary to one another, separated by intervening nucleotides such that the direct repeat can hybridize to form the double stranded RNA duplex (dsRNA duplex) resulting in a stem-loop structure where the two complementary stretches of nucleotides form a stem and the intervening nucleotides form a loop or hair-pin (FIG. 3). For example, the intervening nucleotides that form the "loop" have a length of from about 6 nucleotides to about 8 nucleotides, or about 7 nucleotides. In different embodiments, the stem can include at least 2, at least 3, at least 4, or 5 base pairs.

Suitably, the direct repeat can include two complementary stretches of nucleotides that are about 5 nucleotides in length separated by about seven intervening nucleotides.

Some exemplary direct repeats of Type V-I systems are illustrated in FIG. 3, suitably when departing from naturally occurring Type V-I direct repeats, the skilled person may mimic the structure of such direct repeats illustrated in FIG. 3.

The direct repeat can include or consist of about 22 to 40 nucleotides, or about 23 to 38 nucleotides or about 23 to 36 nucleotides.

In some embodiments, the CRISPR systems described herein include a plurality of RNA guides (e.g., 2, 3, 4, 5, 10, 15, or more) or a plurality of nucleic acids encoding a plurality of RNA guides.

In some embodiments, the CRISPR system described herein includes an RNA guide or a nucleic acid encoding the RNA guide. In some embodiments, the RNA guide comprises or consists of a direct repeat sequence and a spacer sequence capable of hybridizing (e.g., hybridizes under appropriate conditions) to a target nucleic acid, wherein the direct repeat sequence comprises 5'-CCGU-CNNNNNNNGACGG-3' (SEQ ID NO: 202) proximal to its 3' end and adjacent to the spacer sequence. In some embodiments, the RNA guide comprises or consists of a direct repeat sequence and a spacer sequence capable of hybridizing (e.g., hybridizes under appropriate conditions) to a target nucleic acid, wherein the direct repeat sequence comprises 5'-GUGCCNNNNNNNGGCAC-3' (SEQ ID NO: 203) proximal to its 3' end and adjacent to the spacer sequence. In some embodiments, the RNA guide comprises or consists of a direct repeat sequence and a spacer sequence capable of hybridizing (e.g., hybridizes under appropriate conditions) to a target nucleic acid, wherein the direct repeat sequence comprises 5'-GUGUCN$_{5-6}$UGACAX$_1$-3' (SEQ ID NO: 204) proximal to the 3' end and adjacent to the spacer sequence, wherein N5-6 refers to a contiguous sequence of any 5 or 6 nucleobases, and X$_1$ refers to C or T or U.

Examples of RNA guide direct repeat sequences and effector protein pairs are provided in Table 5A. In some embodiments, the direct repeat sequence comprises or consists of a nucleic acid sequence listed in Table 5A (e.g., SEQ ID NOs: 6-10, 19-24). In some embodiments, the direct repeat sequence comprises or consists of a nucleic acid having a nucleic acid sequence listed in Table 5A with a truncation of the initial three 5' nucleotides. In some embodiments, the direct repeat sequence comprises or consists of a nucleic acid having a nucleic acid sequence listed in Table 5A with a truncation of the initial four 5' nucleotides. In some embodiments, the direct repeat sequence comprises or consists of a nucleic acid having a nucleic acid sequence listed in Table 5A with a truncation of the initial five 5' nucleotides. In some embodiments, the direct repeat sequence comprises or consists of a nucleic acid having a nucleic acid sequence listed in Table 5A with a truncation of the initial six 5' nucleotides. In some embodiments, the direct repeat sequence comprises or consists of a nucleic acid having a nucleic acid sequence listed in Table 5A with a truncation of the initial seven 5' nucleotides. In some embodiments, the direct repeat sequence comprises or consists of a nucleic acid having a nucleic acid sequence listed in Table 5A with a truncation of the initial eight 5' nucleotides.

Multiplexing RNA Guides

CLUST.029130 (Type V-I) CRISPR-Cas effectors have been demonstrated to employ more than one RNA guide, thus enabling the ability of these effectors, and systems and complexes that include them, to target multiple different nucleic acid targets. In some embodiments, the CRISPR systems described herein include multiple RNA guides (e.g., two, three, four, five, six, seven, eight, nine, ten, fifteen, twenty, thirty, forty, or more RNA guides). In some embodiments, the CRISPR systems described herein include a single RNA strand or a nucleic acid encoding a single RNA strand, wherein the RNA guides are arranged in tandem. The single RNA strand can include multiple copies of the same RNA guide, multiple copies of distinct RNA guides, or combinations thereof.

In some embodiments, the CLUST.029130 (Type V-I) CRISPR-Cas effector proteins are delivered complexed with multiple RNA guides directed to different target nucleic acids. In some embodiments, the CLUST.029130 (Type V-I) CRISPR-Cas effector proteins can be co-delivered with multiple RNA guides, each specific for a different target nucleic acid. Methods of multiplexing using CRISPR-associated proteins are described, for example, in U.S. Pat. No. 9,790,490, and EP 3009511, the entire contents of each of which are expressly incorporated herein by reference.

RNA Guide Modifications
Spacer Lengths

The spacer length of RNA guides can range from about 15 to 50 nucleotides. In some embodiments, the spacer length of an RNA guide is at least 16 nucleotides, at least 17 nucleotides, at least 18 nucleotides, at least 19 nucleotides, at least 20 nucleotides, at least 21 nucleotides, or at least 22 nucleotides. In some embodiments, the spacer length is from 15 to 17 nucleotides, from 15 to 23 nucleotides, from 16 to 22 nucleotides, from 17 to 20 nucleotides, from 20 to 24 nucleotides (e.g., 20, 21, 22, 23, or 24 nucleotides), from 23 to 25 nucleotides (e.g., 23, 24, or 25 nucleotides), from 24 to 27 nucleotides, from 27 to 30 nucleotides, from 30 to 45 nucleotides (e.g., 30, 31, 32, 33, 34, 35, 40, or 45 nucleotides), from 30 or 35 to 40 nucleotides, from 41 to 45 nucleotides, from 45 to 50 nucleotides, or longer. In some embodiments, the spacer length of an RNA guide is 31 nucleotides. In some embodiments, the direct repeat length of the RNA guide is at least 21 nucleotides, or is from 21 to 37 nucleotides (e.g., 23, 24, 25, 30, 35, or 36 nucleotides). In some embodiments, the direct repeat length of the RNA guide is 23 nucleotides.

The RNA guide sequences can be modified in a manner that allows for formation of the CRISPR effector complex and successful binding to the target, while at the same time not allowing for successful nuclease activity (i.e., without nuclease activity/without causing indels). These modified guide sequences are referred to as "dead guides" or "dead guide sequences." These dead guides or dead guide sequences may be catalytically inactive or conformationally inactive with regard to nuclease activity. Dead guide sequences are typically shorter than respective guide sequences that result in active RNA cleavage. In some embodiments, dead guides are 5%, 10%, 20%, 30%, 40%, or 50%, shorter than respective RNA guides that have nuclease activity. Dead guide sequences of RNA guides can be from 13 to 15 nucleotides in length (e.g., 13, 14, or 15 nucleotides in length), from 15 to 19 nucleotides in length, or from 17 to 18 nucleotides in length (e.g., 17 nucleotides in length).

Thus, in one aspect, the disclosure provides non-naturally occurring or engineered CRISPR systems including a functional CRISPR enzyme as described herein, and a RNA guide (gRNA) wherein the gRNA comprises a dead guide sequence whereby the gRNA is capable of hybridizing to a target sequence such that the CRISPR system is directed to a genomic locus of interest in a cell without detectable cleavage activity.

A detailed description of dead guides is described, e.g., in WO 2016094872, which is incorporated herein by reference in its entirety.
Inducible Guides RNA guides can be generated as components of inducible systems. The inducible nature of the systems allows for spatiotemporal control of gene editing or gene expression. In some embodiments, the stimuli for the inducible systems include, e.g., electromagnetic radiation, sound energy, chemical energy, and/or thermal energy.

In some embodiments, the transcription of RNA guide can be modulated by inducible promoters, e.g., tetracycline or doxycycline controlled transcriptional activation (Tet-On and Tet-Off expression systems), hormone inducible gene expression systems (e.g., ecdysone inducible gene expression systems), and arabinose-inducible gene expression systems. Other examples of inducible systems include, e.g., small molecule two-hybrid transcription activations systems (FKBP, ABA, etc.), light inducible systems (Phytochrome, LOV domains, or cryptochrome), or Light Inducible Transcriptional Effector (LITE). These inducible systems are described, e.g., in WO 2016205764 and U.S. Pat. No. 8,795,965, both of which are incorporated herein by reference in their entirety.
Chemical Modifications Chemical modifications can be applied to the RNA guide's phosphate backbone, sugar, and/or base. Backbone modifications such as phosphorothioates modify the charge on the phosphate backbone and aid in the delivery and nuclease resistance of the oligonucleotide (see, e.g., Eckstein, "Phosphorothioates, essential components of therapeutic oligonucleotides," Nucl. Acid Ther., 24 (2014), pp. 374-387); modifications of sugars, such as 2'-O-methyl (2'-OMe), 2'-F, and locked nucleic acid (LNA), enhance both base pairing and nuclease resistance (see, e.g., Allerson et al. "Fully 2'-modified oligonucleotide duplexes with improved in vitro potency and stability compared to unmodified small interfering RNA," J. Med. Chem., 48.4 (2005): 901-904). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," Front. Genet., 2012 Aug. 20; 3:154). Additionally, RNA is amenable to both 5' and 3' end conjugations with a variety of functional moieties including fluorescent dyes, polyethylene glycol, or proteins.

A wide variety of modifications can be applied to chemically synthesized RNA guide molecules. For example, modifying an oligonucleotide with a 2'-OMe to improve nuclease resistance can change the binding energy of Watson-Crick base pairing. Furthermore, a 2'-OMe modification can affect how the oligonucleotide interacts with transfection reagents, proteins or any other molecules in the cell. The effects of these modifications can be determined by empirical testing.

In some embodiments, the RNA guide includes one or more phosphorothioate modifications. In some embodiments, the RNA guide includes one or more locked nucleic acids for the purpose of enhancing base pairing and/or increasing nuclease resistance.

A summary of these chemical modifications can be found, e.g., in Kelley et al., "Versatility of chemically synthesized guide RNAs for CRISPR-Cas9 genome editing," J. Biotechnol. 2016 Sep. 10; 233:74-83; WO 2016205764; and U.S. Pat. No. 8,795,965 B2; each which is incorporated by reference in its entirety.
Sequence Modifications The sequences and the lengths of the RNA guides and crRNAs described herein can be optimized. In some embodiments, the optimized length of RNA guide can be determined by identifying the processed form of the crRNA, or by empirical length studies for RNA guides, of crRNAs.

The RNA guides can also include one or more aptamer sequences. Aptamers are oligonucleotide or peptide molecules that can bind to a specific target molecule. The aptamers can be specific to gene effectors, gene activators, or gene repressors. In some embodiments, the aptamers can be specific to a protein, which in turn is specific to and recruits/binds to specific gene effectors, gene activators, or gene repressors. The effectors, activators, or repressors can be present in the form of fusion proteins. In some embodiments, the RNA guide has two or more aptamer sequences that are specific to the same adaptor proteins. In some embodiments, the two or more aptamer sequences are specific to different adaptor proteins. The adaptor proteins can include, e.g., MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, and PRR1. Accordingly, in some embodiments, the aptamer is selected from binding proteins specifically binding any one of the adaptor proteins as described herein. In some embodiments, the aptamer sequence is a MS2 loop. A detailed description of aptamers can be found, e.g., in Nowak et al., "Guide RNA engineering for versatile Cas9 functionality," *Nucl. Acid. Res.,* 2016 Nov. 16; 44(20):9555-9564; and WO 2016205764, which are incorporated herein by reference in their entirety.

Guide: Target Sequence Matching Requirements

In classic CRISPR systems, the degree of complementarity between a guide sequence and its corresponding target sequence can be about 50%, 60%, 75%, 80%, 85%, 90%, 95%, 97.5%, 99%, or 100%. In some embodiments, the degree of complementarity is 100%. The RNA guides can be about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length.

To reduce off-target interactions, e.g., to reduce the guide interacting with a target sequence having low complementarity, mutations can be introduced to the CRISPR systems so that the CRISPR systems can distinguish between target and off-target sequences that have greater than 80%, 85%, 90%, or 95% complementarity. In some embodiments, the degree of complementarity is from 80% to 95%, e.g., about 83%, 84%, 85%, 86%, 87%, 88%, 89%, 90%, 91%, 92%, 93%, 94%, or 95% (for example, distinguishing between a target having 18 nucleotides from an off-target of 18 nucleotides having 1, 2, or 3 mismatches). Accordingly, in some embodiments, the degree of complementarity between a guide sequence and its corresponding target sequence is greater than 94.5%, 95%, 95.5%, 96%, 96.5%, 97%, 97.5%, 98%, 98.5%, 99%, 99.5%, or 99.9%. In some embodiments, the degree of complementarity is 100%.

It is known in the field that complete complementarity is not required provided that there is sufficient complementarity to be functional. Modulations of cleavage efficiency can be exploited by introduction of mismatches, e.g., one or more mismatches, such as 1 or 2 mismatches between spacer sequence and target sequence, including the position of the mismatch along the spacer/target. The more central (i.e., not at the 3' or 5' ends) a mismatch, e.g., a double mismatch, is located; the more cleavage efficiency is affected. Accordingly, by choosing mismatch positions along the spacer sequence, cleavage efficiency can be modulated. For example, if less than 100% cleavage of targets is desired (e.g., in a cell population), 1 or 2 mismatches between spacer and target sequence can be introduced in the spacer sequences.

Optimization of CRISPR Systems for use in Select Organisms

Codon-Optimization

The invention contemplates all possible variations of nucleic acids, such as cDNA, that could be made by selecting combinations based on possible codon choices. These combinations are made in accordance with the standard triplet genetic code as applied to the polynucleotide encoding naturally occurring variant, and all such variations are to be considered as being specifically disclosed. Nucleotide sequences encoding type V-I CRISPR-Cas-associated effector protein variants that have been codon-optimized for expression in bacteria (e.g., *E. coli*) and in human cells are disclosed herein. For example, the codon-optimized sequences for human cells can be generated by substituting codons in the nucleotide sequence that occur at lower frequency in human cells for codons that occur at higher frequency in human cells. The frequency of occurrence for codons can be computationally determined by methods known in the art. An example of a calculation of these codon frequencies for various host cells (e.g., *E. coli,* yeast, insect, *C. elegans, D. melanogaster,* human, mouse, rat, pig, *P. pastoris, A. thalian,* maize, and tobacco) have been published or made available by sources such as the GenScript® Codon Usage Frequency Table Tool (example codon usage tables for *E. coli* and Humans are included below.

TABLE 1

*E. coli* Codon Usage Table

| Triplet | Amino acid | Fraction | Number | Triplet | Amino acid | Fraction | Number |
|---------|------------|----------|--------|---------|------------|----------|--------|
| TTT | F | 0.58 | 80995 | TCT | S | 0.17 | 38027 |
| TTC | F | 0.42 | 58774 | TCC | S | 0.15 | 33430 |
| TTA | L | 0.14 | 52382 | TCA | S | 0.14 | 32715 |
| TTG | L | 0.13 | 47500 | TCG | S | 0.14 | 31146 |
| TAT | Y | 0.59 | 63937 | TGT | C | 0.46 | 19138 |
| TAC | Y | 0.41 | 44631 | TGC | C | 0.54 | 22188 |
| TAA | * | 0.61 | 7356 | TGA | * | 0.3 | 3623 |
| TAG | * | 0.09 | 989 | TGG | W | 1 | 50991 |
| CTT | L | 0.12 | 43449 | CCT | P | 0.18 | 27340 |
| CTC | L | 0.1 | 37347 | CCC | P | 0.13 | 19666 |
| CTA | L | 0.04 | 15409 | CCA | P | 0.2 | 31534 |
| CTG | L | 0.47 | 177210 | CCG | P | 0.49 | 76644 |
| CAT | H | 0.57 | 45879 | CGT | R | 0.36 | 73197 |
| CAC | H | 0.43 | 34078 | CGC | R | 0.36 | 72212 |
| CAA | Q | 0.34 | 53394 | CGA | R | 0.07 | 13844 |
| CAG | Q | 0.66 | 104171 | CGG | R | 0.11 | 21552 |
| ATT | I | 0.49 | 109072 | ACT | T | 0.19 | 37842 |
| ATC | I | 0.39 | 86796 | ACC | T | 0.4 | 80547 |
| ATA | I | 0.11 | 24984 | ACA | T | 0.17 | 33910 |
| ATG | M | 1 | 96695 | ACG | T | 0.25 | 50269 |
| AAT | N | 0.49 | 75436 | AGT | S | 0.16 | 36097 |
| AAC | N | 0.51 | 78443 | AGC | S | 0.25 | 55551 |
| AAA | K | 0.74 | 129153 | AGA | R | 0.07 | 13152 |
| AAG | K | 0.26 | 45459 | AGG | R | 0.04 | 7607 |
| GTT | V | 0.28 | 72584 | GCT | A | 0.18 | 62479 |
| GTC | V | 0.2 | 52439 | GCC | A | 0.26 | 88721 |
| GTA | V | 0.17 | 42420 | GCA | A | 0.23 | 77547 |
| GTG | V | 0.35 | 89265 | GCG | A | 0.33 | 110308 |

TABLE 1-continued

E. coli Codon Usage Table

| Triplet | Amino acid | Fraction | Number | Triplet | Amino acid | Fraction | Number |
|---|---|---|---|---|---|---|---|
| GAT | D | 0.63 | 119939 | GGT | G | 0.35 | 93325 |
| GAC | D | 0.37 | 70394 | GGC | G | 0.37 | 99390 |
| GAA | E | 0.68 | 143353 | GGA | G | 0.13 | 34799 |
| GAG | E | 0.32 | 68609 | GGG | G | 0.15 | 41277 |

TABLE 2

Human Codon Usage Table

| Triplet | Amino acid | Fraction | Number | Triplet | Amino acid | Fraction | Number |
|---|---|---|---|---|---|---|---|
| TTT | F | 0.45 | 336562 | TCT | S | 0.18 | 291040 |
| TTC | F | 0.55 | 406571 | TCC | S | 0.22 | 346943 |
| TTA | L | 0.07 | 143715 | TCA | S | 0.15 | 233110 |
| TTG | L | 0.13 | 249879 | TCG | S | 0.06 | 89429 |
| TAT | Y | 0.43 | 239268 | TGT | C | 0.45 | 197293 |
| TAC | Y | 0.57 | 310695 | TGC | C | 0.55 | 243685 |
| TAA | * | 0.28 | 14322 | TGA | * | 0.52 | 25383 |
| TAG | * | 0.2 | 10915 | TGG | W | 1 | 255512 |
| CTT | L | 0.13 | 253795 | CCT | P | 0.28 | 343793 |
| CTC | L | 0.2 | 386182 | CCC | P | 0.33 | 397790 |
| CTA | L | 0.07 | 138154 | CCA | P | 0.27 | 331944 |
| CTG | L | 0.41 | 800774 | CCG | P | 0.11 | 139414 |
| CAT | H | 0.41 | 207826 | CGT | R | 0.08 | 93458 |
| CAC | H | 0.59 | 297048 | CGC | R | 0.19 | 217130 |
| CAA | Q | 0.25 | 234785 | CGA | R | 0.11 | 126113 |
| CAG | Q | 0.75 | 688316 | CGG | R | 0.21 | 235938 |
| ATT | I | 0.36 | 313225 | ACT | T | 0.24 | 255582 |
| ATC | I | 0.48 | 426570 | ACC | T | 0.36 | 382050 |
| ATA | I | 0.16 | 140652 | ACA | T | 0.28 | 294223 |
| ATG | M | 1 | 443795 | ACG | T | 0.12 | 123533 |
| AAT | N | 0.46 | 331714 | AGT | S | 0.15 | 237404 |
| AAC | N | 0.54 | 387148 | AGC | S | 0.24 | 385113 |
| AAA | K | 0.42 | 476554 | AGA | R | 0.2 | 228151 |
| AAG | K | 0.58 | 654280 | AGG | R | 0.2 | 227281 |
| GTT | V | 0.18 | 216818 | GCT | A | 0.26 | 370873 |
| GTC | V | 0.24 | 290874 | GCC | A | 0.4 | 567930 |
| GTA | V | 0.11 | 139156 | GCA | A | 0.23 | 317338 |
| GTG | V | 0.47 | 575438 | GCG | A | 0.11 | 150708 |
| GAT | D | 0.46 | 443369 | GGT | G | 0.16 | 215544 |
| GAC | D | 0.54 | 517579 | GGC | G | 0.34 | 453917 |
| GAA | E | 0.42 | 577846 | GGA | G | 0.25 | 325243 |
| GAG | E | 0.58 | 810842 | GGG | G | 0.25 | 326879 |

Methods of Using CRISPR Systems

The CRISPR systems described herein have a wide variety of utilities including modifying (e.g., deleting, inserting, translocating, inactivating, or activating) a target polynucleotide in a multiplicity of cell types. The CRISPR systems have a broad spectrum of applications in, e.g., DNA/RNA detection (e.g., specific high sensitivity enzymatic reporter unlocking (SHERLOCK)), tracking and labeling of nucleic acids, enrichment assays (extracting desired sequence from background), detecting circulating tumor DNA, preparing next generation library, drug screening, disease diagnosis and prognosis, and treating various genetic disorders. Without wishing to be bound by any particular theory, CRISPR systems including a Cas12i protein may exhibit increased activity or may be preferentially active when targeting in certain environments, such as DNA plasmids, supercoiled DNA, or transcriptionally-active genomic loci.

Genome Editing Systems Generally

The term "genome editing system" refers to an engineered CRISPR system of the present disclosure having RNA-guided DNA editing activity. Genome editing systems of the present disclosure include at least two components of the CRISPR systems described above: an RNA guide and a cognate CRISPR effector protein. In certain embodiments of this disclosure the effector is a Cas12i protein and the RNA guide is a cognate Type V-I RNA guide. As described above, these two components form a complex that is capable of associating with a specific nucleic acid sequence and editing the DNA in or around that nucleic acid sequence, for instance by making one or more of a single strand break (an SSB or nick), a double strand break (a DSB), a nucleobase modification, a DNA methylation or demethylation, a chromatin modification, etc.

In certain embodiments, a genome editing system is transiently active (e.g., incorporating an inducible CRISPR effector as discussed above), while in other embodiments the system is constitutively (e.g., encoded by nucleic acids in which expression of CRISPR system components is controlled by one or more strong promoters).

Genome editing systems of the present disclosure, when introduced into cells, may alter (a) endogenous genomic DNA (gDNA) including, without limitation, DNA encoding e.g., a gene target of interest, an exonic sequence of a gene, an intronic sequence of a gene, a regulatory element of a gene or group of genes, etc.; (b) endogenous extra-genomic DNA such as mitochondrial DNA (mtDNA); and/or (c) exogenous DNA such as a non-integrated viral genome, a plasmid, an artificial chromosome, etc. Throughout this disclosure, these DNA substrates are referred to as "target DNA."

In instances where a genome editing operates by generating SSBs or DSBs, alterations caused by the system may take the form of short DNA insertions or deletions, which are collectively referred to as "indels." These indels may be formed within or proximate to a predicted cleavage site that is typically proximate to the PAM sequence and/or within a region of complementarity to the spacer sequence, though in some cases indels may occur outside of such predicted cleavage site. Without wishing to be bound by any theory, it is believed that indels are often the result of the repair of an SSB or DSB by "error-prone" DNA damage repair pathways, such as non-homologous end joining (NHEJ).

In some cases, a genome editing is used to generate two DSBs within 50, 60, 70, 80, 90, 100, 200, 300, 400, 500, 600, 700, 800, 900, 1000, 1250, 1500, 1750, or 2000 base pairs of one another, which results in one or more outcomes, including the formation of an indels at one or both sites of cleavage, as well as deletion or inversion of a DNA sequence disposed between the DSBs.

Alternatively, genome editing systems of this disclosure may alter target DNA via integration of new sequences. These new sequences may be distinct from the existing sequence of the target DNA (as a non-limiting example, integrated by NHEJ by ligation of blunt-ends) or the may correspond to a DNA template having one or more regions that are homologous to a region of the targeted DNA. Integration of templated homologous sequences is also referred to as "homology-directed repair" or "HDR." Template DNA for HDR may be endogenous to the cell, including without limitation in the form of a homologous sequence located on another copy of the same chromosome as the target DNA, a homologous sequence from the same gene cluster as the target DNA, etc. Alternatively, or additionally, the template DNA may be provided exogenously, including without limitation as a free linear or circular DNA, as a DNA bound (covalently or non-covalently) to one or more genome editing system components, or as part of a vector genome.

In some instances, editing comprises a temporary or permanent silencing of a gene by CRISPR-mediated interference, as described by Matthew H. Larson et al. "CRISPR interference (CRISPRi) for sequence-specific control of gene expression," *Nature Protocols* 8, 2180-2196 (2013), which is incorporated by reference in its entirety and for all purposes.

Genome editing systems may include other components, including without limitation one or more heterologous functional domains which mediate site specific nucleobase modification, DNA methylation or demethylation, or chromatin modification. In some cases, the heterologous functional domain covalently bound to a CRISPR-associated protein such as a Cas12i, for instance by means of a direct peptide bond or an intervening peptide linker. Fusions of this type are described in greater detail below. In some embodiments, the heterologous functional domain is covalently bound to the crRNA, for instance by means of a chemical cross-link. And in some embodiments, one or more functional groups may be non-covalently associated with a CRISPR associated protein and/or a crRNA. This is done, variously, by means of an aptamer appended to the crRNA and/or the heterologous functional group, a peptide motif fused to the CRISPR-associated protein and a binding domain configured to bind such motif fused to the heterologous functional domain, or vice versa.

Genome editing system designs and genome editing outcomes are described in greater detail elsewhere in this specification.

DNA RNA Detection

In one aspect, the CRISPR-Cas system described herein can be used in DNA/RNA detection by DNA sensing. Single effector RNA-guided DNases can be reprogrammed with RNA guides to provide a platform for specific single-stranded DNA (ssDNA) sensing. Upon recognition of its DNA target, an activated CRISPR Type V-I effector protein engages in "collateral" cleavage of nearby ssDNA with no sequence similarity to the target sequence. This RNA-programmed collateral cleavage activity allows the CRISPR systems to detect the presence of a specific DNA by non-specific degradation of labeled ssDNA.

The collateral ssDNase activity can be combined with a reporter in DNA detection applications such as a method called the DNA Endonuclease-Targeted CRISPR trans reporter (DETECTR) method, which when combined with amplification achieves attomolar sensitivity for DNA detection (see, e.g., Chen et al., Science, 360(6387):436-439, 2018), which is incorporated herein by reference in its entirety. One application of using the enzymes described herein is to degrade non-target ssDNA in an in vitro environment. A "reporter" ssDNA molecule linking a fluorophore and a quencher can also be added to the in vitro system, along with an unknown sample of DNA (either single-stranded or double-stranded). Upon recognizing the target sequence in the unknown piece of DNA, the surveillance complex containing a Type V-I effector cleaves the reporter ssDNA resulting in a fluorescent readout.

In other embodiments, the SHERLOCK method (Specific High Sensitivity Enzymatic Reporter UnLOCKing) also provides an in vitro nucleic acid detection platform with attomolar (or single-molecule) sensitivity based on nucleic acid amplification and collateral cleavage of a reporter ssDNA, allowing for real-time detection of the target. Methods of using CRISPR in SHERLOCK are described in detail, e.g., in Gootenberg, et al. "Nucleic acid detection with CRISPR-Cas13a/C2c2," *Science,* 356(6336):438-442 (2017), which is incorporated herein by reference in its entirety.

In some embodiments, the CRISPR systems described herein can be used in multiplexed error-robust fluorescence in situ hybridization (MERFISH). These methods are described in, e.g., Chen et al., "Spatially resolved, highly multiplexed RNA profiling in single cells," *Science,* 2015 Apr. 24; 348(6233):aaa6090, which is incorporated herein by reference in its entirety.

In some embodiments, the CRISPR systems described herein can be used to detect a target DNA in a sample (e.g., a clinical sample, a cell, or a cell lysate). The collateral DNase activity of the CLUST.029130 (Type V-I) CRISPR-Cas effector proteins described herein is activated when the effector proteins bind to a target nucleic acid. Upon binding to the target DNA of interest, the effector protein cleaves a labeled detector ssDNA to generate or change a signal (e.g., an increased signal or a decreased signal) thereby allowing for the qualitative and quantitative detection of the target DNA in the sample. The specific detection and quantification of DNA in the sample allows for a multitude of applications including diagnostics.

In some embodiments, the methods include a) contacting a sample with: (i) an RNA guide (e.g., crRNA) and/or a nucleic acid encoding the RNA guide, wherein the RNA guide consists of a direct repeat sequence and a spacer sequence capable of hybridizing to the target RNA; (ii) a CLUST.029130 (Type V-I) CRISPR-Cas effector protein and/or a nucleic acid encoding the effector protein; and (iii) a labeled detector ssDNA; wherein the effector protein associates with the RNA guide to form a surveillance complex; wherein the surveillance complex hybridizes to the target DNA; and wherein upon binding of the surveillance complex to the target DNA, the effector protein exhibits collateral DNase activity and cleaves the labeled detector ssDNA; and b) measuring a detectable signal produced by cleavage of the labeled detector ssDNA, wherein said measuring provides for detection of the target DNA in the sample.

In some embodiments, the methods further include comparing the detectable signal with a reference signal and determining the amount of target DNA in the sample. In some embodiments, the measuring is performed using gold nanoparticle detection, fluorescence polarization, colloid phase transition/dispersion, electrochemical detection, and semiconductor based-sensing. In some embodiments, the labeled detector ssDNA includes a fluorescence-emitting dye pair, a fluorescence resonance energy transfer (FRET) pair, or a quencher/fluorophore pair. In some embodiments, upon cleavage of the labeled detector ssDNA by the effector protein, an amount of detectable signal produced by the labeled detector ssDNA is decreased or increased. In some embodiments, the labeled detector ssDNA produces a first detectable signal prior to cleavage by the effector protein and a second detectable signal after cleavage by the effector protein.

In some embodiments, a detectable signal is produced when the labeled detector ssDNA is cleaved by the effector protein. In some embodiments, the labeled detector ssDNA includes a modified nucleobase, a modified sugar moiety, a modified nucleic acid linkage, or a combination thereof.

In some embodiments, the methods include the multi-channel detection of multiple independent target DNAs in a sample (e.g., two, three, four, five, six, seven, eight, nine, ten, fifteen, twenty, thirty, forty, or more target RNAs) by using multiple CLUST.029130 (Type V-I) CRISPR-Cas systems, each including a distinct orthologous effector protein and corresponding RNA guides, allowing for the differentiation of multiple target DNAs in the sample. In some embodiments, the methods include the multi-channel detection of multiple independent target DNAs in a sample, with the use of multiple instances of CLUST.029130 (Type V-I) CRISPR-Cas systems, each containing an orthologous effector protein with differentiable collateral ssDNase substrates. Methods of detecting a DNA in a sample using CRISPR-associated proteins are described, for example, in U.S. Patent Publication No. 2017/0362644, the entire contents of which are incorporated herein by reference.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and DNAs in the vicinity of a protein or DNA of interest in vitro. After UV irradiation, the photoactivatable groups react with proteins and other molecules that are in close proximity to the tagged molecules, thereby labelling them. Labelled interacting molecules can subsequently be recovered and identified. The DNA targeting effector proteins can for instance be used to target probes to selected DNA sequences. These applications can also be applied in animal models for in vivo imaging of diseases or difficult-to culture cell types. The methods of tracking and labeling of nucleic acids are described, e.g., in U.S. Pat. No. 8,795,965; WO 2016205764; and WO 2017070605; each of which is incorporated herein by reference in its entirety.

Genome Editing Using Paired CRISPR Nickases

The CRISPR systems described herein can be used in tandem such that two Cas12i nicking enzymes, or one Cas12i enzyme and one other CRISPR Cas enzyme with nicking activity, targeted by a pair of RNA guides to opposite strands of a target locus, can generate a double-strand break with overhangs. This method may reduce the likelihood of off-target modifications, because a double-strand break is expected to occur only at loci where both enzymes generate a nick, thereby increasing genome editing specificity. This method is referred to as a 'double nicking' or 'paired nickase' strategy and is described, e.g., in Ran et al., "Double nicking by RNA-guided CRISPR Cas9 for enhanced genome editing specificity," *Cell*, 2013 Sep. 12; 154(6):1380-1389, and in Mali et al., "CAS9 transcriptional activators for target specificity screening and paired nickases for cooperative genome engineering," *Nature Biotechnology*, 2013 Aug. 1; 31:833-838, which are both incorporated herein by reference in their entireties.

The first applications of paired nickases demonstrated the utility of this strategy in mammalian cell lines. Applications of paired nickases have been described in the model plant *Arabidopsis* (e.g., in Fauser et al., "Both CRISPR/Cas-based nucleases and nickases can be used efficiently for genome engineering in *Arabidopsis thaliana*," *The Plant Journal* 79(2):348-59 (2014), and Shiml et al., ""The CRISPR/Cas system can be used as nuclease for in planta gene targeting and as paired nickases for directed mutagenesis in *Arabidopsis* resulting in heritable progeny," *The Plant Journal* 80(6):1139-50 (2014); in crops such as in rice (e.g., in Mikami et al., "Precision Targeted Mutagenesis via Cas9 Paired Nickases in Rice," *Plant and Cell Physiology* 57(5): 1058-68 (2016) and in wheat (e.g., in Čermák et al., "A Multipurpose Toolkit to Enable Advanced Genome Engineering in Plants," *Plant Cell* 29: 1196-1217 (2017); in bacteria (e.g., in Standage-Beier et al., "Targeted Large-Scale Deletion of Bacterial Genomes Using CRISPR-Nickases," *ACS Synthetic Biology* 4(11):1217-25 (2015); and in primary human cells for therapeutic purposes (e.g., in Dabrowska et al., "Precise Excision of the CAG Tract from the Huntingtin Gene by Cas9 Nickases," *Frontiers in Neuroscience* 12:75 (2018), and in Kocher et al., "Cut and Paste: Efficient Homology-Directed Repair of a Dominant Negative KRT14 Mutation via CRISPR/Cas9 Nickases," *Molecular Therapy* 25(11):2585-2598 (2017)), all of which are incorporated herein by reference in their entireties.

The CRISPR systems described herein can also be used as paired nickases to detect splice junctions as described e.g., in Santo & Paik, "A splice junction-targeted CRISPR approach (spJCRISPR) reveals human FOXO3B to be a protein-coding gene," *Gene* 673:95-101 (2018).

The CRISPR systems described herein can also be used as paired nickases to insert DNA molecules into target loci as described in e.g., Wang et al, "Therapeutic Genome Editing for Myotonic Dystrophy Type 1 Using CRISPR/Cas9," *Molecular Therapy* 26(11):2617-2630 (2018). The CRISPR systems described herein can also be used as single nickases to insert genes as described in e.g., Gao et al, "Single Cas9 nickase induced generation of NRAMP1 knockin cattle with reduced off-target effects," *Genome Biology* 18(1):13 (2017).

Enhancing Base Editing Using CRISPR Nickases

The CRISPR systems described herein can be used to augment the efficiency of CRISPR base editing. In base editing, a protein domain with DNA nucleotide modifying activity (e.g., cytidine deamination) is fused to a programmable CRISPR Cas enzyme that has been deactivated by mutation so as to no longer possess double-strand DNA cleavage activity. In some embodiments, using a nickase as the programmable Cas protein has been shown to improve the efficiency of base editing as described e.g., in Komor et al., "Programmable editing of a target base in genomic DNA without double-stranded DNA cleavage," *Nature* 533:420-424 (2016), and Nishida et al., "Targeted nucleotide editing using hybrid prokaryotic and vertebrate adaptive immune systems," *Science* 353 (6305): aaf8729 (2016), both of which are incorporated herein by reference in their entirety. A nickase that nicks the non-edited strand of the target locus is hypothesized to stimulate endogenous DNA repair pathways-such as mismatch repair or long-patch base excision repair, which preferentially resolves a mismatch generated by base editing to a desired allele or to provide better accessibility of the catalytic editing domain to the target DNA.

Targeted Mutagenesis and DNA Labeling with Nickases and DNA Polymerases

The CRISPR systems described herein can be used in conjunction with proteins that act on nicked DNA. One such class of proteins is nick-translating DNA polymerases, such as *E. coli* DNA polymerase I or Taq DNA polymerase.

In some embodiments, the CRISPR system (e.g., a CRISPR nickase) can be fused to an error-prone DNA polymerase I. This fusion protein can be targeted with an RNA guide to generate a nick at a target DNA site. The DNA polymerase then initiates DNA synthesis at the nick, displacing downstream nucleotides, and, because an error-prone polymerase is used, resulting in mutagenesis of the target locus. Polymerase variants with varying processivity, fidelity, and misincorporation biases may be used to influence characteristics of the mutants that are generated. This method, called EvolvR, is described in detail, e.g., in Halperin et al., "CRISPR-guided DNA polymerases enable diversification of all nucleotides in a tunable window," *Nature* 560, 248-252 (2018), which is incorporated herein by reference in its entirety.

In some embodiments, a CRISPR nickase can be used in a nick translation DNA labeling protocol. Nick translation, first described by Rigby et al in 1977, involves incubating DNA with a DNA nicking enzyme, such as DNase I, which creates one or more nicks in the DNA molecule. Next, a nick-translating DNA polymerase, such as DNA polymerase I, is used to incorporate labeled nucleic acid residues at the nicked sites. Methods of harnessing the programmability of CRISPR nickases to covalently tag telomeric repeats with fluorescent dyes, using a variant of a classical nick translation labeling protocol, are described in detail e.g., in McCaffery et al., "High-throughput single-molecule telomere characterization," *Genome Research* 27:1904-1915 (2017), which is incorporated herein by reference in its entirety. This method enables haplotype-resolved analysis of telomere lengths at the single-molecule level.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and RNAs in the vicinity of a protein or RNA of interest in vitro. After UV irradiation, the photoactivatable groups react with proteins and other molecules that are in close proximity to the tagged molecules, thereby labelling them. Labelled interacting molecules can subsequently be recovered and identified. The RNA targeting effector proteins can for instance be used to target probes to selected RNA sequences. These applications can also be applied in animal models for in vivo imaging of diseases or difficult-to culture cell types. The methods of tracking and labeling of nucleic acids are described, e.g., in U.S. Pat. No. 8,795,965; WO 2016205764; and WO 2017070605; each of which is incorporated herein by reference in its entirety.

High-Throughput Screening

The CRISPR systems described herein can be used for preparing next generation sequencing (NGS) libraries. For example, to create a cost-effective NGS library, the CRISPR systems can be used to disrupt the coding sequence of a target gene, and the CRISPR enzyme transfected clones can be screened simultaneously by next-generation sequencing (e.g., on the Ion Torrent PGM system). A detailed description regarding how to prepare NGS libraries can be found, e.g., in Bell et al., "A high-throughput screening strategy for detecting CRISPR-Cas9 induced mutations using next-generation sequencing," BMC Genomics, 15.1 (2014): 1002, which is incorporated herein by reference in its entirety.

Engineered Microorganisms

Microorganisms (e.g., *E. coli*, yeast, and microalgae) are widely used for synthetic biology. The development of synthetic biology has a wide utility, including various clinical applications. For example, the programmable CRISPR systems described herein can be used to split proteins of toxic domains for targeted cell death, e.g., using cancer-linked RNA as target transcript. Further, pathways involving protein-protein interactions can be influenced in synthetic biological systems with e.g. fusion complexes with the appropriate effectors such as kinases or enzymes.

In some embodiments, RNA guide sequences that target phage sequences can be introduced into the microorganism. Thus, the disclosure also provides methods of vaccinating a microorganism (e.g., a production strain) against phage infection.

In some embodiments, the CRISPR systems provided herein can be used to engineer microorganisms, e.g., to improve yield or improve fermentation efficiency. For example, the CRISPR systems described herein can be used to engineer microorganisms, such as yeast, to generate biofuel or biopolymers from fermentable sugars, or to degrade plant-derived lignocellulose derived from agricultural waste as a source of fermentable sugars. More particularly, the methods described herein can be used to modify the expression of endogenous genes required for biofuel production and/or to modify endogenous genes, which may interfere with the biofuel synthesis. These methods of engineering microorganisms are described e.g., in Verwaal et al., "CRISPR/Cpf1 enables fast and simple genome editing of *Saccharomyces cerevisiae*," Yeast, 2017 Sep. 8. doi: 10.1002/yea.3278; and Hlavova et al., "Improving microalgae for biotechnology—from genetics to synthetic biology," Biotechnol. Adv., 2015 Nov. 1; 33:1194-203, both of which are incorporated herein by reference in their entirety.

In some embodiments, the CRISPR systems described herein can be used to engineer microorganisms that have defective repair pathways, such as the mesophilic cellulolytic bacterium *Clostridium cellylolyticum*, a model organism for bioenergy research. In some embodiments, a CRISPR nickase can be used to introduce single nicks at a target locus, which may result in insertion of an exogenously provided DNA template by homologous recombination. A detailed method regarding how to use a CRISPR nickase to edit repair-defective microbes is described e.g., in Xu et al., "Efficient Genome Editing in *Clostridium cellulolyticum* via CRISPR-Cas9 Nickase," *Appl Environ Microbiology* 81:4423-4431 (2015), which is incorporated herein in its entirety.

In some embodiments, the CRISPR systems provided herein can be used to induce death or dormancy of a cell (e.g., a microorganism such as an engineered microorganism). These methods can be used to induce dormancy or death of a multitude of cell types including prokaryotic and eukaryotic cells, including, but not limited to, mammalian cells (e.g., cancer cells, or tissue culture cells), protozoans, fungal cells, cells infected with a virus, cells infected with an intracellular bacteria, cells infected with an intracellular protozoan, cells infected with a prion, bacteria (e.g., pathogenic and non-pathogenic bacteria), protozoans, and unicellular and multicellular parasites. For instance, in the field of synthetic biology it is highly desirable to have mechanisms of controlling engineered microorganisms (e.g., bacteria) to prevent their propagation or dissemination. The systems described herein can be used as "kill-switches" to regulate and/or prevent the propagation or dissemination of an engineered microorganism. Further, there is a need in the art for alternatives to current antibiotic treatments.

The systems described herein can also be used in applications where it is desirable to kill or control a specific microbial population (e.g., a bacterial population). For example, the systems described herein may include an RNA guide (e.g., a crRNA) that targets a nucleic acid (e.g., a DNA) that is genus-, species-, or strain-specific, and can be delivered to the cell. Upon complexing and binding to the target nucleic acid, the nuclease activity of the CLUST.029130 (Type V-I) CRISPR-Cas effector proteins disrupts essential functions within the microorganisms, ultimately resulting in dormancy or death. In some embodiments, the methods comprise contacting the cell with a system described herein including a CLUST.029130 (Type V-I) CRISPR-Cas effector proteins or a nucleic acid encoding the effector protein, and a RNA guide (e.g., a crRNA) or a nucleic acid encoding the RNA guide, wherein the spacer sequence is complementary to at least 15 nucleotides (e.g., 16, 17, 18, 19, 20, 21, 22, 23, 24, 25, 26, 27, 28, 29, 30, 35, 40, 45, 50 or more nucleotides) of a target nucleic acid.

Without wishing to be bound by any particular theory, the nuclease activity of the CLUST.029130 (Type V-I) CRISPR-Cas effector proteins can induce programmed cell death, cell toxicity, apoptosis, necrosis, necroptosis, cell death, cell cycle arrest, cell anergy, a reduction of cell growth, or a reduction in cell proliferation. For example, in bacteria, the cleavage of DNA by the CLUST.029130 (Type V-I) CRISPR-Cas effector proteins can be bacteriostatic or bactericidal.

Application in Plants

The CRISPR systems described herein have a wide variety of utility in plants. In some embodiments, the CRISPR systems can be used to engineer genomes of plants (e.g., improving production, making products with desired post-translational modifications, or introducing genes for producing industrial products). In some embodiments, the CRISPR systems can be used to introduce a desired trait to a plant (e.g., with or without heritable modifications to the genome), or regulate expression of endogenous genes in plant cells or whole plants. Plants that can be edited using CRISPR systems of this disclosure (e.g., Cas12i systems) can be monocots or dicots and include, without limitation safflower, maize, *cannabis*, rice, sugarcane, canola, sorghum, tobacco, rye, barley, wheat, millet, oats, peanut, potato, switchgrass, turfgrass, soybean, alfalfa, sunflower, cotton, and *Arabidopsis*. The present disclosure also encompasses a plant having a trait made according to a method of the disclosure and/or utilizing a CRISPR system of the disclosure.

In some embodiments, the CRISPR systems can be used to identify, edit, and/or silence genes encoding specific proteins, e.g., allergenic proteins (e.g., allergenic proteins in peanuts, soybeans, lentils, peas, green beans, and mung beans). A detailed description regarding how to identify, edit, and/or silence genes encoding proteins is described, e.g., in Nicolaou et al., "Molecular diagnosis of peanut and legume allergy," *Curr. Opin. Allergy Clin. Immunol.*, 11(3): 222-8 (2011), and WO 2016205764 A1; both of which are incorporated herein by reference in their entirety.

Gene Drives

Gene drive is the phenomenon in which the inheritance of a particular gene or set of genes is favorably biased. The CRISPR systems described herein can be used to build gene drives. For example, the CRISPR systems can be designed to target and disrupt a particular allele of a gene, causing the cell to copy the second allele to fix the sequence. Because of the copying, the first allele will be converted to the second allele, increasing the chance of the second allele being transmitted to the offspring. A detailed method regarding how to use the CRISPR systems described herein to build gene drives is described, e.g., in Hammond et al., "A CRISPR-Cas9 gene drive system targeting female reproduction in the malaria mosquito vector *Anopheles gambiae*," *Nat. Biotechnol.*, 2016 January; 34(1):78-83, which is incorporated herein by reference in its entirety.

Pooled-Screening

As described herein, pooled CRISPR screening is a powerful tool for identifying genes involved in biological mechanisms such as cell proliferation, drug resistance, and viral infection. Cells are transduced in bulk with a library of RNA guide (gRNA)-encoding vectors described herein, and the distribution of gRNAs is measured before and after applying a selective challenge. Pooled CRISPR screens work well for mechanisms that affect cell survival and proliferation, and they can be extended to measure the activity of individual genes (e.g., by using engineered reporter cell lines). Arrayed CRISPR screens, in which only one gene is targeted at a time, make it possible to use RNA-seq as the readout. In some embodiments, the CRISPR systems as described herein can be used in single-cell CRISPR screens. A detailed description regarding pooled CRISPR screenings can be found, e.g., in Datlinger et al., "Pooled CRISPR screening with single-cell transcriptome read-out," *Nat. Methods.*, 2017 March; 14(3):297-301, which is incorporated herein by reference in its entirety.

Saturation Mutagenesis ("Bashing")

The CRISPR systems described herein can be used for in situ saturating mutagenesis. In some embodiments, a pooled RNA guide library can be used to perform in situ saturating mutagenesis for particular genes or regulatory elements. Such methods can reveal critical minimal features and discrete vulnerabilities of these genes or regulatory elements (e.g., enhancers). These methods are described, e.g., in Canver et al., "BCL11A enhancer dissection by Cas9-mediated in situ saturating mutagenesis," *Nature,* 2015 Nov. 12; 527(7577):192-7, which is incorporated herein by reference in its entirety.

Therapeutic Applications

The CRISPR systems described herein that have activity in a mammalian cellular context (e.g., Cas12i2) can have a diverse range of therapeutic applications. Moreover, each nuclease ortholog may have unique properties (e.g., size, PAM, etc.) that render it advantaged for certain targeting, treatment, or delivery modalities, so the ortholog selection is important in allocating the nuclease that provides maximum therapeutic benefit.

There are numerous factors that influence the suitability of gene editing as a therapeutic for a particular disease. With nuclease-based gene therapies, the primary approaches to therapeutic editing have been gene disruption and gene correction. In the former, gene disruption generally occurs with an event (such as a nuclease-induced, targeted double stranded break) that activates the endogenous non homologous end joining DNA repair mechanism of the target cell, yielding indels that often result in a loss of function mutation that is intended to benefit the patient. The latter, gene correction utilizes the nuclease activity to induce alternative DNA repair pathways (such as homology directed repair, or HDR) with the help of a template DNA (whether endogenous or exogenous, single stranded or double stranded). The templated DNA can either be an endogenous correction of a disease-causing mutation, or otherwise the insertion of a therapeutic transgene into an alternate locus (commonly safe harbor loci such as AAVS1). Methods of designing exogenous donor template nucleic acids are described, for example, in PCT Publication No. WO 2016094874 A1, the entire contents of which are expressly incorporated herein by reference. A requisite of therapies that use either of these editing modalities is an understanding of the genetic modulators of a certain disease; the diseases do not necessarily have to be monogenic, but insight into how mutations can effect the disease progress or outcome are important to providing guidance as to the potential efficacy of a gene therapy.

Without wishing to be limited, the CRISPR systems described herein can be utilized to treat the following diseases, wherein the specific gene targets are identified, in addition to the relevant references to aid in the adaption of the Type V-I CRISPR systems to specific disease areas; Cystic fibrosis by targeting CFTR (WO2015157070A2), Duchenne Muscular Dystrophy and Becker Muscular Dystrophy by targeting Dystrophin (DMD) (WO2016161380A1), Alpha-1-antitrypsin deficiency by targeting Alpha-1-antitrypsin (A1AT) (WO2017165862A1), lysosomal storage disorders such as Pompe Disease aka Glycogen storage disease type II by targeting acid alpha-glucosidase (GAA), myotonic dystrophy by targeting DMPK, Huntington disease by targeting HTT, Fragile X by targeting FMR1, Friedreich's ataxia by targeting Frataxin, amyotrophic lateral sclerosis (ALS) and frontotemporal dementia (FTD) by targeting C9orf72, hereditary chronic kidney disease by targeting ApoL1, cardiovascular disease and hyperlipidemia by targeting PCSK9, APOC3, ANGPTL3, LPA (*Nature* 555, S23-S25 (2018)), and congenital blindness such as Leber Congenital Amaurosis Type 10 (LCA10) by targeting CEP290 (Maeder et al., *Nat Med.* 2019 February; 25(2):229-233). The majority of the aforementioned diseases are best treated with an in vivo gene editing approach, in which the cell types and tissues involved in the disease need to be edited in situ with a sufficient dose and efficiency to yield a therapeutic benefit. Some challenges of in vivo delivery are described in the "Delivery of CRISPR Systems" section below, though in general the smaller gene size of the Type V-I CRISPR effectors enables more versatile packaging into viral vectors with a payload restriction, such as adeno-associated viruses.

Ex vivo editing, in which cells are removed from the patient's body and then edited prior to transplantation back into the patient, present a prime therapeutic opportunity for gene editing technologies. The ability to manipulate cells outside the body presents multiple advantages, ranging from the ability to use technologies for high efficiency delivery of protein, DNA, and RNA into cells such as electroporation and nucleofection that are not amenable in an in vivo context, to being able to evaluate toxicity (such as from off-target effects), then further select and expand successfully edited cells to yield a population that provides a therapeutic advantage. These advantages are counterbalanced by the relatively few cell types and populations that can be successfully harvested, processed, and then returned to the body while preserving functionality. Without wishing to be limited, there nevertheless are serious diseases that are amenable to ex vivo genome editing using the systems described herein. For example, sickle cell disease (SCD) as referenced in WO2015148863A2, and beta-thalassemia as referenced in WO2015148860A1, both are examples of diseases in which the understanding of the pathophysiology has enabled a number of different editing modalities in hematopoietic stem cells for disease treatment. Beta thalassemia and SCD can both be treated with the disruption of the BCL11A erythroid enhancer to increase the levels of fetal hemoglobin (as illustrated using Zinc Finger Nucleases by Psatha et al. *Mol Ther Methods Clin Dev.* 2018 Sep. 21). In addition, methods of gene correction can be used to reverse the deleterious mutations in SCD and beta thalassemia. In another instance, the addition of a beta globin expressed from a safe harbor locus provides another alternative therapeutic strategy for ex vivo gene editing.

As a corollary of ex vivo editing of hematopoietic stem cells, immune cells can also be edited. In cancer immunotherapy, one therapeutic mode is to modify immune cells such as T-cells to recognize and fight cancer, as referenced in WO2015161276A2. To increase the efficacy and availability while decreasing cost, the creation of 'off-the-shelf' allogeneic T-cell therapies is attractive, and gene editing has the potential to modify surface antigens to minimize any immunological side effects (Jung et al., *Mol Cell.* 2018 Aug. 31).

In another embodiment, the invention be used to target viruses or other pathogens with a double stranded DNA intermediate stage of their life cycle. Specifically, targeting viruses whose initial infection leaves a latent infection that persists permanently would be of significant therapeutic value. In the following examples, the Type V-I CRISPR systems can be used to directly target the viral genome (such as with HSV-1, HSV-2 or HIV), or used to edit the host cells to reduce or eliminate the receptors enabling infection to make them impervious to the virus (HIV), as referenced for HSV-1 and HSV-2 in WO2015153789A1, WO2015153791A1, and WO2017075475A1, and for HIV in WO2015148670A1 and WO2016183236A1.

In another aspect, the CRISPR systems described herein can be engineered to enable additional functions that utilize enzymatically inactive Cas12i as a chassis on top of which protein domains can be attached to confer activities such as transcriptional activation, repression, base editing, and methylation/demethylation.

Thus, this disclosure provides CRISPR-Cas systems and cells for use in the treatment or prevention of any of the disease disclosed herein.

Delivery of CRISPR Systems

The CRISPR systems described herein, or components thereof, nucleic acid molecules thereof, or nucleic acid molecules encoding or providing components thereof, can be delivered by various delivery systems such as vectors, e.g., plasmids, viral delivery vectors, such as adeno-associated viruses (AAV), lentiviruses, adenoviruses, and other viral vectors, or methods, such as nucleofection or electroporation of ribonucleoprotein complexes consisting of Type V-I effectors and their cognate RNA guide or guides. The proteins and one or more RNA guides can be packaged into one or more vectors, e.g., plasmids or viral vectors. For bacterial applications, the nucleic acids encoding any of the components of the CRISPR systems described herein can be delivered to the bacteria using a phage. Exemplary phages, include, but are not limited to, T4 phage, Mu, λ phage, T5 phage, T7 phage, T3 phage, Φ29, M13, MS2, Qβ, and ΦX174.

In some embodiments, the vectors, e.g., plasmids or viral vectors, are delivered to the tissue of interest by, e.g., intramuscular injection, intravenous administration, transdermal administration, intranasal administration, oral administration, or mucosal administration. Such delivery may be either via a single dose or multiple doses. One skilled in the art understands that the actual dosage to be delivered herein may vary greatly depending upon a variety of factors, such as the vector choices, the target cells, organisms, tissues, the general conditions of the subject to be treated, the degrees of transformation/modification sought, the administration routes, the administration modes, the types of transformation/modification sought, etc.

In certain embodiments, the delivery is via adeno-associated viruses (AAV), e.g., AAV2, AAV8, or AAV9, which can be administered in a single dose containing at least $1 \times 10^5$ particles (also referred to as particle units, pu) of adenoviruses or adeno-associated viruses. In some embodiments, the dose is at least about $1 \times 10^6$ particles, at least about $1 \times 10^7$ particles, at least about $1 \times 10^8$ particles, or at least about $1 \times 10^9$ particles of the adeno-associated viruses. The delivery methods and the doses are described, e.g., in WO 2016205764 and U.S. Pat. No. 8,454,972, both of which are incorporated herein by reference in their entirety. Due to the limited genomic payload of recombinant AAV, the smaller size of the Type V-I CRISP-Cas effector proteins described herein enables greater versatility in packaging the effector and RNA guides with the appropriate control sequences (e.g., promoters) required for efficient and cell-type specific expression.

In some embodiments, the delivery is via a recombinant adeno-associated virus (rAAV) vector. For example, in some embodiments, a modified AAV vector may be used for delivery. Modified AAV vectors can be based on one or more of several capsid types, including AAV1, AV2, AAV5, AAV6, AAV8, AAV8.2. AAV9, AAV rhlO, modified AAV vectors (e.g., modified AAV2, modified AAV3, modified AAV6) and pseudotyped AAV (e.g., AAV2/8, AAV2/5 and AAV2/6). Exemplary AAV vectors and techniques that may be used to produce rAAV particles are known in the art (see, e.g., Aponte-Ubillus et al. (2018) Appl. Microbiol. Biotechnol. 102(3): 1045-54; Zhong et al. (2012) J. Genet. Syndr. Gene Ther. S1: 008; West et al. (1987) Virology 160: 38-47 (1987); Tratschin et al. (1985) Mol. Cell. Biol. 5: 3251-60); U.S. Pat. Nos. 4,797,368 and 5,173,414; and International Publication Nos. WO 2015/054653 and WO 93/24641, each of which is incorporated by reference).

In some embodiments, the delivery is via plasmids. The dosage can be a sufficient number of plasmids to elicit a response. In some cases, suitable quantities of plasmid DNA in plasmid compositions can be from about 0.1 to about 2 mg. Plasmids will generally include (i) a promoter; (ii) a sequence encoding a nucleic acid-targeting CRISPR enzymes, operably linked to the promoter; (iii) a selectable marker; (iv) an origin of replication; and (v) a transcription terminator downstream of and operably linked to (ii). The plasmids can also encode the RNA components of a CRISPR-Cas system, but one or more of these may instead be encoded on different vectors. The frequency of administration is within the ambit of the medical or veterinary practitioner (e.g., physician, veterinarian), or a person skilled in the art.

In another embodiment, the delivery is via liposomes or lipofectin formulations and the like, and can be prepared by methods known to those skilled in the art. Such methods are described, for example, in WO 2016205764 and U.S. Pat. Nos. 5,593,972; 5,589,466; and 5,580,859; each of which is incorporated herein by reference in its entirety.

In some embodiments, the delivery is via nanoparticles or exosomes. For example, exosomes have been shown to be particularly useful in the delivery of RNA.

Further means of introducing one or more components of the new CRISPR systems into cells is by using cell penetrating peptides (CPP). In some embodiments, a cell penetrating peptide is linked to the CRISPR enzymes. In some embodiments, the CRISPR enzymes and/or RNA guides are coupled to one or more CPPs to transport them inside cells effectively (e.g., plant protoplasts). In some embodiments, the CRISPR enzymes and/or RNA guide(s) are encoded by one or more circular or non-circular DNA molecules that are coupled to one or more CPPs for cell delivery.

CPPs are short peptides of fewer than 35 amino acids derived either from proteins or from chimeric sequences capable of transporting biomolecules across cell membrane in a receptor independent manner. CPPs can be cationic peptides, peptides having hydrophobic sequences, amphipathic peptides, peptides having proline-rich and anti-microbial sequences, and chimeric or bipartite peptides. Examples of CPPs include, e.g., Tat (which is a nuclear transcriptional activator protein required for viral replication by HIV type 1), penetratin, Kaposi fibroblast growth factor (FGF) signal peptide sequence, integrin 33 signal peptide sequence, polyarginine peptide Args sequence, Guanine rich-molecular transporters, and sweet arrow peptide. CPPs and methods of using them are described, e.g., in Hallbrink et al., "Prediction of cell-penetrating peptides," *Methods Mol. Biol.*, 2015; 1324:39-58; Ramakrishna et al., "Gene disruption by cell-penetrating peptide-mediated delivery of Cas9 protein and guide RNA," *Genome Res.*, 2014 June; 24(6):1020-7; and WO 2016205764 A1; each of which is incorporated herein by reference in its entirety.

Delivery of the Type V-I CRISPR system as a ribonucleoprotein complex by electroporation or nucleofection, in which purified Cas12i protein is pre-incubated with a RNA guide and electroporated (or nucleofected) into cells of interest, is another method of efficiently introducing the CRISPR system to cells for gene editing. This is particularly useful for ex vivo genome editing and the development of cellular therapies, and such methods are described in Roth et al. "Reprogramming human T cell function and specificity with non-viral genome targeting," *Nature*, 2018 July; 559 (7714): 405-409.

Various delivery methods for the CRISPR systems described herein are also described, e.g., in U.S. Pat. No. 8,795,965, EP 3009511, WO 2016205764, and WO 2017070605; each of which is incorporated herein by reference in its entirety Kits This disclosure also encompasses kits for carrying out the various methods of the disclosure utilizing the CRISPR systems described herein. One exemplary kit of the present disclosure comprises (a) one or more nucleic acids encoding a CRISPR-associated protein and a cognate crRNA, and/or (b) a ribonucleoprotein complex of a CRISPR-associated protein and a cognate crRNA. In some embodiments, the kit comprises a Cas12i protein and a Cas12i guide RNA. As described above, a complex of the protein and guide RNA has an editing activity such as SSB formation, DSB formation, CRISPR interference, nucleobase modification, DNA methylation or demethylation, chromatin modification, etc. In certain embodiments, the CRISPR-associated protein is a variant, such as a variant having reduced endonuclease activity.

Kits of this disclosure also optionally include additional reagents, including one or more of a reaction buffer, a wash buffer, one or more control materials (e.g., a substrate or a nucleic acid encoding a CRISPR system component), etc. A kit of the present disclosure also optionally includes instructions for performing a method of this disclosure using materials provided in the kit. The instructions are provided in physical form, e.g., as a printed document physically packaged with another item of the kit, and/or in digital form, e.g., a digitally published document downloadable from a website or provided on computer readable media.

EXAMPLES

The invention is further described in the following examples, which do not limit the scope of the invention described in the claims.

Example 1: Identification of Minimal Components for the CLUST.029130 (Type V-I) CRISPR-Cas System (FIGS. 1-3)

This protein family describes a large single effector associated with CRISPR systems found in uncultured metagenomic sequences collected from freshwater environments (Table 3). CLUST.029130 (Type V-I) effectors, designated Cas12i, include the exemplary proteins detailed in Tables 3 and 4. Exemplary direct repeat sequences for these systems are shown in Table 5.

Genome and metagenome sequences were downloaded from NCBI (Benson et al. (2013) GenBank. Nucleic Acids Res. 41, D36-42; Pruitt et al. (2012) NCBI Reference Sequences (RefSeq): current status, new features and genome annotation policy. Nucleic Acids Res. 40, D130-135), NCBI whole genome sequencing (WGS), and DOE JGI Integrated Microbial Genomes (Markowitz et al. (2012) IMG: the Integrated Microbial Genomes database and comparative analysis system. Nucleic Acids Res. 40, D115-122) and compiled to construct a database of 293,985 putative CRISPR-Cas systems within which we identified novel nuclease systems. This approach to pipeline engineering performs minimal filtering in the intermediate stages to expand the search space for novel CRISPR effector discovery and reduce biases.

Figure 1A:
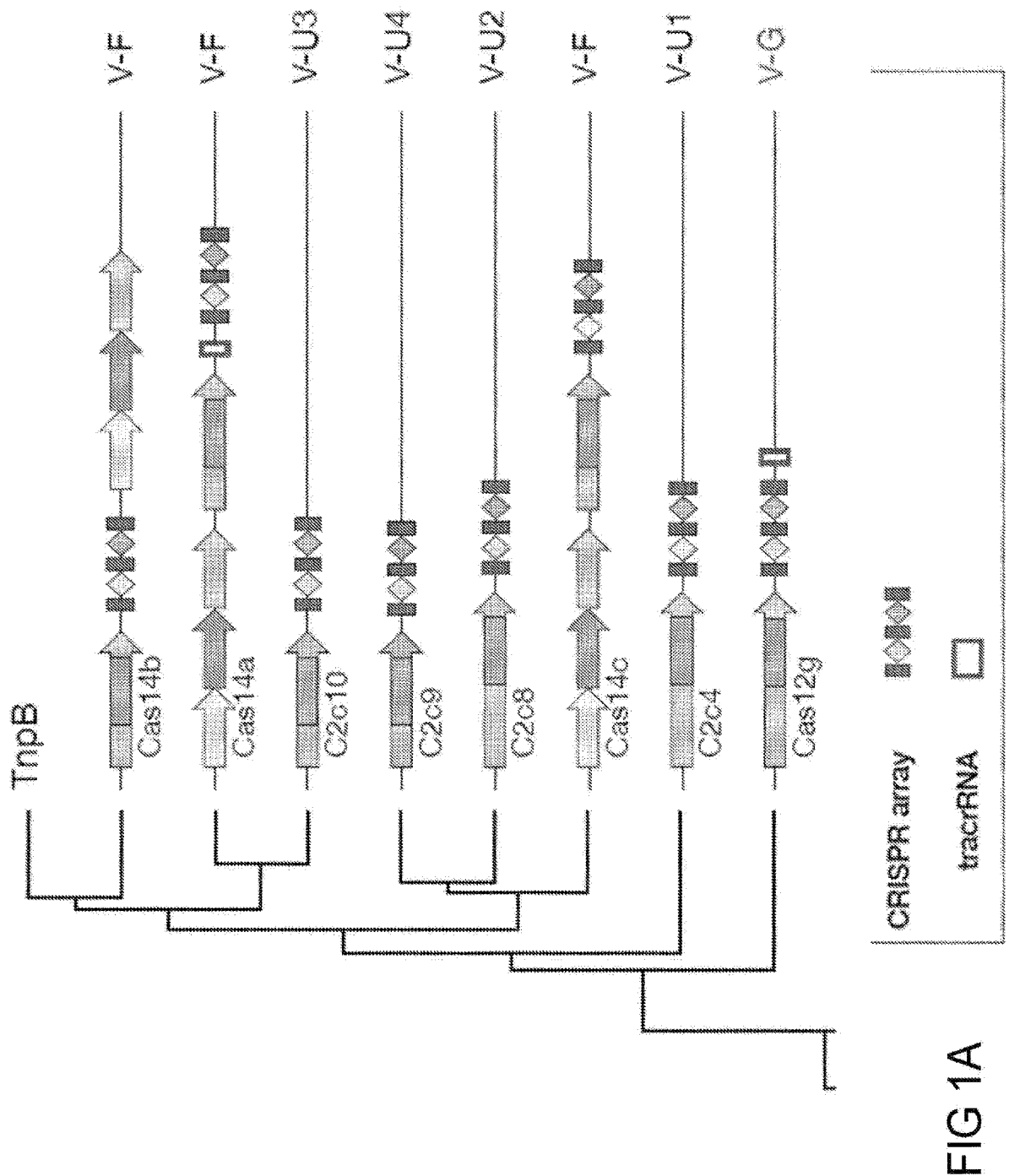
Figure 1B:
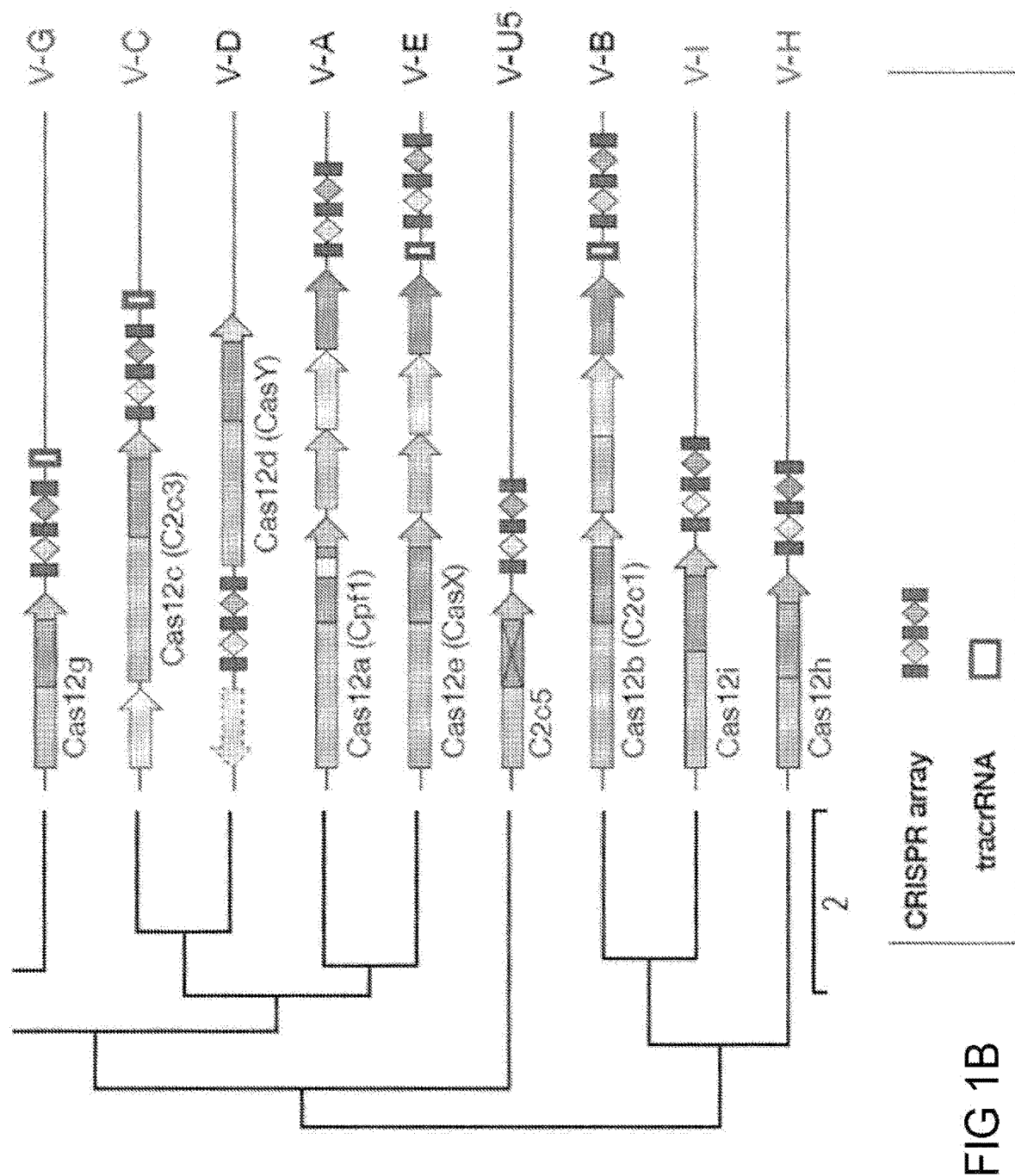

The classification tree depicted in FIGS. 1A-1B was constructed by comparing sequence profiles extracted from multiple alignments of groups of readily alignable Cas12 proteins. Profile-profile comparisons were performed using HHsearch (Söding et al. (2005) Protein homology detection by HMM-HMM comparison. Bioinforma. Oxf Engl. 21, 951-960); scores between two profiles were normalized by the minimum of the self-scores and converted to a distance matrix on the natural log scale. The UPGMA dendrogram was reconstructed from the distance matrix. The tree at the depth of 2 distance unites (corresponding to the pairwise HHsearch score of $e^{-2D}$=0.02 relative to the self-score) typically reliably recovers profile similarity and can serve as a guide for subtype classification (Shmakov et al., 2017).

Figure 2A:
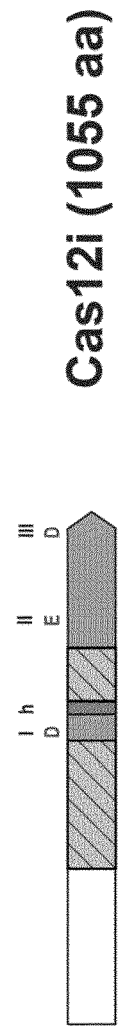
FIG. 2B is a schematic representation of a multiple sequence alignment of Cas12i effector proteins, with the relative locations of the conserved catalytic residues of the RuvC domain denoted by RuvC I/II/III.
Figure 2B:
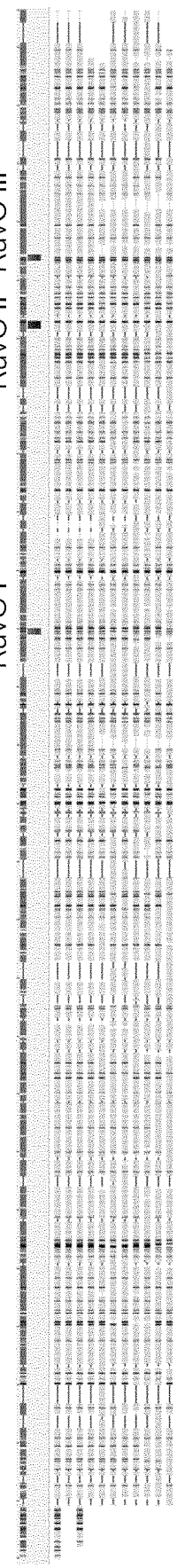

The domain architecture of Cas12i, depicted in FIGS. 2A and 2B indicate that the effector contains the active catalytic residues of the RuvC nuclease domain. Additionally, the predicted secondary structure of the most prevalent direct repeat for Type V-I loci, depicted in FIG. 3, indicates a stem-loop structure that is conserved in the crRNA of many exemplary Type V-I CRISPR-Cas systems.

TABLE 3

Representative CLUST.029130 (Type V-I) Effector Proteins

| species | Cas12i accession | # spacers | cas1 | cas2 | effector size |
|---|---|---|---|---|---|
| SRR1522973 (SRR1522973) | SRR1522973_megahit_k177_1081830_2\|M | 9 | N | N | 1098 |
| SRR1522973 (SRR1522973) | SRR1522973_megahit_k177_427371_1\|M | 20 | N | N | 1088 |
| SRR2179954 (SRR2179954) | SRR2179954_megahit_k177_1417524_4\|M | 7 | N | N | 1074 |
| SRR6475631 (SRR6475631) | SRR6475631_megahit_k177_2773783_7\|M | 22 | N | N | 1031 |
| SRR6837575 (SRR6837575) | SRR6837575_megahit_k177_919599_7\|M | 4 | N | N | 1066 |
| SRR6837577 (SRR6837577) | SRR6837577_megahit_k177_410843_33\|P | 20 | N | N | 1066 |
| 3300020508 (3300020508\|Ga0208225_1000010) | 3300020508\|Ga0208225_1000010_34\|M | 10 | N | N | 1093 |
| aquatic-freshwater (3300002408\|release\|scaffold05697) | 3300002408\|release\|scaffold05697_22\|M | 13 | N | N | 1091 |
| aquatic-freshwater (3300002408\|release\|scaffold05697) | 3300002408\|release\|scaffold05697_22\|P | 13 | N | N | 1046 |
| aquatic-freshwater (3300002408\|release\|scaffold08426) | 3300002408\|release\|scaffold08426_1\|P | 6 | N | N | 1093 |
| aquatic-freshwater (3300028569\|Ga0247843_1000055) | 3300028569\|Ga0247843_1000055_230\|M | 12 | N | N | 1080 |
| aquatic-freshwater (3300028569\|Ga0247843_1000055) | 3300028569\|Ga0247843_1000055_232\|P | 12 | N | N | 1046 |

TABLE 3-continued

Representative CLUST.029130 (Type V-I) Effector Proteins

| species | Cas12i accession | # spacers | cas1 | cas2 | effector size |
|---|---|---|---|---|---|
| aquatic-freshwater (3300028571\|Ga0247844_1000101) | 3300028571\|Ga0247844_1000101_90\|M | 12 | N | N | 1080 |
| aquatic-freshwater (3300028571\|Ga0247844_1000101) | 3300028571\|Ga0247844_1000101_88\|P | 12 | N | N | 1046 |
| aquatic-freshwater-freshwater lake (3300009183\|Ga0114974_10028552) | 3300009183\|Ga0114974_10028552_1\|M | 7 | N | N | 1033 |
| aquatic-freshwater-freshwater lake (3300010885\|Ga0133913_10053227) | 3300010885\|Ga0133913_10053227_5\|M | 26 | N | N | 1046 |
| aquatic-freshwater-freshwater lake (3300020193\|Ga0194131_10013618) | 3300020193\|Ga0194131_10013618_4\|P | 5 | N | N | 1054 |
| aquatic-freshwater-freshwater lake (3300020214\|Ga0194132_10015959) | 3300020214\|Ga0194132_10015959_3\|M | 8 | N | N | 1054 |

TABLE 4

Amino Acid Sequences of Representative CLUST.029130 (Type V-I) Effector Proteins >SRR1522973_megahit_k177_1081830_2|M [SRR1522973]
MSISNNNILPYNPKLLPDDRKHKMLVDTFNQLDLIRNNLHDMIIA
LYGALKYDNIKQFASKEKPHISADALCSINWFRLVKTNERKPAIE
SNQIISKFIQYSGHTPDKYALSHITGNHEPSHKWIDCREYAINYA
RIMHLSFSQFQDLATACLNCKILILNGTLTSSWAWGANSALFGGS
DKENFSVKAKILNSFIENLKDEMNTTKFQVVEKVCQQIGSSDAAD
LFDLYRSTVKDGNRGPATGRNPKVMNLFSQDGEISSEQREDFIES
FQKVMQEKNSKQIIPHLDKLKYHLVKQSGLYDIYSWAAAIKNANS
TIVASNSSNLNTILNKTEKQQTFEELRKDEKIVACSKILLSVNDT
LPEDLHYNPSTSNLGKNLDVFFDLLNENSVHTIENKEEKNKIVKE
CVNQYMEECKGLNKPPMPVLLTFISDYAHKHQAQDFLSAAKMNFI
DLKIKSIKVVPTVHGSSPYTWISNLSKKNKDGKMIRTPNSSLIGW
IIPPEEIHDQKFAGQNPIIWAVLRVYCNNKWEMHHFPFPSDSRFFT
EVYAYKPNLPYLPGGENRSKRFGYRHSTNLSNESRQILLDKSKYA
KANKSVLRCMENMTHNVVFDPKTSLNIRIKTDKNNSPVLDDKGRI
TFVMQINHRILEKYNNTKIEIGDRILAYDQNQSENHTYAILQRTE
EGSHAHQFNGWYVRVLETGKVTSIVQGLSGPIDQLNYDGMPVTSH
KFNCWQADRSAFVSQFASLKISETETFDEAYQAINAQGAYTWNLF
YLRILRLKALRVCHMENINQFREEILAISKNRLSPMSLGSLSQNSL
KMIRAFKSIINCYMSRMSFVDELQKKEGDLELHTIMRLTDNKLND
KRVEKINRASSFLTNKAHSMGCKMIVGESDLPVADSKTSKKQNVD
RMDWCARALSHKVEYACKLMGLAYRGIPAYMSSHQDPLVHLVESK
RSVLRPRFVVADKSDVKQHHLDNLRRMLNSKTKVGTAVYYREAVE
LMCEELGIHKTDMAKGKVSLSDFVDKFIGEKAIFPQRGGRFYMST
KRLTTGAKLICYSGSDVWLSDADEIAAINIGMFVVCDQTGAFKKK
KKEKLDDEECDILPFRPM
(SEQ ID NO: 14)

>SRR1522973_megahit_k177_427371_1|M [SRR1522973]
MSSQVVRPYNAKFLPDDRKHKMLTDTINQLDKISSKHFDLLVAFY
GSIQHKHVSINDKQEEHITPDSVCAINWFRPMSKDYAKYQVKIDS
MITNFKEYAGHIPDKYAIEYMGSNIDTDRFVWVDCRNFAKDYVRN
MDMSFSEFQNLVDALVFCKILALNESTSTNWAWGAISAIYGGGDK
EDSQFKAKVLNTFVKALNDENNKTKFDVINKVCSDLGYNDHLSLI
EDFRSTIDENGNKKSASGSPPAIAKFTEDGEISDNYRRACISSFS
KTAKEKQDKKSIPHLDILKTHMIAMCGEYNTYAWTEAIKNANTDI
TSRNTRNMTFIKEKIESRNSLKIYDTEENMKAAKILNGINHKLTP
DLHYTPAPKHLGKNLKDLFEMLEEKNILAQNEKEKKAALDECIKQ
YIDDCKGLNQQPIASLLAHISNYHKEITAENFLDGAKLLVLLQKI
NRQKAHPSVFSPKAYTWGSKLEKNRRAANSALLGWIVPPEEKHKD
RHAGQHPVMWVTMTLLNNGKWEKHHVPFTNSRFFSEVYAYQPELP
YKEGGYARNSKTATKPSQIMLPAYAESMRHHIATKGNGHKKSEKI
VLRALSNIRHNVRFDPSTSFFVRIMRDKKGNHRLDTKGRITFGLQ
INHRITVGKTKSEINIGDRLLAFDQNQSENHTFAIMQRVEENTPN
SHQFNGWNIRVLETGKVVSMTKGIESYYDQLSYDGVPYETKKFED
WRNERKAFVKKNKDIVIKEENTFLKAEIKKSSLYKWNLSYLKI
LRMAIRAKSGDTVSLFREELISIAKNRFGPLGLGSLSASSLKMLG
AFCGVIQSYFSVLNCLDDKDKSNFDSELYFYLVSAFEKRVFKRNE
KTSRASSFIMAMAYNHGCKMIVCEDDLPTAGAGANKRQNSDRMDW
CARSLAQKIKTGCEAMSIAYRAIPAYMSSHQDPLVHLADGKTSVL
CPRFALVSKDDIKQYLQDGMRRMLNSKSKIGTAVYYRAAVELLCK
ELGINKTDIAKGKLSVSQFADIVNGEILLPQRGGRVYLATKELTN

GAKLVSYNGSDVWLSNADEIAAINIGMFVVCTQTGVFGKKKKKDE
QDGDIEIA
(SEQ ID NO: 15)

>SRR2179954_megahit_k177_1417524_4|M [SRR2179954]
MASISRPYGTKLRPDARKKEMLDKFFNTLTKGQRVFADLALCIYG
SLTLEMAKSLEPESDSELVCAIGWFRLVDKTIWSKDGIKQENLVK
QYEAYSGKEASEVVKTYLNSPSSDKYVWIDCRQKFLRFQRELGTR
NLSEDFECMLFEQYIRLTKGEIEGYAAISNMFGNGEKEDRSKKRM
YATRMKDWLEANENITWEQYREALKNQLNAKNLEQVVANYKGNAG
GADPFFKYSFSKEGMVSKKEHAQQLDKFKTVLKNKARDLNFPNKE
KLKQYLEAEIGIPVDANVYSQMFSNGVSEVQPKTTRNMSFSNEKL
DLLTELKDLNKGDGFEYAREVLNGFFDSELHTTEDKFNITSRYLG
GDKSNRLSKLYKIWKKEGVDCEEGIQQFCEAVKDKMGQIPIRNVL
KYLWQFRETVSAEDFEAAAKANHLEEKISRVKAHPIVISNRYWAF
GTSALVGNIMPADKRHQGEYAGQNFKMWLEAELHYDGKKAKHHLP
FYNARFFEEVYCYHPSVAEITPFKTKQFGCEIGKDIPDYVSVALK
DNPYKKATKRILRAIYNPVANTTGVDKTTNCSFMIKRENDEYKLV
INRKISVDRPKRIEVGRTIMGYDRNQTASDTYWIGRLVPPGTRGA
YRIGEWSVQYIKSGPVLSSTQGVNNSTTDQLVYNGMPSSSERFKA
WKKARMAFIRKLIRQLNDEGLESKGQDYIPENPSSFDVRGETLYV
FNSNYLKALVSKHRKAKKPVEGILDEIEAWTSKDKDSCSLMRLSS
LSDASMQGIASLKSLINSYFNKNGCKTIEDKEKFNPVLYAKLVEV
EQRRTNKRSEKVGRIAGSLEQLALLNGVEVVIGEADLGEVEKGKS
KKQNSRNMDWCAKQVAQRLEYKLAFHGIGYFGVNPMYTSHQDPFE
HRRVADHIVMRARFEEVNVENIAEWHVRNFSNYLRADSGTGLYYK
QATMDFLKHYGLEEHAEGLENKKIKFYDFRKILEDKNLTSVIIPK
RGGRIYMATNPVTSDSTPITYAGKTYNRCNADEVAAANIVISVLA
PRSKKNEEQDDIPLITKKAESKSPPKDRKRSKTSQLPQK
(SEQ ID NO: 16)

>SRR6475631_megahit_k177_2773783_7|M [SRR6475631]
MVSDSTIRPYTSKLAPNDPKRKMLNDTFNWLDHAYKVFFDVSVAL
FGGIDYEAAEELIDEKSTFDADLLCAIMWFRLEEKSNNPGPLQTT
EQRTRLFQKYSGHEPSSFAQEYIKGNTDTEKYEWVDCRLKFADLA
RNIHTTQESLKTDAYTLFMNKLIPVSKDDEFNAYGFISQLFGTDK
KEDRSVKASMLEEISNIIEDKKPNTWEEYQDLIKKTFNVSNYKEL
KEKLSAGSSGRDGSLVIDLKEEKTGLLQPNFIKNRIVKFREDADK
KRTVFSLPNRMKLREFISSQIGPFEQNWSAVLNRSMAAIQSKNS
SNILYTNQKQERNNEIQELLKEDILSAASILNDFRRGEFNSSVVS
KNHLGSRLNELFEMWQALKMNDGIEKYTDLCKDNFSRRPVSALLQ
YIYPYFDKITAKQFLDAASYNTLVETNNRKKIHPTVTGPTVCNWG
PKSTINGSITPPNQMVKDRPAGSHGMIWVTMTVRDNGRWVKHHLP
FHNSRYYEEHYCYREGLPTKNQPRTKQLGTQVGSIISAPSLAILK
SQEEQDRRNDRKSRFKAHKSIIRSQENIKYNVAFDKSTNFDVTRK
NGEFFITISSRVTTPKYSHKLNVGDIIMGLDNNQTAPCTYSIWRI
VEKDTEGSFFHNKIWLQLVTDGKITSIVDNNRQVDQLSYAGVEYS
NFAEWRKDRRQFLRSINEDYVKKSDNWLNMNLYQWNAEYSRLLLG
VMKDNKDKNIQNTFRAEIEELICGKFGIRLGSLSHHSLQFLTNCK
SLISSYFMLNNKKEEHDQESFDSFFRLMRSIDDKRIRKRKEKSS
RISSSVLQIARENNVKSLCVEGDLPTATKKTKPKQNQKSIDWCAR
AVVKKLNDGCKVLGINLQAIDPRDTSHLDPFVYYGKKSTKVGKEA TABLE 4-continued Amino Acid Sequences of Representative
CLUST.029130 (Type V-I) Effector Proteins RYVIVEPSNIKEYMTKKFTDWHRGVSKKSKKGDVQTSTTAPLYQE
ALKQFADHYKLDFDSLPKMKFYELAKILEDHKQVIIPCRGGRAYL
STYPITKDSSKINFNGRERWYNQSDVVAAVNIVLRGIRDEN
(SEQ ID NO: 17)

>SRR6837575_megahit_k177_919599_7|M
[SRR6837575]
MPDPIKSYKSPIIIDPNNAHDVEKLDFLRETFVYLSNGTKCFMHV
FLSLLGGMNETLAKKIVSLETPKKEKKKKSNKPSHKIELFLAICW
FRLVKISKNESSVLPALLGNRFEKYFGAKATPEVMEYFSANYDEA
TYAWKDMREEFVSLKSKLKVSEKDLISDIGSMINERYIGLKFGKP
WGIISGLFGEGKKVDRSLKVELLKNVLEEIEKNPPKTKDQLAKMI
LKCADCKNGQEIHAKCGKIGRMSSVSNWADEVGSEKEIVLSFVKS
KISQDLAKQSNERNWKCVNALKSYILSEIGNCFDQSSWSEMLNNS
LSVIQSKTTRNYNFCIEQLEEKKNLNQNHRKFGTMIEDYFSSRFF
TGENKFIICNPHVGDKDKVSALLASCEGLSEEELEEKIQNFCESQ
KQESKMPIPALLMYLNSLKDSITVDQMFQGILYNKIRDKIERQKL
HPIVPNNDSFDWGMSSKINGRIISPKEKAKHNAQNNRSLYDSGIW
IEISVLKNKEWAKHHYKISNTRFVEEFYYPSSNDENSLDQVFRTG
RNGFNNPAKNNLSLEQVSNIKNAPKNRRRAIKRQMRVEAAHQQNV
LPHVKWDDNYCITISKYGDKFVTFISKKFKSKKSKEYVVFLGFDQ
NQTASHTFAAVQICDSKDENVIPYCGLFVKPLECGHITSVQKVKD
RSIDQLSYSGLPWKDFISWSQERKEFVSKWRMVEVKTRNGEKLDD
LTVKINKLDENKHGLYAYNSKYFWYLKSIMRKKTKDELFEIRKEL
LTVIKTGRLCVLRLSSLNHSSFLMLKNAKSAISCYFNNLLKGVSN
DQEKYEADPEMFELRREVEAKRQNKCMSKKNLISSQIVSKAIELR
GNYGSVAIIGEDLSDYVPDKGKKSTQNANLLDWLSRGVANKVKQI
ANMHDNISFKDVSPQWTSHQDSFVDRNPNSALRVRFGSCDPEEMY
EKDFESLIKFLKEDCGHYTNSMNDFLSHYGVSRKDMLEIKFSAFK
ILMKNILNKTGEKSLLYPKRGGRLYLATHKLGQCTRRTYNGVDFW
ECDADCVAAFNIALSGIRKYYGIKSEAVSPV
(SEQ ID NO: 18)

>SRR6837577_megahit_k177_410843_33|P
[SRR6837577]
MPDPIKSYKSPIIIDPNNAHDVEKLDFLRETFVYLSNGTKCFMHV
FLSLLGGMNETLAKKIVSLETPKKEKKKKSNKPSHKIELFLAICW
FRLVKISKNESSVLPALLGNRFEKYFGAKATPEVMEYFSANYDEA
TYAWKDMREEFVSLKSKLKVSEKDLISDIGSMINERYIGLKFGKP
WGIISGLFGEGKKVDRSLKVELLKNVLEEIEKNPPKTKDQLAKMI
LKCADCKNGQEIHAKCGKIGRMSSVSNWADEVGSEKEIVLSFVKS
KISQDLAKQSNERNWKCVNALKSYILSEIGNCFDQSSWSEMLNNS
LSVIQSKTTRNYNFCIEQLEEKKNLNQNHRKFGTMIEDYFSSRFF
TGENKFIICNPHVGDKDKVSALLASCEGLSEEELEEKIQNFCESQ
KQESKMPIPALLMYLNSLKDSITVDQMFQGILYNKIRDKIERQKL
HPIVPNNDSFDWGMSSKINGRIISPKEKAKHNAQNNRSLYDSGIW
IEISVLKNKEWAKHHYKISNTRFVEEFYYPSSNDENSLDQVFRTG
RNGFNNPAKNNLSLEQVSNIKNAPKNRRRAIKRQMRVEAAHQQNV
LPHVKWDDNYCITISKYGDKFVTFISKKFKSKKSKEYVVFLGFDQ
NQTASHTFAAVQICDSKDENVIPYCGLFVKPLECGHITSVQKVKD
RSIDQLSYSGLPWKDFISWSQERKEFVSKWRMVEVKTRNGEKLDD
LTVKINKLDENKHGLYAYNSKYFWYLKSIMRKKTKDELFEIRKEL
LTVIKTGRLCVLRLSSLNHSSFLMLKNAKSAISCYFNNLLKGVSN
DQEKYEADPEMFELRREVEAKRQNKCMSKKNLISSQIVSKAIELR
GNYGSVAIIGEDLSDYVPDKGKKSTQNANLLDWLSRGVANKVKQI
ANMHDNISFKDVSPQWTSHQDSFVDRNPNSALRVRFGSCDPEEMY
EKDFESLIKFLKEDCGHYTNSMNDFLSHYGVSRKDMLEIKFSAFK
ILMKNILNKTGEKSLLYPKRGGRLYLATHKLGQCTRRTYNGVDFW
ECDADCVAAFNIALSGIRKYYGIKSEAVSPV
(SEQ ID NO: 18)

>3300020508|Ga0208225_1000010_34|M
[3300020508]
MSNKEKNASETRKAYTTKMIPRSHDRMKLLGNFMDYLMDGTPIFF
ELWNQFGGGIDRDIISGTANKDKISDDLLLAVNWFKVMPINSKPQ
GVSPSNLANLFQQYSGSEPDIQAQEYFASNFDTEKHQWKDMRVEY
ERLLAELQLSRSDMHHDLKLMYKEKCIGLSLSTAHYITSVMFGTG
AKNNRQTKHQFYSKVIQLLEESTQINSVEQLASIILKAGDCDSYR
KLRIRCSRKGATPSILKIVQDYELGTNHDDEVNVPSLIANLKEKL
GRFEYECEWKCMEKIKAFLASKVGPYYLGSYSAMLENALSPIKGM
TTKNCKFVLKQIDAKNDIKYENEPFGKIVEGFFDSPYFESDTNVK
WVLHPHHIGESNIKTLWEDLNAIHSKYEEDIASLSEDKKEKRIKV
YQGDVCQTINTYCEEVGKEAKTPLVQLLRYLYSRKDDIAVDKIID
GITFLSKKHKVEKQKINPVIQKYPSFNFGNNSKLLGKIISPKDKL
KHNLKCNRNQVDNYIWIEIKVLNTKTMRWEKHHYALSSTRFLEEV
YYPATSENPPDALAARFRTKTNGYEGKPALSAEQIEQIRSAPVGL
RKVKKRQMRLEAARQQNLLPRYTWGKDFNINICKRGNNFEVTLAT

TABLE 4-continued

Amino Acid Sequences of Representative
CLUST.029130 (Type V-I) Effector Proteins KVKKKKEKNYKVVLGYDANIVRKNTYAAIEAHANGDGVIDYNDLP
VKPIESGFVTVESQVRDKSYDQLSYNGVKLLYCKPHVESRRSFLE
KYRNGTMKDNRGNNIQIDFMKDFEAIADDETSLYYFNMKYCKLLQ
SSIRNHSSQAKEYREEIFELLRDGKLSVLKLSSLSNLSFVMFKVA
KSLIGTYFGHLLKKPKNSKSDVKAPPITDEDKQKADPEMFALRLA
LEEKRLNKVKSKKEVIANKIVAKALELRDKYGPVLIKGENISDTT
KKGKKSSTNSFLMDWLARGVANKVKEMVMMHQGLEFVEVNPNFTS
HQDPFVHKNPENTFRARYSRCTPSELTEKNRKEILSFLSDKPSKR
PTNAYYNEGAMAFLATYGLKKNDVLGVSLEKFKQIMANILHQRSE
DQLLFPSRGGMFYLATYKLDADATSVNWNGKQFWVCNADLVAAYN
VGLVDIQKDFKKK
(SEQ ID NO: 3)

>3300002408|release|scaffold05697_22|M
[aquatic-freshwater]
MFTLLLSDISQQNFNKFLKNFFFTRNKTVVHCSSEIRHKGYRSNV
MVSESTIRPYTSKLAPNDPKLKMLNDTFNWLDHAYKVFFDVSVAL
FGAIEHETAQELIGEKSKFDADLLCAIMWFRLEEKSDNPGPLQTV
EQRMRLFQKYSGHEPSSFTQEYIKGNIDSEKYQWVDCRLKFIDLA
RNINTTQESLKIDAYTLFMNKLIPVSKDDEFNAYGLISQLFGTGK
KEDRSIKASMLEEISNIIEDKKPNTWEEYHDLIKKTFNVDNYKEL
KEKLSAGSSGRDSSLVIDLKEEKTGLLQPNFIKNRIVKFREDADK
KRTVFLLPNRMKLREFIASQIGPFEQNSWSAVLNRSMAAIQSKNS
SNILYTNEKEERNNEIQELLKKDILSAASILGDFRRGEFNRSVVS
KNHLGARLNELFEIWQELTMDDGIKKYVDLCKDKFSRRPVKALLQ
YIYPYFDKINAKQFLDAASYNTLVETNNRKKIHPTVTGPTVCNWG
PKSTINGSITPPNQMVKGRPAGSHGMIWVTMTVIDNGRWIKHHLP
FHNSRYYEEHYCYREGLPTKNKPRTKQLGTQVGSTISAPSLAILK
SQEEQDRRNDRKNRFKAHKSIIRSQENIEYNVAFDKSTNFDVTRK
NGEFFITISSRVATPKYSYKLNIGDMIMGLDNNQTAPCTYSIWRV
VEKDTEGSFFHNKIWLQLVTDGKVTSIVDNNRQVDQLSYAGIEYS
NFAEWRKDRRQFLRSINEDYVKKSDNWRNMNLYQWNAEYSRLLLD
VMKENKGKNIQNTFRAEIEELICGKFGIRLGSLFHHSLQFLTNCK
SLISSYFMLNNKKEEYDQELFDSDFFRLMKSIGDKRVRKRKEKSS
RISSTVLQIARENNVKSLCVEGYLPTSTKKTKPKQNQKSIDWCAR
AVVKKLNDGCKVLGINLQAIDPRDTSHLDPFVYYGKKSTKVGKEA
RYTIVEPSNIKEYMTNRFDDWHRGVTKKSKKGDVQTSTTVLLYQE
ALRQFASHYKLDFDSLPKMKFYELAKILGDHEKVIIPCRGGRAYL
STYPVTKDSSKITFNGRERWYNESDVVAAVNIVLRGIIDEDEQPD
GAKKQALARTK
(SEQ ID NO: 2)

>3300002408|release|scaffold05697_22|P
[aquatic-freshwater]
MVSESTIRPYTSKLAPNDPKLKMLNDTFNWLDHAYKVFFDVSVAL
FGAIEHETAQELIGEKSKFDADLLCAIMWFRLEEKSDNPGPLQTV
EQRMRLFQKYSGHEPSSFTQEYIKGNIDSEKYQWVDCRLKFIDLA
RNINTTQESLKIDAYTLFMNKLIPVSKDDEFNAYGLISQLFGTGK
KEDRSIKASMLEEISNIIEDKKPNTWEEYHDLIKKTFNVDNYKEL
KEKLSAGSSGRDSSLVIDLKEEKTGLLQPNFIKNRIVKFREDADK
KRTVFLLPNRMKLREFIASQIGPFEQNSWSAVLNRSMAAIQSKNS
SNILYTNEKEERNNEIQELLKKDILSAASILGDFRRGEFNRSVVS
KNHLGARLNELFEIWQELTMDDGIKKYVDLCKDKFSRRPVKALLQ
YIYPYFDKINAKQFLDAASYNTLVETNNRKKIHPTVTGPTVCNWG
PKSTINGSITPPNQMVKGRPAGSHGMIWVTMTVIDNGRWIKHHLP
FHNSRYYEEHYCYREGLPTKNKPRTKQLGTQVGSTISAPSLAILK
SQEEQDRRNDRKNRFKAHKSIIRSQENIEYNVAFDKSTNFDVTRK
NGEFFITISSRVATPKYSYKLNIGDMIMGLDNNQTAPCTYSIWRV
VEKDTEGSFFHNKIWLQLVTDGKVTSIVDNNRQVDQLSYAGIEYS
NFAEWRKDRRQFLRSINEDYVKKSDNWRNMNLYQWNAEYSRLLLD
VMKENKGKNIQNTFRAEIEELICGKFGIRLGSLFHHSLQFLTNCK
SLISSYFMLNNKKEEYDQELFDSDFFRLMKSIGDKRVRKRKEKSS
RISSTVLQIARENNVKSLCVEGYLPTSTKKTKPKQNQKSIDWCAR
AVVKKLNDGCKVLGINLQAIDPRDTSHLDPFVYYGKKSTKVGKEA
RYTIVEPSNIKEYMTNRFDDWHRGVTKKSKKGDVQTSTTVLLYQE
ALRQFASHYKLDFDSLPKMKFYELAKILGDHEKVIIPCRGGRAYL
STYPVTKDSSKITFNGRERWYNESDVVAAVNIVLRGIIDEDEQPD
GAKKQALARTK
(SEQ ID NO: 1)

>3300002408|release|scaffold08426_1|P
[aquatic-freshwater]
MSNKEKNASETRKAYTTKMIPRSHDRMKLLGNFMDYLMDGTPIFF
ELWNQFGGGIDRDIISGTANKDKISDDLLLAVNWFKVMPINSKPQ
GVSPSNLANLFQQYSGSEPDIQAQEYFASNFDTEKHQWKDMRVEY
ERLLAELQLSRSDMHHDLKLMYKEKCIGLSLSTAHYITSVMFGTG
AKNNRQTKHQFYSKVIQLLEESTQINSVEQLASIILKAGDCDSYR TABLE 4-continued Amino Acid Sequences of Representative
CLUST.029130 (Type V-I) Effector Proteins KLRIRCSRKGATPSILKIVQDYELGTNHDDEVNVPSLIANLKEKL
GRFEYECEWKCMEKIKAFLASKVGPYYLGSYSAMLENALSPIKGM
TTKNCKFVLKQIDAKNDIKYENEPPFGKIVEGFFDSPYFESDTNVK
WVLHPHHIGESNIKTLWEDLNAIHSKYEEDIASLSEDKKEKRIKV
YQGDVCQTINTYCEEVGKEAKTPLVQLLRYLYSRKDDIAVDKIID
GITFLSKKHKVEKQKINPVIQKYPSFNFGNNSKLLGKIISPKDKL
KHNLKCNRNQVDNYIWIEIKVLNTKTMRWEKHHYALSSTRFLEEV
YYPATSENPPDALAARFRTKTNGYEGKPALSAEQIEQIRSAPVGL
RKVVKKRQMRLEAARQQNLLPRYTWGKDFNINICKRGNNFEVTLAT
KVKKKKEKNYKVVLGYDANIVRKNTYAAIEAHANGDGVIDYNDLP
VKPIESGFVTVESQVRDKSYDQLSYNGVKLLYCKPHVESRRSFLE
KYRNGTMKDNRGNNIQIDFMKDFEAIADDETSLYYFNMKYCKLLQ
SSIRNHSSQAKEYREEIFELLRDGKLSVLKLSSLSNLSFVMFKVA
KSLIGTYFGHLLKKPKNSKSDVKAPPITDEDKQKADPEMFALRLA
LEEKRLNKVKSKKEVIANKIVAKALELRDKYGPVLIKGENISDTT
KKGKKSSTNSFLMDWLARGVANKVKEMVMMHQGLEFVEVNPNFTS
HQDPFVHKNPENTFRARYSRCTPSELTEKNRKEILSFLSDKPSKR
PTNAYYNEGAMAFLATYGLKKNDVLGVSLEKFKQIMANILHQRSE
DQLLFPSRGGMFYLATYKLDADATSVNWNGKQFWVCNADLVAAYN
VGLVDIQKDFKKK
(SEQ ID NO: 3)

>3300028569|Ga0247843_1000055_230|M
[aquatic-freshwater]
MPRNYFLGIFSLQKNKSVVHCSVEIRHKGYRSSVMVSDSTIRPYA
SKLAPNDPKLKMLNDTFNWLDHAYKVFFDVSVALFGAIEHETAQE
LIGEKSKFDADLICAIMWFRLEEKSDNPGPLQTVEQRMRLFQKYS
GHEPSSFTQEYIKGNIDSEKYEWVDCRLKFIDLARNINTTQESLK
IDAYTLFMNKLIPVSKDDEFNAYGLISQLFGTGKKEDRSIKAAML
EEISNILADKKPDTWEEYHDLIKKNFNVDNYKELKEKLSAGSSGR
DSSLVIDLKEEKTGLLQPNFIKNRIVKFREDADKKKTVFLLPNRM
KLREFIASQIGPFEQNSWSAVLNRSMAAIQSKNSSNILYTNEKEE
RNNEIQELLKKDILSAASILGDFRRGEFNRSVVSKNHLGARLNEL
FEIWQDLTMDDGIRKYVDLCKDKFSRRPVKALLQYIYPYFDKITA
KQFLDAASYNTLVETNNRKKIHPTVTGPTVCNWGPKSTINGSITP
PNQMVKGRPAGSHGMIWVTMTVIDNGRWIKHHLPFYNSRYYEEHY
CYREGLPTKNQPRTKQLGTQVGSTISATSLAALKSQEEQDRRNDR
KNRFKAHKSIIRSQENIEYNVAFDKSTNFDVTRKNGEFFITISSR
VATPKYSYKLNIGDMIMGLDNNQTAPCTYSIWRVVEKDTEGSFFH
NKIWLQLVTDGKITSIVDNNRQVDQLSYAGIEYSNFAEWRKDRRQ
FLRSINEDYVKKSDNWRNMNLYQWNAEYSRLLLDVMKENKGKNIQ
NTFRAEIEELICGKFGIRLGSLFHHSLQFLTNCKSLISSYFMLNN
KKEEYDQELFDSDFFRLMKSIGDKRVRKRKEKSSRISSTVLQIAR
ENNIKSLCVEGDLPTATKKTKPKQNQKSIDWCARAVVKKLNDGCK
VLGINLQAIDPRDTSHLDPFVYYGKKSTKVGKEARYTIVEPSNIK
EYMTNRFDDWHRGVTKKSKKGDVQTSTTVLLYQEALRQFASHYEL
DFDSLPKMKFYDLAKRLGDHEKVIIPCRGGRAYLSTYPVTKDSSK
ITFNGRERWYNESDvvAAVNIVLRGIRDEDEQPDDAKKQALARTK
(SEQ ID NO: 11)

>3300028569|Ga0247843_1000055_232|P
[aquatic-freshwater]
MVSDSTIRPYASKLAPNDPKLKMLNDTFNWLDHAYKVFFDVSVAL
FGAIEHETAQELIGEKSKFDADLICAIMWFRLEEKSDNPGPLQTV
EQRMRLFQKYSGHEPSSFTQEYIKGNIDSEKYEWVDCRLKFIDLA
RNINTTQESLKIDAYTLFMNKLIPVSKDDEFNAYGLISQLFGTGK
KEDRSIKAAMLEEISNILADKKPDTWEEYHDLIKKNFNVDNYKEL
KEKLSAGSSGRDSSLVIDLKEEKTGLLQPNFIKNRIVKFREDADK
KKTVFLLPNRMKLREFIASQIGPFEQNSWSAVLNRSMAAIQSKNS
SNILYTNEKEERNNEIQELLKKDILSAASILGDFRRGEFNRSVVS
KNHLGARLNELFEIWQDLTMDDGIRKYVDLCKDKFSRRPVKALLQ
YIYPYFDKITAKQFLDAASYNTLVETNNRKKIHPTVTGPTVCNWG
PKSTINGSITPPNQMVKGRPAGSHGMIWVTMTVIDNGRWIKHHLP
FYNSRYYEEHYCYREGLPTKNQPRTKQLGTQVGSTISATSLAALK
SQEEQDRRNDRKNRFKAHKSIIRSQENIEYNVAFDKSTNFDVTRK
NGEFFITISSRVATPKYSYKLNIGDMIMGLDNNQTAPCTYSIWRV
VEKDTEGSFFHNKIWLQLVTDGKITSIVDNNRQVDQLSYAGIEYS
NFAEWRKDRRQFLRSINEDYVKKSDNWRNMNLYQWNAEYSRLLLD
VMKENKGKNIQNTFRAEIEELICGKFGIRLGSLFHHSLQFLTNCK
SLISSYFMLNNKKEEYDQELFDSDFFRLMKSIGDKRVRKRKEKSS
RISSTVLQIARENNIKSLCVEGDLPTATKKTKPKQNQKSIDWCAR
AVVKKLNDGCKVLGINLQAIDPRDTSHLDPFVYYGKKSTKVGKEA
RYTIVEPSNIKEYMTNRFDDWHRGVTKKSKKGDVQTSTTVLLYQE
ALRQFASHYELDFDSLPKMKFYDLAKRLGDHEKVIIPCRGGRAYL
STYPVTKDSSKITFNGRERWYNESDVVAAVNIVLRGIRDEDEQPD
DAKKQALARTK
(SEQ ID NO: 12)

TABLE 4-continued

Amino Acid Sequences of Representative
CLUST.029130 (Type V-I) Effector Proteins >3300028571|Ga0247844_1000101_90|M
[aquatic-freshwater]
MPRNYFLGIFSLQKNKSVVHCSVEIRHKGYRSSVMVSDSTIRPYA
SKLAPNDPKLKMLNDTFNWLDHAYKVFFDVSVALFGAIEHETAQE
LIGEKSKFDADLICAIMWFRLEEKSDNPGPLQTVEQRMRLFQKYS
GHEPSSFTQEYIKGNIDSEKYEWVDCRLKFIDLARNINTTQESLK
IDAYTLFMNKLIPVSKDDEFNAYGLISQLFGTGKKEDRSIKAAML
EEISNILADKKPDTWEEYHDLIKKNFNVDNYKELKEKLSAGSSGR
DSSLVIDLKEEKTGLLQPNFIKNRIVKFREDADKKKTVFLLPNRM
KLREFIASQIGPFEQNSWSAVLNRSMAAIQSKNSSNILYTNEKEE
RNNEIQELLKKDILSAASILGDFRRGEFNRSVVSKNHLGARLNEL
FEIWQDLTMDDGIRKYVDLCKDKFSRRPVKALLQYIYPYFDKITA
KQFLDAASYNTLVETNNRKKIHPTVTGPTVCNWGPKSTINGSITP
PNQMVKGRPAGSHGMIWVTMTVIDNGRWIKHHLPFYNSRYYEEHY
CYREGLPTKNQPRTKQLGTQVGSTISATSLAALKSQEEQDRRNDR
KNRFKAHKSIIRSQENIEYNVAFDKSTNFDVTRKNGEFFITISSR
VATPKYSYKLNIGDMIMGLDNNQTAPCTYSIWRVVEKDTEGSFFH
NKIWLQLVTDGKITSIVDNNRQVDQLSYAGIEYSNFAEWRKDRRQ
FLRSINEDYVKKSDNWRNMNLYQWNAEYSRLLLDVMKENKGKNIQ
NTFRAEIEELICGKFGIRLGSLFHHSLQFLTNCKSLISSYFMLNN
KKEEYDQELFDSDFFRLMKSIGDKRVRKRKEKSSRISSTVLQIAR
ENNIKSLCVEGDLPTATKKTKPKQNQKSIDWCARAVVKKLNDGCK
VLGINLQAIDPRDTSHLDPFVYYGKKSTKVGKEARYTIVEPSNIK
EYMTNRFDDWHRGVTKKSKKGDVQTSTTVLLYQEALRQFASHYEL
DFDSLPKMKFYDLAKRLGDHEKVIIPCRGGRAYLSTYPVTKDSSK
ITFNGRERWYNESDVVAAVNIVLRGIRDEDEQPDDAKKQALARTK
(SEQ ID NO: 11)

>3300028571|Ga0247844_1000101_88|P
[aquatic-freshwater]
MVSDSTIRPYASKLAPNDPKLKMLNDTFNWLDHAYKVFFDVSVAL
FGAIEHETAQELIGEKSKFDADLICAIMWFRLEEKSDNPGPLQTV
EQRMRLFQKYSGHEPSSFTQEYIKGNIDSEKYEWVDCRLKFIDLA
RNINTTQESLKIDAYTLFMNKLIPVSKDDEFNAYGLISQLFGTGK
KEDRSIKAAMLEEISNILADKKPDTWEEYHDLIKKNFNVDNYKEL
KEKLSAGSSGRDSSLVIDLKEEKTGLLQPNFIKNRIVKFREDADK
KKTVFLLPNRMKLREFIASQIGPFEQNSWSAVLNRSMAAIQSKNS
SNILYTNEKEERNNEIQELLKKDILSAASILGDFRRGEFNRSVVS
KNHLGARLNELFEIWQDLTMDDGIRKYVDLCKDKFSRRPVKALLQ
YIYPYFDKITAKQFLDAASYNTLVETNNRKKIHPTVTGPTVCNWG
PKSTINGSITPPNQMVKGRPAGSHGMIWVTMTVIDNGRWIKHHLP
FYNSRYYEEHYCYREGLPTKNQPRTKQLGTQVGSTISATSLAALK
SQEEQDRRNDRKNRFKAHKSIIRSQENIEYNVAFDKSTNFDVTRK
NGEFFITISSRVATPKYSYKLNIGDMIMGLDNNQTAPCTYSIWRV
VEKDTEGSFFHNKIWLQLVTDGKITSIVDNNRQVDQLSYAGIEYS
NFAEWRKDRRQFLRSINEDYVKKSDNWRNMNLYQWNAEYSRLLLD
VMKENKGKNIQNTFRAEIEELICGKFGIRLGSLFHHSLQFLTNCK
SLISSYFMLNNKKEEYDQELFDSDFFRLMKSIGDKRVRKRKEKSS
RISSTVLQIARENNIKSLCVEGDLPTATKKTKPKQNQKSIDWCAR
AVVKKLNDGCKVLGINLQAIDPRDTSHLDPFVYYGKKSTKVGKEA
RYTIVEPSNIKEYMTNRFDDWHRGVTKKSKKGDVQTSTTVLLYQE
ALRQFASHYELDFDSLPKMKFYDLAKRLGDHEKVIIPCRGGRAYL
STYPVTKDSSKITFNGRERWYNESDVVAAVNIVLRGIRDEDEQPD
DAKKQALARTK
(SEQ ID NO: 12)

>3300009183|Ga0114974_10028552_1|M
[aquatic-freshwater-freshwater lake]
MMSDNIILPYNSKLAPDERKQRLLNDTFNWFDMCNEVFFDFVKNL
YGGVKHEHLILVNFAEKPKKVSNSKKPKKKDQEVNIHVEPNQAEW
VDNACATFWFRLQAKSTVQLDQSVQTAEEERIRRFRDYAGHEPSSF
AKSYLNGNYDPEKTEWVDCRLLYVNFCRNLNVNLDADIRTMVEHN
LLPVLPGQDFKTNNVFSNLEGPVKDKGQKTNWLNTVSEGLQSK
EIWNWDEYRDLISRSTGCSTAAELRSEESIGRPSMLAVDFASEKSG
QISQEWLAERVKSFRAAASQKSKIYDMPNRLVLKEYIASKIGPFK
LERWSAAAVSAYKDVRSKNSINLLYSKERLWRCKEIAQILVDNTQ
VAEAQQILVNYSSGDTNSFTCKNAKASKMYLRTIQNMTHNVAFQQ
TQFAVRRYADNNFTITIQARVVGRKYKKEISVGDRVMGVDQNTT
SNTYSVWEVVAEGTENSYPYKGNNYRLVEDGFIRSECGSRDQLSY
DGLDFQDFAQWRRERYAFLSSVGCILNDEIEPQIPVSAEKAKKKK
KFSKWRGCSLYSWNLCYAYYLKGLMHENLANNPAGFRQEILNPIQ
GSRGVRLCSLNHTSFRLLSKAKSLIHSFFGLNNIKDPESQRDFDP TABLE 4-continued Amino Acid Sequences of Representative
CLUST.029130 (Type V-I) Effector Proteins EIYDIMVNLTQRKTNKRKEKANRITSSILQIANRLNVSRIVIEND
LPNASSKNKASANQRATDWCARNVSEKLEYACKMLGISLWQIDPR
DTSHLDPFVVGKEARFMKIKVSDINEYTISNFKKWHANIATTSTT
APLYHDALKAFSSHYGIDWDNLPEMKFWELKNALKDHKEVFIPNR
GGRCYLSTLPVTSTSEKIVFNGRERWLNASDIVAGVNIVLRSV
(SEQ ID NO: 4)

>3300010885|Ga0133913_10053227_5|M
[aquatic-freshwater-freshwater lake]
MVSESTIRPYTSKLAPNDSKLKMLNDTFNWLDHAYKVFFDVSVAL
FGAIEHETAQELIGEKSKFDADLLCAIMWFRLEEKSDNPGPLQTV
EQRMRLFQKYSGHEPSSFTQEYIKGNIDSEKYQWVDCRLKFIDLA
RNINTTQESLKIDAYTLFMNKLIPVSKDDEFNAYGLISQLFGTGK
KEDRSIKASMLEEISNILADKNPNTWEEYQDLIKKTFNVDNYKEL
KEKLSAGSSGRDGSLVIDLKEEKTGLLQPNFIKNRIVKFREDADK
KRTVFLLPNRMKLREFIASQIGPFEQNSWSAVLNRSMAAIQSKNS
SNILYTNEKEERNNEIQELLKKDILSAASILGDFRRGEFNRSVVS
KNHLGARLNELFEIWQELTMDDGIKKYVDLCKDKFSRRPVKALLQ
YIYPYFDKINAKQFLDAASYNTLVETNNRKKIHPTVTGPTVCNWG
PKSTINGSITPPNQMVKGRPAGSHGMIWVTMTVIDNGRWIKHHLP
FHNSRYYEEHYCYREGLPTKNKPRTKQLGTQVGSTISAPSLAILK
SQEEQDRRNDRKNRFKAHKSIIRSQENIEYNVAFDKSTNFDVTRK
NGEFFITISSRVATPKYSYKLNIGDMIMGLDNNQTAPCTYSIWRV
VEKDTEGSFFHNKIWLQLVTDGKVTSIVDNNRQVDQLSYAGIEYS
NFAEWRKDRRQFLRSINEDYVKKSDNWRNMNLYQWNAEYSRLLLD
VMKENKGKNIQNTFRAEIEELICGKFGIRLGSLPHHSLQFLTNCK
SLISSYFMLNNKKEEYDQELFDSDFFRLMKSIGDKRVRKRKEKSS
RISSTVLQIARENNVKSLCVEGYLPTSTKKTKPKQNQKSIDWCAR
AVVKKLNDGCKVLGIYLQAIDPRDTSHLDPFVYYGKKSTKVGKEA
RHTIVEPSNIKEYMTNRFDDWHRGVTKKSKKGDVQTSTTVLLYQE
ALRQFASHYKLDFDSLPKMKFYELAKILGDHEKVIIPCRGGRAYL
STYPVTKDSSKITFNGRERWYNESDVVAAVNIVLRGIIDEDEQPD
GAKKQATTRRT
(SEQ ID NO: 13)

>3300020193|Ga0194131_10013618_4|P
[aquatic-freshwater-freshwater lake]
MSSAIKSYKSVLRPNERKNQLLKSTIQCLEDGSAFFFKMLQGLFG
GITPEIVRFSTEQEKQQQDIALWCAVNWFRPVSQDSLTHTIASDN
LVEKFEEYYGGTASDAIKQYFSASIGESYYWNDCRQQYYDLCREL
GVEVSDLTHDLEILCREKCLAVATESNQNNSIISVLFGTGEKEDR
SVKLRITKKILEAISNLKEIPKNVAPIQEIILNVAKATKETFRQV
YAGNLGAPSTLEKFIAKDGQKEFDLKKLQTDLKKVIRGKSKERDW
CCQEELRSYVEQNTIQYDLWAWGEMFNKAHTALKIKSTRNYNFAK
QRLEQFKEIQSLNNLLVVKKLNDFFDSEFFSGEETYTICVHHLGG
KDLSKLYKAWEDDPADPENAIVVLCDDLKNNFKKEPIRNILRYIF TABLE 4-continued Amino Acid Sequences of Representative
CLUST.029130 (Type V-I) Effector Proteins TIRQECSAQDILAAAKYNQQLDRYKSQKANPSVLGNQGFTWTNAV
ILPEKAQRNDRPNSLDLRIWLYLKLRHPDGRWKKHHIPFYDTRFF
QEIYAAGNSPVDTCQFRTPRFGYHLPKLTDQTAIRVNKKHVKAAK
TEARIRLAIQQGTLPVSNLKITEISATINSKGQVRIPVKFDVGRQ
KGTLQIGDRFCGYDQNQTASHAYSLWEVVKEGQYHKELGCFVRFI
SSGDIVSITENRGNQFDQLSYEGLAYPQYADWRKKASKFVSLWQI
TKKNKKKEIVTVEAKEKFDAICKYQPRLYKFNKEYAYLLRDIVRG
KSLVELQQIRQEIFRFIEQDCGVTRLGSLSLSTLETVKAVKGIIY
SYFSTALNASKNNPISDEQRKEFDPELFALLEKLELIRTRKKKQK
VERIANSLIQTCLENNIKFIRGEGDLSTTNNATKKKANSRSMDWL
ARGVFNKIRQLAPMHNITLFGCGSLYTSHQDPLVHRNPDKAMKCR
WAAIPVKDIGDWVLRKLSQNLRAKNIGTGEYYHQGVKEFLSHYEL
QDLEEEELLKWRSDRKSNIPCWVLQNRLAEKLGNKEAVVYIPVRGG
RIYFATHKVATGAVSIVFDQKQVWVCNADHVAAANIALTVKGIGE
QSSDEENPDGSRIKLQLTS
(SEQ ID NO: 5)

>3300020214|Ga0194132_10015959_3|M
[aquatic-freshwater-freshwater lake]
MSSAIKSYKSVLRPNERKNQLLKSTIQCLEDGSAFFFKMLQGLFG
GITPEIVRFSTEQEKQQQDIALWCAVNWFRPVSQDSLTHTIASDN
LVEKFEYYGGTASDAIKQYFSASIGESYYWNDCRQQYYDLCREL
GVEVSDLTHDLEILCREKCLAVATESNQNNSIISVLFGTGEKEDR
SVKLRITKKILEAISNLKEIPKNVAPIQEIILNVAKATKETFRQV
YAGNLGAPSTLEKFIAKDGQKEFDLKKLQTDLKKVIRGKSKERDW
CCQEELRSYVEQNTIQYDLWAWGEMFNKAHTALKIKSTRNYNFAK
QRLEQFKEIQSLNNLLVVKKLNDFFDSEFFSGEETYTICVHHLGG
KDLSKLYKAWEDDPADPENAIVVLCDDLKNNFKKEPIRNILRYIF
TIRQECSAQDILAAAKYNQQLDRYKSQKANPSVLGNQGFTWTNAV
ILPEKAQRNDRPNSLDLRIWLYLKLRHPDGRWKKHHIPFYDTRFF
QEIYAAGNSPVDTCQFRTPRFGYHLPKLTDQTAIRVNKKHVKAAK
TEARIRLAIQQGTLPVSNLKITEISATINSKGQVRIPVKFDVGRQ
KGTLQIGDRFCGYDQNQTASHAYSLWEVVKEGQYHKELGCFVRFI
SSGDIVSITENRGNQFDQLSYEGLAYPQYADWRKKASKFVSLWQI
TKKNKKKEIVTVEAKEKFDAICKYQPRLYKFNKEYAYLLRDIVRG
KSLVELQQIRQEIFRFIEQDCGVTRLGSLSLSTLETVKAVKGIIY
SYFSTALNASKNNPISDEQRKEFDPELFALLEKLELIRTRKKKQK
VERIANSLIQTCLENNIKFIRGEGDLSTTNNATKKKANSRSMDWL
ARGVFNKIRQLAPMHNITLFGCGSLYTSHQDPLVHRNPDKAMKCR
WAAIPVKDIGDWVLRKLSQNLRAKNIGTGEYYHQGVKEFLSHYEL
QDLEEEELLKWRSDRKSNIPCWVLQNRLAEKLGNKEAVVYIPVRGG
RIYFATHKVATGAVSIVFDQKQVWVCNADHVAAANIALTVKGIGE
QSSDEENPDGSRIKLQLTS
(SEQ ID NO: 5)

TABLE 5A

Representative CLUST.029130 (Type V-I) Effector Proteins and Direct Repeats

| CLUST.201934 Effector Protein Accession | Direct Repeat Nucleotide Sequence |
|---|---|
| SRR1522973_megahit_k177_1081830_2\|M (SEQ ID NO: 11) | CTAGCAATGACCTAATAGTGTGTCCTTAGTTGACAT (SEQ ID NO: 19) |
| SRR1522973_megahit_k177_427371_1\|M (SEQ ID NO: 12) | CTAGCAATGACCTAATAGTGTGTCCTTAGTTGACAT (SEQ ID NO: 19) |
| SRR2179954_megahit_k177_1417524_4\|M (SEQ ID NO: 13) | TCTCAACGATAGTCAGACATGTGTCCTCAGTGACAC (SEQ ID NO: 20) |
| SRR6475631_megahit_k177_2773783_7\|M (SEQ ID NO: 14) | CCTACAATACCTAAGAAATCCGTCCTAAGTTGACGG (SEQ ID NO: 21) |
| SRR6837575_megahit_k177_919599_7\|M (SEQ ID NO: 15) | GTAGCAATCAGTACATATTGTGCCTTTCATTGGCACA (SEQ ID NO: 22) |
| SRR6837577_megahit_k177_410843_33\|P (SEQ ID NO: 15) | GTAGCAATCAGTACATATTGTGCCTTTCATTGGCAC (SEQ ID NO: 23) |
| 3300020508\|Ga0208225_1000010_34\|M (SEQ ID NO: 3) | GTTGGAATGACTAATTTTTGTGCCCACCGTTGGCAC (SEQ ID NO: 24) |

TABLE 5A-continued

Representative CLUST.029130 (Type V-I) Effector Proteins and Direct Repeats

| CLUST.201934 Effector Protein Accession | Direct Repeat Nucleotide Sequence |
|---|---|
| 3300002408\|release\|scaffold05697_22\|M (SEQ ID NO: 2) | CCCACAATACCTGAGAAATCCGTCCTACGTTGACGG (SEQ ID NO: 6) |
| 3300002408\|release\|scaffold05697_22\|P (SEQ ID NO: 1) | CCCACAATACCTGAGAAATCCGTCCTACGTTGACGG (SEQ ID NO: 6) |
| 3300002408\|release\|scaffold08426_1\|P (SEQ ID NO: 3) | AATTTTTGTGCCCATCGTTGGCAC (SEQ ID NO: 7) |
| 3300028569\|Ga0247843_1000055_230\|M (SEQ ID NO: 16) | CCCACAATACCTGAGAAATCCGTCCTACGTTGACGG (SEQ ID NO: 6) |
| 3300028569\|Ga0247843_1000055_232\|P (SEQ ID NO: 17) | CCCACAATACCTGAGAAATCCGTCCTACGTTGACGG (SEQ ID NO: 6) |
| 3300028571\|Ga0247844_1000101_90\|M (SEQ ID NO: 16) | CCCACAATACCTGAGAAATCCGTCCTACGTTGACGG (SEQ ID NO: 6) |
| 3300028571\|Ga0247844_1000101_88\|P (SEQ ID NO: 17) | CCCACAATACCTGAGAAATCCGTCCTACGTTGACGG (SEQ ID NO: 6) |
| 3300009183\|Ga0114974_10028552_1\|M (SEQ ID NO: 4) | CTCTCAATGCCTTAGAAATCCGTCCTTGGTTGACGG (SEQ ID NO: 8) |
| 3300010885\|Ga0133913_10053227_5\|M (SEQ ID NO: 18) | CCCACAATACCTGAGAAATCCGTCCTACGTTGACGG (SEQ ID NO: 6) |
| 3300020193\|Ga0194131_10013618_4\|P (SEQ ID NO: 5) | GCAACACCTAAGAAATCCGTCTTTCATTGACGGG (SEQ ID NO: 9) |
| 3300020214\|Ga0194132_10015959_3\|M (SEQ ID NO: 5) | GTTGCAAAACCCAAGAAATCCGTCTTTCATTGACGG (SEQ ID NO: 10) |

TABLE 5B

Example CLUST.029130 (Type V-I) pre-crRNA sequences

| Effector Accession | Example pre-crRNA sequence | Spacer Lens 1 | Spacer Lens 2 | Spacer Lens 3 |
|---|---|---|---|---|
| SRR1522973_megahit _k177_1081830_ 2\|M (SEQ ID NO: 11) | CUAGCAAUGACCUAAUAGUGUGUCCUUAGUUGACAUNNNN NNNNNNNNNNNNNNNNNNNNNNNNNNNNNNNNCUAGCAAUGA CCUAAUAGUGUGUCCUUAGUUGACAU (SEQ ID NO: 150) | 34-36 | 33-37 | 20-41 |
| SRR1522973_megahit _k177_427371_1\|M (SEQ ID NO: 12) | CUAGCAAUGACCUAAUAGUGUGUCCUUAGUUGACAUNNNN NNNNNNNNNNNNNNNNNNNNNNNNNNNNNNNNCUAGCAAUG ACCUAAUAGUGUGUCCUUAGUUGACAU (SEQ ID NO: 151) | 35-36 | 33-37 | 23-38 |
| SRR2179954_ megahit_k177_ 1417524_4\|M (SEQ ID NO: 13) | UCUCAACGAUAGUCAGACAUGUGUCCUCAGUGACACNNNN NNNNNNNNNNNNNNNNNNNNNNNNNNNNNNNNUCUCAACG AUAGUCAGACAUGUGUCCUCAGUGACAC (SEQ ID NO: 152) | 36-45 | 36-51 | 36-59 |
| SRR6475631_megahit _k177_2773783_ 7\|M (SEQ ID NO: 14) | CCUACAAUACCUAAGAAAUCCGUCCUAAGUUGACGGNNNN NNNNNNNNNNNNNNNNNNNNNNNNNNNNNNNNCCUACAAUA CCUAAGAAAUCCGUCCUAAGUUGACGG (SEQ ID NO: 153) | 35-38 | 27-44 | 21-47 |
| SRR683757_5_megahit _k177_919599_7 \|M (SEQ ID NO: 15) | GUAGCAAUCAGUACAUAUUGUGCCUUUCAUUGGCACANNN NNNNNNNNNNNNNNNNNNNNNNNNNNNNNNNNNGUAGCAAUCA GUACAUAUUGUGCCUUUCAUUGGCACA (SEQ ID NO: 154) | 33-34 | 30-35 | 26-36 |
| SRR6837577_megahit _k177_410843_3 3\|P (SEQ ID NO: 15) | GUAGCAAUCAGUACAUAUUGUGCCUUUCAUUGGCACNNNN NNNNNNNNNNNNNNNNNNNNNNNNNNNNNNNNGUAGCAAUCA GUACAUAUUGUGCCUUUCAUUGGCAC (SEQ ID NO: 155) | 34-37 | 27-38 | 20-42 |

TABLE 5B-continued

Example CLUST.029130 (Type V-I) pre-crRNA sequences

| Effector Accession | Example pre-crRNA sequence | Spacer Lens 1 | Spacer Lens 2 | Spacer Lens 3 |
|---|---|---|---|---|
| 3300020508\|Ga020 8225_1000010_34\| M (SEQ ID NO: 3) | GUUGGAAUGACUAAUUUUUGUGCCCACCGUUGGCACNNNN NNNNNNNNNNNNNNNNNNNNNNNNNNNNNNNNNNGUUGGAAU GACUAAUUUUUGUGCCCACCGUUGGCAC (SEQ ID NO: 156) | 36-38 | 35-43 | 28-47 |
| 3300002408\|release \|scaffold08426 _1\|P (SEQ ID NO: 3) | AAUUUUUGUGCCCAUCGUUGGCACNNNNNNNNNNNNNNNNN NNNNNNNNNNNNNNNNNNNNNNNAAUUUUUGUGCCCAUCGUUG GCAC (SEQ ID NO: 157) | 36-38 | 36-42 | 28-47 |
| 3300028569\|Ga024 7843_1000055_230 \|M (SEQ ID NO: 16) | CCCACAAUACCUGAGAAAUCCGUCCUACGUUGACGGNNNN NNNNNNNNNNNNNNNNNNNNNNNNNNNNNNNNNCCCACAAU ACCUGAGAAAUCCGUCCUACGUUGACGG (SEQ ID NO: 158) | 36-37 | 20-38 | 19-41 |
| 3300028569\|Ga024 7843_1000055_232 \|P (SEQ ID NO: 17) | CCCACAAUACCUGAGAAAUCCGUCCUACGUUGACGGNNNN NNNNNNNNNNNNNNNNNNNNNNNNNNNNNNNNNCCCACAAU ACCUGAGAAAUCCGUCCUACGUUGACGG (SEQ ID NO: 159) | 36-37 | 20-38 | 19-41 |
| 3300009183\|Ga011 4974_10028552_1\| M (SEQ ID NO: 4) | CUCUCAAUGCCUUAGAAAUCCGUCCUUGGUUGACGGNNNN NNNNNNNNNNNNNNNNNNNNNNNNNNNNNNNNNCUCUCAAU GCCUUAGAAAUCCGUCCUUGGUUGACGG (SEQ ID NO: 160) | 36-37 | 36-40 | 36-46 |
| 3300010885\|Ga013 3913_10053227_5\| M (SEQ ID NO: 18) | CCCACAAUACCUGAGAAAUCCGUCCUACGUUGACGGNNNN NNNNNNNNNNNNNNNNNNNNNNNNNNNNNNNCCCACAAUAC CUGAGAAAUCCGUCCUACGUUGACGG (SEQ ID NO: 161) | 34-37 | 26-38 | 19-39 |
| 3300020193\|Ga019 4131_10013618_4\| P (SEQ ID NO: 5) | GCAACACCUAAGAAAUCCGUCUUUCAUUGACGGGNNNNNN NNNNNNNNNNNNNNNNNNNNGCAACACCUAAGAAAUCCGUCU UUCAUUGACGGG (SEQ ID NO: 162) | 24-25 | 21-26 | 20-33 |
| 3300020214\|Ga019 4132_10015959_3\| M (SEQ ID NO: 5) | GUUGCAAAACCCAAGAAAUCCGUCUUUCAUUGACGGNNNN NNNNNNNNNNNNNNNNNNNNNNNNNNNGUUGCAAAACCCA AGAAAUCCGUCUUUCAUUGACGG (SEQ ID NO: 163) | 31-33 | 29-35 | 20-47 |

Example 2: In Vivo Bacterial Validation of Engineered CLUST.029130 (Type V-I) CRISPR-Cas Systems (FIGS. 4A-10B)

Having identified the minimal components of Type V-I CRISPR-Cas systems, we selected two systems for functional validation, one comprising the effector designated Cas12i1 (SEQ TD NO: 3), and the other comprising the effector designated Cas12i2 (SEQ ID NO: 5).

Methods

Gene Synthesis and Oligo Library Cloning

The *E. coli* codon-optimized protein sequences for CRISPR effectors, accessory proteins were cloned into pET-28a(+) (EMD-Millipore) to create the Effector Plasmid. Noncoding sequences flanking Cas genes (including 150 nt of terminal CDS coding sequence) or the CRISPR array were synthesized (Genscript) into pACYC184 (New England Biolabs) to create the Non-coding Plasmid (FIG. 4A). Effector mutants (e.g., D513A or A513D) plasmids were cloned by site directed mutagenesis using the indicated primers in the sequence table: sequence changes were first introduced into PCR fragments, which were then re-assembled into a plasmid using NEBuilder HiFi DNA Assembly Master Mix or NEB Gibson Assembly Master Mix (New England Biolabs) following the manufacturer's instructions.

For the pooled spacer library, we first computationally designed an oligonucleotide library synthesis (OLS) pool (Agilent) to express a minimal CRISPR array of "repeat-spacer-repeat" sequences. The "repeat" elements were derived from the consensus direct repeat sequence found in the CRISPR array associated with the effector, and "spacer" represents ~8,900 sequences targeting the pACYC184 plasmid and *E. coli* essential genes, or negative control non-targeting sequences. The spacer length was determined by the mode of the spacer lengths found in the endogenous CRISPR array. Flanking the minimal CRISPR array were unique PCR priming sites that enabled amplification of a specific library from a larger pool of oligo synthesis.

We next cloned the minimal CRISPR array library into the Effector Plasmid to create an Effector Plasmid library. We appended flanking restriction sites, a unique molecular identifier, and a J23119 promoter for array expression onto the oligo library using PCR (NEBNext High-Fidelity 2×PCR Master Mix), and then used NEB Golden Gate Assembly Master Mix (New England Biolabs) to assemble the full plasmid library of effectors with their targeting arrays. This represented the "input library" for the screen.

In Vivo *E. coli* Screen

We performed the in vivo screen using electrocompetent E. cloni EXPRESS BL21(DE3) *E. coli* cells (Lucigen), unless otherwise indicated. Competent cells were co-transformed with the Effector Plasmid and/or Non-coding (FIG. 4B). The cells were electroporated with the "input library" according to the manufacturer's protocols using a Gene Pulser Xcell® (Bio-rad) with a 1.0 mm cuvette. The cells were plated onto bioassay plates containing both Chloramphenicol (Fisher) and Kanamycin (Alfa Aesar), and grown for 11 hours, after which we estimated the approximate colony count to ensure sufficient library representation and harvested the cells.

Plasmid DNA fractions were extracted from the harvested cells to create the 'output library' using a QIAprep® Spin Miniprep Kit (Qiagen), while total RNA=17nt was harvested by lysing the harvested cells in Direct-zol® (Zymo Research), followed by extraction using the Direct-zol RNA miniprep kit (Zymo Research).

The next generation sequencing library for the DNA depletion signal was prepared by performing a PCR on both the input and output libraries, using custom primers flanking the CRISPR array cassette of the Effector Plasmid library and containing barcodes and handles compatible with Illumina sequencing chemistry. This library was then normalized, pooled, and loaded onto a Nextseq 550 (Illumina) to evaluate the activity of the effectors.

Bacterial Screen Sequencing Analysis

Next generation sequencing data for screen input and output libraries were demultiplexed using Illumina bcl2fastq. Reads in resulting fastq files for each sample contained the CRISPR array elements for the screening plasmid library. The direct repeat sequence of the CRISPR array was used to determine the array orientation, and the spacer sequence was mapped to the source (pACYC184 or E. coli essential genes) or negative control sequence (GFP) to determine the corresponding target. For each sample, the total number of reads for each unique array element ($r_a$) in a given plasmid library was counted and normalized as follows: ($r_a$+1)/total reads for all library array elements. The depletion score was calculated by dividing normalized output reads for a given array element by normalized input reads.

To identify specific parameters resulting in enzymatic activity and bacterial cell death, we used next generation sequencing (NGS) to quantify and compare the representation of individual CRISPR arrays (i.e., repeat-spacer-repeat) in the PCR product of the input and output plasmid libraries. We defined the fold depletion for each CRISPR array as the normalized input read count divided by the normalized output read count (with 1 added to avoid division by zero). An array was considered to be "strongly depleted" if the fold depletion was greater than 3. When calculating the array fold depletion across biological replicates, we took the maximum fold depletion value for a given CRISPR array across all experiments (i.e. a strongly depleted array must be strongly depleted in all biological replicates). We generated a matrix including array fold depletion and the following features for each spacer target: target strand, transcript targeting, ORI targeting, target sequence motifs, flanking sequence motifs, and target secondary structure. We investigated the degree to which different features in this matrix explained target depletion for Type V-I systems, thereby yielding a broad survey of functional parameters within a single screen.

Results

FIGS. 5A-D depict the location of strongly depleted targets for Cas12i1 and Cas12i2 targeting pACYC184 and E. coli E. Cloni® essential genes. Notably, the location of strongly depleted targets appears dispersed throughout the potential target space.

We found that dsDNA interference activities of the Type V-I effectors, Cas12i1 (1094aa), and Cas12i2 (1054aa), are abolished by mutation of the conserved aspartate in the RuvC I motif (FIGS. 6A, and 6B). The RuvC-dependent dsDNA interference activity of Cas12i shows no requirement for non-coding sequences flanking the CRISPR array or cas genes (FIGS. 7A and 7B), indicating that the minimal V-I interference module includes only the effector and crRNA (FIGS. 8A and 8B).

Analysis of the target-flanking sequences corresponding to strongly depleted arrays from in vivo screens show that dsDNA interference by Cas12i is PAM-dependent. Specifically, we found that Cas12i1 and Cas12i2 both showed a 5' TTN PAM preference (FIGS. 9A-B and 10A-B). These results suggest that the compact Cas12i effectors are capable of autonomous PAM-dependent dsDNA interference.

Example 3: Biochemical Mechanistic Characterization of Engineered CLUST.029130 (Type V-I) CRISPR-Cas Systems (FIGS. 11A-13, 15-17B)

Cas12i Processes Pre-crRNAs in Vivo

To investigate crRNA biogenesis for Type V-I CRISPR-Cas systems, we purified and sequenced small RNAs from E. coli expressing Cas12i and the minimal CRISPR array library from the bacterial screen. FIGS. 11A and 11B show the pile-up of RNA-sequencing reads, showing a strong consensus form of the Cas12i1 and Cas12i2 mature crRNA, respectively, as well as a distribution of spacer lengths. The most common spacer length observed was 21, with length variation between 16 nt and 22 nt.

For the Type V-I CRISPR-Cas system containing Cas12i1, the mature crRNA can take the form 5'-AUUUUU-GUGCCCAUCGUUGGCAC[spacer]-3' (SEQ ID NO: 100).

For the Type V-I CRISPR-Cas system containing Cas12i2, the mature crRNA can take the form 5'-AGAAAUCCGUCUUUCAUUGACGG[spacer]-3' (SEQ ID NO: 101).

Sequencing the small RNA from the in vivo bacterial screen was performed by extracting total RNA from harvested bacteria using the Direct-zol RNA MiniPrep Plus with TRI Reagent (Zymo Research). Ribosomal RNA was removed using a Ribo-Zero rRNA Removal Kit for Bacteria, followed by cleanup using a RNA Clean and Concentrator-5 kit. The resultant ribosomal RNA depleted-total RNA was treated with T4 PNK for 3 hours without ATP to enrich for 3'-P ends, after which ATP was added and the reaction incubated for another hour to enrich for 5'-OH ends. The samples were then column purified, incubated with RNA 5' polyphosphatase (Lucigen) and column purified again prior to preparation for next-generation sequencing using the NEBNext Multiplex Small RNA Library Prep Set for Illumina (New England Biolabs). The library was paired-end sequenced on a Nextseq 550 (Illumina), and the resulting paired end alignments were analyzed using Geneious 11.0.2 (Biomatters).

Cas12i Effector Purification

Effector vectors were transformed into E. coli NiCo21 (DE3) (New England BioLabs) and expressed under a T7 promoter. Transformed cells were initially grown overnight in 3 mL Luria Broth (Sigma)+50 ug/mL kanamycin, followed by inoculation of 1 L of Terrific Broth media (Sigma)+50 ug/mL kanamycin with 1 mL of overnight culture. Cells were grown at 37° C. until an OD600 of 1-1.5, then protein expression was induced with 0.2 mM IPTG. Cultures were then grown at 20° C. for an additional 14-18 hours. Cultures were harvested and pelleted via centrifugation, then resuspended in 80 mL of lysis buffer (50 mM HEPES pH 7.6, 0.5M NaCl, 10 mM imidazole, 14 mM 2-mercaptoethanol, and 5% glycerol)+protease inhibitors (Sigma). Cells were lysed via cell disruptor (Constant System Limited), then centrifuged twice at 28,000×g for 20 minutes at 4° C. to clarify the lysate. The lysate was loaded onto a 5 mL HisTrap FF column (GE Life Sciences), then purified via FPLC (AKTA Pure, GE Life Sciences) over an imidazole gradient from 10 mM to 250 mM. Cas12i1 was purified in low salt buffer (50 mM HEPES-KOH pH 7.8, 500 mM KCl, 10 mM MgCl2, 14 mM 2-mercaptoethanol, and 5% glycerol). After purification, fractions were run on SDS-PAGE gels and fractions containing protein of the appropriate size were pooled and concentrated using 10 kD Amicon Ultra-15 Centrifugal Units. Protein concentration was determined by Qubit protein assay (Thermo Fisher).

Cas12i Processes Pre-crRNAs in Vitro

To determine whether Cas12i1 is capable of autonomous crRNA biogenesis, we incubated the effector protein purified from E. coli with a pre-crRNA expressed from a minimal CRISPR array (repeat-spacer-repeat-spacer-repeat). We observed that purified Cas12i1 processes the pre-crRNA into fragments matching the mature crRNAs identified from the in vivo small RNAseq, suggesting Cas12i1 is capable of autonomous pre-crRNA processing (FIG. 12).

Pre-crRNA processing assays for Cas12i1 were performed at 37° C. for 30 minutes in cleavage buffer at a final pre-cr-RNA concentration of 100 nM. The reaction was performed in optimized cleavage buffer (50 mM Tris-HCl pH 8.0, 50 mM NaCl, 1 mM DTT, 10 mM $MgCl_2$, 50 ug/ml BSA) for Cas12i. Reactions were quenched with the addition of 1 ug/uL of proteinase K (Ambion) and incubated at 37° C. for 15 minutes. 50 mM EDTA was added to the reactions before mixing with equal volume of 2×TBE-Urea sample buffer (Invitrogen) and denaturing at 65° C. for 3 minutes. Samples were analyzed on 15% TBE-Urea gels (Invitrogen). Gels were stained for 5 minutes with SYBR Gold nucleic acid stain (Invitrogen) and imaged on Gel Doc EZ (Biorad). Gels containing labeled pre-crRNA were first imaged on Odyssey CLx scanner (LI-COR Biosciences) prior to SYBR staining.

Cas12i1 DNA Manipulation using Strongly Depleted Arrays

To explore the mechanism of the interference activity of Cas12i1, we selected strongly depleted CRISPR array sequences from the in vivo negative selection screen and generated pre-crRNAs with the DR-spacer-DR-spacer-DR arrangement. The pre-crRNAs were designed to target Cas12i1 to 128 nt ssDNA and dsDNA substrates containing target sequences complementary to the second spacer of the pre-crRNA. We observed that Cas12i1 binary complex consisting of the effector protein and pre-crRNA cleaved 100 nM of target ssDNA to saturation at a 62.5 nM complex concentration (FIG. 13). Additional degradation of cleaved ssDNA to short fragments or single nucleotides was observed at increasing concentrations of the complex, suggestive of collateral ssDNA cleavage activated by binding of the binary complex to an ssDNA target (FIG. 13).

To explore the dsDNA interference activity of Cas12i, we targeted the Cas12i1 binary complex to target dsDNA substrates containing a 5' end label on the non-spacer-complementary strand. To assess both dsDNA cleavage and nicking activity comprehensively, the resulting dsDNA cleavage reactions were split into three fractions for different analyses. The first two fractions were quenched and analyzed by denaturing or nondenaturing gel electrophoresis conditions, respectively. The third fraction was treated with 0.1U of S1 nuclease to convert any dsDNA nicks to double-stranded breaks, quenched, and analyzed by nondenaturing gel electrophoresis.

We observed dose-dependent cleavage under denaturing conditions, suggestive of either target nicking or dsDNA cleavage (FIG. 15). Under non-denaturing conditions with no S1 nuclease treatment, we observed a dose-dependent increase in a primary product that migrated with slightly lower electrophoretic mobility than the input dsDNA, suggestive of a nicked dsDNA product (FIG. 16). When these products were incubated with S1 nuclease, the upward shifted band was converted to a smaller dsDNA product indicative of the S1-mediated conversion of nicked dsDNA to double-stranded breaks (FIG. 16). We also observed minor dsDNA cleavage products at high concentrations and incubation times, indicating that Cas12i1 is a dsDNA nuclease that cleaves the spacer complementary ("SC") and non-spacer complementary ("NSC") strands of target dsDNA with substantially different efficiencies (FIG. 17A).

The observation of nicking activity accompanying 5' labeling of the spacer complementary strand of dsDNA substrates suggests that Cas12i1 preferentially nicks the DNA strand opposing the crRNA-target DNA hybrid. To validate this bias in DNA strand cleavage by Cas12i1, we generated dsDNA substrates that were IR800 dye-labeled at either the 5' end of the spacer complementary or at the 5' end of the non-spacer complementary strand. At lower concentrations of the effector complex, we observed only cleavage of the NSC strand of the DNA duplex, whereas at higher concentrations of the effector complex, cleavage of both the NSC and the SC strand was observed (FIG. 17A-B). Comparing the SYBR stain labeling all nucleic acid products versus the strand-specific labeling using IR800 dye reveals a difference in the rate of stranded product formation versus the overall accumulation of cleavage products. These results suggest an ordered series of events leading to dsDNA interference, whereby the Cas12i1 binary complex first nicks the NSC strand and then cleaves the SC strand with a lower efficiency, resulting in dsDNA cleavage. Taken together, these findings indicate that Cas12i is an effector capable of autonomous pre-crRNA processing, ssDNA target and collateral cleavage, and dsDNA cleavage. This spectrum of catalytic activities closely parallels those of Cas12a and Cas12b except for the notable bias towards non-spacer complementary strand cleavage, resulting in preferential dsDNA nicking.

crRNA and Substrate RNA Preparation

Single stranded DNA oligo templates for crRNA and substrate RNA were ordered from IDT. Substrate RNA and pre-crRNA templates were PCR amplified to generate a double stranded in vitro transcription (IVT) template DNA using NEBNEXT Hifi 2× master mix (New England Biolabs). Double stranded DNA templates for mature cr-RNA was generated by annealing T7 primer with templates followed by extension using DNA Polymerase I, Large (Klenow) Fragment (New England Biolabs). Annealing was performed by incubating for 5 min at 95° C. followed by a −5° C./min ramp down to 4° C. In vitro transcription was performed by incubating the dsDNA templates with T7 RNA polymerase at 37° C. for 3 hours using HiScribe T7 Quick High Yield RNA kit (New England Biolabs). After incubation, IVT samples were treated with Turbo DNase® (Thermo Scientific) and then purified using RNA Clean & Concentrator kit (Zymo Research). Mature cr-RNA generated from IVT was treated with Calf Intestinal Alkaline Phosphatase (Thermo Fisher) or RNA 5'-polyphosphatase (Lucigen) for 2 hours at 37° C. to generate 5'-hydroxyl or 5'-monophosphate, respectively, followed by clean up with RNA Clean & Concentrator kit (Zymo Research). Concentrations were measured via Nanodrop 2000 (Thermo Fisher).

Pre-crRNA sequences used in biochemical characterization Cas12i are included in Table 6. Oligonucleotide templates and primers for preparation of crRNAs are included in Table 9.

Preparation of IR-800 Labeled Substrate RNA and DNA

RNA substrates from IVT were treated with Calf Intestinal Alkaline Phosphatase (Thermo Fisher) for 30 minutes at 37° C. to convert the 5'-triphosphate to 5' terminal hydroxyl group and purified using RNA Clean & Concentrator kit (Zymo Research). A thiol end group was added to the 5' terminal hydroxyl group of the DNA and RNA substrates via 5' EndTag Labeling Kit (Vector Labs), then substrates were labeled with IRDye 800CW Maleimide (LI-COR Biosciences). Substrates were purified using DNA Clean & Concentrator kit or RNA Clean & Concentrator kit (Zymo Research). Labeled dsDNA substrates were generated by labeling the non-target (non-spacer complementary) ssDNA strand, annealing with a primer, then extending with DNA Polymerase I, Large (Klenow) Fragment (New England Biolabs) for 15 minutes at 25° C. These substrates were purified with DNA Clean & Concentrator kit (Zymo Research). Concentrations were measured via Nanodrop 2000 (Thermo Fisher).

RNA and DNA substrate sequences used in the biochemical characterization of Cas12i are included in Tables 7 and 8.

nM dsDNA substrate. Reactions were first treated with RNAse cocktail with incubation at 37° C. for 15 minutes. Next, they were treated with proteinase K with incubation at 37° C. for 15 minutes. To detect dsDNA cleavage products the reactions were analyzed with 15% TBE-Urea gel as described before. To detect nicking activity of Cas12i, reactions were SPRI purified after proteinase K treatment and split into three fractions. One fraction was analyzed on a 15% TBE-Urea gel as described above. Another fraction was mixed with 5× hi-density TBE sample buffer and analyzed on a non-denaturing 4-0 TBE gel to detect nicked dsDNA products. The last fraction was incubated with 0.01U/uL of S1 Nuclease (Thermo Scientific) at 50° C. for 1 hour to convert nicks into double stranded breaks followed by mixing with 5×hi-density TBE sample buffer and analyzed on a non-denaturing 4-20% TBE gel. All gels were imaged on Odyssey CLx scanner followed by a 5 minute SYBR stain and image on Gel Doc imager.

To identify the nicked strand, dsDNA was prepared by labeling either the target strand (complementary to crRNA) or the non-target strand (non-spacer complementary, same sequence as the crRNA). The cleavage reaction was performed as described. The labeled strands were then annealed with the corresponding primers and extended with DNA Polymerase I, Large (Klenow) Fragment (New England Biolabs) for 15 minutes at 25° C. The dsDNA substrates were then purified using SPRI purification.

TABLE 6

Pre-crRNAs used for CLUST.029130 (Type V-I) in vitro

| Name | Sequence | DR | Spacer1 | Spacer2 | Target | FIG |
|---|---|---|---|---|---|---|
| Cas12i1 pre-crRNA 1 | gggAAUUUUUGUGCCC AUCGUUGGCACCCUA AUGCGGAAGUAGUGG GUAACCCGGAAUUUU UGUGCCCAUCGUUGG CACUCCGCAAGAAUU GAUUGGCUCCAAUUC UAAUUUUUGUGCCCA UCGUUGGCAC (SEQ ID NO: 400) | AAUUUUU GUGCCCAU CGUUGGC AC (SEQ ID NO: 401) | CCUAA UGCGG AAGUA GUGGG UAACC CGG (SEQ ID NO: 402) | UCCGC AAGAA UUGAU UGGCU CCAAU UCU (SEQ ID NO: 403) | Cas12i1 Target 1 | FIG. 12 |
| Cas12i1 pre-crRNA 2 | gggAAUUUUUGUGCCC AUCGUUGGCACAGGC AUCAUCAGCAUUAAC CACGCAAACAAUUUU UGUGCCCAUCGUUGG CACGCGUGCUGGAUU GCUUCGAUGGUCUGC GAAUUUUUGUGCCCA UCGUUGGCAC (SEQ ID NO: 404) | AAUUUUU GUGCCCAU CGUUGGC AC (SEQ ID NO: 405) | AGGCA UCAUC AGCAU UAACC ACGCA AAC (SEQ ID NO: 406) | GCGUG CUGGA UUGCU UCGAU GGUCU GCG (SEQ ID NO: 407) | Cas12i1 Target 2 | FIGS. 13-17B |

Target Cleavage Assays with Cas12i ssDNA: Cas12i target cleavage assays with ssDNA were performed in optimized cleavage buffer (50 mM Tris-HCl pH 8.0, 50 mM NaCl, 1 mM DTT, 10 mM MgCl2, 50 ug/ml BSA). Binary complex was formed by incubating a 1:2 molar ratio of Cas12i:pre-crRNA for 10 minutes at 37° C., followed by transfer to ice. All further complex dilutions were done on ice keeping the protein:RNA ratio fixed. The complex was added to 100 nM IR800 labeled substrates and incubated at 37° C. for 30 minutes. Reactions were treated with RNAse cocktail and proteinase K and analyzed as above.

dsDNA: dsDNA target cleavage assays were set up in the optimized cleavage buffer at 37° C. for 1 hour. Binary complex was formed as described above and added to 100

TABLE 7

Substrates used for CLUST.029130 (Type V-I) in vitro biochemistry

| Name | Sequence | Nucleic acid | FIG |
|---|---|---|---|
| Cas12i1 ssDNA1, dsDNA1 | CATGTGGACCACATTAGGCT GCAAAACTGCGCATTTACGA AAACGCGAAAGTTTGCGTGG TTAATGCTGATGATGCCTTA ACAATGCCGATTCGCGGTGC GGATGAACGTAATTTCTCGA GGCGTATT (SEQ ID NO: 408) | DNA | FIG. 12 |

TABLE 7-continued

Substrates used for CLUST.029130 (Type V-I) in vitro biochemistry

| Name | Sequence | Nucleic acid | FIG |
|---|---|---|---|
| Cas12i1 ssDNA2, dsDNA2 | CATGTGGACCACATTAGGCT TGGTTGTTGCTGCCGACGAC GGTGTGATGCCGCAGACCAT CGAAGCAATCCAGCACGCGA AAGCGGCGCAGGTACCGGTG GTGGTTGCGTAATTTCTCGA GGCGTATT (SEQ ID NO: 409) | DNA | FIGS. 13-17B |

TABLE 8

Collateral nucleic acids used for CLUST.029130 (Type V-I) in vitro Biochemistry

| Name | Sequence | Nucleic acid | Fig |
|---|---|---|---|
| Cas12i1 ssDNA6_RC | AATACGCCTCGAGAAATTACAAA GTGATGCAGGCGTTTCCAGGTGC TTTCCCTAATGCGGAAGTAGTGG GTAACCCGGTGCGTACCGATGTG TTGGCGCTGCCGTTGCAGCCTAA TGTGGTCCACATG (SEQ ID NO: 410) | DNA | FIG. 14 |

TABLE 9

IDT Template oligos and primers for crRNAs used for CLUST.029130 (Type V-I) in vitro biochemistry

| Name | Template Sequence | T7 fwd primer | Rev primer |
|---|---|---|---|
| Cas12i1 pre-crRNA 1 | GTGCCAACGATGGGC ACAAAAATTAGAATT GGAGCCAATCAATTC TTGCGGAGTGCCAAC GATGGGCACAAAAAT TAGAATTGGAGCCAA TCAATTCTTGCGGAG TGCCAACGATGGGCA CAAAAATTccctata gtgagtcgtattact cgagggatccTTATT ACATTT (SEQ ID NO: 411) | TAATACGA CTCACTAT AG (SEQ ID NO: 412) | GTGCCAACGAT GGGCACAAAAA TTAGAATTGGA GCCAATCAATTC TTGCGGA (SEQ ID NO: 413) |
| Cas12i1 pre-crRNA 2 | GTGCCAACGATGGGC ACAAAAATTCGCAGA CCATCGAAGCAATCC AGCACGCGTGCCAAC GATGGGCACAAAAAT TGTTTGCGTGGTTAA TGCTGATGATGCCTG TGCCAACGATGGGCA CAAAAATTccctata gtgagtcgtattact cgagggatccTTATT ACATTT (SEQ ID NO: 414) | TAATACGA CTCACTAT AG (SEQ ID NO: 415) | GTGCCAACGAT GGGCACAAAAA TTCGCAGACCAT CGAAGCAATCC AGCACGC (SEQ ID NO: 416) |

Example 4: In Vitro Pooled Screening for Rapid Evaluation of CRISPR-Cas Systems (FIGS. 20-25)

As described herein, in vitro pooled screening serves as an efficient and high throughput method to perform biochemical evaluation. As an overview, we begin by in vitro reconstitution of the CRISPR-Cas system (FIG. 20). In one embodiment, the effector protein is produced using an in vitro transcription and translation reagent that uses dsDNA template containing a T7-RNA polymerase promoter driving the expression of the effector protein(s), and produces proteins for the reaction. In another embodiment, the minimal CRISPR arrays and the tracrRNAs include T7 promoter sequences appended onto either the top strand or bottom strand transcription directions using PCR in order to interrogate all possible RNA orientations. As shown in FIG. 20, the Apo form contains the effector only, the Binary form contains the effector protein and T7 transcript minimal CRISPR array, and the Binary+tracrRNA form adds any T7 transcribed tracrRNA elements to the complex for incubation.

In one embodiment, the endonucleolytic activity of the CRISPR-Cas systems is the primary biochemical activity assayed. FIG. 21 shows one form of the ssDNA and dsDNA substrates, in which a target sequence is flanked on both sides by 6 degenerate bases to create a pool of possible PAM sequences that may gate ssDNA and dsDNA cleavage activity. Apart from the PAM sequence, the substrates include 5' and 3' fiducial marks designed to facilitate downstream next generation sequencing library preparation protocols that selectively enrich for the substrate ssDNA or dsDNA, as well as provide unique sequences that facilitate mapping of the cleavage products. In one embodiment, the dsDNA substrate is generated by second strand synthesis in the 5'-to-3' direction using a short DNA primer and DNA polymerase I. Similar reactions can be performed using pools of different targets in the minimal CRISPR array, as well as libraries of different ssDNA and dsDNA sequences.

The CRISPR-Cas cleavage reaction is performed by mixing and incubating the preformed Apo/Binary/Binary-tracrRNA complexes with either targeting or non-targeting substrates. While other methods such as gel electrophoresis are possible, a useful embodiment for maximum sensitivity and base-pair resolution capture of the cleavage is next generation sequencing of the ssDNA or dsDNA substrate after incubation with the effector complex. FIG. 22 is a schematic that describes the library preparation for enrichment of the ssDNA substrates. By annealing a primer to well-defined sequences within the fiducial marks, the second strand synthesis and end repair occurs to produce fragments of dsDNA that represent both cut and uncut ssDNA. Afterwards, the newly-formed dsDNA molecules are a substrate for adaptor ligation, after which a selective PCR is performed using one primer (I5/P5) complementary to the ligation adaptor and another (I7/P7) that is complementary to the 3' fiducial of the original ssDNA substrate. This ultimately produces a sequencing library that contains both the full length, as well as cleaved and degraded ssDNA products, as demonstrated in FIG. 24A. The dsDNA readout NGS library prep begins without requiring the primer annealing and second strand synthesis, so the end repair and subsequent adaptor ligation can be directly performed. FIG. 23 describes the general overview of the library preparation that, similar to the ssDNA prep, labels both the cleaved/degraded as well as uncleaved fragments. Of note, either end of the dsDNA cleavage fragment can be enriched based on the PCR primer choice. In one embodiment, illustrated in FIG. 24A, dsDNA manipulation next generation sequencing libraries for readout can be prepared with a first primer complementary to a handle ligated to the 5' end of the full length or cleaved substrate (and containing I5/P5 sequences) and a second primer complementary to the 3' fiducial sequence of the substrate (and containing I7/P7 sequences). In one embodiment, illustrated in FIG. 24B, DNA manipulation next generation sequencing libraries for readout can be prepared with a first primer complementary to the 5' fiducial sequence of the substrate (and containing I5/P5 sequences) and a second primer complementary to a handle ligated to the 3' end of the full length or cleaved substrate (and containing I7/P7 sequences). Target length and substrate length can be extracted from resulting NGS reads from RNA/ssDNA/dsDNA manipulation experiments as depicted in FIGS. 25A-B, respectively. Target length and substrate lengths extracted can be used to investigate the presence of RNA/ssDNA/dsDNA nicking or cleavage.

Example 5: Characterization of dsDNA Cleavage Activity for the Type V-I1 CRISPR-Cas System (FIGS. 26-32)

Having computationally identified the minimal components of Type V-I CRISPR-Cas systems, we investigated double stranded DNA (dsDNA) cleavage activity from the Type V-I1 system containing effector Cas12i1.

IVTT-expressed Cas12i1 in complex with a top-strand expressed crRNA targeting dsDNA resulted in a population of truncated target lengths not present in the apo (effector-only) controls as shown in FIG. 26A-B. Libraries prepared using a 5' ligation adapter and selecting for the 3' fiducial (as depicted in FIG. 24A) showed a cleavage product not present in the Apo control at the +24 position within the target sequence. This result indicates either nicking of the non-target dsDNA strand or both strands of the dsDNA between the +24 and +25 nucleotides relative to the PAM. Target length analysis shows a peak at +24 indicating truncation of the target between nucleotides +24 and +25 (FIG. 27A). This population of truncated target sequences coincides with substrate lengths indicating cleavage of the non-target dsDNA strand between between nucleotides +24 and +25 of the target sequence (FIG. 28A).

Libraries prepared using a 3' ligation adapter and selecting for the 5' fiducial (as depicted in FIG. 24B) showed a cleavage product not present in the Apo control at the −9 position. (+19 given a 28nt target) within the target sequence. This result indicates either nicking of the target dsDNA strand or both strands of the dsDNA between the +19 and +20 nucleotides relative to the PAM. Target length analysis shows a peak at −9 nucleotides from the PAM (28nt full length target) indicating truncation of the target between nucleotides +19 and +20 (FIG. 27B). This population of truncated target sequences coincides with substrate lengths indicating cleavage of the target dsDNA strand between nucleotides +19 and +20 of the target sequence (FIG. 28B).

Sequence motif analysis for substrates showing non-target strand cleavage between the +24/+25 nucleotides relative to the PAM revealed a 5' TTN PAM motif to the left of the target sequence for Cas 12i1 (FIG. 29). No PAM sequence requirement was observed on the right side of the Cas12i1 target. Taken together, in vitro screening of Cas12i1 indicates predominant nicking between the +24/+25 nucleotides of the non-target strand relative to a TTN PAM with a significant fraction of these products converted to double strand breaks with a 5nt 3' overhang by cleavage of the target strand between the +19/+20 nucleotides relative to the PAM (FIG. 30).

Targeting of Cas12i1 in complex with a top-strand expressed non-target crRNA resulted in no manipulation of dsDNA relative, indicating that Cas12i1 cleavage specificity is conferred by the crRNA spacer (FIG. 31A-B). Cas12i1 showed no cleavage cleavage activity in the presence of a bottom strand-expressed crRNA targeting the dsDNA substrate indicating that the top-strand oriented crRNA is required for formation of the active Cas12i1 complex (FIG. 32A-B).

Example 6: Characterization of dsDNA Cleavage Activity for the Type V-I2 CRISPR-Cas System (FIGS. 33-39)

Having computationally identified the minimal components of Type V-I CRISPR-Cas systems, we investigated double stranded DNA (dsDNA) cleavage activity from the Type V-I2 system containing effector Cas12i2.

IVTT-expressed Cas12i2 in complex with a top-strand expressed crRNA targeting dsDNA resulted in a population of truncated target lengths not present in the apo (effector-only) controls as shown in FIG. 33A-B. Libraries prepared using a 5' ligation adapter and selecting for the 3' fiducial (as depicted in FIG. 24A) showed a cleavage product not present in the Apo control at the +24 position within the target sequence. This result indicates either nicking of the non-target dsDNA strand or both strands of the dsDNA between the +24 and +25 nucleotides relative to the PAM. Target length analysis shows a peak at +24 indicating truncation of the target between nucleotides +24 and +25 (FIG. 34A). This population of truncated target sequences coincides with substrate lengths indicating cleavage of the non-target dsDNA strand between nucleotides +24 and +25 of the target sequence (FIG. 35A).

Libraries prepared using a 3' ligation adapter and selecting for the 5' fiducial (as depicted in FIG. 33B) showed a cleavage product not present in the Apo control at the −7 position (+24 given 31nt target) within the target sequence. This result indicates either nicking of the target dsDNA strand or both strands of the dsDNA between the +24 and +25 nucleotides relative to the PAM. Target length analysis shows a peak at −7 nucleotides from the PAM (28nt full length target) indicating truncation of the target between nucleotides +24 and +25 (FIG. 34B). This population of truncated target sequences coincides with substrate lengths indicating cleavage of the target dsDNA strand between nucleotides +24 and +25 of the target sequence (FIG. 35B).

Sequence motif analysis for substrates showing non-target strand cleavage between the +24/+25 nucleotides relative to the PAM revealed a 5' TTN PAM motif to the left of the target sequence for Cas12i2 (FIG. 36). No PAM sequence requirement was observed on the right side of the Cas12i2 target. Taken together, in vitro screening of Cas12i2 indicates predominant nicking between the +24/+25 nucleotides of the non-target strand relative to a TTN PAM with a significant fraction of these products converted to double strand breaks with a blunt cut by cleavage of the target strand between the +24/+25 nucleotides relative to the PAM (FIG. 37).

Targeting of Cas12i2 in complex with a top-strand expressed non-target crRNA resulted in no manipulation of dsDNA relative, indicating that Cas12i2 cleavage specificity is conferred by the crRNA spacer (FIG. 38A-B). Cas12i2 showed no cleavage cleavage activity in the presence of a bottom strand-expressed crRNA targeting the dsDNA substrate indicating that the top-strand oriented crRNA is required for formation of the active Cas12i2 complex (FIG. 39A-B).

Example 7: CLUST.029130 (Type V-I) CRISPR Cas Systems can be Used for Gene Silencing In Vitro An in vitro gene-silencing assay (FIGS. 18A and 18B) was developed to mimic in vivo gene silencing activity for rapid validation of the activity of a novel CRISPR-Cas system. This assay can simultaneously evaluate in an unbiased manner different activity mechanisms and functional parameters outside the natural cellular environment.

First, a reconstituted IVTT (in vitro transcription and translation) system was supplemented with E. coli RNA polymerase core enzyme to allow gene expression (protein synthesis) to occur from not only T7 promoter but also any E. coli promoter, as long as the corresponding E. coli sigma factor is present.

Second, to facilitate rapid and high throughput experimentation, linear DNA templates generated from PCR reactions were directly used. These linear DNA templates included those encoding the Type V-I effector, a RNA guide, and E. coli sigma factor 28. Incubation of these DNA templates with the reconstituted IVTT reagent results in co-expression of the Type V-I effector and a RNA guide, and the formation of the RNP (ribonucleoprotein complex). E. coli sigma factor 28 was also expressed for subsequent expression of GFP and REP as described below.

Third, as the target substrate, a linear or plasmid DNA encoding GFP expressed from the sigma factor 28 promoter was included in the above incubation reaction such that the newly synthesized RNP has the immediate access to the target substrate. As an internal control, a non-target linear DNA encoding RFP expressed from the sigma factor 28 promoter was also included. The RNA polymerase core enzyme alone does not recognize the sigma factor 28 promoter until sufficient sigma factor 28 protein is synthesized. This delay in the GFP and RFP expression allows the newly synthesized RNP to interfere with the GFP target substrate, which could result in a decrease in the GFP expression and a depletion of the GFP fluorescence. The RFP expression, on the other hand, was not negatively affected, which serves as the internal control for protein synthesis and fluorescence measurement.

Certain important advantages of the in vitro gene-silencing assay described herein include:
(1) Modularity—The reconstituted IVTT is a synthetic system consisting of individually purified components, which allows the assay to be custom designed fora variety of controls and activities. Each component of the CRISPR-Cas system is encoded in a separate linear DNA template, allowing rapid assays of a combination of different effectors, effector variants, and RNA guides;
(2) Complexity—The assay contains all essential components for RNA transcription and protein synthesis, allowing diverse mechanisms of interference to be tested in a single one-pot reaction, such as DNA and RINA cleavage, and transcription-dependent interference. The kinetic fluorescence readouts of the assay provide significantly more data points than endpoint activity assays;
(3) Sensitivity—The assay couples effector and RNA guide synthesis with substrate interference, allowing newly synthesized RNPs (ribonucleoprotein complexes of effector protein and RNA guide) to immediately interact with the substrate in the same reaction, There are no separate purification steps, thus potentially allowing small amounts of RNPs to be sufficient to generate signal. Furthermore, the interference of the GFP expression is amplified due to the coupled transcription and translation of GFP that can generate >100 GFP protein per DNA template.
(4) Efficiency—The assay is designed to be highly compatible to high throughput platforms. Due to its modularity, all components of the assay can be added in 96-, 384- and 1536-well formats by commonly available liquid handling instruments, and fluorescence can be measured by commonly available plate fluorometers.
(5) Relevance—The assay tests the ability of a CRISPR-Cas effector protein to interfere with the gene expression during transcription and translation in an in vitro engineered system outside of its natural cellular environment. It may be possible that a highly active CRISPR-Cas effector measured by this gene-silencing assay is also highly efficient for gene editing in mammalian cells.

This assay has been used to measure the gene-silencing effect of a Cas12i effector complex as illustrated here when targeting GFP encoded in plasmid DNA. Multiple Type V-I RNA guides are designed—one with a spacer sequence complementary to the template strand of the GFP sequence, and another with a spacer sequence complementary to the coding strand of the GFP sequence. The degree of gene-silencing by the Cas12i1 effector protein was then compared with that of the mutants Cas12i1 D647A, Cas12i1 E894A, and Cas12i1 D948A.

FIG. 19A depicts the fold-depletion of each of the four tested Cas12i effectors when complexed with an RNA guide complementary to the template strand. In this case, the non-target strand, preferentially being nicked, is the coding strand. While Cas12i1 shows approximately 2-fold depletion of GFP expression after 400 minutes, each of the three mutant forms shows smaller degrees of depletion.

FIG. 19B depicts the fold-depletion of each of the four tested Cas12i1 effectors when complexed with an RNA guide complementary to the coding strand. In this case, the non-target strand, preferentially being nicked, is the template strand. The ability for RNA polymerase to produce a functional RNA transcript appears to be significantly impaired by Cas12i1 in this configuration, with greater than 4-fold depletion in the case of Cas12i. The gene-silencing ability of the three mutant forms appears significantly diminished.

Taken together, the data shown in FIG. 19A and FIG. 19B indicate that the assay is effective in detecting the gene silencing activity of Cas12i1 when using RNA guides targeting both the coding and template strands. The significant higher depletion when targeting the coding strand than targeting the template strand suggests Cas12i1 interferes with the GFP expression by preferentially nicking the non-target strand. All three Cas12i1 mutants substitute the postulated catalytic residues (aspartic acid (D) and glutamic acid (E)) with alanine (A). The diminishing silencing activities of these Cas12i1 mutants further support that DNA stand cleavage, rather than just binding, underlies the mechanism of the gene silencing by Cas12i1

Example 8: CLUST.029130 (Type V-I) CRISPR-Cas Systems can be Used with a Fluorescent Reporter for the Specific Detection of Nucleic Acid Species The nuclease activities of Cas12i proteins (i.e., non-specific collateral DNase activities activated by a target ssDNA substrate complementary to the crRNA spacer) make these effectors promising candidates for use in the detection of nucleic acid species. Some of these methods have been previously described (see, e.g., East-Seletsky et al. "Two distinct RNase activities of CRISPR-C2c2 enable guide-RNA processing and RNA detection," *Nature*. 2016 Oct. 13; 538(7624):270-273), Gootenberg et al. (2017), Chen et al. 2018, and Gootenberg et al. (2018) "Multiplexed and portable nucleic acid detection platform with Cas13, Cas12a, and Csm6" *Science* 15 Feb. 2018: eaaq0179), describing the general principle of RNA detection using Cas13a (East-Seletsky et al. (2016)), supplemented by amplification to increase the detection sensitivity and optimization of additional Cas13a enzymes (Gootenberg et al. (2017)), and most recently, the inclusion of additional RNA targets, orthologous and paralogous enzymes, and Csm6 activator to enable multiplexed detection of nucleic acids along with an increase in detection sensitivity (Gootenberg et al. (2018)). The addition of Cas12i to this toolkit provides an additional channel of orthogonal activity for nucleic acid detection.

The in vitro biochemical activity of Cas12i1 suggests that it may have promise in applications for sensitive nucleic acid detection, given that a dye-labeled, collateral DNA was efficiently cleaved at low target ssDNA concentrations and background nuclease activity was limited with a non-targeting substrate (FIG. 14). Adapting Cas12i1 towards sensitive nucleic acid detection application requires several steps, including, but not limited to, optimizing the substrate for sensitive readout of the collateral activity and identifying per-base mismatch tolerance between the spacer and the target substrate.

Identification of the optimal substrate for nucleic acid detection can be informed by performing next generation sequencing (NGS) on the cleavage products of Cas12i collateral activity on both DNA substrates. The enzyme concentration may have to be titrated or incubation time adjusted in order to yield cleavage fragments that are still of a sufficient size to be prepared into a next generation sequencing library. The NGS data reveal the enzyme cleavage sites and the adjacent base preferences. It has been demonstrated that the individual effectors within the Cas13a and b families have different dinucleotide base preferences for RNA cleavage, yielding markedly different cleavage magnitudes and signal to noise ratios (Gootenberg et al. (2018)). The collateral NGS data thus enable better insight into the preferences for Cas12i. A separate experimental approach to identifying the dinucleotide preference of Cas12i collateral cleavage is to create a collateral DNA substrate with degenerate N's in consecutive positions so as to have a broader sequence space than a defined sequence. The library prep and analysis of the NGS data would proceed similarly to identify base preferences for cleavage. To verify the preference, collateral substrates containing synthesized short DNAs with a fluorophore/quencher pair on the 5' and 3' ends can be introduced into a cleavage reaction to assess the signal to noise ratio. Further optimization can be done on the length of the collateral DNA substrate to determine whether Cas12i1 has a length preference.

Having identified the preferred substrate, another important parameter to determine is the mismatch tolerance of the Cas12i system, as it has implications for guide design that affects the ability of the enzyme to distinguish single base pair mismatches. The mismatch tolerance can be determined by designing a panel of targets bearing different positions and types of mismatches (for example, insertion/deletions, single base pair mismatches, adjacent double mismatches, separated double mismatches, triple mismatches, and more).

Mismatch tolerance can be measured by assessing the amount of cleavage of collateral DNA for targets containing varying amounts of mismatches. As an example, the collateral DNA substrate could be a short ssDNA probe containing a fluorophore and quencher on opposite sides. For reactions containing the Cas12i effector, an RNA guide, and a target substrate containing different numbers of mismatches, insertions and deletions in the target sequence, successful activation of the Cas12i system by targeting of altered target DNA sequence will result in collateral cleavage of the fluorescent probe. Hence resulting fluorescent measurements denoting cleaved collateral substrate can be background subtracted using negative control samples and normalized to the signal from perfectly matching targets to estimate the impact of target alterations on the efficiency of collateral cleavage by Cas12i. Resulting maps of mismatch, insertion, and deletion tolerance by the Cas12i enzyme over the target length relative to the PAM can be used to design optimal RNA guides to distinguish between different DNA sequences or genotypes for specific detection or distinction between different Nucleic Acid Species. Using the fluorometric cleavage readout and the preferred collateral substrate, the fluorescence activity would be compared against the fully matched sequence to determine the position and types of mismatch to which the enzyme is most sensitive.

The optimization process can be furthermore applied to other Cas12i orthologs to yield other systems that may have different properties. For example, orthogonal dinucleotide preferences of collateral cleavage would be helpful in generating separate channels of detection.

Example 9. CLUST.029130 (Type V-I) CRISPR Cas Systems can be Used for Paired Nicking to Enable Highly Specific dsDNA Manipulation The CLUST.029130 effector Cas12i is capable of manipulating dsDNA via nicking of the non-target strand (FIGS. 15, 16, 17A-B). Catalytically inactivated Cas12i can also be fused with a FokI nuclease domain to create a fusion protein capable of binding and nicking dsDNA. Some of these methods have been previously described. Ran et al. (2013) "Double Nicking by RNA-Guided CRISPR Cas9 for Enhanced Genome Editing Specificity" Science 29 Aug. 2013 describes the general principle and optimization of double nicking using Cas9; Guilinger et al. (2014) "Fusion of catalytically inactive Cas9 to FokI nuclease improves the specificity of genome modification" Science 25 Apr. 2014 described the principle of double nicking using a FokI-dCas9 fusion.

The use of paired Cas12i nickases enables highly specific dsDNA manipulation as follows. A first Cas12i complex with a crRNA targeting one strand of a dsDNA target region and second Cas12i-crRNA complex targeting the opposing strand of the dsDNA are introduced together to enable a dsDNA cleavage reaction. By targeting the Cas12i complexes to different dsDNA strands, the first and second Cas12i complexes cleave opposing dsDNA strands resulting in a double strand break.

To optimize the efficiency of dsDNA double strand break formation by double nicking, pairs of crRNA spacer sequences are chosen with different lengths separating their expected nuclease cleavage sites. Cleavage of the top and bottom strand of dsDNA by Cas12i paired nickases with different target displacements produces different length sequence overhangs, resulting in different efficiencies of double strand break formation. Paired nickase targets can be selected with specific orientations to generate either 3' or 5' overhangs, or a blunt (overhang length of 0) double strand breaks.

For nicking applications with the Cas12i1 and Cas12i2-WT enzymes containing 5' TTN PAMs, orientation of the paired nickase targets with PAMs 'out' (PAMs at the outside of the paired targets) results in a 5' overhang, whereas pairing of nickase targets with PAMs at the inside of the target pair results in a 3' overhang. In some instances 3' and 5' overhangs range from 1-200 nt. In some instances, 3' and 5' overhangs are between 20 and 100 nt.

Autonomous pre-crRNA processing facilitates Cas12i delivery for double nicking applications (FIG. 12), as two separate genomic loci can be targeted from a single crRNA transcript. Therein, Cas12i and a CRISPR array containing two spacer sequences targeting the Cas12i to nick opposing strands of dsDNA can be expressed from a single viral vector or plasmid. Cas12i and the CRISPR array can also be delivered on separate plasmids or viral vectors. The Cas12i protein then processes the CRISPR array into two cognate crRNAs that result in the formation of paired nicking complexes. Viral vectors can include phage or adeno-associated virus for delivery to bacteria or mammalian cells, respectively.

Apart from viral or plasmid delivery methods, paired nicking complexes can be delivered directly using nanoparticle or other direct protein delivery methods, such that complexes containing both paired crRNA elements are co-delivered. Furthermore, protein can be delivered to cells by viral vector or directly, followed by the direct delivery of a CRISPR array containing two paired spacers for double nicking. In some instances, for direct RNA delivery the RNA may be conjugated to at least one sugar moiety, such as N-acetyl galactosamine (GalNAc) (particularly, triantennary GalNAc).

Example 10: Adaptation of CLUST.029130 (Type V-I) CRISPR Cas System Effectors for Eukaryotic and Mammalian Activity To develop CLUST.029130 (Type V-I) CRISPR Cas systems for eukaryotic applications, the constructs encoding the protein effectors were first codon-optimized for expression in mammalian cells, and specific localization tags were optionally appended to either or both the N-terminus or C-terminus of the effector protein. These localization tags can include sequences such as nuclear localization signal (NLS) sequences, which localize the effector to the nucleus for modification of genomic DNA. These sequences are described above in the "Functional Mutations" section. Some examples of non-naturally occurring, engineered nucleotide sequences to encode mammalian codon-optimized Cas12i effectors with a localization tag are provided in TABLE 10. Other accessory proteins, such as fluorescent proteins, may be further appended. It has been demonstrated that the addition of robust, "superfolding" proteins such as superfolding green fluorescent protein (GFP) can increase the activity of CRISPR enzymes in mammalian cells when appended to the effector (Abudayyeh et al. (2017) *Nature* 550(7675): 280-4, and Cox et al. (2017) *Science* 358(6366): 1019-27).

The codon-optimized sequence coding for the Cas12i and appended accessory proteins and localization signals was then cloned into a eukaryotic expression vector with the appropriate 5' Kozak eukaryotic translation initiation sequence, eukaryotic promoters, and polyadenylation signals. In mammalian expression vectors, these promoters can include, e.g., general promoters such as CMV, EF1a, EFS, CAG, SV40, and cell-type specific RNA polymerase II promoters such as Syn and CamKIIa for neuronal expression, and thyroxine binding globulin (TBG) for hepatocyte expression to name a few. Similarly, useful polyadenylation signals include, but are not limited to, SV40, hGH, and BGH. Additional transcript stabilization or transcript nuclear export elements such as WPRE can be used for increasing the expression of such constructs. For expression of the pre-crRNA or mature crRNA, RNA polymerase III promoters such as H1 or U6 can be used.

Depending on the application and mode of packaging, the eukaryotic expression vector can be a lentiviral plasmid backbone, adeno-associated viral (AAV) plasmid backbone, or similar plasmid backbone capable of use in recombinant viral vector production. Notably, the small size of CLUST.029130 (Type V-I) CRISPR Cas effector proteins, e.g., Cas12i proteins, make them ideally suited for packaging along with its crRNA and appropriate control sequences into a single adeno-associated virus particle; the packaging size limit of 4.7 kb for AAV may preclude the use of larger effectors, particularly if large cell-type specific promoters are used for expression control.

After adapting the sequences, delivery vectors, and methods for eukaryotic and mammalian use, different Cas12i constructs as described herein were characterized for performance. An initial characterization was performed by lipofection of DNA constructs expressing the minimal components of the Cas12i system with the adaptations for eukaryotic use as described above. In one embodiment, the Cas12i effector is mammalian codon optimized and a nucleoplasmin nuclear localization sequence (npNLS) is appended to the C-terminus of the protein. The expression of the effector is driven by the elongation factor 1alpha short (EFS) promoter, and terminated using a bGH poly(A) signal (TABLE 10). A double-stranded, linear PCR product containing a U6 promoter was used to express the cognate RNA guides for the Cas12i system, as adapted from (Ran et al. "Genome engineering using the CRISPR-Cas9 system," *Nat Protoc.* 2013 November; 8(11):2281-2308.). This approach is well suited to testing a larger number of sgRNAs over plasmid cloning and sequence verification. (FIG. 40) The effector plasmid and U6-guide PCR fragment were co-transfected into 293T cells at an approximately 1:2 molar ratio of plasmid to PCR product with 400 ng of effector plasmid and 30 ng of U6-guide PCR product for a 24 well plate format. The resulting gene editing event was evaluated using next generation sequencing of a targeted PCR amplicon surrounding the target site (Hsu et al., "DNA targeting specificity of RNA-guided Cas9 nucleases," *Nat Biotechnol.* 2013 September; 31(9):827-32.).

Initial evaluation of Cas12i2 yielded indel activity of 13% at the VEGFA locus at a target site with a TTC PAM. We tested different RNA guide designs as described in FIG. 41, with the strongest indel efficiency achieved using pre-crRNA, and with indel rates decreasing with shorter spacer lengths. Examining the indels created by Cas12i2 reveals that the predominant location of the indels are centered around +20 relative to the PAM sequence.

Multiplexing of Type V-I effectors is accomplished using the pre-crRNA processing capability of the effectors, where multiple targets with different sequences can be programmed on a single RNA guide. As such, multiple genes or DNA targets can be manipulated simultaneously for therapeutic applications. One embodiment of a RNA guide design is a pre-crRNA expressed from a CRISPR array consisting of target sequences interleaved by unprocessed DR sequences, repeated to enable targeting of one, two, or more loci simultaneously by the intrinsic pre-crRNA processing of the effector.

In addition to testing various construct configurations and accessory sequences on individual targets, pooled library-based approaches are used to determine 1) any targeting dependency of specific Cas12i proteins in mammalian cells as well as 2) the effect of mismatch locations and combinations along the length of the targeting crRNA. Briefly, the pooled library includes a plasmid that expresses a target DNA containing different flanking sequences as well as mismatches to the guide or guides used in the screening experiment, such that the successful target recognition and cleavage results in depletion of the sequence from the library. Furthermore, targeted indel sequencing or unbiased genome-wide cleavage assays can be used to evaluate the specificity of the CLUST.029130 (Type V-I) CRISPR-Cas system (Hsu et al. (2013), Tsai et al. "GUIDE-seq enables genome-wide profiling of off-target cleavage by CRISPR-Cas nucleases." *Nat Biotechnol.* 2015 February; 33(2):187-197, Kim et al. "Digenome-seq: genome-wide profiling of CRISPR-Cas9 off-target effects in human cells," *Nat Methods.* 2015 March; 12(3):237-43, Tsai et al., "CIRCLE-seq: a highly sensitive in vitro screen for genome-wide CRISPR-Cas9 nuclease off-targets," *Nat Methods.* 2017 June; 14(6): 607-614).

Mutations are additionally created to extend the functional range of Cas12i proteins. In some embodiment, catalytically-inactive Cas12i proteins can be made in which the conserved residues of the RuvC domain are mutated to alanine (such as the D647A mutation for Cas12i1 and D599A mutation for Cas12i2). Catalytically inactive Cas12i versions (referred to as dCas12i) retains its programmable DNA binding activity, though it will no longer be able to cleave target or collateral ssDNA or dsDNA. Direct uses of dCas12i include immunoprecipitation and transcriptional repression. Further functionality is provided by appending other domains onto the dCas12i protein Activities of these domains include, but are not limited to, DNA base modification (ex: ecTAD and its evolved forms, APOBEC), DNA methylation ($m^6A$ methyltransferases and demethylases), localization factors (KDEL retention sequence, mitochondrial targeting signal), transcription modification factors (ex: KRAB, VP64). Additionally, domains can be appended to provide additional control, such as light-gated control (cryptochromes) and chemically inducible components (FKBP-FRB chemically inducible dimerization).

Optimizing the activity of such fusion proteins requires a systematic way of comparing linkers that connect the dCas12i with the appended domain. These linkers may include, but are not limited to, flexible glycine-serine (GS) linkers in various combinations and lengths, rigid linkers such as the alpha-helix forming EAAAK sequence, XTEN linker (Schellenberger V, et al. *Nat. Biotechnol.* 2009; 27:1186-1190), as well as different combinations thereof (see TABLE 11). The various designs are then assayed in parallel over the same crRNA target complex and functional readout to determine which one yields the desired properties.

For adapting Cas12i for use in targeted DNA base modification (see, e.g., Gaudelli et al. (2017) "Programmable base editing of A·T to G·C in genomic DNA without DNA cleavage" Science 25 Oct. 2017), we begin with the Cas12i ortholog and NLS combination that yielded the highest endogenous mammalian DNA cleavage activity and mutate the conserved residues of the RuvC domain to create a catalytically inactive enzyme (dCas12i). Next, a linker is used to create the fusion protein between dCas12i-NLS and the base editing domain. Initially, this domain will consist of the ecTadA(wt)/ecTadA*(7.10)heterodimer (hereafter referred to as the dCas12i-TadA heterodimer) engineered previously for hyperactivity and modification of dsDNA A·T dinucleotides to G·C (TABLE 11). Given the likely structural differences between the smaller Cas12i versus the previously characterized Cas9 effectors, alternate linker designs and lengths may yield the optimal design of the base editing fusion protein.

To evaluate the activity of the dCas12i-derived base editors, the HEK 293T cells are transiently transfected with the dCas12i-TadA heterodimer construct, a plasmid expressing the crRNA, and optionally, a reporter plasmid if targeting the reporter and not an endogenous locus. The cells are harvested 48 hours after transient transfection, the DNA is extracted and prepared for next generation sequencing. Analysis of the base composition of loci of samples containing the targeting vs. negative control non-targeting crRNAs provide information about the editing efficiency, and analysis of broader changes to the transcriptome will yield information about the off-target activity.

One particular advantage of developing a DNA base editing system using Cas12i is that the small size, smaller than the existing Cas9 and Cas12a effectors, enables more ready packaging in AAV of dCas12i-TadA heterodimer along with its crRNA and control elements without the need for protein truncations. This all-in-one AAV vector enables greater efficacy of in vivo base editing in tissues, which is particularly relevant as a path towards therapeutic applications of Cas12i.

In additional to editing using Cas12i and an RNA guide, additional template DNA sequences can be co-delivered either in a vector, such as an AAV viral vector, or as linear single stranded or double stranded DNA fragments. For insertion of template DNA by homology directed repair (HDR), template sequences are designed containing a payload sequence to be inserted into the locus of interest as well as flanking sequences that are homologous to endogenous sequences flanking the desired insertion site. In some instances, for insertion of short DNA payloads less than (for example: less than 1 kb in length), flanking homologous sequences can be short (for example: ranging from 15 to 200nt in length). In other instances, for the insertion of long DNA payloads (for example: 1 kb or greater in length), long homologous flanking sequences are required to facilitate efficient HDR (for example: greater than 200nt in length). Cleavage of target genomic loci for HDR between sequences homologous to template DNA flanking regions can significantly increase the frequency of HDR. Cas12i cleavage events facilitating HDR include, but are not limited to dsDNA cleavage, double nicking, and single strand nicking activity.

DsDNA fragments may contain overhang sequences complementary to the overhangs resulting from double nicking using Cas12i. Pairing of the insert and double-nicking overhangs and subsequent ligation by endogenous DNA repair machinery result in the seamless insertion of the template DNA at the site of double-nicking.

TABLE 10

Sequences enabling mammalian expression of Cas12i effectors with included N-terminal mH6 tag and C-terminal nucleoplasmin NLS sequence (bolded)

>EF1alpha short (EFS) promoter
GGGCAGAGCGCACATCGCCCACAGTCCCCGAGAAGTTGGG
GGGAGGGGTCGGCAATTGATCCGGTGCCTAGAGAAGGTGG
CGCGGGGTAAACTGGGAAAGTGATGTCGTGTACTGGCTCC
GCCTTTTTCCCGAGGGTGGGGGAGAACCGTATATAAGTGC
AGTAGTCGCCGTGAACGTTCTTTTTCGCAACGGGTTTGCC
GCCAGAACACAG
(SEQ ID NO: 500)

>Cas12i1_mammalian_effector
atg**AAAATCGAAGAAGGTAAAGGTCACCATCACCATCACC
A**CATGTCTAACAAGGAGAAGAATGCCAGCAGACCCGGAA
GGCCTACACCACAAAGATGATCCCCAGGAGCCACGACCGC
ATGAAGCTGCTGGGCAACTTTATGGACTATCTGATGGATG
GCACCCCTATCTTCTTTGAGCTGTGGAATCAGTTCGGCGG
CGGCATCGACAGAGATATCATCAGCGGCACAGCCAACAAG
GATAAGATCTCCGACGATCTGCTGCTGGCCGTGAACTGGT
TTAAAGTGATGCCAATCAATTCTAAGCCCCAGGGCGTGTC
CCCTTCTAACCTGGCCAATCTGTTCCAGCAGTACAGCGGA
TCCGAGCCTGACATCCAGGCACAGGAGTATTTCGCCTCCA
ACTTTGACACCGAGAAGCACCAGTGGAAGGATATGCGGGT
GGAGTACGAGAGACTGCTGGCCGAGCTGCAGCTGTCTAGG
AGCGACATGCATCACGATCTGAAGCTGATGTACAAGGAGA
AGTGCATCGGCCTGTCCCTGTCTACCGCCACTATATCAC
AAGCGTGATGTTTGGCACCGGCGCCAAGAACAATCGCCAG
ACAAAGCACCAGTTCTATTCCAAAGTGATCCAGCTGCTGG
AGGAGAGCACCCAGATCAATTCCGTGGAGCAGCTGGCCTC
CATCATCCTGAAGGCCGGCGACTGCGATTCTTACAGGAAG
CTGAGGATCAGGTGTTCCGCAAGGGAGCAACCCCATCTA
TCCTGAAGATCGTGCAGGACTATGAGCTGGGCACAAACCA
CGACGATGAAGTGAATGTGCCCTCCCTGATCGCCAACCTG
AAGGAGAAGCTGGGCAGGTTTGAGTACGAGTGCGAGTGGA
AGTGTATGGAAGATCAAGGCCTTCCTGGCCTCTAAAGT
GGGCCCTTACTATCTGGGCAGCTATTCCGCCATGCTGGAG
AATGCCCTGAGCCCAATCAAGGGCATGACCACAAAGAACT
GTAAGTTCGTGCTGAAGCAGATCGACGCCAAGAACGATAT
CAAGTACGAGAATGAGCCCTTTGGCAAGATCGTGGAGGGC
TTCTTTGACTCTCCTTATTCTGAGAGCGATACCAATGTGA
AGTGGGTGCTGCACCCTCACCACATCGGCGAGTCTAACAT
CAAGACACTGTGGGAGGACCTGAATGCCATCCACAGCAAG
TACGAGGAGGACATCGCCTCTCTGAGCCAGGAGATCATCC
AGAAGCGGATCAAGGTGTACCAGGGCGATGTGTGCCAGAC
CATCAACACATATTGTGAGGAAGTGGGCAAGGAGGCCAAG
ACCCCACTGGTGCAGCTGCTGAGGTACCTGTATTCCCGCA
AGGACGATATCGCCGTGGACAAGATCATCGATGCATCAC
ATTCCTGTCTAAGAAGCACAAGGTGGAAGCAGAAGATC
AACCCAGTGATCCAGAAGTACCCCAGCTTCAATTTTGGCA
ACAATTCCAAGCTGCTGGGCAAGATCATCAGCCCAAAGGA
CAAGCTGAAGCACAACCTGAAGTGCAACAGAAATCAGGTG
GATAATTACATCTGGATCGAGATCAAGGTGCTGAACACCA
AGACAATGCGGTGGGAGAAGCACCACTATGCCCTGAGCTC
CACCAGATTTCTGGAGGAGGTGTACTATCCCGCCACATCC
GAGAATCCAACCTGACGCACTGGCAGCACGGTTCAGAACCA
AGACAAACGGCTACGAGGGCAAGCCAGCCCTGTCTGCCGA
GCAGATCGAGCAGATCAGGAGCGCACCAGTGGGACTGAGA
AAGGTGAAGAAGCGGCAGATGAGACTGGAGGCAGCAAGGC
AGCAGAATCTGCTGCCACGCTATACCTGGGGCAAGGATTT
TAACATCAATATCTGTAAGAGGGGCAACAATTTCGAGGTG
ACCCTGGCCACAAAGGTGAAGAAGAAGAAGGAGAAGAACT
ACAAGGTGGTGCTGGGCTATGACGCCAACATCGTGCGCAA
GAATACCTACGCAGCAATCGAGGCACACGCAAACGGCGAT
GGCGTGATCGACTATAATGATCTGCCTGTGAAGCCAATCA
AGTCTGGCTTTGTGACAGTGGAGAGCAGGTGAGGGACAA
GTCCTACGATCAGCTGTCTTATAACGGCGTGAAGCTGCTG
TACTGCAAGCCTCACGTGGAGAGCCGGAGATCCTTCCTGG
AGAAGTATCGGAACGGCACCATGAAGGACAATAGAGGCAA
CAATATCCAGATCGACTTCATGAAGGATTTTGAGGCCATC
GCCGACGATGAGACAAGCCTGTACTACTTCAACATGAAGT
ACTGTAAGCTGCTGCAGTCTAGCATCCGCAACCACTCCTC
TCAGGCCAAGGAGTATAGGGAGAAGGATCTTCGAGCTGTC
CGCGATGGCAAGCTGTCCGTGCTGAAGCTGAGCTCCCTGT
CTAATCTGAGCTTCGTGATGTTTAAGGTGGCCAAGTCTCT
GATCGGCACCTACTTTGGCCACCTGCTGAAGAAGCCTAAG
AACTCCAAGTCTGACGTGAAGGCCCCACCCATCACAGACG
AGGATAAGCAGAAGGCCGATCCAGAGATGTTCGCACTGCG GCTGGCACTGGAGGAGAAGAGACTGAATAAGGTGAAGAGC
AAGAAGGAAGTGATCGCCAACAAGATCGTGGCCAAGGCAC
TGGAGCTGAGGGACAAGATTACGGACCAGTGCTGATCAAGGG
CGAGAATATCAGCGATACCACAAAGAAGGGCAAGAAGTCT
AGCACCCAATTCCTTCCTGATGGACTGGCTGGCCAGAGGCG
TGGCCAACAAGGTGAAGGAGATGGTCATGATGCACCAGGG
CCTGGAGTTCGTGGAGGTGAACCCCAATTTTACCTCCCAC
CAGGATCCTTTCGTGCACAAGAACCCAGAGAATACCTTCC
GGGCAAGGTACAGCAGGTGCACCCCTTCCGAGCTGACAGA
GAAGAACCGCAAGGAGATCCTGTCCTTCCTGTCTGACAAG
CCCAGCAAGCGGCCTACTAACGCCTACTATAATGAGGGCG
CCATGGCCTTTCTGGCCACATATGGCCTGAAGAAGAATGA
CGTGCTGGGCGTGTCCCTGGAGAAGTTCAAGCAGATCATG
GCCAACATCCTGCACCAGCGGTCCGAGGATCAGCTGCTGT
TTCCCTCTAGAGGCGGCATGTTCTACCTGGCCACCTATAA
GCTGGACGCGATGCCACAGCGTGAACTGGAATGGCAAG
CAGTTTTGGGTGTGTAACGCCGACCTGGTGGCCGCCTACA
ATGTGGGCCTGGTGGACATCCAGAAGGATTTCAAGAAGAA
GAAAAGGCCGGCGGCCACG**AAAAGGCCGGCGGCCACGAAA
AAGGCCGGCCAGGCCGGCCAGGCAAAAAAGAAAAAG**TAAT
AA
(SEQ ID NO: 501)

>Cas12i2_mammalian_effector
atgGAAAATCGAAGAAGGTAAAGGTCACCATCACCATCACC
ACATGAGCTCCGCCATCAAGTCCTACAAGTCTGTGCTGCG
GCCAAACGAGAGAAAGAATCAGCTGCTGAAGAGCACCATC
CAGTGCCTGGAGGACGGCTCCGCCTTCTTTTTTCAAGATGC
TGCAGGGCCTGTTTGGCGGCATCACCCCCGAGATCGTGAG
ATTCAGCACAGAGCAGGAGAAGCAGCAGCAGGATATCGCC
CTGTGGTGTGCCGTGAATTGGTTCAGGCCTGTGAGCCAGG
ACTCCCTGACCCACACAATCGCCTCCGATAACCTGGTGGA
GAAGTTTGAGGAGTACTATGGCGGCAACAGCCAGCGACGCC
ATCAAGCAGTACTTCAGCGCCTCCATCGGCGAGTCCTACT
ATTGGAATGACTGCCGCCAGCAGTACTATGATCTGTGTCG
GGAGCTGGGCGTGGAGGTGTCTGACCTGACCCACGATCTG
GAGATCCTGTGCCGGGAGAAGTGTCTGGCCGTGGCCACAG
AGAACAACCAGAACAATTCTATCATCAGCGTGCTGTTTGG
CACCGGCGAGAAGGAGGATAGGTCTGTGAAGCTGCGCATC
ACAAAGAAGATCCTGGAGGCCATCAGCAACCTGAAGGAGA
TCCCAAAGAATGTGGCCCCCATCCAGGAGATCATCCTGAA
TGTGGCCAAGGCCACCAAGGAGACATTCAGACAGGTGTAC
GCAGGAAACCTGGGAGCACCATCCACCCTGGAGAAGTTTA
TCGCCAAGGACGGCCAGAAGGAGTTCGATCTGAAGAAGCT
GCAGCAGACCCTGGAGAAGACTGATCCGGGGCAAGTCTAAG
GAGAGAGATTGGTGCTGTCAGGAGGAGCTGAGGAGCTACG
TGGAGCAGAATACCATCCAGTATGACCTGTGGGCCTGGGG
CGAGATGTTCAACAAGGCCCACACCGCCCTGAAGATCAAG
TCCACAAGAAACTACAATTTTGCCAAGCAGAGGCTGGAGC
AGTTCAAGGAGATCCAGTCTCTGAACAATCTGCTGGTGGT
GAAGAAGCTGAACGACTTTTTCGATAGCGAGTTTTTCTCC
GGCGAGGAGACCTACACAATCTGCGTGCACCACCTGGGCG
GCAAGGACCTGTCCAGCCGGCACGGTTCTGGCCTGTGGAGGACGA
TCCCGCCGATCCTGAGAATGCCATCGTGGTGCTGTGCGAC
GATCTGAAGAACAATTTTAAGAAGGAGCCTATCAGGAACA
TCCTGCGCTACATCTTCACCATCCGCCAGGAGTGTAGCGC
ACAGGACATCCTGGCCAGCAGCAAATACAATCAGCAGCTG
GATCGGTATAAGAGCCAGAAGGCCAACCCATCCGTGCTGG
GCAATCAGGGCTTTACCTGGACAAACGCCGTGATCCTGCC
AGAGAAGGCCCAGCGGAACGACAGACCCAATTCTCTGGAT
CTGCGCATCTGGCTGTACCTGAAGCTGCGGCACCCTGACG
GCAGATGGAAGAAGCACCATATCCCATTCTACGATACCCG
GTTTTTCCAGGAGATCTATGCCGCCGGCAATAGCCCTGTG
GACACCTGTCAGTTTAGGACACCCCGCTTCGGCTATCACC
TGCCTAAGCTGACCGATCAGACAGCCATCCGCGTGAACAA
GAAGCACGTGAAGGCAGCAAAGACCGAGGCACGGATCAGA
CTGGCCATCCAGCAGGGACACTGCCAGTGTCCAATCTGA
AGATCACCGAGATCTCCGCCACAATCAACTCTAAGGGCCA
GGTGCGCATCCCCGTGAAGTTTGACGTGGGAAGGCAGAAG
GGAACCCTGCAGATCGGCGACCGGTTCTGCGGCTACGATC
AGAACCAGACAGCCTCTCACGCCTATAGCCTGTGGGAGGT
GGTGAAGGAGGGCCAGTACCACAAGGAGCTGGGCTGTTTT
GTGCGCTTCATCTCTAGCGGCGACATCGTGTCCATCACCG
AGAACCGGGGCAATCAGTTTGATCAGCTGTCTTATGAGGG
CCTGGCCTACCCCCAGTATGCCGACTGGAGAAAGAAGGCC TABLE 10-continued Sequences enabling mammalian expression of Cas12i effectors with included N-terminal mH6 tag and C-terminal nucleoplasmin NLS sequence (bolded)

TCCAAGTTCGTGTCTCTGTGGCAGATCACCAAGAAGAACA
AGAAGAAGGAGATCGTGACAGTGGAGGCCAAGGAGAAGTT
TGACGCCATCTGCAAGTACCAGCCTAGGCTGTATAAGTTC
AACAAGGAGTACGCCTATCTGCTGCGGGATATCGTGAGAG
GCAAGAGCCTGGTGGAGCTGCAGCAGATCAGGCAGGAGAT
CTTTCGCTTCATCGAGCAGGACTGTGGAGTGACCCGCCTG
GGATCTCTGAGCCTGTCCACCCTGGAGACAGTGAAGGCCG
TGAAGGGCATCATCTACTCCTATTTTTCTACAGCCCTGAA
TGCCTCTAAGAACAATCCCATCAGCGACGAGCAGCGGAAG
GAGTTTGATCCTGAGCTGTTCGCCCTGCTGGAGAAGCTGG
AGCTGATCAGGACTCGGAAGAAGAAGCAGAAGGTGGAGAG
AATCGCCAATAGCCTGATCCAGACATGCCTGGAGAACAAT
ATCAAGTTCATCAGGGGCGAGGGCGACCTGTCCACCACAA
ACAATGCCACCAAGAAGAAGGCCAACTCTAGGAGCATGGA
TTGGCTGGCCAGAGGCGTGTTTAATAAGATCCGGCAGCTG
GCCCCAATGCACAACATCACCCTGTTCGGCTGCGGCGACC
TGTACACATCCCACCAGGACCCTCTGGTGCACAGAAACCC
AGATAAGGCCATGAAGTGTAGATGGGCAGCAATCCCAGTG
AAGGACATCGGCGATTGGGTGCTGAGAAAGCTGTCCCAGA
ACCTGAGGGCCAAGAATATCGGCACCGGCGAGTACTATCA
CCAGGGCGTGAAGGAGTTCCTGTCTCACTATGAGCTGCAG
GACCTGGAGGAGGAGCTGCTGAAGTGGCGGTCTGATAGAA
AGAGCAACATCCCTTGCTGGGTGCTGCAGAATAGACTGGC
CGAGAAGCTGGGCAACAAGGAGGCCGTGGTGTACATCCCA
GTGAGGGGCGGCCGCATCTATTTTGCAACCCACAAGGTGG
CAACAGGAGCCGTGAGCATCGTGTTCGACCAGAAGCAAGT
GTGGGTGTGTAATGCAGATCACGTGGCAGCAGCAAACATC
GCACTGACCGTGAAGGGCATCGGCGAGCAGTCCTCTGACG
AGGAGAACCCCGATGGCTCCAGGATCAAGCTGCAGCTGAC
ATCT**AAAAGGCCGGCGGCCACGAAAAAGGCCGGCCAGGCA
AAAAAGAAAAAG**TAATAA
(SEQ ID NO: 502)

>bGH polyA Tail
CGACTGTGCCTTCTAGTTGCCAGCCATCTGTTGTTTGCCC
CTCCCCCGTGCCTTCCTTGACCCTGGAAGGTGCCACTCCC
ACTGTCCTTTCCTAATAAAATGAGGAAATTGCATCGCATT
GTCTGAGTAGGTGTCATTCTATTCTGGGGGGTGGGGTGGG
GCAGGACAGCAAGGGGGAGGATTGGGAAGACAATAGCAGG
CATGCTGGGGATGCGGTGGGCTCTATGG
(SEQ ID NO: 503)

TABLE 11

Amino Acid Sequences of Motifs and Functional Domains in Engineered Variants of CLUST.029130 (Type V-I) CRISPR-Cas Effector Proteins

>LINKER_1
GS (SEQ ID NO: 600)

>LINKER_2
GSGGGGS (SEQ ID NO: 601)

>LINKER_3
GGGGSGGGSGGGGS (SEQ ID NO: 602)

>LINKER_4
GGSGGSGGSGGSGSGS (SEQ ID NO: 603)

>LINKER 5 (Gaudelli et al., 2017)
SGGSSGGSSGSETPGTSESATPESSGGSSGGS
(SEQ ID NO: 604)

>ecTadA(wt) (Gaudelli et al., 2017)
[N-term fusion to ecTadA* (7.10)]
MSEVEFSHEYWMRHALTLAKRAWDEREVPVGAVLV
HNNRVIGEGWNRPIGRHDPTAHAEIMALRQGGLVM
QNYRLIDATLYVTLEPCVMCAGAMIHSRIGRVVFG
ARDAKTGAAGSLMDVLHHPGMNHRVEITEGILADE
CAALLSDFFRMRRQEIKAQKKAQSSTD
(SEQ ID NO: 605)

TABLE 11-continued

Amino Acid Sequences of Motifs and Functional Domains in Engineered Variants of CLUST.029130 (Type V-I) CRISPR-Cas Effector Proteins >ecTadA*(7.10) (Gaudelli et al., 2017)
[N-term fusion to CRISPR nuclease]
MSEVEFSHEYWMRHALTLAKRAWDEREVPVGAVLV
HNNRVIGEGWNRPIGRHDPTAHAEIMALRQGGLVM
QNYRLIDATLYVTLEPCVMCAGAMIHSRIGRVVFG
ARDAKTGAAGSLMDVLHHPGMNHRVEITEGILADE
CAALLSDFFRMRRQEIKAQKKAQSSTD
(SEQ ID NO: 606)

[Cytidine deaminase, AID, APOBEC1:
N-term fusion (or optionally C-term)]
>AID-APOBEC1 (Dickerson et al., 2003,
Komor et al., 2017)
MDSLLMNRRKFLYQFKNVRWAKGRRETYLCYVVKR
RDSATSFSLDFGYLRNKNGCHVELLFLRYISDWDL
DPGRCYRVTWFTSWSPCYDCARHVADFLRGNPNLS
LRIFTARLYFCEDRKAEPEGLRRLHRAGVQIAIMT
FKDYFYCWNTFVENHERTFKAWEGLHENSVRLSRQ
LRRILLPLYEVDDLRDAFRTLGL
(SEQ ID NO: 607)

>Lamprey_AID-APOBEC1
(Rogozin et al., 2007,
Komor et al., 2017)
MTDAEYVRIHEKLDIYTFKKQFFNNKKSVSHRCYV
LFELKRRGERRACFWGYAVNKPQSGTERGIHAEIF
SIRKVEEYLRDNPGQFTINWYSSWSPCADCAEKIL
EWYNQELRGNGHTLKIWACKLYYEKNARNQIGLWN
LRDNGVGLNVMVSEHYQCCRKIFIQSSHNQLNENR
WLEKTLKRAEKRRSELSIMIQVKILHTTKSPAV
(SEQ ID NO: 608)

>APOBEC1_BE1 (Komor et al., 2016)
MSSETGPVAVDPTLRRRIEPHEFEVFFDPRELRKE
TCLLYEINWGGRHSIWRHTSQNTNKHVEVNFIEKF
TTERYFCPNTRCSITWELSWSPCGECSRAITEFLS
RYPHVTLFIYIARLYHHADPRNRQGLRDLISSGVT
IQIMTEQESGYCWRNFVNYSPSNEAHWPRYPHLWV
RLYVLELYCIILGLPPCLNILRRKQPQLTFFTIAL
QSCHYQRLPPHILWATGLK
(SEQ ID NO: 609)

These results suggest that members of the compact Type V-I CRISPR family can be engineered for activity in eukaryotic cells, and specifically, for genome editing in mammalian cells. A mammalian functional Type V-I effector enables the development of additional technologies based on further engineering on top of a DNA binding chassis.

Example 11. Type V-I CRISPR-Cas Systems can be Used to Provide Genotype-Gated Control of Genome Replication, Viral Propagation, Plasmid Propagation, Cell Death, or Cell Dormancy Hybridization of the Type V-I CRISPR-Cas effector protein and crRNA with a specific ssDNA or dsDNA target results in nicking or cleavage of the substrate. The dependence of such activity on the presence of a specific DNA target in a cell is valuable since it enables targeting of specific genomic material or cell populations based on specific underlying genotypes. Numerous applications exist in both eukaryotic, prokaryotic, and viral/plasmid settings for such control of genome replication, cell death, or cell dormancy.

For prokaryotic, viral, and plasmid applications, a Type V-I CRISPR-Cas system (e.g., including a Type V-I effector and a RNA guide) can be delivered (e.g., in vitro or in vivo) in order to stop genome replication and/or induce cell death or dormancy of specific prokaryote populations (e.g., bacterial populations) in a genotype-specific way. For instance, the Type V-I CRISPR-Cas system can include one or more RNA guides that specifically target a particular virus, plasmid, or prokaryotic genus, species, or strain. As shown in FIG. 5A-D cleavage, nicking, or interference with the *E. coli* genome or plasmid DNA conferring antibiotic resistance in *E. coli* by a Type V-I system results in specific depletion of the *E. coli* containing these sequences. Specific targeting of viruses, plasmids, or prokaryotes has many therapeutic benefits as it may be used to induce death or dormancy of undesirable bacteria (e.g., pathogenic bacteria such as *Clostridium difficile*). In addition, the Type V-I systems provided herein may be used to target prokaryotic cells having specific genotypes. Within the microbial diversity that colonizes humans, only a small number of bacterial strains can induce pathogenesis. Further, even within pathogenic strains such as *Clostridium difficile*, not all members of the bacterial population exist continuously in active, disease-causing states. Thus, targeting the Type V-I system based on the genotype of a virus, plasmid, or prokaryotic cell allows for specific control of which genomes or cell populations are targeted without disrupting the entire microbiome.

Additionally, bacterial strains can be readily engineered with genetic circuits or environmentally-controlled expression elements to generate genetic kill switches that limit the growth, colonization, and/or shedding of the engineered bacterial strains. For example, the expression of a TypeV-I effector and specific crRNA, can be controlled using promoters derived from the regulatory regions of genes encoding proteins expressed in response to external stimuli, such as cold sensitive proteins (PcspA), heat shock proteins (Hsp), chemically inducible systems (Tet, Lac, AraC). The controlled expression of one or more elements of the Type V-I system allows for the full functional system to be expressed only upon exposure to an environmental stimulus, which results in genotype-specific DNA interference activity of the system and thereby induces cell death or dormancy. Kill switches including Cas12i effectors as those described herein may be advantageous over traditional kill switch designs such as toxin/antitoxin systems (e.g., CcdB/CcdA Type II toxin/antitoxin systems), since they are not dependent on relative protein expression ratios which may be affected by leaky expression from a promoter (e.g., an environmental-stimulus dependent promoter), and thus allow for more precise control of the kill-switch.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An engineered, non-naturally occurring Clustered Regularly Interspaced Short Palindromic Repeat (CRISPR)—associated (Cas) system comprising:
   (a) an RNA guide or a nucleic acid encoding the RNA guide, wherein the RNA guide comprises a direct repeat sequence and a spacer sequence; and
   (b) a CRISPR-Cas effector protein or a nucleic acid encoding the CRISPR-Cas effector protein, wherein the CRISPR-Cas effector protein comprises an amino acid sequence with at least 95% identity to SEQ ID NO: 5, and a nuclear localization sequence (NLS) having an amino acid sequence having at least 90% identical to KRPAATKKAGQAKKKK (SEQ ID NO: 301);
   wherein the CRISPR-Cas effector protein binds to the RNA guide, and wherein the spacer sequence is complementary to at least 15 nucleotides of a target nucleic acid.

2. The system of claim 1, wherein the NLS has an amino acid sequence according to KRPAATKKAGQAKKKK (SEQ ID NO: 301).

3. The system of claim 1, wherein the CRISPR-Cas effector protein comprises one or more of:
   (a) a RuvC domain comprising the amino acid sequence $X_1SHX_4DX_6X_7$ (SEQ ID NO: 200, wherein $X_1$ is S or T, $X_4$ is Q or L, $X_6$ is P or S, and $X_7$ is F or L,
   (b) a RuvC domain comprising the amino acid sequence $X_1XDXNX_6X_7XXXX_{11}$ (SEQ ID NO: 201), wherein $X_1$ is A, G, or S, X is any amino acid, $X_6$ is Q or I, $X_7$ is T, S, or V, and $X_{11}$ is T or A; and
   (c) a RuvC domain comprising the amino acid sequence $X_1X_2X_3$ E (SEQ ID NO: 210), wherein $X_1$ is C, F, I, L, M, P, V, W, or Y, $X_2$ is C, F, I, L, M, P, R, V, W, or Y, and $X_3$ is C, F, G, I, L, M, P, V, W, or Y.

4. The system of claim 1, wherein the CRISPR-Cas effector protein comprises the amino acid sequence set forth in SEQ ID NO: 5.

5. The system of claim 1, wherein the direct repeat sequence comprises any one of:
   (a) 5'-CCGUCNNNNNNUGACGG-3' (SEQ ID NO: 202) proximal to the 3' end, wherein N is any nucleobase; or
   (b) 5'-UCX$_3$UX$_5$X$_6$X$_7$UUGACGG-3' (SEQ ID NO: 205) proximal to the 3' end, wherein $X_3$ is C, T, or U, $X_5$ is A, T, or U, $X_6$ is A, C, or G, and $X_7$ is A or G.

6. The system of claim 1, wherein the RNA guide comprises a nucleotide sequence with at least 95% sequence identity to SEQ ID NO: 101.

7. The system of claim 1, wherein the RNA guide comprises a nucleotide sequence set forth in SEQ ID NO: 101.

8. The system of claim 1, wherein the direct repeat sequence comprises an RNA transcript of a nucleotide sequence with at least 95% sequence identity to SEQ ID NO: 9 or SEQ ID NO: 10.

9. The system of claim 1, wherein the direct repeat sequence comprises an RNA transcript of a nucleotide sequence set forth in SEQ ID NO: 9 or SEQ ID NO: 10.

10. The system of claim 1, wherein the direct repeat sequence comprises a stem-loop structure proximal to a 3' end of the direct repeat sequence, wherein the stem-loop structure comprises:
    (a) a first stem nucleotide strand 5 nucleotides in length;
    (b) a second stem nucleotide strand 5 nucleotides in length, wherein the first and second stem nucleotide strands bind with each other; and
    (c) a loop nucleotide strand arranged between the first and second stem nucleotide strands, wherein the loop nucleotide strand comprises 6, 7, or 8 nucleotides.

11. The system of claim 1, wherein the spacer sequence comprises between 15 and 47 nucleotides in length.

12. The system of claim 11, wherein the spacer sequence comprises between 24 and 38 nucleotides in length or between 20 and 33 nucleotides in length.

13. The system of claim 11, wherein the spacer sequence has at least 90%, 95%, or 100% complementarity to the target nucleic acid.

14. The system of claim 1, wherein the NLS is attached to the C-terminus of the CRISPR-Cas effector protein.

15. The system of claim 1, wherein the NLS is attached to the N-terminus of the CRISPR-Cas effector protein.

16. The system of claim 1, wherein the CRISPR-Cas effector protein recognizes a protospacer adjacent motif (PAM) sequence, wherein the PAM sequence comprises a nucleotide sequence set forth as 5'-TTN-3', wherein N is any nucleotide.

17. The system of claim 16, wherein the PAM sequence comprises a nucleotide sequence set forth as 5'-TTY-3', wherein Y is C or T, or 5'-TTH-3', wherein H is A or C or T.

18. The system of claim 1, wherein the CRISPR-Cas effector protein further comprises a second NLS.

19. The system of claim 1, wherein the CRISPR-Cas effector protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

20. The system of claim 1, wherein the CRISPR-Cas effector protein further includes a linker sequence.

21. The system of claim 1, wherein the nucleic acid encoding the CRISPR-Cas effector protein is in a vector.

22. The system of claim 21, wherein the vector comprises a retroviral vector, a lentiviral vector, a phage vector, an adenoviral vector, an adeno-associated vector, or a herpes simplex vector.

23. The system of claim 1, wherein the system is present in a delivery system comprising a nanoparticle, a liposome, an exosome, a microvesicle, or a gene-gun.

24. A cell comprising the system of claim 1.

25. The cell of claim 24, wherein the cell is a human cell.

26. A method of binding the system of claim 1 to the target nucleic acid in a cell comprising:
   (a) providing the system; and
   (b) delivering the system to the cell,
   wherein the cell comprises the target nucleic acid, wherein the CRISPR-Cas effector protein binds to the RNA guide, and wherein the spacer sequence binds to the target nucleic acid.

27. The method of claim 26, wherein the target nucleic acid is a double-stranded DNA.

28. The method of claim 26, wherein binding the system to the target nucleic acid results in cleavage, or a formation of an insertion or a deletion the target nucleic acid.

* * * * *